(12) United States Patent
Findlay et al.

(10) Patent No.: US 10,717,734 B2
(45) Date of Patent: Jul. 21, 2020

(54) INDOLE AND AZAINDOLE HALOALLYLAMINE DERIVATIVE INHIBITORS OF LYSYL OXIDASES AND USES THEREOF

(71) Applicant: PHARMAXIS LTD., Frenchs Forest, NSW (AU)

(72) Inventors: Alison Dorothy Findlay, Frenchs Forest (AU); Craig Ivan Turner, Frenchs Forest (AU); Mandar Deodhar, Frenchs Forest (AU); Jonathan Stuart Foot, Frenchs Forest (AU); Wolfgang Jarolimek, Frenchs Forest (AU); Wenbin Zhou, Frenchs Forest (AU); Alan Duncan Robertson, Warrawee (AU)

(73) Assignee: Pharmaxis Ltd., Frenchs Forest, New South Wales (AU)

( * ) Notice: Subject to any disclaimer, the term of this patent is extended or adjusted under 35 U.S.C. 154(b) by 0 days.

(21) Appl. No.: 16/076,985

(22) PCT Filed: Feb. 10, 2017

(86) PCT No.: PCT/AU2017/000040
§ 371 (c)(1),
(2) Date: Aug. 9, 2018

(87) PCT Pub. No.: WO2017/136871
PCT Pub. Date: Aug. 17, 2017

(65) Prior Publication Data
US 2019/0119269 A1 Apr. 25, 2019

(30) Foreign Application Priority Data

Feb. 12, 2016 (AU) .................. 2016900478
Jul. 1, 2016 (AU) .................. 2016902593

(51) Int. Cl.
| | | |
|---|---|---|
| *C07D 471/04* | (2006.01) | |
| *C07D 487/04* | (2006.01) | |
| *A61K 45/06* | (2006.01) | |
| *C07D 209/42* | (2006.01) | |
| *A61P 1/16* | (2006.01) | |
| *A61P 13/12* | (2006.01) | |
| *A61P 11/00* | (2006.01) | |
| *A61K 31/4025* | (2006.01) | |
| *A61K 31/4045* | (2006.01) | |
| *A61K 31/41* | (2006.01) | |
| *A61K 31/4245* | (2006.01) | |
| *A61K 31/437* | (2006.01) | |
| *A61K 31/4439* | (2006.01) | |
| *A61K 31/506* | (2006.01) | |
| *C07D 209/14* | (2006.01) | |
| *C07D 401/04* | (2006.01) | |
| *C07D 403/04* | (2006.01) | |
| *C07D 403/10* | (2006.01) | |
| *C07D 413/10* | (2006.01) | |
| *A61K 31/5025* | (2006.01) | |
| *A61K 31/519* | (2006.01) | |
| *C07D 209/20* | (2006.01) | |
| *C07D 209/36* | (2006.01) | |

(52) U.S. Cl.
CPC ........ *C07D 471/04* (2013.01); *A61K 31/4025* (2013.01); *A61K 31/4045* (2013.01); *A61K 31/41* (2013.01); *A61K 31/4245* (2013.01); *A61K 31/437* (2013.01); *A61K 31/4439* (2013.01); *A61K 31/506* (2013.01); *A61K 31/5025* (2013.01); *A61K 31/519* (2013.01); *A61K 45/06* (2013.01); *A61P 1/16* (2018.01); *A61P 11/00* (2018.01); *A61P 13/12* (2018.01); *C07D 209/14* (2013.01); *C07D 209/20* (2013.01); *C07D 209/36* (2013.01); *C07D 209/42* (2013.01); *C07D 401/04* (2013.01); *C07D 403/04* (2013.01); *C07D 403/10* (2013.01); *C07D 413/10* (2013.01); *C07D 487/04* (2013.01)

(58) Field of Classification Search
CPC .......................... C07D 209/14; A61K 31/4025
See application file for complete search history.

(56) References Cited

U.S. PATENT DOCUMENTS

| | | |
|---|---|---|
| 4,358,603 A | 11/1982 | Yu |
| 4,522,811 A | 6/1985 | Eppstein et al. |
| 4,699,928 A | 10/1987 | McDonald |

(Continued)

FOREIGN PATENT DOCUMENTS

| | | |
|---|---|---|
| AU | 2014200520 A1 | 2/2014 |
| WO | WO 2007/120528 | 10/2007 |

(Continued)

OTHER PUBLICATIONS

International Search Report dated Mar. 29, 2017 in connection with PCT International Application No. PCT/AU2017/000040.

(Continued)

*Primary Examiner* — Golam M Shameem
(74) *Attorney, Agent, or Firm* — Gary J. Gershik; Cooper & Dunham LLP

(57) ABSTRACT

The present invention relates to novel compounds which are capable of inhibiting certain amine oxidase enzymes. These compounds are useful for treatment of a variety of indications, e.g., fibrosis, cancer and/or angiogenesis in human subjects as well as in pets and livestock. In addition, the present invention relates to pharmaceutical compositions containing these compounds, as well as various uses thereof.

19 Claims, 2 Drawing Sheets

(56) References Cited

U.S. PATENT DOCUMENTS

| | | | |
|---|---|---|---|
| 4,943,593 | A | 7/1990 | Palfreyman et al. |
| 4,965,288 | A | 10/1990 | Palfreyman et al. |
| 4,997,854 | A | 3/1991 | Kagan et al. |
| 5,021,456 | A | 6/1991 | Palfreyman et al. |
| 5,059,714 | A | 10/1991 | Palfreyman et al. |
| 5,182,297 | A | 1/1993 | Palfreyman et al. |
| 5,252,608 | A | 10/1993 | Palfreyman et al. |
| 2008/0199933 | A1 | 8/2008 | Sayre |
| 2009/0053224 | A1 | 2/2009 | Smith et al. |
| 2011/0044907 | A1 | 2/2011 | Marshall et al. |
| 2015/0158813 | A1 | 6/2015 | Deodhar et al. |
| 2019/0040007 | A1 | 2/2019 | Findlay et al. |

FOREIGN PATENT DOCUMENTS

| | | |
|---|---|---|
| WO | WO 2009/017833 A2 | 2/2009 |
| WO | WO 2009/066152 | 5/2009 |

OTHER PUBLICATIONS

Written Opinion of the International Searching Authority dated Mar. 29, 2017 in connection with PCT International Application No. PCT/AU2017/000040.

Gacheru, S.N. et al., "Vicinal Diamines as Pyrroloquinoline Quinone-directed Irreversible Inhibitors of Lysyl Oxidase", *The Journal of Biological Chemistry*, 1989, vol. 264, No. 22, pp. 12963-12968.

Eleftheriadis, N et al ., Rational Development of a Potent 15-Lipoxygenase-1 Inhibitors with in Vivo and ex Vivo Anti-inflammatory Properties, *Journal of Medicinal Chemistry*, 2015, vol. 58, No. 19, pp. 7850-7862.

Choppara, P. et al., "Design, Synthesis of Novel N Prenylated Indole-3-carbazones and Evaluation of in Vitro Cytotoxicity and 5-LOX Inhibition Activities", 2015, *Arabian Journal of Chemistry*.

Chanoki, M., et al., "Increased expression of lysyl oxidase in skin with scleroderma", Br J Dermatol, 1995; 133: 710-715.

Counts, D.F., et al., "Collagen lysyl oxidase activity in the lung decreases during bleomycin induced lung fibrosis", J Pharmacol Exp Ther, 1981; 219: 675-678.

Di Donato, A., et al., "Lysyl oxidase expression and collagen cross-linking during chronic adriamycin nephropathy", Nephron, 1997; 76: 192-200.

Halberg et al., "Hypoxia inducible factor 1α induces fibrosis and insulin resistance in white adipose tissue", Cell Biol, 2009; 29: 4467-4483.

Holt A. and Palcic M., "A peroxidase-coupled continuous absorbance plate-reader assay for flavin monoamine oxidases, copper-containing amine oxidases and related enzymes" Nat. Protoc., 2006; 1: 2498-2505.

Hee-Jung M. et al., "MCF-7 Cells Expressing Nuclear Associated Lysyl Oxidase-like 2 (LOXL2) Exhibit an Epithelial-to-Mesenchymal Transition (EMT) Phenotype and are Highly Invasive in Vitro", J Biol Chem., 2013;288: 30000-30008.

Jones et al., "Three-dimensional characterization of fibroblast foci in idiopathic pulmonary fibrosis", AJRCCM 191;2015:1-11.

Saito et al. "Characterization of hepatic lipid profiles in a mouse model with nonalcoholic steatohepatitis and subsequent fibrosis", Sci Rep. Aug. 20, 2015;5:1-11.

Kagan H.M. and Li W., "Lysyl oxidase: properties, specificity, and biological roles inside and outside of the cell", J Cell Biochem 2003; 88: 660-672.

Kagan, H.M., "Lysyl oxidase: Mechanism, regulation and relationship to liver fibrosis", Pathology—Research and Practice, 1994; 190: 910-919.

Kagan, H.M. et al., "Changes in aortic lysyl oxidase activity in diet induced atherosclerosis in the rabbit", Arteriosclerosis, 1981; 1: 287-291.

Kleiner DE. et al., "Design and validation of a histological scoring system for nonalcoholic fatty liver disease", Hepatology, 2005;41:1313.

Lopez, B. et al., "Role of lysyl oxidase in myocardial fibrosis: from basic science to clinical aspects" Am J Physiol Heart Circ Physiol, 2010; 299: H1-H9.

Natsume, M. et al., "Attenuated liver fibrosis and depressed serum albumin levels in carbon tetrachloride-treated IL-6-deficient mice", J. Leukoc. Biol., 1999, 66, 601-608.

S.P. Robins, "Biochemistry and functional significance of collagen cross-linking", Biochem Soc Trans 2007; 35(5): 849-852.

Saito et al, "Single-Column High-Performance Liquid Chromatographic-Fluorescence Detection of Immature, Mature, and Senescent Cross-Links of Collagen", Anal. Biochem., 1997; 253: 26-32.

Siddikiuzzaman et al., "Lysyl oxidase: a potential target for cancer therapy", Inflammapharmacol 2011; 19: 117-129.

Siegel, R.C. et al., "Biochemical and immunochemical study of lysyl oxidase in experimental hepatic fibrosis in the rat", Proc. Natl. Acad. Sci. USA 1978; 75: 2945-2949.

Stewart, C.D. et al., "Analysis of hypoxia-associated gene expression in prostate cancer: lysyl oxidase and glucose transporter-1 expression correlate with Gleason score", Oncol Rep 2008; 20: 1561-1567.

Tang, S.S. et al., "Reaction of aortic lysyl oxidase with beta aminoproprionitrile", J Biol Chem 1983; 258: 4331-4338.

Woznick, A.R. et al., "Lysyl oxidase expression in bronchogenic carcinoma", Am J Surg 2005; 189: 297-301.

Yao, Q.Y. et al., "Inhibition by curcumin of multiple sites of the transforming growth factor-betel signalling pathway ameliorates the progression of liver fibrosis induced by carbon tetrachloride in rats" BMC Complement Altern Med., Sep. 16, 2012;12(1):156.

Nov. 15, 2019 European Search Report issued in connection with European Patent Application No. 17749813.6.

Martinez-Martinez, E. et al. (2016) "The lysyl oxidase inhibitor (β-aminopropionitrile) reduces leptin profibrotic effects and ameliorates cardiovascular remodeling in diet-induced obesity in rats", *Journal of Molecular and Cellular Cardiology*, vol. 92, pp. 96-104.

INDOLE AND AZAINDOLE HALOALLYLAMINE DERIVATIVE INHIBITORS OF LYSYL OXIDASES AND USES THEREOF

CROSS-REFERENCE TO RELATED APPLICATIONS

This application is a § 371 national stage of PCT International Application No. PCT/AU2017/000040, filed Feb. 10, 2017, claiming priority of Australian Patent Applications Nos. 2016902593, filed Jul. 1, 2016, and 2016900478, filed Feb. 12, 2016, the contents of each of which are hereby incorporated by reference into the application.

TECHNICAL FIELD

The present invention relates to novel compounds which are capable of inhibiting certain amine oxidase enzymes. These compounds are useful for treatment of a variety of indications, e.g., fibrosis, cancer and/or angiogenesis in human subjects as well as in pets and livestock. In addition, the present invention relates to pharmaceutical compositions containing these compounds, as well as various uses thereof.

BACKGROUND

A family of five closely relating enzymes have been linked to fibrotic disease and to metastatic cancer. The enzymes are related to lysyl oxidase (LOX), the first family member to be described and four closely related enzymes, LOX-like1 (LOXL1), LOXL2, LOXL3, and LOXL4 (Kagan H. M. and Li W., Lysyl oxidase: properties, specificity, and biological roles inside and outside of the cell. *J Cell Biochem* 2003; 88: 660-672). Lysyl oxidase isoenzymes are copper-dependent amine oxidases which initiate the covalent cross-linking of collagen and elastin. A major function of lysyl oxidase isoenzymes is to facilitate the cross-linking of collagen and elastin by the oxidative deamination of lysine and hydroxylysine amino acid side chains to aldehydes which spontaneously react with neighbouring residues. The resulting cross-linked strands contribute to extracellular matrix (ECM) stability. Lysyl oxidase activity is essential to maintain the tensile and elastic features of connective tissues of skeletal, pulmonary, and cardiovascular systems, among others. The biosynthesis of LOX is well understood; the protein is synthesized as a pre-proLOX that undergoes a series of post-translational modifications to yield a 50 kDa pro-enzyme which is secreted into the extracellular environment. For LOX and LOXL1 proteolysis by bone morphogenetic protein-1 (BMP-1) and other procollagen C-proteinases releases the mature and active form. LOXL2, LOXL3 and LOXL4 contain scavenger receptor cysteine-rich protein domains and are directly secreted as active forms.

Lysyl oxidase isoenzymes belong to a larger group of amine oxidases which include flavin-dependent and copper-dependent oxidases which are described by the nature of the catalytic co-factor. Flavin-dependent enzymes include monoamine oxidase-A (MAO-A), MAO-B, polyamine oxidase and lysine demethylase (LSD1), and the copper-dependent enzymes include semicarbazide sensitive amine oxidase (vascular adhesion protein-1, SSAO/VAP-1), retinal amine oxidase, diamine oxidase and the lysyl oxidase isoenzymes. The copper-dependent amine oxidases have a second co-factor which varies slightly from enzyme to enzyme. In SSAO/VAP-1 it is an oxidized tyrosine residue (TPQ, oxidized to a quinone), whereas in the lysyl oxidase isoenzymes the TPQ has been further processed by addition of a neighboring lysine residue (to form LTQ); see Kagan, H. M. and Li, W., Lysyl oxidase: Properties, specificity, and biological roles inside and outside of the cell. *J Cell Biochem* 2003; 88: 660-672.

Since lysyl oxidase isoenzymes exhibit different in vivo expression patterns it is likely that specific isoenzymes will have specific biological roles. Catalytically active forms of LOX have been identified in the cytosolic and nuclear compartments which suggest the existence of undefined roles of LOX in cellular homeostasis. Significant research is currently underway to define these roles. LOX itself, for example, plays a major role in epithelial-to-mesenchymal transition (EMT), cell migration, adhesion, transformation and gene regulation. Different patterns of LOX expression/activity have been associated with distinct pathological processes including fibrotic diseases, Alzheimer's disease and other neurodegenerative processes, as well as tumour progression and metastasis. See, for example, Woznick, A. R., et al. Lysyl oxidase expression in bronchogenic carcinoma. *Am J Surg* 2005; 189: 297-301. Catalytically active forms of LOXL2 can be also found in the nucleus (J Biol Chem. 2013; 288: 30000-30008) and can deaminate lysine 4 in histone H3 (*Mol Cell* 2012 46: 369-376).

Directed replacement of dead or damaged cells with connective tissue after injury represents a survival mechanism that is conserved throughout evolution and appears to be most pronounced in humans serving a valuable role following traumatic injury, infection or diseases. Progressive scarring can occur following more chronic and/or repeated injuries that causes impaired function to parts or all of the affected organ. A variety of causes, such as chronic infections, chronic exposure to alcohol and other toxins, autoimmune and allergic reactions or radio- and chemotherapy can all lead to fibrosis. This pathological process, therefore, can occur in almost any organ or tissue of the body and, typically, results from situations persisting for several weeks or months in which inflammation, tissue destruction and repair occur simultaneously. In this setting, fibrosis most frequently affects the lungs, liver, skin and kidneys.

Liver fibrosis occurs as a complication of haemochromatosis, Wilson's disease, alcoholism, schistosomiasis, viral hepatitis, bile duct obstruction, exposure to toxins and metabolic disorders. Liver fibrosis is characterized by the accumulation of extracellular matrix that can be distinguished qualitatively from that in normal liver. This fibrosis can progress to cirrhosis, liver failure, cancer and eventually death. This is reviewed in Kagan, H. M. Lysyl oxidase: Mechanism, regulation and relationship to liver fibrosis. *Pathology-Research and Practice* 1994; 190: 910-919.

Fibrotic tissues can accumulate in the heart and blood vessels as a result of hypertension, hypertensive heart disease, atherosclerosis and myocardial infarction where the accumulation of extracellular matrix or fibrotic deposition results in stiffening of the vasculature and stiffening of the cardiac tissue itself. See Lopez, B., et al. Role of lysyl oxidase in myocardial fibrosis: from basic science to clinical aspects. *Am J Physiol Heart Circ Physiol* 2010; 299: H1-H9.

A strong association between fibrosis and increased lysyl oxidase activity has been demonstrated. For example, in experimental hepatic fibrosis in rat (Siegel, R. C., Chen, K. H. and Acquiar, J. M, Biochemical and immunochemical study of lysyl oxidase in experimental hepatic fibrosis in the rat. *Proc. Natl. Acad. Sci. USA* 1978; 75: 2945-2949), in models of lung fibrosis (Counts, D. F., et al., Collagen lysyl oxidase activity in the lung decreases during bleomycin-induced lung fibrosis. *J Pharmacol Exp Ther* 1981; 219: 675-678) in arterial fibrosis (Kagan, H. M., Raghavan, J. and Hollander, W., Changes in aortic lysyl oxidase activity in diet-induced atherosclerosis in the rabbit. *Arteriosclerosis* 1981; 1: 287-291.), in dermal fibrosis (Chanoki, M., et al., Increased expression of lysyl oxidase in skin with scleroderma. *Br J Dermatol* 1995; 133: 710-715) and in adriamycin-induced kidney fibrosis in rat (Di Donato, A., et al., Lysyl oxidase expression and collagen cross-linking during chronic adriamycin nephropathy. *Nephron* 1997; 76: 192-200). Of these experimental models of human disease, the most striking increases in enzyme activity are seen in the rat model of $CCl_4$-induced liver fibrosis. In these studies, the low level of enzyme activity in the healthy liver increased 15- to 30-fold in fibrotic livers. The rationale for the consistent and strong inhibition of fibrosis by lysyl oxidase isoenzyme blockers is that the lack of cross-linking activity renders the collagen susceptible to matrix metalloproteinases and causes degradation. Hence, any type of fibrosis should be reversed by treatment with lysyl oxidase isoenzyme inhibitors. In humans, there is also a significant association between lysyl oxidase activity measured in the plasma and liver fibrosis progression. Lysyl oxidase activity level is normally negligible in the serum of healthy subjects, but significantly increased in chronic active hepatitis and even more in cirrhosis, therefore lysyl oxidase might serve as a marker of internal fibrosis.

BAPN (β-aminopropionitrile) is a widely used, nonselective lysyl oxidase inhibitor. Since the 1960s BAPN has been used in animal studies (mainly rat, mouse and hamster) and has been efficacious in reducing collagen content in various models (eg. $CCl_4$, bleomycin, quartz) and tissues (eg. liver, lung and dermis). See Kagan, H. M. and Li, W., Lysyl oxidase: Properties, specificity and biological roles inside and outside of the cell. *J Cell Biochem* 2003; 88: 660-672.

Lysyl oxidase isoenzymes are highly regulated by Hypoxia-Induced Factor 1α (HIF-1α) and TGF-β, the two most prominent growth factor that cause fibrosis (Halberg et al., Hypoxia-inducible factor 1α induces fibrosis and insulin resistance in white adipose tissue. *Cell Biol* 2009; 29: 4467-4483). Collagen cross linking occurs in every type of fibrosis, hence a lysyl oxidase isoenzyme inhibitor could be used in idiopathic pulmonary fibrosis, scleroderma, kidney or liver fibrosis. Lysyl oxidase isoenzymes are not only involved in the cross-linking of elastin and collagen during wound healing and fibrosis but also regulate cell movement and signal transduction. Its intracellular and intranuclear function is associated with gene regulation and can lead to tumorgenesis and tumor progression (Siddikiuzzaman, Grace, V. M and Guruvayoorappan, C., Lysyl oxidase: a potential target for cancer therapy. *Inflammapharmacol* 2011; 19: 117-129). Both down and upregulation of lysyl oxidase isoenzymes in tumour tissues and cancer cell lines have been described, suggesting a dual role for lysyl oxidase isoenzymes and LOX pro-peptide as a metastasis promoter gene as well as a tumour suppressor gene.

To date, an increase in lysyl oxidase isoenzymes mRNA and/or protein has been observed in breast, CNS cancer cell lines, head and neck squamous cell, prostatic, clear cell renal cell and lung carcinomas, and in melanoma and osteosarcoma cell lines. Statistically significant clinical correlations between lysyl oxidase isoenzymes expression and tumor progression have been observed in breast, head and neck squamous cell, prostatic and clear cell renal cell carcinomas. The role of lysyl oxidase isoenzymes in tumor progression has been most extensively studied in breast cancer using in vitro models of migration/invasion and in in vivo tumorgenesis and metastasis mouse models. Increased lysyl oxidase isoenzymes expression was found in hypoxic patients, and was associated with negative estrogen receptor status (ER−), decreased overall survival in ER− patients and node-negative patients who did not receive adjuvant systemic treatment, as well as shorter metastasis-free survival in ER− patients and node negative patients. Lysyl oxidase isoenzymes mRNA was demonstrated to be up-regulated in invasive and metastatic cell lines (MDA-MB-231 and Hs578T), as well as in more aggressive breast cancer cell lines and distant metastatic tissues compared with primary cancer tissues.

In head and neck squamous cell carcinomas, increased lysyl oxidase isoenzyme expression was found in association with CA-IX, a marker of hypoxia, and was associated with decreased cancer specific survival, decreased overall survival and lower metastasis-free survival. In oral squamous cell carcinoma, lysyl oxidase isoenzyme mRNA expression was upregulated compared to normal mucosa.

Gene expression profiling of gliomas identified overexpressed lysyl oxidase isoenzyme as part of a molecular signature indicative of invasion, and associated with higher-grade tumors that are strongly correlated with poor patient survival. Lysyl oxidase isoenzyme protein expression was increased in glioblastoma and astrocytoma tissues, and in invasive U343 and U251 cultured astrocytoma cells.

In tissues, lysyl oxidase isoenzyme mRNA was upregulated in prostate cancer compared to benign prostatic hypertrophy, correlated with Gleason score, and associated with both high grade and short time to recurrence (Stewart, G. D., et al., Analysis of hypoxia-associated gene expression in prostate cancer: lysyl oxidase and glucose transporter-1 expression correlate with Gleason score. *Oncol Rep* 2008; 20: 1561-1567).

Up-regulation of lysyl oxidase isoenzyme mRNA expression was detected in renal cell carcinoma (RCC) cell lines and tissues. Clear cell RCC also demonstrated lysyl oxidase isoenzyme up-regulation. Indeed, LOX over expression appeared preferentially in clear cell RCC compared to mixed clear and granular, granular, oxyphil, tubulopapillary and chromophobe RCC/ontocytomas. In clear cell RCC, smoking was associated with allelic imbalances at chromosome 5q23.1, where the LOX gene is localized, and may involve duplication of the gene.

SiHa cervical cancer cells demonstrated increased invasion in vitro under hypoxic/anoxic conditions; this was repressed by inhibition of extracellular catalytically active lysyl oxidase activity by treatment with BAPN as well as LOX antisense oligos, LOX antibody, LOX shRNA or an extracellular copper chelator.

The scientific and patent literature describes small molecule inhibitors of lysyl oxidase isoenzymes and antibodies of LOX and LOXL2 with therapeutic effects in animal models of fibrosis and cancer metastasis. Some known MAO inhibitors also are reported to inhibit lysyl oxidase isoenzyme (e.g., the MAO-B inhibitor Mofegiline illustrated below). This inhibitor is a member of the haloallylamine family of MAO inhibitors; the halogen in Mofegiline is fluorine. Fluoroallylamine inhibitors are described in U.S. Pat. No. 4,454,158. There are issued patents claiming fluoroallylamines and chloroallylamines, for example MDL72274 (illustrated below) as inhibitors of lysyl oxidase (U.S. Pat. Nos. 4,943,593; 4,965,288; 5,021,456; 5,059,714; 5,182,297; 5,252,608). Many of the compounds claimed in these patents are also reported to be potent MAO-B and SSAO/VAP-1 inhibitors.

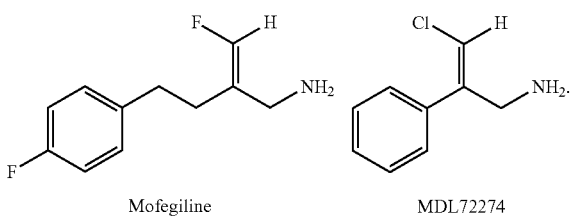

Mofegiline        MDL72274

Additional fluoroallylamine inhibitors are described U.S. Pat. No. 4,699,928. Other examples structurally related to Mofegiline can be found in WO 2007/120528.

WO 2009/066152 discloses a family of 3-substituted 3-haloallylamines that are inhibitors of SSAO/VAP-1 useful as treatment for a variety of indications, including inflammatory disease. None of these documents specifically disclose the fluoroallylamine compounds of formula (I) according to the present invention.

Antibodies to LOX and LOXL2 have been disclosed in US 2009/0053224 with methods to diagnostic and therapeutic applications. Anti-LOX and anti-LOXL2 antibodies can be used to identify and treat conditions such as a fibrotic condition, angiogenesis, or to prevent a transition from an epithelial cell state to a mesenchymal cell state: US 2011/0044907.

SUMMARY

The present invention provides substituted fluoroallylamine compounds that inhibit lysyl oxidase (LOX), lysyl oxidase-like2 (LOXL2) and other lysyl oxidase isoenzymes. Surprisingly, modification of 3-substituted-3-fluoroallylamine structures described previously has led to the discovery of novel compounds that are potent inhibitors of the human LOX and LOXL isoenzymes. Furthermore, certain of these novel compounds also selectively inhibit certain LOX and LOXL isoenzymes with respect to the other enzymes in the amine oxidase family.

A first aspect of the invention provides for a compound of Formula I:

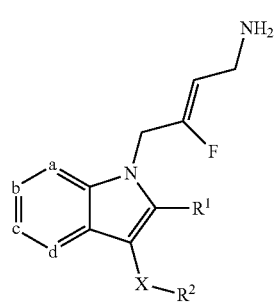

Formula I or a stereoisomer, pharmaceutically acceptable salt, polymorphic form, solvate, tautomeric forth or prodrug thereof; wherein:
  a is N or $CR^3$;
  b is N or $CR^4$;
  c is N or $CR^5$;
  d is N or $CR^6$;
and from 0 to 2 of a, b, c and d are N;
  X is O or —$(CHR^7)_m$—
  m is 1 or 2;

$R^1$ is selected from the group consisting of hydrogen, halogen, $C_{1-6}$alkyl, $C_{3-7}$cycloalkyl, —O—$C_{1-6}$alkyl, —O—$C_{3-7}$cycloalkyl, —C(O)$OR^8$, —C(O)$NR^9R^{10}$ and —$NR^9$C(O)$R^{11}$; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$;

$R^2$ is aryl or heteroaryl; wherein each $R^2$ is optionally substituted by one or more $R^{12}$;

$R^3$, $R^4$, $R^5$ and $R^6$ are each independently selected from the group consisting of hydrogen, halogen, hydroxyl, $C_{1-6}$alkyl, $C_{3-7}$cycloalkyl, —O—$C_{1-6}$alkyl, —O—$C_{3-7}$cycloalkyl, —CN, —$NO_2$, —$NR^9R^{10}$, —C(O)$OR^8$, —C(O)$NR^9R^{10}$, —$NR^9$C(O)$R^{11}$, —S($O_2$)$NR^9R^{10}$, —$NR^9$S($O_2$)$R^{11}$, —S(O)$R^{11}$, —S($O_2$)$R^{11}$, tetrazole and oxadiazole; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —$CF_3$, —$CH_2CF_3$, and —O—$CF_3$;

each $R^7$ is independently selected from the group consisting of hydrogen, hydroxyl and $C_{1-3}$alkyl;

$R^8$ is selected from the group consisting of hydrogen, $C_{1-6}$alkyl, and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —O—$C_{1-3}$alkyl, —$CF_3$, —$CH_2CF_3$, and —O—$CF_3$;

$R^9$ and $R^{10}$ are independently selected from the group consisting of hydrogen, $C_{1-6}$alkyl and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$; or $R^9$ and $R^{10}$ when attached to the same nitrogen atom are combined to form a 3- to 7-membered ring having from 0 to 2 additional heteroatoms as ring members;

$R^{11}$ is selected from the group consisting of $C_{1-6}$alkyl and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —$CF_3$, —$CH_2CF_3$, and —O—$CF_3$; and $R^{12}$ is selected from the group consisting of halogen, $C_{1-6}$alkyl, —O—$C_{1-6}$alkyl, —S—$C_{1-6}$alkyl, $C_{3-7}$cycloalkyl, —O—$C_{3-7}$cycloalkyl, —C(O)$OR^8$, —C(O)$NR^9R^{10}$, —$NR^9$C(O)$R^{11}$, —S($O_2$)$NR^9R^{10}$, —$NR^9$S($O_2$)$R^{11}$, —S(O)$R^{11}$ and —S($O_2$)$R^{11}$; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —$C_{1-3}$alkyl, —O—$C_{1-3}$alkyl, —$CF_3$, —$CH_2CF_3$, and —O—$CF_3$.

A second aspect of the invention provides for a pharmaceutical composition comprising a compound according to the first aspect of the invention, or a pharmaceutically acceptable salt, solvate or prodrug thereof, and at least one pharmaceutically acceptable excipient, carrier or diluent.

A third aspect of the invention provides for a method of inhibiting the amine oxidase activity of LOX, LOXL1, LOXL2, LOXL3 and LOXL4 in a subject in need thereof, comprising administering to the subject an effective amount of a compound according to the first aspect of the invention, or a pharmaceutically acceptable salt, solvate or prodrug thereof, or a pharmaceutical composition according to the second aspect of the invention.

A fourth aspect of the invention provides for a method of treating a condition associated with LOX, LOXL1, LOXL2, LOXL3 and LOXL4 protein, comprising administering to a subject in need thereof a therapeutically effective amount of compound according to the first aspect of the invention, or a pharmaceutically acceptable salt, solvate or prodrug thereof, or a pharmaceutical composition according to the second aspect of the invention.

A fifth aspect of the invention provides for use of a compound according to the first aspect of the invention, or a pharmaceutically acceptable salt, solvate or prodrug thereof, for the manufacture of a medicament for treating a condition associated with LOX, LOXL1, LOXL2, LOXL3 and LOXL4 protein.

A sixth aspect of the invention provides for a compound according to the first aspect of the invention, or a pharmaceutically acceptable salt, solvate or prodrug thereof, for use in treating a condition associated with LOX, LOXL1, LOXL2, LOXL3 and LOXL4 protein.

In one embodiment of the methods and uses of the present invention the condition is selected from a liver disorder, kidney disorder, cardiovascular disease, fibrosis, cancer and angiogenesis.

Contemplated herein is combination therapy in which the methods further comprise co-administering additional therapeutic agents that are used for the treatment of liver disorders, kidney disorders, cardiovascular diseases, cancer, fibrosis, angiogenesis and inflammation.

Definitions

The following are some definitions that may be helpful in understanding the description of the present invention. These are intended as general definitions and should in no way limit the scope of the present invention to those terms alone, but are put forth for a better understanding of the following description.

Unless the context requires otherwise or specifically states to the contrary, integers, steps, or elements of the invention recited herein as singular integers, steps or elements clearly encompass both singular and plural forms of the recited integers, steps or elements.

Throughout this specification, unless the context requires otherwise, the word "comprise", or variations such as "comprises" or "comprising", will be understood to imply the inclusion of a stated step or element or integer or group of steps or elements or integers, but not the exclusion of any other step or element or integer or group of elements or integers. Thus, in the context of this specification, the term "comprising" means "including principally, but not necessarily solely".

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

As used herein, the term "alkyl" includes within its meaning monovalent ("alkyl") and divalent ("alkylene") straight chain or branched chain saturated hydrocarbon radicals having from 1 to 6 carbon atoms, e.g., 1, 2, 3, 4, 5 or 6 carbon atoms. The straight chain or branched alkyl group is attached at any available point to produce a stable compound. For example, the term alkyl includes, but is not limited to, methyl, ethyl, 1-propyl, isopropyl, 1-butyl, 2-butyl, isobutyl, tert-butyl, amyl, 1,2-dimethylpropyl, 1,1-dimethylpropyl, pentyl, isopentyl, hexyl, 4-methylpentyl, 1-methylpentyl, 2-methylpentyl, 3-methylpentyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, and the like.

The term "alkoxy" or "alkyloxy" as used herein refers to straight chain or branched alkyloxy (i.e, O-alkyl) groups, wherein alkyl is as defined above. Examples of alkoxy groups include methoxy, ethoxy, n-propoxy, and isopropoxy.

The term "cycloalkyl" as used herein includes within its meaning monovalent ("cycloalkyl") and divalent ("cycloalkylene") saturated, monocyclic, bicyclic, polycyclic or fused analogs. In the context of the present disclosure the cycloalkyl group may have from 3 to 10 carbon atoms. In the context of the present disclosure the cycloalkyl group may also have from 3 to 7 carbon atoms. A fused analog of a cycloalkyl means a monocyclic ring fused to an aryl or heteroaryl group in which the point of attachment is on the non-aromatic portion. Examples of cycloalkyl and fused analogs thereof include cyclopropyl, cyclobutyl, cyclopentyl, cyclohexyl, cycloheptyl, tetrahydronaphthyl, decahydronaphthyl, indanyl, adamantyl and the like.

The term "aryl" or variants such as "arylene" as used herein refers to monovalent ("aryl") and divalent ("arylene") single, polynuclear, conjugated and fused analogs of aromatic hydrocarbons having from 6 to 10 carbon atoms. A fused analog of aryl means an aryl group fused to a monocyclic cycloalkyl or monocyclic heterocyclyl group in which the point of attachment is on the aromatic portion. Examples of aryl and fused analogs thereof include phenyl, naphthyl, indanyl, indenyl, tetrahydronaphthyl, 2,3-dihydrobenzofuranyl, dihydrobenzopyranyl, 1,3-benzodioxolyl, 1,4-benzodioxanyl, and the like. A "substituted aryl" is an aryl that is independently substituted, with one or more, preferably 1, 2 or 3 substituents, attached at any available atom to produce a stable compound.

The term "alkylaryl" as used herein, includes within its meaning monovalent ("aryl") and divalent ("arylene"), single, polynuclear, conjugated and fused aromatic hydrocarbon radicals attached to divalent, saturated, straight or branched chain alkylene radicals. Examples of alkylaryl groups include benzyl.

The term "heteroaryl" and variants such as "heteroaromatic group" or "heteroarylene" as used herein, includes within its meaning monovalent ("heteroaryl") and divalent ("heteroarylene"), single, polynuclear, conjugated and fused heteroaromatic radicals having from 5 to 10 atoms, wherein 1 to 4 ring atoms, or 1 to 2 ring atoms are heteroatoms independently selected from O, N, NH and S. Heteroaryl is also intended to include oxidized S or N, such as sulfonyl, sulfonyl and N-oxide of a tertiary ring nitrogen. A carbon or nitrogen atom is the point of attachment of the heteroaryl ring structure such that a stable compound is produced. The heteroaromatic group may be $C_{5-8}$heteroaromatic. A fused analog of heteroaryl means a heteroaryl group fused to a monocyclic cycloalkyl or monocyclic heterocyclyl group in which the point of attachment is on the aromatic portion. Examples of heteroaryl groups and fused analogs thereof include pyrazolyl, pyridyl, oxazolyl, oxadiazolyl, thiadiazolyl, tetrazolyl, triazinyl, thienyl, benzoxazolyl, benzothiazolyl, benzimidazolyl, benzofuranyl, benzothiophenyl, furo (2,3-b)pyridyl, quinolyl, indolyl, isoquinolyl, pyrimidinyl, pyridazinyl, pyrazinyl, 2,2'-bipyridyl, phenanthrolinyl, quinolinyl, isoquinolinyl, imidazolinyl, thiazolinyl, pyrrolyl, furanyl, thiophenyl, oxazolyl, isoxazolyl, isothiazolyl, triazolyl, and the like. "Nitrogen containing heteroaryl" refers to heteroaryl wherein any heteroatoms are N. A "substituted heteroaryl" is a heteroaryl that is independently substituted, with one or more, preferably 1, 2 or 3 substituents, attached at any available atom to produce a stable compound.

The term "heterocyclyl" and variants such as "heterocycloalkyl" as used herein, includes within its meaning monovalent ("heterocyclyl") and divalent ("heterocyclylene"), saturated, monocyclic, bicyclic, polycyclic or fused hydrocarbon radicals having from 3 to 10 ring atoms, wherein from 1 to 5, or from 1 to 3, ring atoms are heteroatoms independently selected from O, N, NH, or S, in which the point of attachment may be carbon or nitrogen. A fused analog of heterocyclyl means a monocyclic heterocycle fused to an aryl or heteroaryl group in which the point of attachment is on the non-aromatic portion. The heterocyclyl group may be $C_{3-8}$ heterocyclyl. The heterocycloalkyl group may be $C_{3-6}$ heterocyclyl. The heterocyclyl group may be $C_{3-5}$ heterocyclyl. Examples of heterocyclyl groups and fused analogs thereof include aziridinyl, pyrrolidinyl, thiazolidinyl, piperidinyl, piperazinyl, imidazolidinyl, 2,3-dihydrofuro(2,3-b)pyridyl, benzoxazinyl, tetrahydroquinolinyl, tetrahydroisoquinolinyl, dihydroindolyl, quinuclidinyl, azetidinyl, morpholinyl, tetrahydrothiophenyl, tetrahydrofuranyl, tetrahydropyranyl, and the like. The term also includes partially unsaturated monocyclic rings that are not aromatic, such as 2- or 4-pyridones attached through the nitrogen or N-substituted uracils.

The term "halogen" or variants such as "halide" or "halo" as used herein refers to fluorine, chlorine, bromine and iodine.

The term "heteroatom" or variants such as "hetero-" or "heterogroup" as used herein refers to O, N, NH and S.

In general, "substituted" refers to an organic group as defined herein (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group will be substituted with one or more substituents, unless otherwise specified. In some embodiments, a substituted group is substituted with 1, 2, 3, 4, 5, or 6 substituents.

The term "optionally substituted" as used herein means the group to which this term refers may be unsubstituted, or may be substituted with one or more groups independently selected from alkyl, alkenyl, alkynyl, cycloalkyl, cycloalkenyl, heterocycloalkyl, halo, haloalkyl, haloalkynyl, hydroxyl, hydroxyalkyl, alkoxy, thioalkoxy, alkenyloxy, haloalkoxy, haloalkenyloxy, $NO_2$, NH(alkyl), N(alkyl)$_2$, nitroalkyl, nitroalkenyl, nitroalkynyl, nitroheterocyclyl, alkylamino, dialkylamino, alkenylamine, alkynylamino, acyl, alkenoyl, alkynoyl, acylamino, diacylamino, acyloxy, alkylsulfonyloxy, heterocycloxy, heterocycloamino, haloheterocycloalkyl, alkylsulfenyl, alkylcarbonyloxy, alkylthio, acylthio, phosphorus-containing groups such as phosphono and phosphinyl, aryl, heteroaryl, alkylaryl, aralkyl, alkylheteroaryl, cyano, cyanate, isocyanate, $CO_2H$, $CO_2$alkyl, $C(O)NH_2$, —C(O)NH(alkyl), and —C(O)N(alkyl)$_2$. Preferred substituents include halogen, $C_1$-$C_6$alkyl, $C_2$-$C_6$alkenyl, $C_1$-$C_6$haloalkyl, $C_1$-$C_6$alkoxy, hydroxy($C_{1-6}$) alkyl, $C_3$-$C_6$cycloalkyl, C(O)H, C(O)OH, NHC(O)H, NHC(O)$C_1$-$C_6$alkyl, C(O)$C_1$-$C_4$alkyl, $NH_2$, NH$C_1$-$C_4$alkyl, N($C_1$-$C_4$alkyl)$_2$, $NO_2$, OH and CN. Particularly preferred substituents include $C_{1-3}$alkyl, $C_{1-3}$alkoxy, halogen, OH, hydroxy($C_{1-3}$)alkyl (e.g. $CH_2OH$), C(O)$C_1$-$C_4$alkyl (e.g. C(O)$CH_3$), and $C_{1-3}$haloalkyl (e.g. $CF_3$, $CH_2CF_3$). Further preferred optional substituents include halogen, —OH, —SH, —$C_{1-3}$alkyl, —O—$C_{1-3}$alkyl, —$CF_3$, —$CH_2CF_3$, and —O—$CF_3$.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based.

The present invention includes within its scope all stereoisomeric and isomeric forms of the compounds disclosed herein, including all diastereomeric isomers, racemates, enantiomers and mixtures thereof. It is also understood that the compounds described by Formula I may be present as E and Z isomers, also known as cis and trans isomers. Thus, the present disclosure should be understood to include, for example, E, Z, cis, trans, (R), (S), (L), (D), (+), and/or (−) forms of the compounds, as appropriate in each case. Where a structure has no specific stereoisomerism indicated, it should be understood that any and all possible isomers are encompassed. Compounds of the present invention embrace all conformational isomers. Compounds of the present invention may also exist in one or more tautomeric forms, including both single tautomers and mixtures of tautomers. Also included in the scope of the present invention are all polymorphs and crystal forms of the compounds disclosed herein.

The present invention includes within its scope isotopes of different atoms. Any atom not specifically designated as a particular isotope is meant to represent any stable isotope of that atom. Thus, the present disclosure should be understood to include deuterium and tritium isotopes of hydrogen.

All references cited in this application are specifically incorporated by cross-reference in their entirety. Reference to any such documents should not be construed as an admission that the document forms part of the common general knowledge or is prior art.

In the context of this specification the term "administering" and variations of that term including "administer" and "administration", includes contacting, applying, delivering or providing a compound or composition of the invention to an organism, or a surface by any appropriate means. In the context of this specification, the term "treatment", refers to any and all uses which remedy a disease state or symptoms, prevent the establishment of disease, or otherwise prevent, hinder, retard, or reverse the progression of disease or other undesirable symptoms in any way whatsoever.

In the context of this specification the term "effective amount" includes within its meaning a sufficient but non-toxic amount of a compound or composition of the invention to provide a desired effect. Thus, the term "therapeutically effective amount" includes within its meaning a sufficient but non-toxic amount of a compound or composition of the invention to provide the desired therapeutic effect. The exact amount required will vary from subject to subject depending on factors such as the species being treated, the sex, age and general condition of the subject, the severity of the condition being treated, the particular agent being administered, the mode of administration, and so forth. Thus, it is not possible to specify an exact "effective amount". However, for any given case, an appropriate "effective amount" may be determined by one of ordinary skill in the art using only routine experimentation.

DETAILED DESCRIPTION

Figure 1:
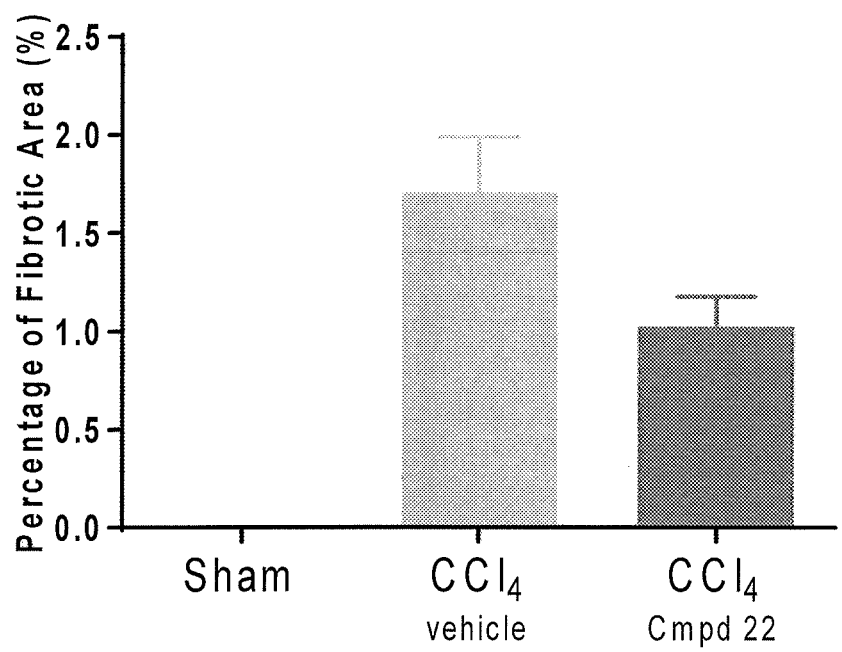
FIG. 1 shows the ability of Compound 22 to reduce fibrosis in a rat model of liver fibrosis.

The present invention relates to substituted fluoroallylamine derivatives which may inhibit lysyl oxidase (LOX), lysyl oxidase-like2 (LOXL2) and other lysyl oxidase isoenzymes. In particular the present invention relates to substituted fluoroallylamine derivatives with an indole or azaindole group.

In particular the present invention relates to compounds of Formula I:

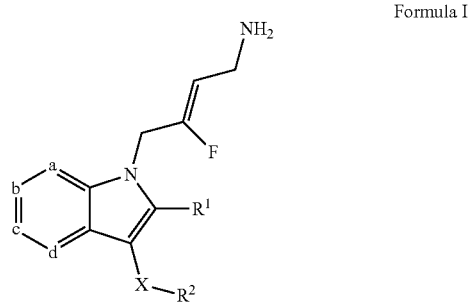

Formula I or a stereoisomer, pharmaceutically acceptable salt, polymorphic form, solvate, tautomeric form or prodrug thereof; wherein:
a is N or $CR^3$;
b is N or $CR^4$;
c is N or $CR^5$;
d is N or $CR^6$;
and from 0 to 2 of a, b, c and d are N;
X is O or $-(CHR^7)_m-$
m is 1 or 2;
$R^1$ is selected from the group consisting of hydrogen, halogen, $C_{1-6}$alkyl, $C_{3-7}$cycloalkyl, $-O-C_{1-6}$alkyl, $-O-C_{3-7}$cycloalkyl, $-C(O)OR^8$, $-C(O)NR^9R^{10}$ and $-NR^9C(O)R^{11}$; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, $-OH$, $-SH$, $-C_{1-3}$alkyl, $-O-C_{1-3}$alkyl, $-CF_3$, $-CH_2CF_3$, and $-O-CF_3$;
$R^2$ is aryl or heteroaryl; wherein each $R^2$ is optionally substituted by one or more $R^{12}$;
$R^3$, $R^4$, $R^5$ and $R^6$ are each independently selected from the group consisting of hydrogen, halogen, hydroxyl, $C_{1-6}$alkyl, $C_{3-7}$cycloalkyl, $-O-C_{1-6}$alkyl, $-O-C_{3-7}$cycloalkyl, $-CN$, $-NO_2$, $-NR^9R^{10}$, $-C(O)OR^8$, $-C(O)NR^9R^{10}$, $-NR^9C(O)R^{11}$, $-S(O_2)NR^9R^{10}$, $-NR^9S(O_2)R^{11}$, $-S(O)R^{11}$, $-S(O_2)R^{11}$, tetrazole and oxadiazole;

wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, $-OH$, $-SH$, $-C_{1-3}$alkyl, $-O-C_{1-3}$alkyl, $-CF_3$, $-CH_2CF_3$, and $-O-CF_3$;
each $R^7$ is independently selected from the group consisting of hydrogen, hydroxyl and $C_{1-3}$alkyl;
$R^8$ is selected from the group consisting of hydrogen, $C_{1-6}$alkyl, and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, $-OH$, $-SH$, $-C_{1-3}$alkyl, $-O-C_{1-3}$alkyl, $-CF_3$, $-CH_2CF_3$, and $-O-CF_3$;
$R^9$ and $R^{10}$ are independently selected from the group consisting of hydrogen, $C_{1-6}$alkyl and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, $-OH$, $-SH$, $-C_{1-3}$alkyl, $-O-C_{1-3}$alkyl, $-CF_3$, $-CH_2CF_3$, and $-O-CF_3$; or
$R^9$ and $R^{10}$ when attached to the same nitrogen atom are combined to form a 3- to 7-membered ring having from 0 to 2 additional heteroatoms as ring members;
$R^{11}$ is selected from the group consisting of $C_{1-6}$alkyl and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, $-OH$, $-SH$, $-C_{1-3}$alkyl, $-O-C_{1-3}$alkyl, $-CF_3$, $-CH_2CF_3$, and $-O-CF_3$; and
$R^{12}$ is selected from the group consisting of halogen, $C_{1-6}$alkyl, $-O-C_{1-6}$alkyl, $-S-C_{1-6}$alkyl, $C_{3-7}$cycloalkyl, $-O-C_{3-7}$cycloalkyl, $-C(O)OR^8$, $-C(O)NR^9R^{10}$, $-NR^9C(O)R^{11}$, $-S(O_2)NR^9R^{10}$, $-NR^9S(O_2)R^{11}$, $-S(O)R^{11}$ and $-S(O_2)R^{11}$; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, $-OH$, $-C_{1-3}$alkyl, $-O-C_{1-3}$alkyl, $-CF_3$, $-CH_2CF_3$, and $-O-CF_3$.

In one embodiment of compounds of the present invention none of a, b, c and d is N and a is $CR^3$, b is $CR^4$, c is $CR^5$ and d is $CR^6$ so that the compounds of Formula I are indole derivatives. In a further embodiment of compounds of the present invention one of a, b, c and d is N so that the compounds of Formula I are azaindole derivatives. In another embodiment of compounds of the present invention a is N, b is $CR^4$, c is $CR^5$ and d is $CR^6$. In a further embodiment of compounds of the present invention a is $CR^3$, b is N, c is $CR^5$ and d is $CR^6$. In another embodiment of compounds of the present invention a is $CR^3$, b is $CR^4$, c is N and d is $CR^6$. In a still further embodiment of compounds of the present invention a is $CR^3$, b is $CR^4$, c is $CR^5$ and d is N. In another embodiment of the present invention two of a, b, c and d are N. In a further embodiment of compounds of the present invention a is $CR^3$, b is $CR^4$, c is N and d is N. In another embodiment of compounds of the present invention a is $CR^3$, b is N, c is $CR^5$ and d is N. In another embodiment of the present invention a is N, b is $CR^4$, c is N and d is $CR^6$. In a further embodiment of compounds of the present invention a is $CR^3$, b is N, c is N and d is $CR^6$. In another embodiment of compounds of the present invention a is N, b is N, c is $CR^5$ and d is $CR^6$. In a further embodiment of compounds of the present invention a is $CR^4$, b is $CR^4$, c is $CR^5$ and d is N.

In one embodiment of compounds of the present invention X is O or —(CHR$^7$)$_m$—; m is 1 or 2; and each R$^7$ is independently selected from the group consisting of hydrogen, hydroxyl and C$_{1-3}$alkyl. In another embodiment of compounds of the present invention X is O. In another embodiment of compounds of the present invention X is —(CHR$^7$)$_m$—, m is 1 and R$^7$ is selected from the group consisting of hydrogen, hydroxyl and C$_{1-3}$alkyl. In a further embodiment of compounds of the present invention X is —(CHR$^7$)$_m$—, m is 1 and R$^7$ is hydrogen so that X is —CH$_2$—. In a further embodiment of compounds of the present invention X is —(CHR$^7$)$_m$—, m is 1 and R$^7$ is hydroxyl so that X is —CHOH—. In another embodiment of compounds of the present invention X is —(CHR$^7$)$_m$—, m is 2 and R$^7$ is selected from the group consisting of hydrogen, hydroxyl and C$_{1-3}$alkyl. In a further embodiment of compounds of the present invention X is —(CHR$^7$)$_m$—, m is 2 and each R$^7$ is hydrogen so that X is —CH$_2$CH$_2$—.

In one embodiment of compounds of the present invention R$^1$ is selected from the group consisting of hydrogen, halogen, C$_{1-6}$alkyl, C$_{3-7}$cycloalkyl, —O—C$_{1-6}$alkyl, —O—C$_{3-7}$cycloalkyl, —C(O)OR$^8$, —C(O)NR$^9$R$^{10}$ and —NR$^9$C(O)R$^{11}$; wherein each C$_{1-6}$alkyl is a straight or branched chain alkyl; and wherein each C$_{1-6}$alkyl and C$_{3-7}$cycloalkyl is optionally substituted by one or more substituents selected from the group consisting of halogen, —OH, —SH, —C$_{1-3}$alkyl, —O—C$_{1-3}$alkyl, —CF$_3$, —CH$_2$CF$_3$, and —O—CF$_3$. In another embodiment of compounds of the present invention each R$^1$ is independently selected from the group consisting of hydrogen, halogen, C$_{1-6}$alkyl, and —C(O)NR$^9$R$^{10}$; wherein each C$_{1-6}$alkyl is a straight or branched chain alkyl; and wherein each C$_{1-6}$alkyl is optionally substituted by one or more substituents selected from the group consisting of halogen, —OH, —O—C$_{1-3}$alkyl, —CF$_3$, —CH$_2$CF$_3$, and —O—CF$_3$. In a further embodiment of compounds of the present invention each R$^1$ is independently selected from the group consisting of hydrogen, halogen, C$_{1-3}$alkyl, and —C(O)N(CH$_3$)$_2$; wherein each C$_{1-3}$alkyl is a straight or branched chain alkyl; and wherein each C$_{1-3}$alkyl is optionally substituted by one or more substituents selected from the group consisting of halogen and —OH. In one embodiment of compounds of the present invention R$^1$ is selected from the group consisting of hydrogen, methyl, ethyl, isopropyl, 1-hydroxyethyl, 2-hydroxyisopropyl, chloro and —C(O)N(CH$_3$)$_2$. In another embodiment of compounds of the present invention R$^1$ is selected from the group consisting of hydrogen, methyl and isopropyl. In a further embodiment of compounds of the present invention R$^1$ is methyl. In another embodiment of compounds of the present invention R$^1$ is isopropyl.

In one embodiment of compounds of the present invention R$^2$ is aryl or heteroaryl where each R$^2$ is optionally substituted by one or more R$^{12}$. In another embodiment of compounds of the present invention R$^2$ is aryl optionally substituted by one or more R$^{12}$. In another embodiment of compounds of the present invention R$^2$ is phenyl substituted by one R$^{12}$. In a further embodiment of compounds of the present invention R$^2$ is heteroaryl substituted by one or more R$^{12}$. In another embodiment of the present invention R$^2$ is heteroaryl substituted by one or more R$^{12}$. In a further embodiment of compounds of the present invention R$^2$ is selected from the group consisting of phenyl

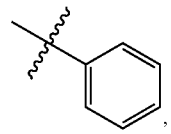

1,3-benzodioxolyl

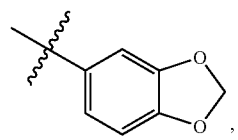 [SMILES: *c1ccc2c(c1)OCO2]

2-pyridinyl

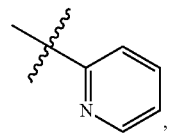 [SMILES: *c1ccccn1]

3-pyridinyl

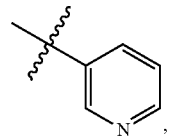 [SMILES: *c1cccnc1]

4-pyridinyl

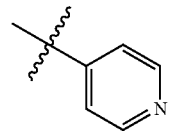 [SMILES: *c1ccncc1]

and 5-pyrimidinyl

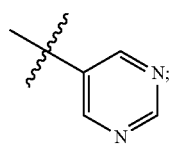

wherein each $R^2$ is optionally substituted by one or more $R^{12}$. In another embodiment of compounds of the present invention $R^2$ is phenyl

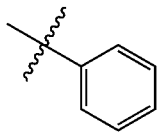 [SMILES: *c1ccccc1]

substituted by one $R^{12}$ or 1,3-benzodioxolyl

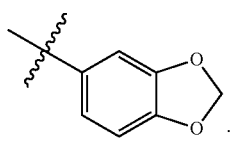 [SMILES: *c1ccc2c(c1)OCO2]

In a further embodiment of compounds of the present invention $R^2$ is a heteroaryl selected from the group consisting of 2-pyridinyl

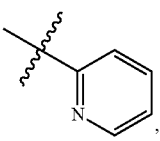 [SMILES: *c1ccccn1]

3-pyridinyl

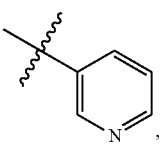

4-pyridinyl

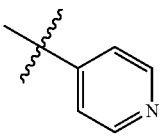

and 5-pyrimidinyl

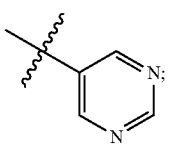

wherein each $R^2$ is optionally substituted by one or more $R^{12}$. In another embodiment of compounds of the present invention $R^2$ is a heteroaryl selected from the group consisting of 2-pyridinyl

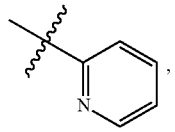 [SMILES: *c1ccccn1]

3-pyridinyl

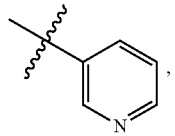 [SMILES: *c1cccnc1]

and 4-pyridinyl

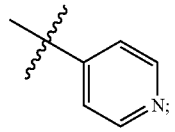

wherein each $R^2$ is substituted by one or two $R^{12}$. In a further embodiment of compounds of the present invention $R^2$ is 3-pyridinyl

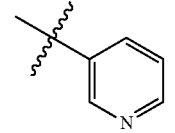 [SMILES: *c1cccnc1]

substituted by one or two $R^{12}$. In another embodiment of compounds of the present invention $R^2$ is 3-pyridinyl

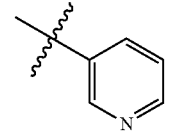 [SMILES: *c1cccnc1]

substituted by —S(O$_2$)NR$^9$R$^{10}$ or —S(O$_2$)R$^{11}$. In a further embodiment of compounds of the present invention $R^2$ is 3-pyridinyl

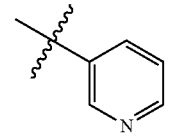 [SMILES: *c1cccnc1]

substituted by —S(O$_2$)N(CH$_3$)$_2$ or —S(O$_2$)CH$_3$.

In one embodiment of compounds of the present invention $R^2$ is substituted by one $R^{12}$. In another embodiment of compounds of the present invention $R^2$ is substituted by two $R^{12}$. In another embodiment of compounds of the present invention $R^2$ is substituted by one or two $R^{12}$. In a further embodiment of compounds of the present invention $R^2$ is substituted by three $R^{12}$. In another embodiment of compounds of the present invention $R^2$ is substituted by four or five $R^{12}$.

In one embodiment of compounds of the present invention $R^3$, $R^4$, $R^5$ and $R^6$ are each independently selected from the group consisting of hydrogen, halogen, hydroxyl, $C_{1-6}$alkyl, $C_{3-7}$cycloalkyl, —O—$C_{1-6}$alkyl, —O—$C_{3-7}$cycloalkyl, —CN, —NO$_2$, —NR$^9$R$^{10}$, —C(O)OR$^8$, —C(O)NR$^9$R$^{10}$, —NR$^9$C(O)R$^{11}$, —S(O$_2$)NR$^9$R$^{10}$, —NR$^9$S(O$_2$)R$^{11}$, —S(O)R$^{11}$, —S(O$_2$)R$^{11}$, tetrazole and oxadiazole; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —CF$_3$, —CH$_2$CF$_3$, and —O—CF$_3$. In another embodiment of compounds of the present invention $R^3$, $R^4$, $R^5$ and $R^6$ are each independently selected from the group consisting of hydrogen, halogen, hydroxyl, $C_{1-6}$alkyl, $C_{3-7}$cycloalkyl, —O—$C_{1-6}$alkyl, —O—$C_{3-7}$cycloalkyl, —CN, —NO$_2$, —NR$^9$R$^{10}$, —C(O)OR$^8$, —C(O)NR$^9$R$^{10}$, —NR$^9$C(O)R$^{11}$, —S(O$_2$)NR$^9$R$^{10}$, —NR$^9$S(O$_2$)R$^{11}$, —S(O)R$^{11}$, —S(O$_2$)R$^{11}$; wherein each $C_{1-6}$alkyl is a straight or branched chain alkyl; and wherein each $C_{1-6}$alkyl is optionally substituted by one or more substituents selected from the group consisting of halogen, —OH and —O—$C_{1-3}$alkyl. In a further embodiment of compounds of the present invention $R^3$, $R^4$, $R^5$ and $R^6$ are each independently selected from the group consisting of hydrogen, fluoro, chloro, hydroxyl, methyl, cyclopropyl, —CN, —NO$_2$, —NH$_2$, —C(O)OH, —C(O)OMe, —C(O)OEt, —C(O)NR$^9$R$^{10}$, —S(O$_2$)NR$^9$R$^{10}$, —NR$^9$S(O$_2$)R$^{11}$, —S(O)R$^{11}$, —S(O$_2$)R$^{11}$, tetrazole, oxadiazole, —CH$_2$F, —CHF$_2$, —OCF$_3$, —CH$_2$OCH$_3$, —CF$_3$, —CHF$_2$CH$_3$, —C(CH$_3$)$_2$OH.

In one embodiment of compounds of the present invention each $R^7$ is independently selected from the group consisting of hydrogen, hydroxyl and $C_{1-3}$alkyl. In another embodiment of compounds of the present invention each $R^7$ is selected from the group consisting of hydrogen and hydroxyl. In another embodiment of compounds of the present invention each $R^7$ is selected from the group consisting of hydrogen, hydroxyl and methyl. In a further embodiment of compounds of the present invention each $R^7$ is hydrogen. In another embodiment of compounds of the present invention each $R^7$ is hydroxyl.

In one embodiment of compounds of the present invention $R^8$ is selected from the group consisting of hydrogen, $C_{1-6}$alkyl and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —CF$_3$, —CH$_2$CF$_3$, and —O—CF$_3$. In another embodiment of compounds of the present invention $R^8$ is hydrogen. In a further embodiment of compounds of the present invention $R^8$ is $C_{1-6}$alkyl or $C_{3-7}$cycloalkyl. In a still further embodiment of compounds of the present invention $R^8$ is hydrogen or $C_{1-6}$alkyl. In another embodiment of compounds of the present invention $R^8$ is $C_{1-6}$alkyl. In another embodiment of compounds of the present invention $R^8$ is $C_{1-3}$alkyl. In a further embodiment of compounds of the present invention $R^8$ is methyl or ethyl. In another embodiment of compounds of the present invention $R^8$ is selected from the group consisting of hydrogen, methyl and ethyl.

In one embodiment of compounds of the present invention $R^9$ and $R^{10}$ are independently selected from the group consisting of hydrogen, $C_{1-6}$alkyl and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —CF$_3$, —CH$_2$CF$_3$, and —O—CF$_3$. In another embodiment of compounds of the present invention $R^9$ and $R^{10}$ are independently selected from the group consisting of hydrogen, $C_{1-6}$alkyl and $C_{3-7}$cycloalkyl. In another embodiment of compounds of the present invention $R^9$ and $R^{10}$ are independently selected from the group consisting of hydrogen and $C_{1-6}$alkyl. In another embodiment of compounds of the present invention $R^9$ and $R^{10}$ are hydrogen. In a further embodiment of compounds of the present invention $R^9$ and $R^{10}$ are $C_{1-6}$alkyl. In another embodiment of compounds of the present invention $R^9$ and $R^{10}$ are both methyl. In a further embodiment of compounds of the present invention $R^9$ and $R^{10}$ are independently selected from the group consisting of hydrogen and $C_{3-7}$cycloalkyl. In another embodiment of compounds of the present invention $R^9$ is hydrogen and $R^{10}$ is $C_{1-6}$alkyl. In one embodiment of compounds of the present invention $R^9$ is hydrogen and $R^{10}$ is methyl or isopropyl. In a further embodiment of compounds of the present invention $R^9$ is methyl and $R^{10}$ is isopropyl.

In one embodiment of compounds of the present invention $R^9$ and $R^{10}$ when attached to the same nitrogen atom are combined to form a 3- to 7-membered ring having from 0 to 2 additional heteroatoms as ring members. In another embodiment $R^9$ and $R^{10}$ when attached to the same nitrogen atom are combined to form a 3- to 7-membered ring having from 0 to 1 additional heteroatoms as ring members. In a further embodiment $R^9$ and $R^{10}$ when attached to the same nitrogen atom are combined to form a 3- to 7-membered ring having 1 additional heteroatom as ring members. In another embodiment $R^9$ and $R^{10}$ when attached to the same nitrogen atom are combined to form a 3- to 7-membered ring having 0 additional heteroatoms as ring members.

In one embodiment of compounds of the present invention $R^{11}$ is selected from the group consisting of $C_{1-6}$alkyl and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —CF$_3$, —CH$_2$CF$_3$, and —O—CF$_3$. In another embodiment of compounds of the present invention $R^{11}$ is selected from the group consisting of $C_{1-6}$alkyl and $C_{3-7}$cycloalkyl. In another embodiment of compounds of the present invention $R^{11}$ is $C_{1-6}$alkyl. In a further embodiment of compounds of the present invention $R^{11}$ is selected from the group consisting of methyl, ethyl and isopropyl. In another embodiment of compounds of the present invention $R^{11}$ is selected from the group consisting of methyl and isopropyl. In a further embodiment of compounds of the present invention $R^{11}$ is $C_{3-7}$cycloalkyl. In another embodiment of compounds of the present invention $R^{11}$ is cyclopropyl.

In one embodiment of compounds of the present invention $R^{12}$ is selected from the group consisting of halogen, $C_{1-6}$alkyl, —O—$C_{1-6}$alkyl, —S—$C_{1-6}$alkyl, $C_{3-7}$cycloalkyl, —O—$C_{3-7}$cycloalkyl, —C(O)OR$^8$, —C(O)NR$^9$R$^{10}$, —NR$^9$C(O)R$^{11}$, —S(O$_2$)NR$^9$R$^{10}$, —NR$^9$S(O$_2$)R$^{11}$, —S(O)R$^{11}$ and —S(O$_2$)R$^{11}$; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —$C_{1-3}$alkyl, —O—$C_{1-3}$alkyl, —$CF_3$, —$CH_2CF_3$, and —O—$CF_3$. In a further embodiment of compounds of the present invention $R^{12}$ is selected from the group consisting of halogen, $C_{1-6}$alkyl, —O—$C_{1-6}$alkyl, —S—$C_{1-6}$alkyl, $C_{3-7}$cycloalkyl, —O—$C_{3-7}$cycloalkyl, —C(O)O$R^8$, —C(O)N$R^9R^{10}$, —N$R^9$C(O)$R^{11}$, —S(O$_2$)N$R^9R^{10}$, —N$R^9$S(O$_2$)$R^{11}$, —S(O)$R^{11}$ and —S(O$_2$)$R^{11}$. In another embodiment of compounds of the present invention $R^{12}$ is selected from the group consisting of halogen, $C_{1-6}$alkyl, —O—$C_{1-6}$alkyl, —S—$C_{1-6}$alkyl, —C(O)O$R^8$, —C(O)N$R^9R^{10}$, —S(O$_2$)N$R^9R^{10}$ —N$R^9$S(O$_2$)$R^{11}$ and —S(O$_2$)$R^{11}$. In a further embodiment of compounds of the present invention $R^{12}$ is selected from the group consisting of —S(O$_2$)N$R^9R^{10}$ and —S(O$_2$)$R^{11}$. In another embodiment of compounds of the present invention $R^{12}$ is —S(O$_2$)N$R^9R^{10}$. In a further embodiment of compounds of the present invention $R^{12}$ is —S(O$_2$)N(CH$_3$)$_2$. In another embodiment of compounds of the present invention $R^{12}$ is —S(O$_2$)$R^{11}$. In a further embodiment of compounds of the present invention $R^{12}$ is —S(O$_2$)CH$_3$. In another embodiment of compounds of the present invention $R^{12}$ is —S(O$_2$)$^i$Pr.

In one embodiment the present invention also relates to compounds of Formula Ia:

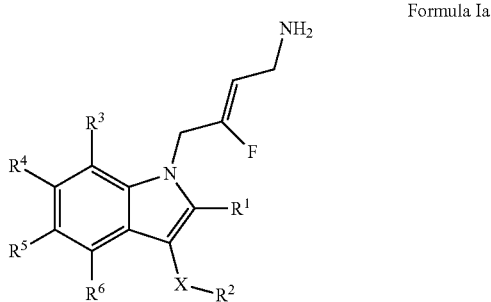

Formula Ia or a pharmaceutically acceptable salt, solvate or prodrug thereof; wherein:

X is O or —(CHR$^7$)$_m$— m is 1 or 2;

$R^1$ is selected from the group consisting of hydrogen, halogen, $C_{1-6}$alkyl, $C_{3-7}$cycloalkyl, —O—$C_{1-6}$alkyl, —O—$C_{3-7}$cycloalkyl, —C(O)O$R^8$, —C(O)N$R^9R^{10}$ and —N$R^9$C(O)$R^{11}$; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$;

$R^2$ is aryl or heteroaryl; wherein each $R^2$ is optionally substituted by one or more $R^{12}$;

$R^3$, $R^4$, $R^5$ and $R^6$ are each independently selected from the group consisting of hydrogen, halogen, hydroxyl, $C_{1-6}$alkyl, $C_{3-7}$cycloalkyl, —O—$C_{1-6}$alkyl, —O—$C_{3-7}$cycloalkyl, —CN, —NO$_2$, —N$R^9R^{10}$, —C(O)O$R^8$, —C(O)N$R^9R^{10}$, —N$R^9$C(O)$R^{11}$, —S(O$_2$)N$R^9R^{10}$, —N$R^9$S(O$_2$)$R^{11}$, —S(O)$R^{11}$, —S(O$_2$)$R^{11}$, tetrazole and oxadiazole; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$;

each $R^7$ is independently selected from the group consisting of hydrogen, hydroxyl and $C_{1-3}$alkyl;

$R^8$ is selected from the group consisting of hydrogen, $C_{1-6}$alkyl, and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$;

$R^9$ and $R^{10}$ are independently selected from the group consisting of hydrogen, $C_{1-6}$alkyl and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$; or $R^9$ and $R^{10}$ when attached to the same nitrogen atom are combined to form a 3- to 7-membered ring having from 0 to 2 additional heteroatoms as ring members;

$R^{11}$ is selected from the group consisting of $C_{1-6}$alkyl and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$; and $R^{12}$ is selected from the group consisting of halogen, $C_{1-6}$alkyl, —O—$C_{1-6}$alkyl, —S—$C_{1-6}$alkyl, $C_{3-7}$cycloalkyl, —O—$C_{3-7}$cycloalkyl, —C(O)O$R^8$, —C(O)N$R^9R^{10}$, —N$R^9$C(O)$R^{11}$, —S(O$_2$)N$R^9R^{10}$, —N$R^9$S(O$_2$)$R^{11}$, —S(O)$R^{11}$ and —S(O$_2$)$R^{11}$; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —$C_{1-3}$alkyl, —O—$C_{1-3}$alkyl, —$CF_3$, —$CH_2CF_3$, and —O—$CF_3$.

In one embodiment of compounds of Formula Ia of the invention X is CH$_2$; $R^1$ is hydrogen, methyl or —C(O)N$R^9R^{10}$; $R^2$ is phenyl optionally substituted by —S(O$_2$)N$R^9R^{10}$; and $R^3$, $R^4$, $R^5$ and $R^6$ are independently selected from the group consisting of hydrogen, C(O)O$R^8$, —C(O)N$R^9R^{10}$ and —S(O$_2$)N$R^9R^{10}$.

In another embodiment the present invention also relates to compounds of Formula Ib:

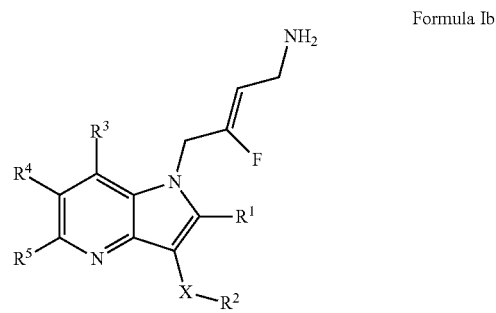

Formula Ib or a pharmaceutically acceptable salt, solvate or prodrug thereof; wherein:

X is O or —(CHR$^7$)$_m$— m is 1 or 2;

$R^1$ is selected from the group consisting of hydrogen, halogen, $C_{1-6}$alkyl, $C_{3-7}$cycloalkyl, —O—$C_{1-6}$alkyl, —O—$C_{3-7}$cycloalkyl, —C(O)O$R^8$, —C(O)N$R^9R^{10}$ and —N$R^9$C(O)$R^{11}$; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —C$_{1-3}$alkyl, —O—C$_{1-3}$alkyl, —CF$_3$, —CH$_2$CF$_3$ and —O—CF$_3$;

R$^2$ is aryl or heteroaryl; wherein each R$^2$ is optionally substituted by one or more R$^{12}$;

R$^3$, R$^4$ and R$^5$ are each independently selected from the group consisting of hydrogen, halogen, hydroxyl, C$_{1-6}$alkyl, C$_{3-7}$cycloalkyl, —S—C$_{1-6}$alkyl, —O—C$_{3-7}$cycloalkyl, —CN, —NO$_2$, —NR$^9$R$^{10}$, —C(O)OR$^8$, —C(O)NR$^9$R$^{10}$, —NR$^9$C(O)R$^{11}$, —S(O$_2$)NR$^9$R$^{10}$, —NR$^9$S(O$_2$)R$^{11}$, —S(O)R$^{11}$, —S(O$_2$)R$^{11}$, tetrazole and oxadiazole; wherein each C$_{1-6}$alkyl is a straight or branched chain alkyl; and wherein each C$_{1-6}$alkyl and C$_{3-7}$cycloalkyl is optionally substituted by one or more substituents selected from the group consisting of halogen, —OH, —SH, —C$_{1-3}$alkyl, —O—C$_{1-3}$alkyl, —CF$_3$, —CH$_2$CF$_3$, and —O—CF$_3$;

each R$^7$ is independently selected from the group consisting of hydrogen, hydroxyl and C$_{1-3}$alkyl;

R$^8$ is selected from the group consisting of hydrogen, C$_{1-6}$alkyl, and C$_{3-7}$cycloalkyl; wherein each C$_{1-6}$alkyl is a straight or branched chain alkyl; and wherein each C$_{1-6}$alkyl and C$_{3-7}$cycloalkyl is optionally substituted by one or more substituents selected from the group consisting of halogen, —OH, —SH, —C$_{1-3}$alkyl, —O—C$_{1-3}$alkyl, —CF$_3$, —CH$_2$CF$_3$, and —O—CF$_3$;

R$^9$ and R$^{10}$ are independently selected from the group consisting of hydrogen, C$_{1-6}$alkyl and C$_{3-7}$cycloalkyl; wherein each C$_{1-6}$alkyl is a straight or branched chain alkyl; and wherein each C$_{1-6}$alkyl and C$_{3-7}$cycloalkyl is optionally substituted by one or more substituents selected from the group consisting of halogen, —OH, —SH, —C$_{1-3}$alkyl, —O—C$_{1-3}$alkyl, —CF$_3$, —CH$_2$CF$_3$, and —O—CF$_3$; or R$^9$ and R$^{10}$ when attached to the same nitrogen atom are combined to form a 3- to 7-membered ring having from 0 to 2 additional heteroatoms as ring members;

R$^{11}$ is selected from the group consisting of C$_{1-6}$alkyl and C$_{3-7}$cycloalkyl; wherein each C$_{1-6}$alkyl is a straight or branched chain alkyl; and wherein each C$_{1-6}$alkyl and C$_{3-7}$cycloalkyl is optionally substituted by one or more substituents selected from the group consisting of halogen, —OH, —SH, —C$_{1-3}$alkyl, —O—C$_{1-3}$alkyl, —CF$_3$, —CH$_2$CF$_3$, and —O—CF$_3$; and R$^{12}$ is selected from the group consisting of halogen, C$_{1-6}$alkyl, —O—C$_{1-6}$alkyl, —S—C$_{1-6}$alkyl, C$_{3-7}$cycloalkyl, —O—C$_{3-7}$cycloalkyl, —C(O)OR$^8$, —C(O)NR$^9$R$^{10}$, —NR$^9$C(O)R$^{11}$, —S(O$_2$)NR$^9$R$^{10}$, —NR$^9$S(O$_2$)R$^{11}$, —S(O)R$^{11}$ and —S(O$_2$)R$^{11}$; wherein each C$_{1-6}$alkyl is a straight or branched chain alkyl; and wherein each C$_{1-6}$alkyl and C$_{3-7}$cycloalkyl is optionally substituted by one or more substituents selected from the group consisting of halogen, —OH, —C$_{1-3}$alkyl, —O—C$_{1-3}$alkyl, —CF$_3$, —CH$_2$CF$_3$, and —O—CF$_3$.

In one embodiment of compounds of Formula Ib of the invention m is 1 or 2; R$^1$ is hydrogen, methyl, chlorine, isopropyl, 1-hydroxyethyl, 2-hydroxyisopropyl; R$^2$ is phenyl or 3-pyridyl optionally substituted by one or more R$^{12}$; R$^3$, R$^4$ and R$^5$ are each independently selected from the group consisting of hydrogen, halogen, hydroxyl, C$_{1-6}$alkyl, cyclopropyl, —O—C$_{1-6}$alkyl, —NR$^9$R$^{10}$, —C(O)OR$^8$ and —C(O)NR$^9$R$^{10}$; wherein each C$_{1-6}$alkyl is a straight or branched chain alkyl; and wherein each C$_{1-6}$alkyl and C$_{3-7}$cycloalkyl is optionally substituted by one or more substituents selected from the group consisting of halogen and —OH; and R$^{12}$ is selected from the group consisting selected from the group consisting of halogen, —S—C$_{1-6}$alkyl, —S(O$_2$)NR$^9$R$^{10}$, —S(O)R$^{11}$ and —S(O$_2$)R$^{11}$.

In a further embodiment of compounds of Formula Ib of the invention in is 1 or 2; R$^1$ is hydrogen, methyl, chlorine, isopropyl, 1-hydroxyethyl, 2-hydroxyisopropyl; R$^2$ is phenyl or 3-pyridyl optionally substituted by one or more R$^{12}$; R$^3$, R$^4$ and R$^5$ are each independently selected from the group consisting of hydrogen, fluorine, chlorine, hydroxyl, methyl, cyclopropyl, —OCH$_3$, —CF$_3$, —CH$_2$F, —CHF$_2$CH$_3$, —CH$_2$OCH$_3$, —C(CH$_3$)$_2$OH, —N(CH$_3$)$_2$, —C(O)OH, —C(O)OEt, —C(O)NHCH$_3$, —C(O)N(CH$_3$)$_2$, —C(O)NH$^i$Pr; R$^7$ is hydrogen or hydroxyl; and R$^{12}$ is selected from the group consisting selected from the group consisting of chlorine, —S—CH$_3$, —S(O$_2$)N(CH$_3$)$_2$, —S(O$_2$)CH$_3$, —S(O$_2$)Et, —S(O$_2$)$^i$Pr and —S(O$_2$)cyclopropyl.

In another embodiment the present invention also relates to compounds of Formula Ic:

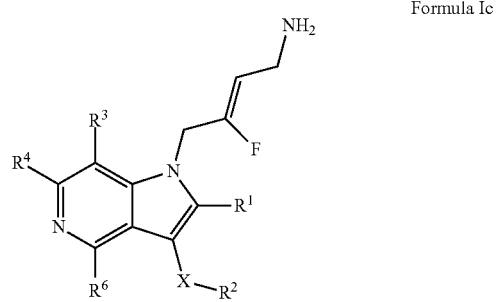

Formula Ic or a pharmaceutically acceptable salt, solvate or prodrug thereof; wherein:

X is O or —(CHR$^7$)$_m$— m is 1 or 2;

R$^1$ is selected from the group consisting of hydrogen, halogen, C$_{1-6}$alkyl, C$_{3-7}$cycloalkyl, —O—C$_{1-6}$alkyl, —O—C$_{3-7}$cycloalkyl, —C(O)OR$^8$, —C(O)NR$^9$R$^{10}$ and —NR$^9$C(O)R$^{11}$; wherein each C$_{1-6}$alkyl is a straight or branched chain alkyl; and wherein each C$_{1-6}$alkyl and C$_{3-7}$cycloalkyl is optionally substituted by one or more substituents selected from the group consisting of halogen, —OH, —SH, —C$_{1-3}$alkyl, —O—C$_{1-3}$alkyl, —CF$_3$, —CH$_2$CF$_3$, and —O—CF$_3$;

R$^2$ is aryl or heteroaryl; wherein each R$^2$ is optionally substituted by one or more R$^{12}$;

R$^3$, R$^4$ and R$^6$ are each independently selected from the group consisting of hydrogen, halogen, hydroxyl, C$_{1-6}$alkyl, C$_{3-7}$cycloalkyl, —O—C$_{1-6}$alkyl, —O—C$_{3-7}$cycloalkyl, —CN, —NO$_2$, —NR$^9$R$^{10}$, —C(O)OR$^8$, —C(O)NR$^9$R$^{10}$, —NR$^9$C(O)R$^{11}$, —S(O$_2$)NR$^9$R$^{10}$, —NR$^9$S(O$_2$)R$^{11}$, —S(O)R$^{11}$, —S(O$_2$)R$^{11}$, tetrazole and oxadiazole; wherein each C$_{1-6}$alkyl is a straight or branched chain alkyl; and wherein each C$_{1-6}$alkyl and C$_{3-7}$cycloalkyl is optionally substituted by one or more substituents selected from the group consisting of halogen, —OH, —SH, —C$_{1-3}$alkyl, —O—C$_{1-3}$alkyl, —CF$_3$, —CH$_2$CF$_3$, and —O—CF$_3$;

each R$^7$ is independently selected from the group consisting of hydrogen, hydroxyl and C$_{1-3}$alkyl;

R$^8$ is selected from the group consisting of hydrogen, C$_{1-6}$alkyl, and C$_{3-7}$cycloalkyl; wherein each C$_{1-6}$alkyl is a straight or branched chain alkyl; and wherein each C$_{1-6}$alkyl and C$_{3-7}$cycloalkyl is optionally substituted by one or more substituents selected from the group consisting of halogen, —OH, —SH, —C$_{1-3}$alkyl, —O—C$_{1-3}$alkyl, —CF$_3$, —CH$_2$CF$_3$, and —O—CF$_3$;

$R^9$ and $R^{10}$ are independently selected from the group consisting of hydrogen, $C_{1-6}$alkyl and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$; or $R^9$ and $R^{10}$ when attached to the same nitrogen atom are combined to form a 3- to 7-membered ring having from 0 to 2 additional heteroatoms as ring members;

$R^{11}$ is selected from the group consisting of $C_{1-6}$alkyl and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$; and $R^{12}$ is selected from the group consisting of halogen, $C_{1-6}$alkyl, —O—$C_{1-6}$alkyl, —S—$C_{1-6}$alkyl, $C_{3-7}$cycloalkyl, —O—$C_{3-7}$cycloalkyl, —C(O)O$R^8$, —C(O)N$R^9R^{10}$, —N$R^9$C(O)$R^{11}$, —S($O_2$)N$R^9R^{10}$, —N$R^9$S($O_2$)$R^{11}$, —S(O)$R^{11}$ and —S($O_2$)$R^{11}$; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —$C_{1-3}$alkyl, —O—$C_{1-3}$alkyl, —$CF_3$, —$CH_2CF_3$, and —O—$CF_3$.

In one embodiment of compounds of Formula Ic of the invention X is $CH_2$; $R^1$ is methyl, $R^2$ is phenyl optionally substituted by $S(O_2)N(CH_3)_2$ or —$S(O_2)CH_3$; and $R^3$, $R^4$ and $R^6$ are independently selected from the group consisting of hydrogen and methyl.

In another embodiment the present invention also relates to compounds of Formula Id:

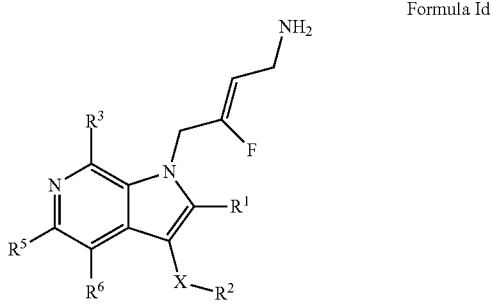

Formula Id or a pharmaceutically acceptable salt, solvate or prodrug thereof; wherein:

X is O or —$(CHR^7)_m$— m is 1 or 2;

$R^1$ is selected from the group consisting of hydrogen, halogen, $C_{1-6}$alkyl, $C_{3-7}$cycloalkyl, —O—$C_{1-6}$alkyl, —O—$C_{3-7}$cycloalkyl, —C(O)O$R^8$, —C(O)N$R^9R^{10}$ and —N$R^9$C(O)$R^{11}$; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$;

$R^2$ is aryl or heteroaryl; wherein each $R^2$ is optionally substituted by one or more $R^{12}$;

$R^3$, $R^5$ and $R^6$ are each independently selected from the group consisting of hydrogen, halogen, hydroxyl, $C_{1-7}$alkyl, $C_{3-7}$cycloalkyl, —O—$C_{1-6}$alkyl, —O—$C_{3-7}$cycloalkyl, —CN, —$NO_2$, —N$R^9R^{10}$, —C(O)O$R^8$, —C(O)N$R^9R^{10}$, —N$R^9$C(O)$R^{11}$, —S($O_2$)N$R^9R^{10}$, —N$R^9$S($O_2$)$R^{11}$, —S(O)$R^{11}$, —S($O_2$)$R^{11}$, tetrazole and oxadiazole; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$;

each $R^7$ is independently selected from the group consisting of hydrogen, hydroxyl and $C_{1-3}$alkyl;

$R^8$ is selected from the group consisting of hydrogen, $C_{1-6}$alkyl, and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$;

$R^9$ and $R^{10}$ are independently selected from the group consisting of hydrogen, $C_{1-6}$alkyl and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —$CF_3$, —$CH_2CF_3$, and —O—$CF_3$; or $R^9$ and $R^{10}$ when attached to the same nitrogen atom are combined to form a 3- to 7-membered ring having from 0 to 2 additional heteroatoms as ring members;

$R^{11}$ is selected from the group consisting of $C_{1-6}$alkyl and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$; and $R^{12}$ is selected from the group consisting of halogen, $C_{1-6}$alkyl, —S—$C_{1-6}$alkyl, $C_{3-7}$cycloalkyl, —O—$C_{3-7}$cycloalkyl, —C(O)O$R^8$, —C(O)N$R^9R^{10}$, —N$R^9$C(O)$R^{11}$, —S($O_2$)N$R^9R^{10}$, —N$R^9$S($O_2$)$R^{11}$, —S(O)$R^{11}$ and —S($O_2$)$R^{11}$; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —$C_{1-3}$alkyl, —O—$C_{1-3}$alkyl, —$CF_3$, —$CH_2CF_3$, and —O—$CF_3$.

In another embodiment the present invention also relates to compounds of Formula Ie:

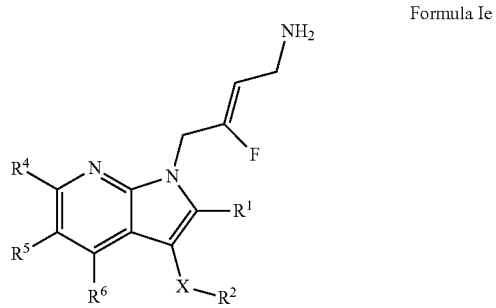

Formula Ie or a pharmaceutically acceptable salt, solvate or prodrug thereof; wherein:

X is O or —$(CHR^7)_m$— m is 1 or 2;

$R^1$ is selected from the group consisting of hydrogen, halogen, $C_{1-6}$alkyl, $C_{3-7}$cycloalkyl, —O—$C_{1-6}$alkyl, —O—$C_{3-7}$cycloalkyl, —C(O)O$R^8$, —C(O)N$R^9R^{10}$ and —NR$^9$C(O)R$^{11}$; wherein each C$_{1-6}$alkyl is a straight or branched chain alkyl; and wherein each C$_{1-6}$alkyl and C$_{3-7}$cycloalkyl is optionally substituted by one or more substituents selected from the group consisting of halogen, —OH, —SH, —C$_{1-3}$alkyl, —O—C$_{1-3}$alkyl, —CF$_3$, —CH$_2$CF$_3$, and —O—CF$_3$;

R$^2$ is aryl or heteroaryl; wherein each R$^2$ is optionally substituted by one or more R$^{12}$;

R$^4$, R$^5$ and R$^6$ are each independently selected from the group consisting of hydrogen, halogen, hydroxyl, C$_{1-6}$alkyl, C$_{3-7}$cycloalkyl, —O—C$_{1-6}$alkyl, —O—C$_{3-7}$cycloalkyl, —CN, —NO$_2$, —NR$^9$R$^{10}$, —C(O)OR$^8$, —C(O)NR$^9$R$^{10}$, —NR$^9$C(O)R$^{11}$, —S(O$_2$)NR$^9$R$^{10}$, —NR$^9$S(O$_2$)R$^{11}$, —S(O)R$^{11}$, —S(O$_2$)R$^{11}$, tetrazole and oxadiazole; wherein each C$_{1-6}$alkyl is a straight or branched chain alkyl; and wherein each C$_{1-6}$alkyl and C$_{3-7}$cycloalkyl is optionally substituted by one or more substituents selected from the group consisting of halogen, —OH, —SH, —C$_{1-3}$alkyl, —O—C$_{1-3}$alkyl, —CF$_3$, —CH$_2$CF$_3$, and —O—CF$_3$;

each R$^7$ is independently selected from the group consisting of hydrogen, hydroxyl and C$_{1-3}$alkyl;

R$^8$ is selected from the group consisting of hydrogen, C$_{1-6}$alkyl, and C$_{3-7}$cycloalkyl; wherein each C$_{1-6}$alkyl is a straight or branched chain alkyl; and wherein each C$_{1-6}$alkyl and C$_{3-7}$cycloalkyl is optionally substituted by one or more substituents selected from the group consisting of halogen, —OH, —SH, —C$_{1-3}$alkyl, —O—C$_{1-3}$alkyl, —CF$_3$, —CH$_2$CF$_3$, and —O—CF$_3$;

R$^9$ and R$^{10}$ are independently selected from the group consisting of hydrogen, C$_{1-6}$alkyl and C$_{3-7}$cycloalkyl; wherein each C$_{1-6}$alkyl is a straight or branched chain alkyl; and wherein each C$_{1-6}$alkyl and C$_{3-7}$cycloalkyl is optionally substituted by one or more substituents selected from the group consisting of halogen, —OH, —SH, —C$_{1-3}$alkyl, —CF$_3$, —CH$_2$CF$_3$, and —O—CF$_3$; or R$^9$ and R$^{10}$ when attached to the same nitrogen atom are combined to form a 3- to 7-membered ring having from 0 to 2 additional heteroatoms as ring members;

R$^{11}$ is selected from the group consisting of C$_{1-6}$alkyl and C$_{3-7}$cycloalkyl; wherein each C$_{1-6}$alkyl is a straight or branched chain alkyl; and wherein each C$_{1-6}$alkyl and C$_{3-7}$cycloalkyl is optionally substituted by one or more substituents selected from the group consisting of halogen, —OH, —SH, —C$_{1-3}$alkyl, —O—C$_{1-3}$alkyl, —CF$_3$, —CH$_2$CF$_3$, and —O—CF$_3$; and R$^{12}$ is selected from the group consisting of halogen, C$_{1-6}$alkyl, —O—C$_{1-6}$alkyl, —S—C$_{1-6}$alkyl, C$_{3-7}$cycloalkyl, —O—C$_{3-7}$cycloalkyl, —C(O)OR$^8$, —C(O)NR$^9$R$^{10}$, —NR$^9$C(O)R$^{11}$, —S(O$_2$)NR$^9$R$^{10}$, —NR$^9$S(O$_2$)R$^{11}$, —S(O)R$^{11}$ and —S(O$_2$)R$^{11}$; wherein each C$_{1-6}$alkyl is a straight or branched chain alkyl; and wherein each C$_{1-6}$alkyl and C$_{3-7}$cycloalkyl is optionally substituted by one or more substituents selected from the group consisting of halogen, —OH, —C$_{1-3}$alkyl, —O—C$_{1-3}$alkyl, —CF$_3$, —CH$_2$CF$_3$, and —O—CF$_3$.

In another embodiment the present invention also relates to compounds of Formula If:

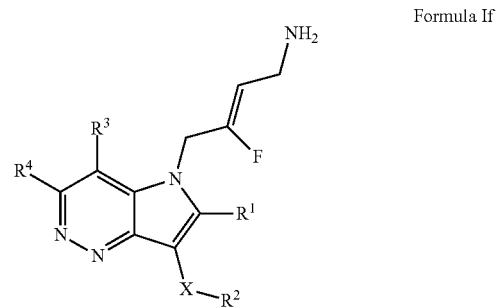

Formula If or a pharmaceutically acceptable salt, solvate or prodrug thereof; wherein:

X is O or —(CHR$^7$)$_m$— m is 1 or 2;

R$^1$ is selected from the group consisting of hydrogen, halogen, C$_{1-6}$alkyl, C$_{3-7}$cycloalkyl, —O—C$_{1-6}$alkyl, —O—C$_{3-7}$cycloalkyl, —C(O)OR$^8$, —C(O)NR$^9$R$^{10}$ and —NR$^9$C(O)R$^{11}$; wherein each C$_{1-6}$alkyl is a straight or branched chain alkyl; and wherein each C$_{1-6}$alkyl and C$_{3-7}$cycloalkyl is optionally substituted by one or more substituents selected from the group consisting of halogen, —OH, —SH, —C$_{1-3}$alkyl, —O—C$_{1-3}$alkyl, —CF$_3$, —CH$_2$CF$_3$, and —O—CF$_3$;

R$^2$ is aryl or heteroaryl; wherein each R$^2$ is optionally substituted by one or more R$^{12}$;

R$^3$ and R$^4$ are each independently selected from the group consisting of hydrogen, halogen, hydroxyl, C$_{1-6}$alkyl, C$_{3-7}$cycloalkyl, —O—C$_{1-6}$alkyl, —O—C$_{3-7}$cycloalkyl, —CN, —NO$_2$, —NR$^9$R$^{10}$, —C(O)OR$^8$, —C(O)NR$^9$R$^{10}$, —NR$^9$C(O)R$^{11}$, —S(O$_2$)NR$^9$R$^{10}$, —NR$^9$S(O$_2$)R$^{11}$, —S(O)R$^{11}$, —S(O$_2$)R$^{11}$, tetrazole and oxadiazole; wherein each C$_{1-6}$alkyl is a straight or branched chain alkyl; and wherein each C$_{1-6}$alkyl and C$_{3-7}$cycloalkyl is optionally substituted by one or more substituents selected from the group consisting of halogen, —OH, —SH, —O—C$_{1-3}$alkyl, —CF$_3$, —CH$_2$CF$_3$, and —O—CF$_3$;

each R$^7$ is independently selected from the group consisting of hydrogen, hydroxyl and C$_{1-3}$alkyl;

R$^8$ is selected from the group consisting of hydrogen, C$_{1-6}$alkyl, and C$_{3-7}$cycloalkyl; wherein each C$_{1-6}$alkyl is a straight or branched chain alkyl; and wherein each C$_{1-6}$alkyl and C$_{3-7}$cycloalkyl is optionally substituted by one or more substituents selected from the group consisting of halogen, —OH, —SH, —C$_{1-3}$alkyl, —O—C$_{1-3}$alkyl, —CF$_3$, —CH$_2$CF$_3$, and —O—CF$_3$;

R$^9$ and R$^{10}$ are independently selected from the group consisting of hydrogen, C$_{1-6}$alkyl and C$_{3-7}$cycloalkyl; wherein each C$_{1-6}$alkyl is a straight or branched chain alkyl; and wherein each C$_{1-6}$alkyl and C$_{3-7}$cycloalkyl is optionally substituted by one or more substituents selected from the group consisting of halogen, —OH, —SH, —C$_{1-3}$alkyl, —O—C$_{1-3}$alkyl, —CF$_3$, —CH$_2$CF$_3$, and —O—CF$_3$; or R$^9$ and R$^{10}$ when attached to the same nitrogen atom are combined to form a 3- to 7-membered ring having from 0 to 2 additional heteroatoms as ring members;

$R^{11}$ is selected from the group consisting of $C_{1-6}$alkyl and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$; and $R^{12}$ is selected from the group consisting of halogen, $C_{1-6}$alkyl, —O—$C_{1-6}$alkyl, —S—$C_{1-6}$alkyl, $C_{3-7}$cycloalkyl, —O—$C_{3-7}$cycloalkyl, —C(O)$OR^8$, —C(O)$NR^9R^{10}$, —$NR^9$C(O)$R^{11}$, —S($O_2$)$NR^9R^{10}$, —$NR^9$S($O_2$)$R^{11}$, —S(O)$R^{11}$ and —S($O_2$)$R^{11}$; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —$C_{1-3}$alkyl, —O—$C_{1-3}$alkyl, —$CF_3$, —$CH_2CF_3$, and —O—$CF_3$.

In one embodiment of compounds of Formula If of the invention $R^1$ is $C_{1-6}$alkyl, X is —$(CHR^7)_m$—, $R^7$ is hydrogen, m is 1, and $R^2$ is aryl, optionally substituted by one or more $R^{12}$. In another embodiment of compounds of Formula If $R^1$ is methyl, X is $CH_2$, $R^2$ is phenyl substituted by S($O_2$)$NR^9R^{10}$; $R^3$ is hydrogen and $R^4$ is methyl.

In another embodiment the present invention also relates to compounds of Formula Ig:

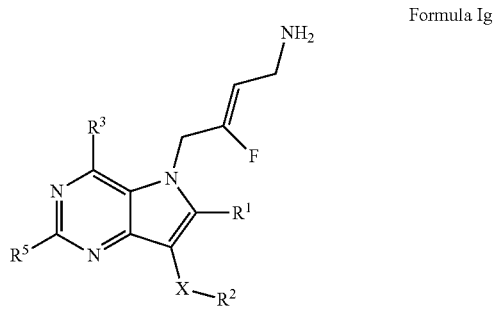

Formula Ig or a pharmaceutically acceptable salt, solvate or prodrug thereof; wherein:

X is O or —$(CHR^7)_m$— m is 1 or 2;

$R^1$ is selected from the group consisting of hydrogen, halogen, $C_{1-6}$alkyl, $C_{3-7}$cycloalkyl, —O—$C_{1-6}$alkyl, —O—$C_{3-7}$cycloalkyl, —C(O)$OR^8$, —C(O)$NR^9R^{10}$ and —$NR^9$C(O)$R^{11}$; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$;

$R^2$ is aryl or heteroaryl; wherein each $R^2$ is optionally substituted by one or more $R^{12}$;

$R^3$ and $R^5$ are each independently selected from the group consisting of hydrogen, halogen, hydroxyl, $C_{1-6}$alkyl, $C_{3-7}$cycloalkyl, —O—$C_{3-7}$cycloalkyl, —CN, —$NO_2$, —$NR^9R^{10}$, —C(O)$OR^8$, —C(O)$NR^9R^{10}$, —$NR^9$C(O)$R^{11}$, —S($O_2$)$NR^9R^{10}$, —$NR^9$S($O_2$)$R^{11}$, —S(O)$R^{11}$, —S($O_2$)$R^{11}$, tetrazole and oxadiazole; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$;

each $R^7$ is independently selected from the group consisting of hydrogen, hydroxyl and $C_{1-3}$alkyl;

$R^8$ is selected from the group consisting of hydrogen, $C_{1-6}$alkyl, and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$;

$R^9$ and $R^{10}$ are independently selected from the group consisting of hydrogen, $C_{1-6}$alkyl and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$; or $R^9$ and $R^{10}$ when attached to the same nitrogen atom are combined to form a 3- to 7-membered ring having from 0 to 2 additional heteroatoms as ring members;

$R^{11}$ is selected from the group consisting of $C_{1-6}$alkyl and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$; and $R^{12}$ is selected from the group consisting of halogen, $C_{1-6}$alkyl, —O—$C_{1-6}$alkyl, —S—$C_{1-6}$alkyl, $C_{3-7}$cycloalkyl, —O—$C_{3-7}$cycloalkyl, —C(O)$OR^8$, —C(O)$NR^9R^{10}$, —$NR^9$C(O)$R^{11}$, —S($O_2$)$NR^9R^{10}$, —$NR^9$S($O_2$)$R^{11}$, —S(O)$R^{11}$ and —S($O_2$)$R^{11}$; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —$C_{1-3}$alkyl, —O—$C_{1-3}$alkyl, —$CF_3$, —$CH_2CF_3$, and —O—$CF_3$.

In one embodiment of compounds of Formula Ig of the invention $R^1$ is $C_{1-6}$alkyl, X is —$(CHR^7)_m$—, $R^7$ is hydrogen, in is 1, and $R^2$ is aryl, optionally substituted by one or more $R^{12}$. In another embodiment of compounds of Formula Ig $R^1$ is methyl, X is $CH_2$, $R^2$ is phenyl substituted by S($O_2$)N($CH_3$)$_2$ or S($O_2$)$CH_3$; $R^3$ is hydrogen and $R^5$ is methyl.

In the context of the present disclosure, any one or more aspect(s) or embodiment(s) may be combined with any other aspect(s) or embodiment(s).

Exemplary compounds according to the present invention include the compounds set forth in Table 1:

TABLE 1
| 1 | 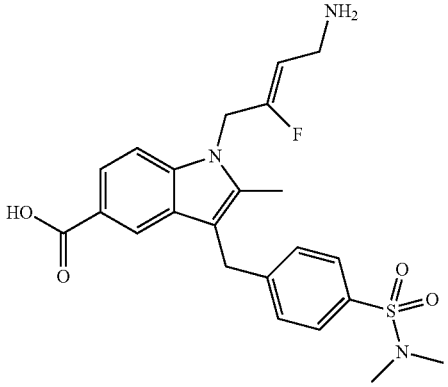 [SMILES: Cc1c(Cc2ccc(S(=O)(=O)N(C)C)cc2)c2cc(C(=O)O)ccc2n1C/C(F)=C/CN] | (Z)-1-(4-amino-2-fluorobut-2-en-1-yl)-3-(4-(N,N-dimethylsulfamoyl)benzyl)-2-methyl-1H-indole-5-carboxylic acid |
| 2 | 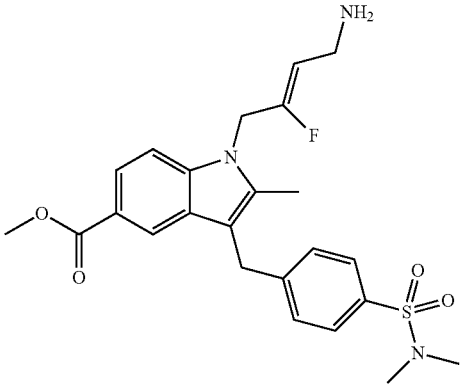 | (Z)-methyl 1-(4-amino-2-fluorobut-2-en-1-yl)-3-(4-(N,N-dimethylsulfamoyl)benzyl)-2-methylindole-5-carboxylate |
| 3 | 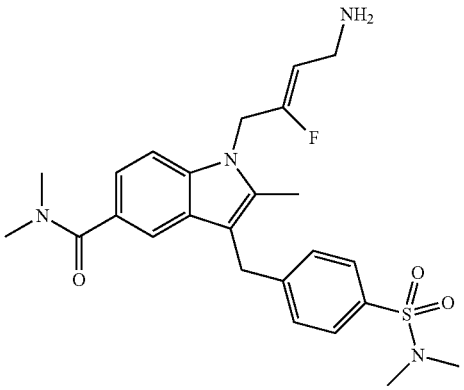 | (Z)-methyl 1-(4-amino-2-fluorobut-2-en-1-yl)-3-(4-(N,N-dimethylsulfamoyl)benzyl)-2-methyl-1H-indole-5-carboxylate |
| 4 | 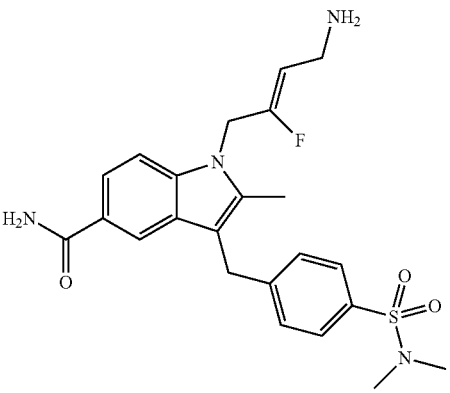 [SMILES: Cc1c(Cc2ccc(S(=O)(=O)N(C)C)cc2)c2cc(C(N)=O)ccc2n1C/C(F)=C/CN] | (Z)-1-(4-amino-2-fluorobut-2-en-1-yl)-3-(4-(N,N-dimethylsulfamoyl)benzyl)-2-methyl-1H-indole-5-carboxamide |

TABLE 1-continued

| | | |
|---|---|---|
| 5 | 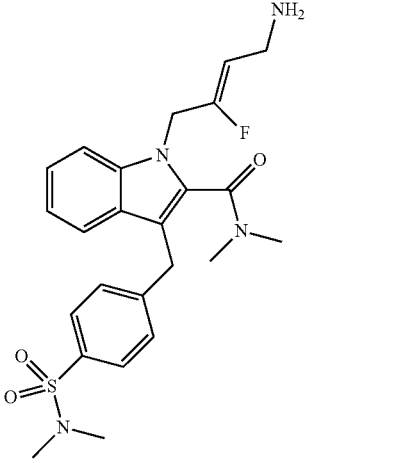 [SMILES: CN(C)C(=O)c1c(Cc2ccc(S(=O)(=O)N(C)C)cc2)c2ccccc2n1C/C(F)=C/CN] | (Z)-1-(4-amino-2-fluorobut-2-en-1-yl)-3-(4-(N,N-dimethylsulfamoyl)benzyl)-N,N-dimethyl-1H-indole-2-carboxamide |
| 6 | 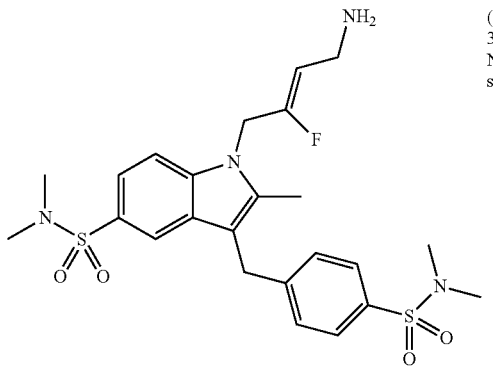 | (Z)-1-(4-amino-2-fluorobut-2-en-1-yl)-3-(4-(N,N-dimethylsulfamoyl)benzyl)-N,N,2-trimethyl-1H-indole-5-sulfonamide |
| 7 | 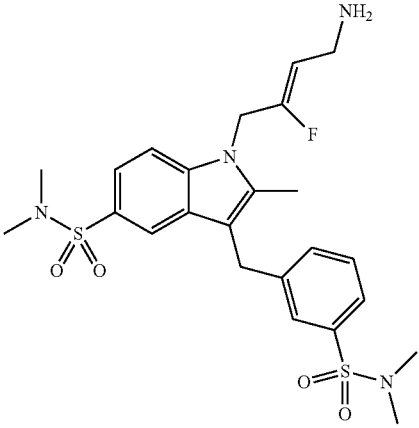 | (Z)-1-(4-amino-2-fluorobut-2-en-1-yl)-3-(3-(N,N-dimethylsulfamoyl)benzyl)-N,N,2-trimethyl-1H-indole-5-sulfonamide |
| 8 | 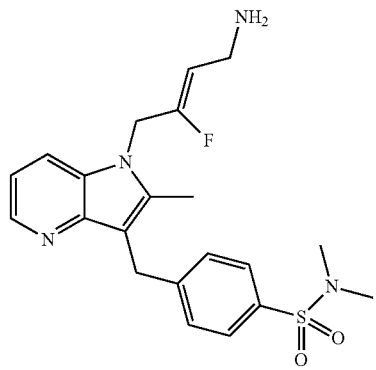 [SMILES: Cc1c(Cc2ccc(S(=O)(=O)N(C)C)cc2)c2ncccc2n1C/C(F)=C/CN] | (Z)-4-((1-(4-amino-2-fluorobut-2-en-1-yl)-2-methyl-1H-pyrrolo[3,2-b]pyridin-3-yl)methyl)-N,N-dimethylbenzenesulfonamide |

TABLE 1-continued

| | Structure | Name |
|---|---|---|
| 9 | 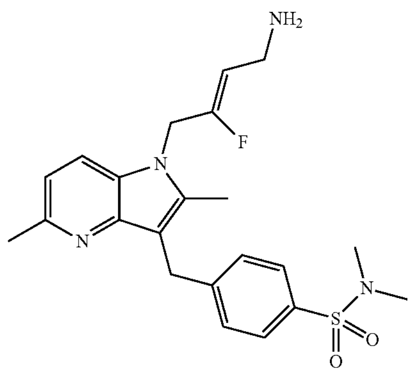 | (Z)-4-((1-(4-amino-2-fluorobut-2-en-1-yl)-2,5-dimethyl-1H-pyrrolo[3,2-b]pyridin-3-yl)methyl)-N,N-dimethylbenzenesulfonamide |
| 10 | 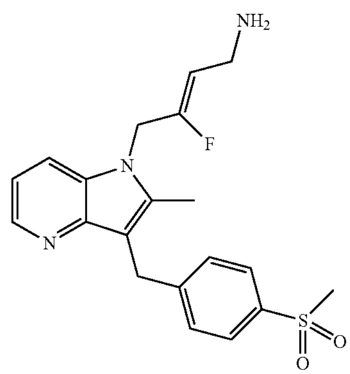 [SMILES: Cc1c(Cc2ccc(S(C)(=O)=O)cc2)c2ncccc2n1C/C(F)=C/CN] | (Z)-3-fluoro-4-(2-methyl-3-(4-(methylsulfonyl)benzyl)-1H-pyrrolo[3,2-b]pyridin-1-yl)but-2-en-1-amine |
| 11 | 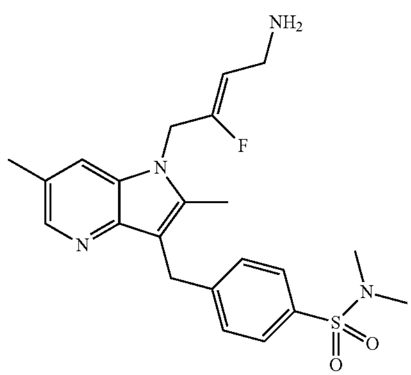 | (Z)-4-((1-(4-amino-2-fluorobut-2-en-1-yl)-2,6-dimethyl-1H-pyrrolo[3,2-b]pyridin-3-yl)methyl)-N,N-dimethylbenzenesulfonamide |
| 12 | 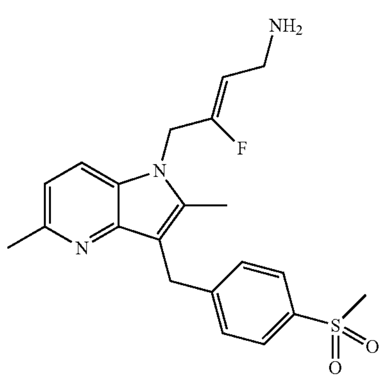 [SMILES: Cc1ccc2c(n1)c(Cc1ccc(S(C)(=O)=O)cc1)c(C)n2C/C(F)=C/CN] | (Z)-4-(2,5-dimethyl-3-(4-(methylsulfonyl)benzyl)-1H-pyrrolo[3,2-b]pyridin-1-yl)-3-fluorobut-2-en-1-amine |

TABLE 1-continued

| | | |
|---|---|---|
| 13 | 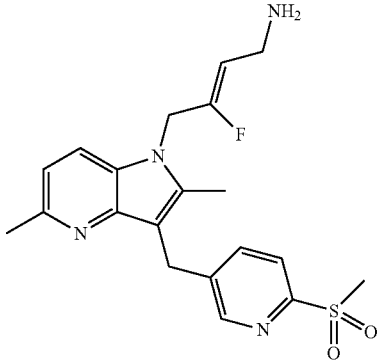 [SMILES: Cc1ccc2c(n1)c(Cc1ccc(S(C)(=O)=O)nc1)c(C)n2C/C(F)=C/CN] | (Z)-4-(2,5-dimethyl-3-((6-(methylsulfonyl)pyridin-3-yl)methyl)-1H-pyrrolo[3,2-b]pyridin-1-yl)-3-fluorobut-2-en-1-amine |
| 14 | 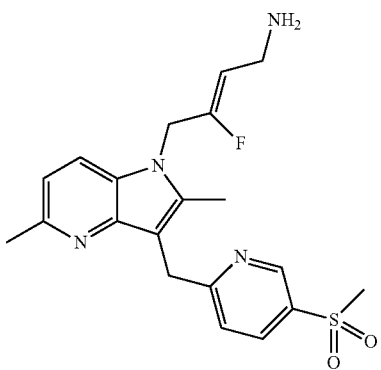 [SMILES: Cc1ccc2c(n1)c(Cc1ccc(S(C)(=O)=O)cn1)c(C)n2C/C(F)=C/CN] | (Z)-4-(2,5-dimethyl-3-((5-(methylsulfonyl)pyridin-2-yl)methyl)-1H-pyrrolo[3,2-b]pyridin-1-yl)-3-fluorobut-2-en-1-amine |
| 15 | 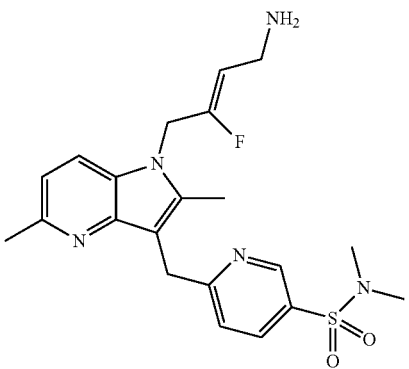 | (Z)-6-((1-(4-amino-2-fluorobut-2-en-1-yl)-2,5-dimethyl-1H-pyrrolo[3,2-b]pyridin-3-yl)methyl)-N,N-dimethylpyridine-3-sulfonamide |
| 16 | 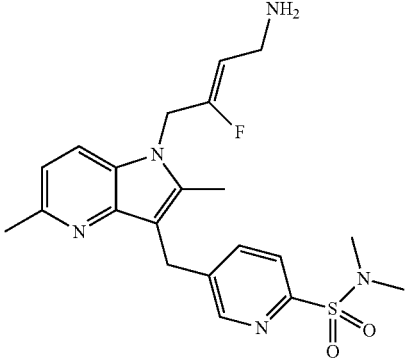 | (Z)-5-((1-(4-amino-2-fluorobut-2-en-1-yl)-2,5-dimethyl-1H-pyrrolo[3,2-b]pyridin-3-yl)methyl)-N,N-dimethylpyridine-2-sulfonamide |

TABLE 1-continued

| | | |
|---|---|---|
| 17 | 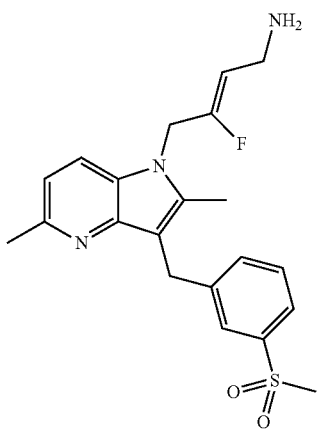 | (Z)-4-(2,5-dimethyl-3-(3-(methylsulfonyl)benzyl)-1H-pyrrolo[3,2-b]pyridin-1-yl)-3-fluorobut-2-en-1-amine |
| 18 | 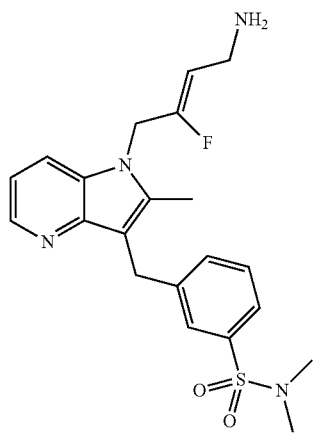 [SMILES: Cc1c(Cc2cccc(S(=O)(=O)N(C)C)c2)c2ncccc2n1C/C(F)=C/CN] | (Z)-3-((1-(4-amino-2-fluorobut-2-en-1-yl)-2-methyl-1H-pyrrolo[3,2-b]pyridin-3-yl)methyl)-N,N-dimethylbenzenesulfonamide |
| 19 | 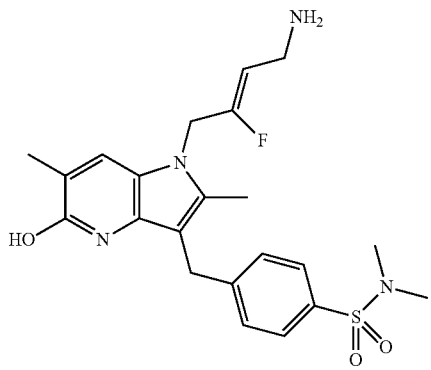 [SMILES: Cc1cc2c(nc1O)c(Cc1ccc(S(=O)(=O)N(C)C)cc1)c(C)n2C/C(F)=C/CN] | (Z)-4-((1-(4-amino-2-fluorobut-2-en-1-yl)-5-hydroxy-2,6-dimethyl-1H-pyrrolo[3,2-b]pyridin-3-yl)methyl)-N,N-dimethylbenzenesulfonamide |
| 20 | 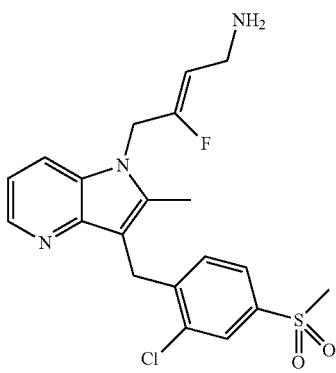 [SMILES: Cc1c(Cc2ccc(S(C)(=O)=O)cc2Cl)c2ncccc2n1C/C(F)=C/CN] | (Z)-4-(3-(2-chloro-4-(methylsulfonyl)benzyl)-2-methyl-1H-pyrrolo[3,2-b]pyridin-1-yl)-3-fluorobut-2-en-1-amine |

TABLE 1-continued

| 21 | 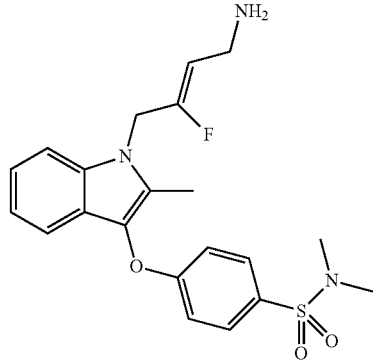 | (Z)-4-((1-(4-amino-2-fluorobut-2-en-1-yl)-2-methyl-1H-indol-3-yl)oxy)-N,N-dimethylbenzenesulfonamide |
| --- | --- | --- |
| 22 | 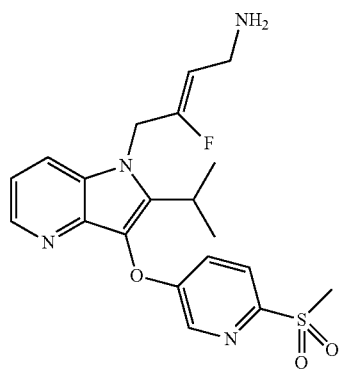 | (Z)-3-fluoro-4-(2-isopropyl-3-((6-(methylsulfonyl)pyridin-3-yl)methyl)-1H-pyrrolo[3,2-b]pyridin-1-yl)but-2-en-1-amine |
| 23 | 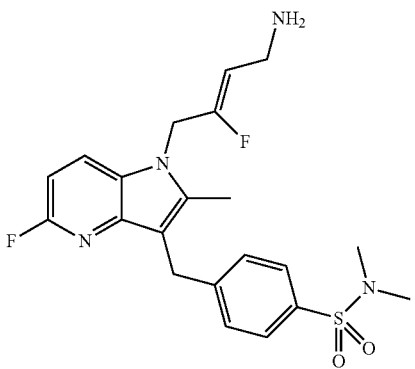 [SMILES: Cc1c(Cc2ccc(S(=O)(=O)N(C)C)cc2)c2nc(F)ccc2n1C/C(F)=C/CN] | (Z)-4-((1-(4-amino-2-fluorobut-2-en-1-yl)-5-fluoro-2-methyl-1H-pyrrolo[3,2-b]pyridin-3-yl)methyl)-N,N-dimethylbenzenesulfonamide |
| 24 | 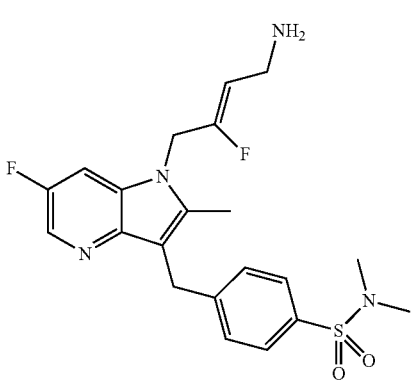 [SMILES: Cc1c(Cc2ccc(S(=O)(=O)N(C)C)cc2)c2ncc(F)cc2n1C/C(F)=C/CN] | (Z)-4-((1-(4-amino-2-fluorobut-2-en-1-yl)-6-fluoro-2-methyl-1H-pyrrolo[3,2-b]pyridin-3-yl)methyl)-N,N-dimethylbenzenesulfonamide |

TABLE 1-continued

| | | |
|---|---|---|
| 25 | 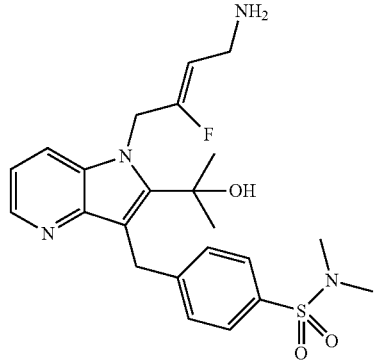 [SMILES: CN(C)S(=O)(=O)c1ccc(Cc2c(C(C)(C)O)n(C/C(F)=C/CN)c3cccnc23)cc1] | (Z)-4-((1-(4-amino-2-fluorobut-2-en-1-yl)-2-(2-hydroxypropan-2-yl)-1H-pyrrolo[3,2-b]pyridin-3-yl)methyl)-N,N-dimethylbenzenesulfonamide |
| 26 | 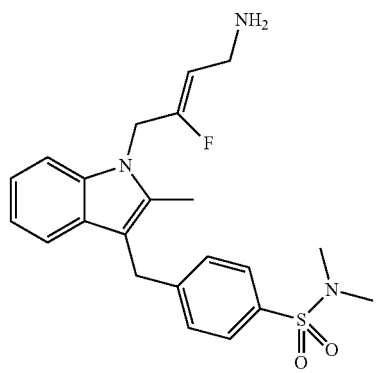 [SMILES: Cc1c(Cc2ccc(S(=O)(=O)N(C)C)cc2)c2ccccc2n1C/C(F)=C/CN] | (Z)-4-((1-(4-amino-2-fluorobut-2-en-1-yl)-2-methyl-1H-indol-3-yl)methyl)-N,N-dimethylbenzenesulfonamide |
| 27 | 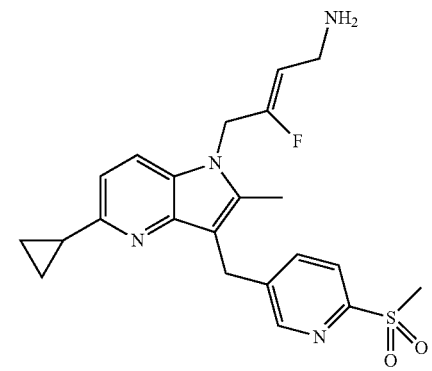 [SMILES: Cc1c(Cc2ccc(S(C)(=O)=O)nc2)c2nc(C3CC3)ccc2n1C/C(F)=C/CN] | (Z)-4-(5-cyclopropyl-2-methyl-3-((6-(methylsulfonyl)pyridin-3-yl)methyl)-1H-pyrrolo[3,2-b]pyridin-1-yl)-3-fluorobut-2-en-1-amine |
| 28 | 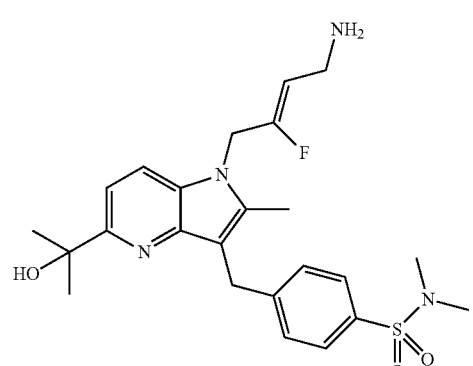 | (Z)-4-((1-(4-amino-2-fluorobut-2-en-1-yl)-5-(2-hydroxypropan-2-yl)-2-methyl-1H-pyrrolo[3,2-b]pyridin-3-yl)methyl)-N,N-dimethylbenzenesulfonamide |

TABLE 1-continued

| | | |
|---|---|---|
| 29 | | (Z)-4-((1-(4-amino-2-fluorobut-2-en-1-yl)-2-(1-hydroxyethyl)-1H-pyrrolo[3,2-b]pyridin-3-yl)methyl)-N,N-dimethylbenzenesulfonamide |
| 30 | | (Z)-4-(5-(1,1-difluoroethyl)-2-methyl-3-((6-(methylsulfonyl)pyridin-3-yl)methyl)-1H-pyrrolo[3,2-b]pyridin-1-yl)-3-fluorobut-2-en-1-amine |
| 31 | | (Z)-3-fluoro-4-(2-methyl-3-((6-(methylsulfonyl)pyridin-3-yl)methyl)-5-(trifluoromethyl)-1H-pyrrolo[3,2-b]pyridin-1-yl)but-2-en-1-amine |
| 32 | | (Z)-4-((1-(4-amino-2-fluorobut-2-en-1-yl)-2-methyl-1H-pyrrolo[3,2-c]pyridin-3-yl)methyl)-N,N-dimethylbenzenesulfonamide |

TABLE 1-continued

| | | |
|---|---|---|
| 33 | (structure) | (Z)-3-fluoro-4-(2-isopropyl-3-(4-(methylsulfonyl)benzyl)-1H-pyrrolo[3,2-b]pyridin-1-yl)but-2-en-1-amine |
| 34 | (structure) | (Z)-3-fluroo-4-(2-methyl-3-(2-methyl-4-(methylsulfonyl)benzyl)-1H-pyrrolo[3,2-b]pyridin-1-yl)but-2-en-1-amine |
| 35 | (structure) | (Z)-4-(3-(3-chloro-4-(methylsulfonyl)benzyl)-2-methyl-1H-pyrrolo[3,2-b]pyridin-1-yl)-3-fluorobut-2-en-1-amine |
| 36 | (structure) | (Z)-4-(2,6-dimethyl-3-(4-(methylsulfonyl)benzyl)-1H-pyrrolo[3,2-c]pyridin-1-yl)-3-fluorobut-2-en-1-amine |

TABLE 1-continued

| | | |
|---|---|---|
| 37 | [structure] | (Z)-4-((5-(4-amino-2-fluorobut-2-en-1-yl)-3,6-dimethyl-5H-pyrrolo[3,2-c]pyridazin-7-yl)methyl)-N,N-dimethylbenzenesulfonamide |
| 38 | [structure] | (Z)-4-(2,6-dimethyl-7-(4-(methylsulfonyl)benzyl)-5H-pyrrolo[3,2-d]pyrimidin-5-yl)-3-fluorobut-2-en-1-amine |
| 39 | [structure] | (Z)-4-((5-(4-amino-2-fluorobut-2-en-1-y)-2,6-dimethyl-5H-pyrrolo[3,2-d]pyrimidin-7-yl)methyl)-N,N-dimethylbenzenesulfon-amide |
| 40 | [structure] | (Z)-4-(2,5-dimethyl-3-(4-(methylsulfonyl)phenethyl)-1H-pyrrolo[3,2-b]pyridin-1-yl)-3-fluorobut-2-en-1-amine |

TABLE 1-continued

| | | |
|---|---|---|
| 41 | 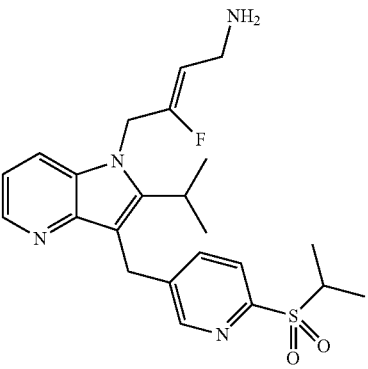 [SMILES: CC(C)c1c(Cc2ccc(S(=O)(=O)C(C)C)nc2)c2ncccc2n1C/C(F)=C/CN] | (Z)-3-fluoro-4-(2-isopropyl-3-((6-(isopropylsulfonyl)pyridin-3-yl)methyl)-1H-pyrrolo[3,2-b]pyridin-1-yl)but-2-en-1-amine |
| 42 | 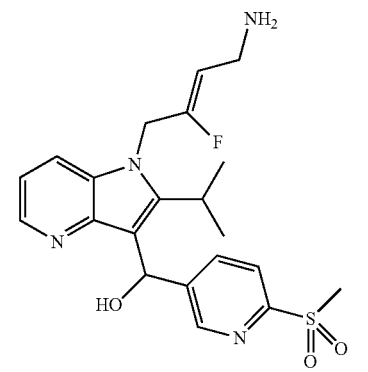 [SMILES: CC(C)c1c(C(O)c2ccc(S(C)(=O)=O)nc2)c2ncccc2n1C/C(F)=C/CN] | (Z)-(1-(4-amino-2-fluorobut-2-en-1-yl)-2-isopropyl-1H-pyrrolo[3,2-b]pyridin-3-yl)(6-(methylsulfonyl)pyridin-3-yl)methanol |
| 43 | 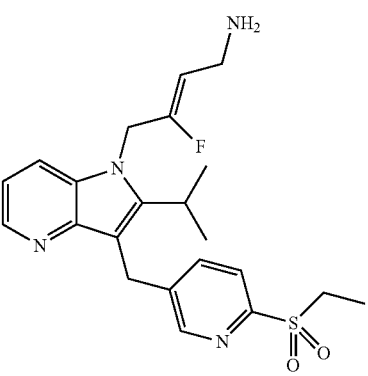 [SMILES: CCS(=O)(=O)c1ccc(Cc2c(C(C)C)n(C/C(F)=C/CN)c3cccnc23)cn1] | (Z)-4-(3-((6-(ethylsulfonyl)pyridin-3-yl)methyl)-2-isopropyl-1H-pyrrolo[3,2-b]pyridin-1-yl)-3-fluorobut-2-en-1-amine |
| 44 | 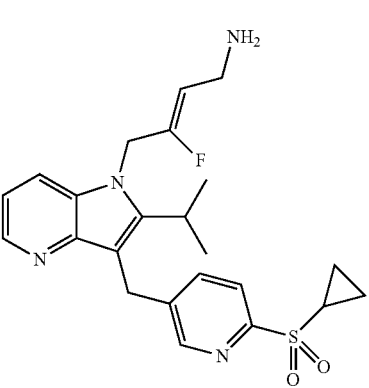 [SMILES: CC(C)c1c(Cc2ccc(S(=O)(=O)C3CC3)nc2)c2ncccc2n1C/C(F)=C/CN] | (Z)-4-(3-((6-(cyclopropylsulfonyl)pyridin-3-yl)methyl)-2-isopropyl-1H-pyrrolo[3,2-b]pyridin-1-yl)-3-fluorobut-2-en-1-amine |

Preparation of Compounds of Formula I

Compounds of Formula I can be readily prepared by those skilled in the art using methods and materials known in the art and with reference to standard textbooks, such as "Advanced Organic Chemistry" by Jerry March (third edition, 1985, John Wiley and Sons) or "Comprehensive Organic Transformations" by Richard C. Larock (1989, VCH Publishers).

Compounds of Formula I may be synthesised as described below. The following schemes provide an overview of representative non-limiting embodiments of the invention. Those skilled in the art will recognize that analogues of Formula I, including different isomeric forms, may also be prepared from the analogous starting materials.

Scheme 1:

The preparation of compounds described by Formula I wherein m=1; $R^7$=H is described in Scheme 1 below.

temperatures for up to 24 hours. The product described by Formula IV can be recovered by standard work-up procedures.

One convenient protocol for the conversion of compounds described by Formula IV to compounds described by Formula V is Method B which involves heating at 155° C. in DMSO/$H_2O$ (10:1) for several hours. The product described by Formula V can be recovered by standard work-up procedures.

In general Scheme 1 Method C involves the reaction of compounds described by Formulae V and VI to afford the coupled product as described by Formula VII. One convenient protocol involves treatment of compounds described by Formulae V with a base such as sodium methoxide in a solvent such as DMSO at ambient temperatures for a short time (5 min) followed by the addition of compounds described by Formulae VI. Following standard extraction

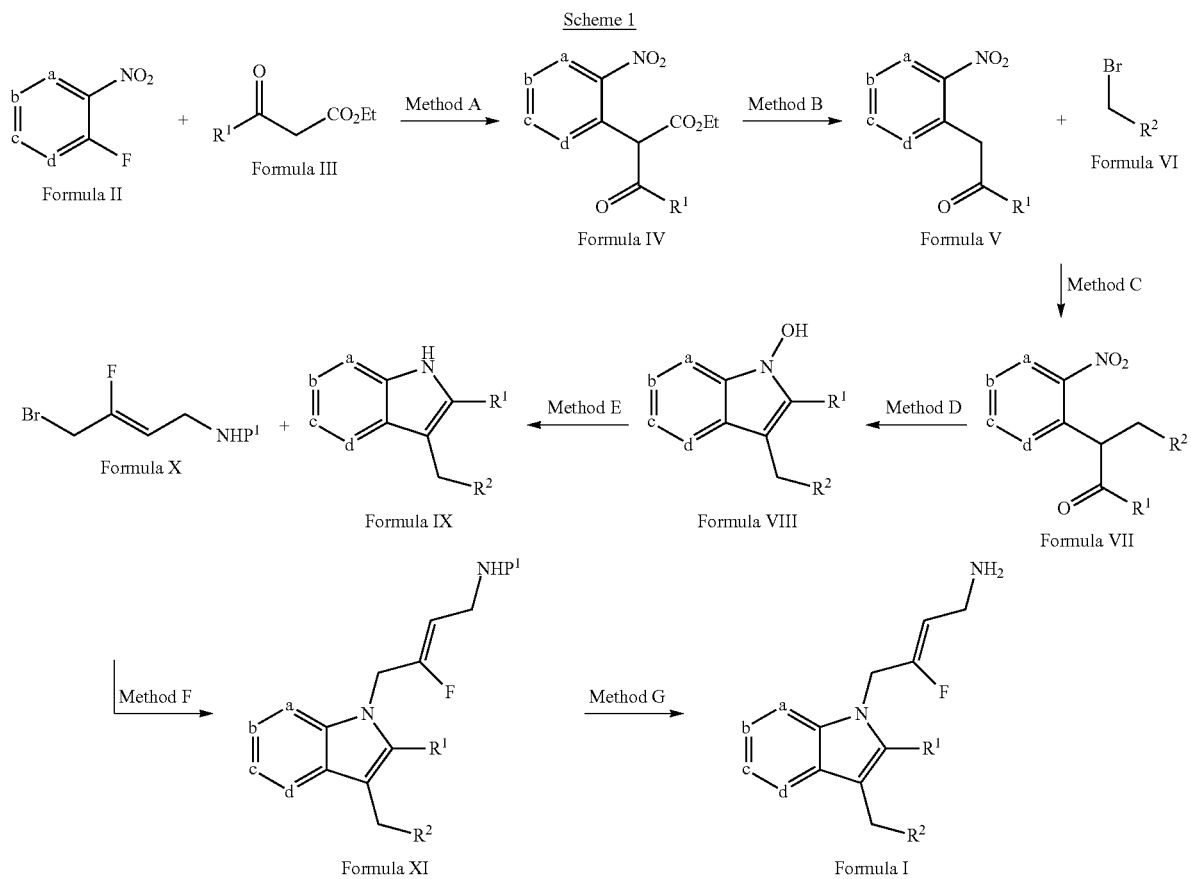

Scheme 1

$P^1$ is a functional group used to protect a nitrogen functionality. Examples of $P^1$ are carbonates such as the tert-butyloxycarbonyl (BOC), the 9-fluorenylmethyloxycarbonyl (FMOC), and the benzyloxycarbonyl (CBZ) groups.

In general Scheme 1 the starting material described by Formula II can be obtained from commercial sources or can be prepared by many methods well known in the art. Method A involves reaction of this starting material with the anion derived from an appropriately substituted 1,3-dicarbonyl compound, as is described by Formula III. For example, a solution of compounds described by Formulae II and III in a solvent such as N,N-dimethylformamide (DMF) can be treated with a base, such as potassium carbonate, at ambient and purification methods the product described by Formula VII can be obtained in good yield and purity.

One convenient protocol for the conversion of compounds described by Formula VII is Method D which involves treatment with zinc powder and ammonium chloride at ambient temperatures in tetrahydrofuran for several hours. The product described by Formula VIII can be recovered by standard work-up procedures.

One convenient protocol for the conversion of compounds described by Formula VIII is Method E which involves treatment with 2-bromoacetophenone and a base such as triethylamine in a solvent such as methanol at ambient temperatures for several hours. The product described by Formula IX can be recovered by standard work-up procedures.

Whilst there are many ways to achieve the reaction described by Method F, one convenient protocol involves reaction of compounds described by Formulae IX and X with a base such as cesium carbonate in a solvent such as N,N-dimethylformamide (DMF) at ambient temperature for approximately 16 hours. Following standard extraction and purification methods the product described by Formula XI can be obtained in good yield and purity.

There are many well established chemical procedures for the deprotection of the compounds described by Formula XI to the compounds described by Formula I (Method G). For example if $P^1$ is a BOC protecting group, compounds described by Formula XI can be treated with an acidic reagent such as dry hydrogen chloride in a solvent such as diethyl ether or dichloromethane to furnish the compounds described by Formula I as the hydrochloride salts. In general, the free amino compounds are converted to acid addition salts for ease of handling and for improved chemical stability. Examples of acid addition salts include but are not limited to hydrochloride, hydrobromide, 2,2,2-trifluoroacetate, methanesulfonate and toluenesulfonate salts.

Cis/trans (E/Z) isomers may be separated by conventional techniques well known to those skilled in the art, for example, chromatography and fractional crystallisation.

Therapeutic Uses and Formulations

Another aspect of the present invention relates to a pharmaceutical composition comprising a compound of Formula I, or a pharmaceutically acceptable salt or stereoisomer thereof, together with a pharmaceutically acceptable diluent, excipient or adjuvant.

The present invention also relates to use of the compounds of Formula I in therapy, in particular to inhibit members of the lysyl oxidase family members, LOX, LOXL1, LOXL2, LOXL3 and LOXL4. In one embodiment the invention provides for the selective inhibition of specific lysyl oxidase isoenzymes. In another embodiment the invention provides for the simultaneous inhibition of 2, 3 or 4 LOX isoenzymes. The relative inhibitory potencies of the compounds can be determined by the amount needed to inhibit the amine oxidase activity of LOX, LOXL1, LOXL2, LOXL3 and LOXL4 in a variety of ways, e.g., in an in vitro assay with recombinant or purified human protein or with recombinant or purified non-human enzyme, in cellular assays expressing normal rodent enzyme, in cellular assays which have been transfected with human protein, in in vivo tests in rodent and other mammalian species, and the like.

Accordingly, a further aspect of the invention is directed to a method of inhibiting the amine oxidase activity of LOX, LOXL1, LOXL2, LOXL3 and LOXL4 in a subject in need thereof, comprising administering to the subject an effective amount of a compound of Formula I, or a pharmaceutically acceptable salt or solvate thereof, or a pharmaceutical composition thereof.

In one embodiment the present invention is directed to a method of inhibiting the amine oxidase activity of LOXL2. In another embodiment the present invention is directed towards inhibiting the amine oxidase activity of LOX and LOXL2.

As discussed previously, LOX and LOXL1-4 enzymes are members of a large family of flavin-dependent and copper-dependent amine oxidases, which includes SSAO/VAP-1, monoamine oxidase-B (MAO-B) and diamine oxidase (DAO). In one embodiment compounds of the present invention selectively inhibit members of the lysyl oxidase isoenzyme family with respect to SSAO/VAP-1, MAO-B and other members of the amine oxidase family.

The present invention also discloses methods to use the compounds described by Formula I to inhibit one or more lysyl oxidase isoenzymes (LOX, LOXL1, LOXL2, LOXL3 and LOXL4) in patients suffering from a fibrotic disease, and methods to treat fibrotic diseases. Furthermore, the present invention discloses methods to use the compounds described by Formula I to inhibit one or more lysyl oxidase isoenzymes (LOX, LOXL1, LOXL2, LOXL3 and LOXL4) in patients suffering from cancer, including metastatic cancer, and methods to treat cancer and metastatic cancer.

In a further aspect of the invention there is provided a method of treating a condition associated with LOX, LOXL1, LOXL2, LOXL3 and LOXL4 protein, comprising administering to a subject in need thereof a therapeutically effective amount of compound of Formula I, or a pharmaceutically acceptable salt or solvate thereof, or a pharmaceutical composition thereof.

In another aspect there is a provided a method of treating a condition modulated by LOX, LOXL1, LOXL2, LOXL3 and LOXL4, comprising administering to a subject in need thereof a therapeutically effective amount of compound of Formula I, or a pharmaceutically acceptable salt or solvate thereof, or a pharmaceutical composition thereof.

In one embodiment of the methods of the present invention the condition is selected from the group consisting of fibrosis, cancer and angiogenesis.

In another aspect, the present invention provides a method for decreasing extracellular matrix formation by treating human subjects, pets and livestock with fluoroallylamine inhibitors of lysyl oxidase isoenzyme family of Formula I as described herein.

The above-described methods are applicable wherein the condition is a liver disorder. As described herein the term "liver disorder" includes any disorder affecting the liver, and in particular any acute or chronic liver disease that involves the pathological disruption, inflammation, degeneration, and/or proliferation of liver cells. In particular, the liver disorder is liver fibrosis, liver cirrhosis, or any other liver disease in which the level in the plasma of some markers of hepatocellular injury, alteration or necrosis, is elevated when compared to normal plasma levels. These biochemical markers associated to liver activity and status can be selected among those disclosed in the literature and in particular Alanine aminotransferase (ALAT), Aspartate aminotransferase (ASAT), Alkaline Phosphatase (AP), Gamma Glutamyl transpeptidase (GGT), Cytokeratin-18 (CK-18) or Resistin. In a particular embodiment, the liver disorder is a fatty liver disease in which the elevation of one or more of these markers is associated to a more or less significant steatosis in the liver, as it can be confirmed by a liver biopsy. A non-exhaustive list of fatty liver diseases includes non-alcoholic fatty liver disease (NAFLD), nonalcoholic steatohepatitis (NASH), and fatty liver disease associated to disorders such as hepatitis or metabolic syndrome (obesity, insulin resistance, hypertriglyceridemia, and the like). In one embodiment the liver disorder is selected from the group consisting of biliary atresia, cholestatic liver disease, chronic liver disease, nonalcoholic steatohepatitis (NASH), non-alcoholic fatty liver disease (NAFLD), hepatitis C infection, alcoholic liver disease, primary biliary cirrhosis (PBC), primary schlerosing cholangitis (PSC), liver damage due to progressive fibrosis, liver fibrosis and liver cirrhosis.

The above-described methods are applicable wherein the condition is a kidney disorder. In one embodiment the kidney disorder is selected from the group consisting of kidney fibrosis, renal fibrosis, acute kidney injury, chronic kidney disease, diabetic nephropathy, glomerulosclerosis, vesicoureteral reflux, tubulointerstitial renal fibrosis and glomerulonephritis.

The above-described methods are applicable wherein the condition is a cardiovascular disease. In one embodiment the cardiovascular disease is selected from the group consisting of atherosclerosis, arteriosclerosis, hypercholesteremia, and hyperlipidemia.

The above-described methods are applicable wherein the condition is fibrosis. As employed here "fibrosis" includes such diseases as cystic fibrosis, idiopathic pulmonary fibrosis, liver fibrosis, kidney fibrosis, scleroderma, radiation-induced fibrosis, ocular fibrosis, Peyronie's disease, scarring and other diseases where excessive fibrosis contributes to disease pathology including Crohn's disease and inflammatory bowel disease.

In one embodiment the fibrosis is selected from the group consisting of liver fibrosis, lung fibrosis, kidney fibrosis, cardiac fibrosis, cystic fibrosis, idiopathic pulmonary fibrosis, radiation-induced fibrosis and scleroderma or is associated with respiratory disease, abnormal wound healing and repair, post-surgical operations, cardiac arrest and all conditions where excess or aberrant deposition of fibrous material is associated with disease. In another embodiment the fibrosis is selected from the group consisting of liver fibrosis, lung fibrosis, kidney fibrosis, cardiac fibrosis, and scleroderma.

In one embodiment, kidney fibrosis includes, but is not limited to, diabetic nephropathy, vesicoureteral reflux, tubulointerstitial renal fibrosis; glomerulonephritis or glomerular nephritis, including focal segmental glomerulosclerosis and membranous glomerulonephritis, and mesangiocapillary glomerular nephritis. In one embodiment, liver fibrosis results in cirrhosis, and includes associated conditions such as chronic viral hepatitis, non-alcoholic fatty liver disease (NAFLD), alcoholic steatohepantis (ASH), non-alcoholic steatohepatiris (NASH), primary biliary cirrhosis (PBC), biliary cirrhosis, and autoimmune hepatitis.

The above-described methods are also applicable wherein the condition is cancer. In one embodiment the cancer is selected from the group consisting of lung cancer; breast cancer; colorectal cancer; anal cancer; pancreatic cancer; prostate cancer; ovarian carcinoma; liver and bile duct carcinoma; esophageal carcinoma; non-Hodgkin's lymphoma; bladder carcinoma; carcinoma of the uterus; glioma, glioblastoma, medulloblastoma, and other tumors of the brain; kidney cancer; myelofibrosis, cancer of the head and neck; cancer of the stomach; multiple myeloma; testicular cancer; germ cell tumor; neuroendocrine tumor; cervical cancer; oral cancer; carcinoids of the gastrointestinal tract, breast, and other organs; signet ring cell carcinoma; mesenchymal tumors including sarcomas, fibrosarcomas, haemangioma, angiomatosis, haemangiopericytoma, pseudoangiomatous stromal hyperplasia, myofibroblastoma, fibromatosis, inflammatory myofibroblastic tumour, lipoma, angiolipoma, granular cell tumour, neurofibroma, schwannoma, angiosarcoma, liposarcoma, rhabdomyosarcoma, osteosarcoma, leiomyoma or a leiomysarcoma.

In one embodiment the cancer is selected from the group consisting of breast cancer, head and neck squamous cell carcinoma, brain cancer, prostate cancer, renal cell carcinoma, liver cancer, lung cancer, oral cancer, cervical cancer and tumour metastasis.

In one embodiment lung cancer includes lung adenocarcinoma, squamous cell carcinoma, large cell carcinoma, bronchoalveolar carcinoma, non-small-cell carcinoma, small cell carcinoma and mesothelioma. In one embodiment breast cancer includes ductal carcinoma, lobular carcinoma, inflammatory breast cancer, clear cell carcinoma, and mucinous carcinoma. In one embodiment colorectal cancer includes colon cancer and rectal cancer. In one embodiment pancreatic cancer includes pancreatic adenocarcinoma, islet cell carcinoma and neuroendocrine tumors.

In one embodiment ovarian carcinoma includes ovarian epithelial carcinoma or surface epithelial-stromal tumour including serous tumour, endometrioid tumor and mucinous cystadenocarcinoma, and sex-cord-stromal tumor. In one embodiment liver and bile duct carcinoma includes hepatocellular carcinoma, cholangiocarcinoma and hemangioma. In one embodiment esophageal carcinoma includes esophageal adenocarcinoma and squamous cell carcinoma. In one embodiment carcinoma of the uterus includes endometrial adenocarcinoma, uterine papillary serous carcinoma, uterine clear-cell carcinoma, uterine sarcomas and leiomyosarcomas and mixed mullerian tumors. In one embodiment kidney cancer includes renal cell carcinoma, clear cell carcinoma and Wilm's tumor. In one embodiment cancer of the head and neck includes squamous cell carcinomas. In one embodiment cancer of the stomach includes stomach adenocarcinoma and gastrointestinal stromal tumor.

In one embodiment, the cancer is selected from the group consisting of colon cancer, ovarian cancer, lung cancer, esophageal carcinoma, breast cancer and prostate cancer.

The above-described methods are applicable wherein the condition is angiogenesis.

In one embodiment of the methods of the present invention the subject is selected from the group consisting of humans, pets and livestock. In another embodiment of the methods of the present invention the subject is a human.

A further aspect of the invention provides for use of a compound of Formula I, or a pharmaceutically acceptable salt or solvate thereof, for the manufacture of a medicament for treating a condition associated with LOX, LOXL1, LOXL2, LOXL3 and LOXL4 protein.

Another aspect of the invention provides for use of a compound of Formula I, or a pharmaceutically acceptable salt or solvate thereof, for the manufacture of a medicament for treating a condition modulated by LOX, LOXL1, LOXL2, LOXL3 and LOXL4.

Pharmaceutical and/or Therapeutic Formulations

In another embodiment of the present invention, there are provided compositions comprising a compound having Formula I and at least one pharmaceutically acceptable excipient, carrier or diluent thereof. The compound(s) of Formula I may also be present as suitable salts, including pharmaceutically acceptable salts.

The phrase "pharmaceutically acceptable carrier" refers to any carrier known to those skilled in the art to be suitable for the particular mode of administration. In addition, the compounds may be formulated as the sole pharmaceutically active ingredient in the composition or may be combined with other active ingredients.

The phrase "pharmaceutically acceptable salt" refers to any salt preparation that is appropriate for use in a pharmaceutical application. By pharmaceutically acceptable salt it is meant those salts which, within the scope of sound medical judgement, are suitable for use in contact with the tissues of humans and lower animals without undue toxicity, irritation, allergic response and the like, and are commensurate with a reasonable benefit/risk ratio. Pharmaceutically acceptable salts are well known in the art and include acid addition and base salts. Hemisalts of acids and bases may also be formed. Pharmaceutically acceptable salts include amine salts of mineral acids (e.g., hydrochlorides, hydrobromides, sulfates, and the like); and amine salts of organic acids (e.g., formates, acetates, lactates, malates, tartrates, citrates, ascorbates, succinates, maleates, butyrates, valerates, fumarates, and the like).

For compounds of formula (I) having a basic site, suitable pharmaceutically acceptable salts may be acid addition salts. For example, suitable pharmaceutically acceptable salts of such compounds may be prepared by mixing a pharmaceutically acceptable acid such as hydrochloric acid, sulfuric acid, methanesulfonic acid, succinic acid, fumaric acid, maleic acid, benzoic acid, phosphoric acid, acetic acid, oxalic acid, carbonic acid, tartaric acid, or citric acid with the compounds of the invention.

S. M. Berge et al. describe pharmaceutically acceptable salts in detail in *J. Pharmaceutical Sciences,* 1977, 66:1-19. The salts can be prepared in situ during the final isolation and purification of the compounds of the invention, or separately by reacting the free base function with a suitable organic acid. Representative acid addition salts include acetate, adipate, alginate, ascorbate, asparate, benzenesulfonate, benzoate, bisulfate, borate, butyrate, camphorate, camphorsulfonate, citrate, digluconate, cyclopentanepropionate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Suitable base salts are formed from bases that form non-toxic salts. Examples include the aluminium, arginine, benzathine, calcium, choline, diethylamine, diolamine, glycine, lysine, magnesium, meglumine, olamine, potassium, sodium, tromethamine and zinc salts. Representative alkali or alkaline earth metal salts include sodium, lithium potassium, calcium, magnesium, and the like, as well as non-toxic ammonium, quaternary ammonium, and amine cations, including, but not limited to ammonium, tetramethylammonium, tetraethylammonium, methylamine, dimethylamine, trimethylamine, triethylamine, ethylamine, triethanolamine and the like.

Pharmaceutically acceptable salts of compounds of formula I may be prepared by methods known to those skilled in the art, including for example:
(i) by reacting the compound of formula I with the desired acid or base;
(ii) by removing an acid- or base-labile protecting group from a suitable precursor of the compound of formula I or by ring-opening a suitable cyclic precursor, for example, a lactone or lactam, using the desired acid or base; or
(iii) by converting one salt of the compound of formula I to another by reaction with an appropriate acid or base or by means of a suitable ion exchange column.

The above reactions (i)-(iii) are typically carried out in solution. The resulting salt may precipitate out and be collected by filtration or may be recovered by evaporation of the solvent. The degree of ionisation in the resulting salt may vary from completely ionised to almost non-ionised.

Thus, for instance, suitable pharmaceutically acceptable salts of compounds according to the present invention may be prepared by mixing a pharmaceutically acceptable acid such as hydrochloric acid, sulfuric acid, methanesulfonic acid, succinic acid, fumaric acid, maleic acid, benzoic acid, phosphoric acid, acetic acid, oxalic acid, carbonic acid, tartaric acid, or citric acid with the compounds of the invention. Suitable pharmaceutically acceptable salts of the compounds of the present invention therefore include acid addition salts.

The compounds of the invention may exist in both unsolvated and solvated forms. The term 'solvate' is used herein to describe a molecular complex comprising the compound of the invention and a stoichiometric amount of one or more pharmaceutically acceptable solvent molecules, for example, ethanol. The term 'hydrate' is employed when the solvent is water.

In one embodiment the compounds of Formula I may be administered in the form of a "prodrug". The phrase "prodrug" refers to a compound that, upon in vivo administration, is metabolized by one or more steps or processes or otherwise converted to the biologically, pharmaceutically or therapeutically active form of the compound. Prodrugs can be prepared by modifying functional groups present in the compound in such a way that the modifications are cleaved, either in routine manipulation or in vivo, to a compound described herein. For example, prodrugs include compounds of the present invention wherein a hydroxy, amino, or sulfhydryl group is bonded to any group that, when administered to a mammalian subject, can be cleaved to form a free hydroxyl, free amino, or free sulfhydryl group, respectively. Representative prodrugs include, for example, amides, esters, enol ethers, enol esters, acetates, formates, benzoate derivatives, and the like of alcohol and amine functional groups in the compounds of the present invention. The prodrug form can be selected from such functional groups as —C(O)alkyl, —C(O)cycloalkyl, —C(O)aryl, —C(O)-arylalkyl, C(O)heteroaryl, —C(O)-heteroarylalkyl, or the like. By virtue of knowledge of pharmacodynamic processes and drug metabolism in vivo, those of skill in this art, once a pharmaceutically active compound is known, can design prodrugs of the compound (see, e.g., Nogrady (1985) *Medicinal Chemistry A Biochemical Approach,* Oxford University Press, New York, pages 388-392).

Compositions herein comprise one or more compounds provided herein. The compounds are, in one embodiment, formulated into suitable pharmaceutical preparations such as solutions, suspensions, tablets, creams, gels, dispersible tablets, pills, capsules, powders, sustained release formulations or elixirs, for oral administration or in sterile solutions or suspensions for parenteral administration, as well as transdermal patch preparation and dry powder inhalers. In one embodiment, the compounds described above are formulated into pharmaceutical compositions using techniques and procedures well known in the art (see, e.g., Ansel *Introduction to Pharmaceutical Dosage Forms,* Fourth Edition 1985, 126).

In the compositions, effective concentrations of one or more compounds or pharmaceutically acceptable derivatives thereof is (are) mixed with a suitable pharmaceutical carrier. The compounds may be derivatized as the corresponding salts, esters, enol ethers or esters, acetals, ketals, orthoesters, hemiacetals, hemiketals, acids, bases, solvates, hydrates or prodrugs prior to formulation, as described above. The concentrations of the compounds in the compositions are effective for delivery of an amount, upon administration, that treats, prevents, or ameliorates one or more of the symptoms of diseases or disorders to be treated.

In one embodiment, the compositions are formulated for single dosage administration. To formulate a composition, the weight fraction of compound is dissolved, suspended, dispersed or otherwise mixed in a selected carrier at an effective concentration such that the treated condition is relieved, prevented, or one or more symptoms are ameliorated.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in in vitro and in vivo systems described herein and in PCT publication WO 04/018997, and then extrapolated from there for dosages for humans.

The concentration of active compound in the pharmaceutical composition will depend on absorption, distribution, inactivation and excretion rates of the active compound, the physicochemical characteristics of the compound, the dosage schedule, and amount administered as well as other factors known to those of skill in the art.

In one embodiment, a therapeutically effective dosage should produce a serum concentration of active ingredient of from about 0.1 ng/mL to about 50-100 µg/mL. The pharmaceutical compositions, in another embodiment, should provide a dosage of from about 0.001 mg to about 2000 mg of compound per kilogram of body weight per day. Pharmaceutical dosage unit forms are prepared to provide from about 0.01 mg, 0.1 mg or 1 mg to about 500 mg, 1000 mg or 2000 mg, and in one embodiment from about 10 mg to about 500 mg of the active ingredient or a combination of essential ingredients per dosage unit form.

Dosing may occur at intervals of minutes, hours, days, weeks, months or years or continuously over any one of these periods. Suitable dosages lie within the range of about 0.1 ng per kg of body weight to 1 g per kg of body weight per dosage. The dosage is preferably in the range of 1 µg to 1 g per kg of body weight per dosage, such as is in the range of 1 mg to 1 g per kg of body weight per dosage. Suitably, the dosage is in the range of 1 µg to 500 mg per kg of body weight per dosage, such as 1 µg to 200 mg per kg of body weight per dosage, or 1 µg to 100 mg per kg of body weight per dosage. Other suitable dosages may be in the range of 1 mg to 250 mg per kg of body weight, including 1 mg to 10, 20, 50 or 100 mg per kg of body weight per dosage or 10 µg to 100 mg per kg of body weight per dosage.

Suitable dosage amounts and dosing regimens can be determined by the attending physician and may depend on the particular condition being treated, the severity of the condition, as well as the general health, age and weight of the subject.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN®, dissolution in aqueous sodium bicarbonate, formulating the compounds of interest as nanoparticles, and the like. Derivatives of the compounds, such as prodrugs of the compounds may also be used in formulating effective pharmaceutical compositions.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are, in one embodiment, formulated and administered in unit-dosage forms or multiple-dosage forms. The active ingredient may be administered at once, or may be divided into a number of smaller doses to be administered at intervals of time. Unit-dose forms as used herein refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoles and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Actual methods of preparing such dosage forms are known, or will be apparent, to those skilled in this art; for example, see Remington's Pharmaceutical Sciences, Mack Publishing Company, Easton, Pa., 15th Edition, 1975.

Dosage forms or compositions containing active ingredient in the range of 0.005% to 100% (wt %) with the balance made up from non-toxic carrier may be prepared. Methods for preparation of these compositions are known to those skilled in the art. The contemplated compositions may contain 0.001%-100% (wt %) active ingredient, in one embodiment 0.1-95% (wt %), in another embodiment 75-85% (wt %).

Modes of Administration

Convenient modes of administration include injection (subcutaneous, intravenous, etc.), oral administration, inhalation, transdermal application, topical creams or gels or powders, vaginal or rectal administration. Depending on the route of administration, the formulation and/or compound may be coated with a material to protect the compound from the action of enzymes, acids and other natural conditions which may inactivate the therapeutic activity of the compound. The compound may also be administered parenterally or intraperitoneally.

Compositions for Oral Administration

Oral pharmaceutical dosage forms are either solid, gel or liquid. The solid dosage forms are tablets, capsules, granules, and bulk powders. Types of oral tablets include compressed, chewable lozenges and tablets which may be enteric-coated, sugar-coated or film-coated.

Capsules may be hard or soft gelatin capsules, while granules and powders may be provided in non-effervescent or effervescent form with the combination of other ingredients known to those skilled in the art.

Solid Compositions for Oral Administration

In certain embodiments, the formulations are solid dosage forms, in one embodiment, capsules or tablets. The tablets, pills, capsules, troches and the like can contain one or more of the following ingredients, or compounds of a similar nature: a binder; a lubricant; a diluent; a glidant; a disintegrating agent; a coloring agent; a sweetening agent; a flavoring agent; a wetting agent; an emetic coating; and a film coating. Examples of binders include microcrystalline cellulose, gum tragacanth, glucose solution, acacia mucilage, gelatin solution, molasses, polyvinylpyrrolidine, povidone, crospovidones, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

The compound, or pharmaceutically acceptable derivative thereof, could be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. The active ingredient is a compound or pharmaceutically acceptable derivative thereof as described herein. Higher concentrations, up to about 98% by weight of the active ingredient may be included.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

Liquid Compositions for Oral Administration

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, solubilizing agents, pH buffering agents and the like, for example, acetate, sodium citrate, cyclodextrine derivatives, sorbitan monolaurate, triethanolamine sodium acetate, triethanolamine oleate, and other such agents.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic acid, sodium benzoate and ethanol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is in one embodiment encapsulated in a gelatin capsule. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. RE28,819 and 4,358,603. Briefly, such formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

Injectables, Solutions and Emulsions

Parenteral administration, in one embodiment characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Implantation of a slow-release or sustained-release system, such that a constant level of dosage is maintained is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, olive oil, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcellulose, hydroxypropyl methylcellulose and polyvinylpyrrolidone. Emulsifying agents include Polysorbate 80 (TWEEN® 80). A sequestering or chelating agent of metal ions include EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations are packaged in an ampule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. In one embodiment, a therapeutically effective dosage is formulated to contain a concentration of at least about 0.1% w/w up to about 90% w/w or more, in certain embodiments more than 1% w/w of the active compound to the treated tissue(s).

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

Lyophilized Powders

Of interest herein are also lyophilized powders, which can be reconstituted for administration as solutions, emulsions and other mixtures. They may also be reconstituted and formulated as solids or gels.

The sterile, lyophilized powder is prepared by dissolving a compound provided herein, or a pharmaceutically acceptable derivative thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. In one embodiment, the resulting solution will be apportioned into vials for lyophilization. Each vial will contain a single dosage or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

Topical Administration

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or pharmaceutically acceptable derivatives thereof may be formulated as aerosols for topical application, such as by inhalation. These formulations for administration to the respiratory tract can be in the form of an aerosol or solution for a nebulizer, or as a microfine powder for insufflation, alone or in combination with an inert carrier such as lactose. In such a case, the particles of the formulation will, in one embodiment, have diameters of less than 50 microns, in one embodiment less than 10 microns.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

These solutions, particularly those intended for ophthalmic use, may be formulated as 0.01%-10% (vol %) isotonic solutions, pH about 5-7, with appropriate salts.

Compositions for Other Routes of Administration

Other routes of administration, such as transdermal patches, including iontophoretic and electrophoretic devices, vaginal and rectal administration, are also contemplated herein.

Transdermal patches, including iontophoretic and electrophoretic devices, are well known to those of skill in the art. For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The weight of a rectal suppository, in one embodiment, is about 2 to 3 gm.

Tablets and capsules for rectal administration are manufactured using the same pharmaceutically acceptable substance and by the same methods as for formulations for oral administration.

Targeted Formulations

The compounds provided herein, or pharmaceutically acceptable derivatives thereof, may also be formulated to be targeted to a particular tissue, receptor, or other area of the body of the subject to be treated. Many such targeting methods are well known to those of skill in the art. All such targeting methods are contemplated herein for use in the instant compositions.

In one embodiment, liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

Co-Administration with Other Drugs

In accordance with another aspect of the present invention, it is contemplated that compounds of Formula I as described herein may be administered to a subject in need thereof in combination with medication considered by those of skill in the art to be current standard of care for the condition of interest. Such combinations provide one or more advantages to the subject, e.g., requiring reduced dosages to achieve similar benefit, obtaining the desired palliative effect in less time, and the like.

Compounds in accordance with the present invention may be administered as part of a therapeutic regimen with other drugs. It may desirable to administer a combination of active compounds, for example, for the purpose of treating a particular disease or condition. Accordingly, it is within the scope of the present invention that two or more pharmaceutical compositions, at least one of which contains a compound of Formula (I) according to the present invention, may be combined in the form of a kit suitable for co-administration of the compositions.

In one embodiment of the methods of the present inventions a compound of Formula I may be administered with a second therapeutic agent. In one embodiment the second therapeutic agent is selected from the group consisting of an anti-cancer agent, an anti-inflammatory agent, an anti-hypertensive agent, an anti-fibrotic agent, an anti-angiogenic agent and an immunosuppressive agent.

When two or more active ingredients are co-administered, the active ingredients may be administered simultaneously, sequentially or separately. In one embodiment the compound of Formula I is co-administered simultaneously with a second therapeutic agent. In another embodiment the compound of Formula I and the second therapeutic agent are administered sequentially. In a further embodiment the compound of Formula I and the second therapeutic agent are administered separately.

The invention will now be described in greater detail, by way of illustration only, with reference to the following non-limiting examples. The examples are intended to serve to illustrate the invention and should not be construed as limiting the generality of the disclosure of the description throughout this specification.

Example 1

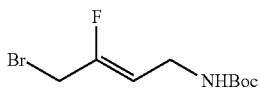

Preparation of (Z-tert-butyl(4-bromo-3-fluorobut-2-en-1-yl)carbamate

Procedure A: Preparation of tert-butyl 2-oxoethylcarbamate

To a stirring solution of 3-amino-1,2-propanediol (20.0 g, 0.22 mol) in water (200 mL) at 0-5° C. was added di-tert-butyl dicarbonate (55.5 mL, 0.24 mol). After adjusting the alkalinity of the solution to pH~9 by addition of aq. NaOH (6 N), the mixture was left to stir at rt for 18 h. The reaction mixture was cooled to 0-5° C. and then acidified to pH~6 before the addition of sodium metaperiodate (56.3 g, 0.26 mol). The resulting suspension was stirred at rt for 2 h. The mixture was filtered to remove all solids and the filtrate was transferred to a separatory funnel and extracted with ethyl acetate (200 mL). Sodium chloride was added to the aqueous layer until a saturated solution was obtained. The aqueous layer was then extracted further with ethyl acetate (100 mL). The combined organics were dried over $Na_2SO_4$ and then concentrated in vacuo to give crude tert-butyl 2-oxoethyl-carbamate (45.7 g) as a yellow gum. The crude material was used in the subsequent step without purification.

Procedure B: Preparation of (E)-ethyl 4-(tert-butoxycarbonylamino)-2-fluorobut-2-enoate and (Z)-ethyl 4-(tert-butoxycarbonylamino)-2-fluorobut-2-enoate

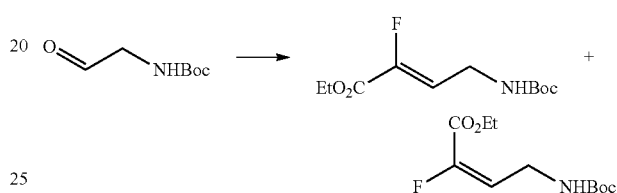

To a stirring suspension of crude text-butyl 2-oxoethyl-carbamate (43.7 g, 0.22 mol) and magnesium sulfate (32.0 g) in acetonitrile (200 mL) at 0° C. under $N_2$ was added sequentially ethyl 2-fluorophosphonoacetate (55.7 mL, 0.27 mol) and 1,8-diazabicyclo[5.4.0]undec-7-ene (32.8 mL, 0.22 mol). The reaction mixture was allowed to warm to rt and stirring was continued for 3 h. After removing the solvent under reduced pressure the residue was taken up in ethyl acetate (200 mL) and then transferred to a separatory funnel. The organics were washed successively with aq. HCl (2 M; 100 mL×2), aq. NaOH (2 M; 100 mL×2) and brine (100 mL). After drying over $MgSO_4$, the organics were concentrated in vacuo to give the crude, desired product as a mixture of E/Z isomers (2:3; 57.0 g). This crude material was progressed to the next step without purification.

Procedure C: Preparation of (E)-tert-butyl 3-fluoro-4-hydroxybut-2-enylcarbamate and (Z)-tert-butyl 3-fluoro-4-hydroxybut-2-enylcarbamate

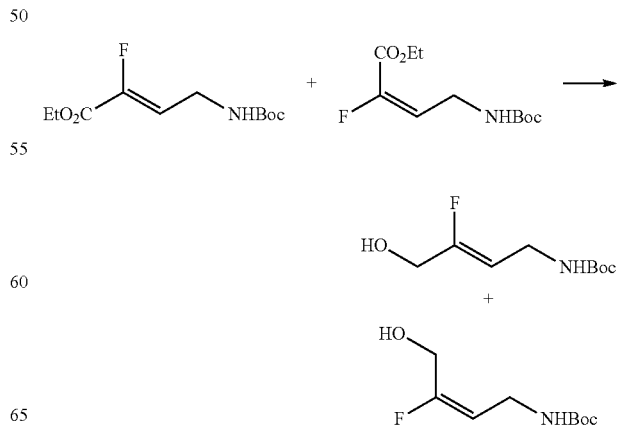

To a stirring solution of crude E/Z-ethyl 4-(tert-butoxy-carbonylamino)-2-fluorobut-2-enoate (18.0 g, 72.8 mmol) in THF (150 mL) at 0° C. under N₂ was added diisobutylaluminum hydride (1 M in toluene, 182 mL, 182 mmol) dropwise over 45 min. After complete addition, the mixture was left to stir at 0° C. for 3 h. The reaction mixture was transferred to a separatory funnel and added dropwise to a stirring mixture of ice (100 g) and aq. NaOH (2 M; 200 mL). Following addition the mixture was stirred for 2 h. The quenched reaction mixture was extracted with diethyl ether (100 mL×2) and the combined organics were washed with brine (100 mL). After drying over MgSO₄ the organics were concentrated in vacuo to give the crude alcohol as a mixture of E/Z isomers. This mixture was purified over silica gel (135 g), eluting with 25% ethyl acetate in n-hexane to give (Z)-tert-butyl 3-fluoro-4-hydroxybut-2-enylcarbamate (6.20 g, 30% over three steps) and (E)-tert-butyl 3-fluoro-4-hydroxybut-2-enylcarbamate (1.85 g, 8.9% over three steps). (E)-tert-butyl 3-fluoro-4-hydroxybut-2-enylcarbamate: ¹H-NMR (200 MHz; CDCl₃) δ ppm: 1.43 (9H, s), 3.72 (2H, dd, J 7.5, 5.4 Hz), 4.25 (2H, d, J 21.5 Hz), 4.85 (1H, br. s), 5.18 (1H, dt, J 19.2, 8.5 Hz). (Z)-tert-butyl 3-fluoro-4-hydroxybut-2-enylcarbamate: ¹H-NMR (300 MHz; CDCl₃) δ ppm: 1.46 (9H, s), 3.84 (2H, dd, J 6.2, 6.2 Hz), 4.13 (2H, d, J 13.9 Hz), 4.68 (1H, br. s), 5.03 (1H, dt, J 36.0, 7.1 Hz).

Procedure D: Preparation of (Z)-tert-butyl 4-bromo-3-fluorobut-2-enylcarbamate

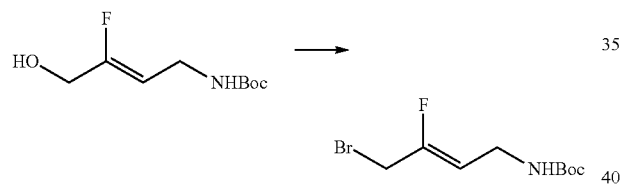

To a stirring solution of (Z)-tert-butyl 3-fluoro-4-hydroxybut-2-enylcarbamate (6.20 g, 30.2 mmol) and triethylamine (6.32 mL, 45.3 mmol) in acetone (100 mL) at 0° C. was added methanesulfonyl chloride (2.81 mL, 36.3 mmol) dropwise. After complete addition the mixture was left to stir at 0° C. for 30 min. After this time, lithium bromide (13.1 g, 0.15 mol) was added portionwise and the resulting suspension was stirred for a further 2 h. The reaction mixture was filtered to remove all solids and the filtrate was concentrated under reduced pressure. The residue was partitioned between water (50 mL) and CH₂Cl₂ (50 mL) and the aqueous layer was extracted with further CH₂Cl₂ (50 mL×2). The combined organics were dried over Na₂SO₄ and concentrated in vacuo. The crude residue was purified over silica gel (100 g) eluting with n-hexane followed by 25% ethyl acetate in n-hexane to afford (Z)-tert-butyl 4-bromo-3-fluorobut-2-enylcarbamate (7.00 g, 86%) as a colourless solid. ¹H-NMR (300 MHz; CDCl₃) δ ppm: 1.46 (9H, s), 3.85 (2H, dd, J 6.2, 6.2 Hz), 3.93 (2H, d, J 19.5 Hz), 4.66 (1H, br. s), 5.16 (1H, dt, J 34.0, 6.5 Hz).

Example 2

The following compound was prepared according to procedures E, F, G, H, I, J and K.

(Z)-4-((1-(4-amino-2-fluorobut-2-en-1-yl)-5-hydroxy-2,6-dimethyl-1H-pyrrolo[3,2-b]pyridin-3-yl) methyl)-N,N-dimethylbenzenesulfonamide dihydrochloride (Compound 19)

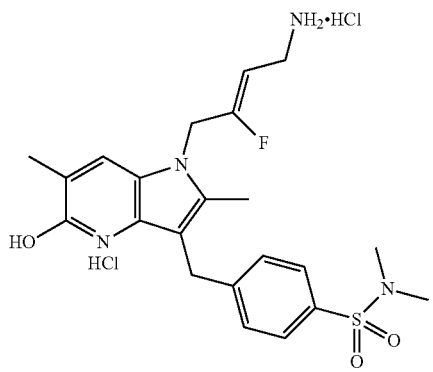

Procedure E: Preparation of 4-(bromomethyl)-N,N-dimethylbenzenesulfonamide

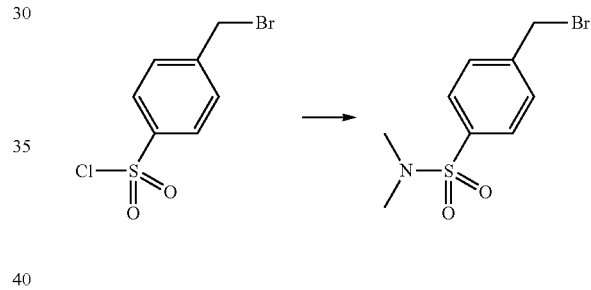

To a stirring solution of 4-(bromomethyl)benzenesulfonyl chloride (5.00 g, 18.6 mmol) in CH₂Cl₂ (40 mL) at 0° C. was added dimethylamine (5.80 mL, 46.4 mmol) drop-wise. Following addition the resulting mixture was left to stir at this temperature for 45 min before partitioning between aq. HCl (1 M, 100 mL) and CH₂Cl₂ (50 mL). The organic layer was washed further with aq. HCl (1 M, 100 mL) and water (50 mL), dried over Na₂SO₄ and concentrated in vacuo to give 4-(bromomethyl)-N,N-dimethylbenzenesulfonamide (2.20 g, 43%) as an off-white solid. ¹H-NMR (300 MHz; CD₃OD) δ ppm: 2.74 (6H, s), 4.52 (2H, s), 7.58 (2H, d, J 8.4 Hz), 7.77 (2H, d, J 8.3 Hz).

Procedure F: Preparation of ethyl 2-(4-(N,N-dimethylsulfamoyl)benzyl)-3-oxobutanoate

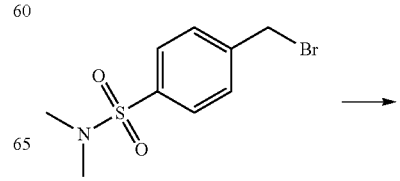

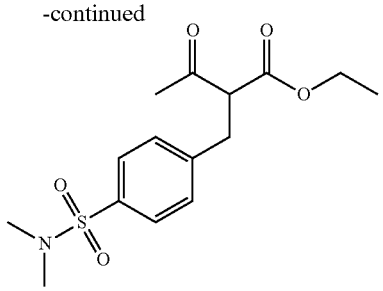

To a stirred solution of ethyl 3-oxobutanoate (0.41 mL, 3.24 mmol) in DMF (2.5 mL) was added cesium carbonate (0.59 g, 180 mmol) and the resulting suspension was stirred at rt for 5 mins. To this was added 4-(bromomethyl)-N,N-dimethylbenzenesulfonamide (0.50 g, 1.80 mmol) and stirring was continued for 2 h. The reaction mixture was partitioned between ethyl acetate (20 mL) and water (20 mL). The organic layer was washed with further water, brine and then dried over $Na_2SO_4$. The solvent was removed in vacuo to afford a crude brown gum. The crude material was purified over silica gel, eluting with 20% in hexane followed by 40% ethyl acetate in hexane to afford the title compound ethyl 2-(4-(N,N-dimethylsulfamoyl)benzyl)-3-oxobutanoate (200 mg, 33%) as a clear oil. $^1$H NMR (300 MHz, $CDCl_3$) δ 7.71 (d, J=8.3 Hz, 2H), 7.38 (d, J=8.1 Hz, 2H), 4.42-4.03 (m, 2H), 3.80 (t, 1H), 3.35-3.13 (m, 2H), 2.71 (s, 6H), 2.25 (s, 3H), 1.38-1.08 (m, 3H).

Procedure G: Preparation of di-tert-butyl 1-(6-methoxy-5-methylpyridin-3-yl)hydrazine-1,2-dicarboxylate

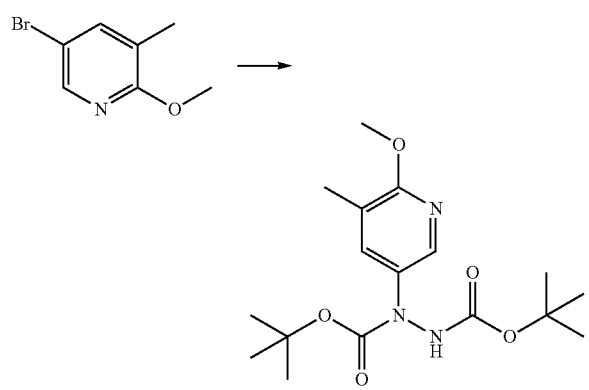

To a stirring solution of 5-bromo-2-methoxy-3-methylpyridine (606 mg, 3.00 mmol) in THF (8 mL) at −40° C. under nitrogen was added n-butyllithium (2 M in hexanes; 1.65 mL, 3.30 mmol) dropwise, ensuring that the dry ice bath remained between −50° C. and −40° C. After complete addition, the reaction mixture was stirred at this temperature for 10 min before dropwise addition of a solution of tert-butyl (NE)-N-tert-butoxycarbonyliminocarbamate (760 mg, 3.30 mmol) in THF (8 mL), again, ensuring temperature was maintained between −50° C. and −40° C. Stirring was continued for 30 mins below −40° C., and then the reaction mixture was allowed to warm to rt. The reaction was quenched onto ice water and extracted with ethyl acetate (2×20 mL). The combined organic layers were washed with brine and dried over $Na_2SO_4$. The solvent was then removed in vacuo to afford crude product. The crude material was purified over silica gel, eluting with 10% ethyl acetate in hexane, followed by 20% ethyl acetate in hexane to afford di-tert-butyl 1-(6-methoxy-5-methylpyridin-3-yl)hydrazine-1,2-dicarboxylate (700 mg, 56%) as a yellow oil. $^1$H NMR (300 MHz, Chloroform-d) δ 8.00 (d, J=2.7 Hz, 1H), 7.51 (s, 1H), 6.94 (s, 1H), 3.93 (s, 3H), 2.16 (s, 3H), 1.48 (s, 18H).

Procedure H: Preparation of N,N-dimethyl-4-(3-oxobutyl)benzenesulfonamide

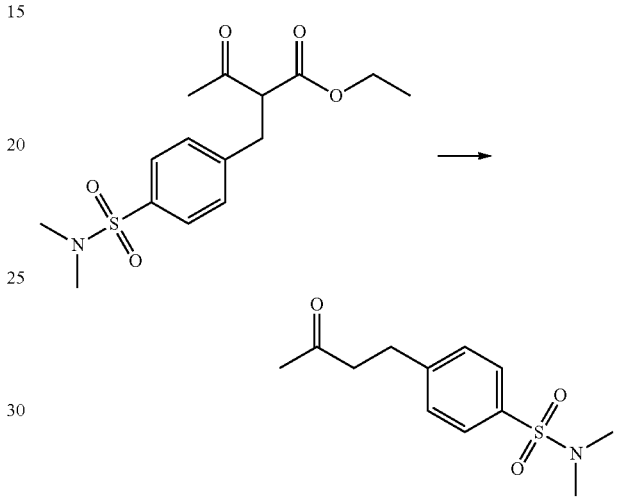

A stirring solution of ethyl 2-(4-(N,N-dimethylsulfamoyl)benzyl)-3-oxobutanoate (200 mg, 0.61 mmol) in DMSO (4 mL) and water (1 mL) was heated at reflux for 6 h. Tlc after this time indicated complete consumption of starting material. The reaction mixture was poured onto a mixture of brine (30 mL), water (10 mL) and ethyl acetate (30 mL). The organic layer was washed with further brine and dried over $MgSO_4$. The solvent was removed in vacuo to afford a crude oil. The crude material was purified using normal phase flash chromatography, eluting in 30%, then 40% ethyl acetate in n-hexane to afford the title compound N,N-dimethyl-4-(3-oxobutyl)benzenesulfonamide (89.0 mg, 57%) as a white solid. H NMR (300 MHz, $CDCl_3$) δ 7.71 (d, J=8.3 Hz, 2H), 7.37 (d, J=8.3 Hz, 2H), 3.00 (t, J=7.4 Hz, 2H), 2.82 (t, J=7.2 Hz, 2H), 2.72 (s, 61-1), 2.19 (s, 3H).

Procedure I: Preparation of 4-((5-methoxy-2,6-dimethyl-1H-pyrrolo[3,2-b]pyridin-3-yl)methyl)-N,N-dimethylbenzenesulfonamide

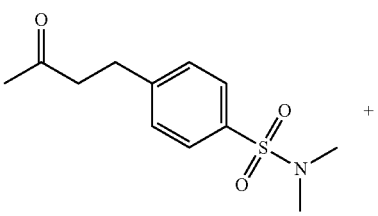

73

-continued

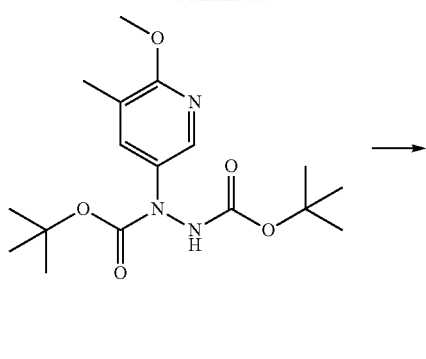

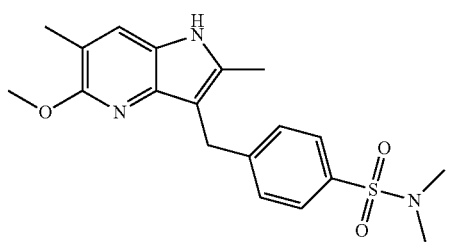

A suspension of di-tert-butyl 1-(6-methoxy-5-methylpyridin-3-yl)hydrazine-1,2-dicarboxylate (153 mg, 0.43 mmol) and N,N-dimethyl-4-(3-oxobutyl)benzenesulfonamide (85.0 mg, 0.33 mmol) in 4% sulfuric acid (2.00 mL) was heated at a gentle reflux for 3 h. The reaction mixture was cooled to rt. Saturated aqueous NaHCO$_3$ (15 mL) was added and the product was extracted with ethyl acetate (3×20 mL). The combined organics were dried over Na$_2$SO$_4$ and concentrated in vacuo. The crude was purified over silica gel eluting with 20% ethyl acetate in n-hexane to afford 4-((5-methoxy-2,6-dimethyl-1H-pyrrolo[3,2-b]pyridin-3-yl)methyl)-N,N-dimethylbenzenesulfonamide (56.0 mg, 41%) as a yellow foam. $^1$H NMR (300 MHz, CDCl$_3$) δ 7.65 (d, J=8.3 Hz, 2H), 7.56 (d, J=8.4 Hz, 2H), 7.29 (d, J=1.0 Hz, 1H), 4.16 (s, 2H), 4.01 (s, 3H), 2.68 (s, 6H), 2.38 (s, 3H), 2.27 (s, 3H).

Procedure J: Preparation of tert-butyl (Z)-(4-(3-(4-(N,N-dimethylsulfamoyl)benzyl)-5-methoxy-2,6-dimethyl-1H-pyrrolo[3,2-b]pyridin-1-yl)-3-fluorobut-2-en-1-yl)carbamate

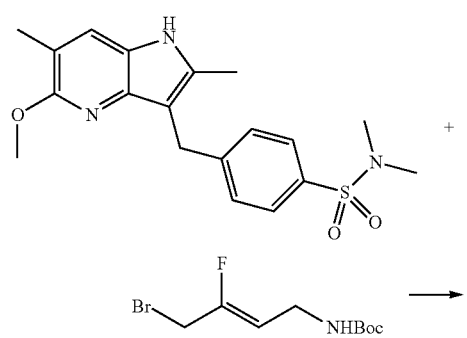

74

-continued

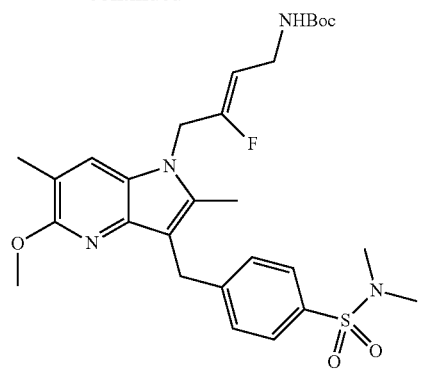

To a stirred solution of potassium hydroxide (15.8 mg, 0.22 mmol) in DMF (1.00 mL) at rt was added first 4-((5-methoxy-2,6-dimethyl-1H-pyrrolo[3,2-b]pyridin-3-yl)methyl)-N,N-dimethylbenzenesulfonamide (56.0 mg, 0.15 mmol) and then tert-butyl (Z)-(4-bromo-3-fluorobut-2-en-1-yl)carbamate (40.2 mg, 0.15 mmol). The reaction mixture was stirred at rt for 1 h. The reaction was quenched by adding water (20 mL). It was extracted with ethyl acetate (3×20 mL). The combined organic layer was washed with sat. aq. NH$_4$Cl (20 mL) and brine (20 mL). Then it was dried over Na$_2$SO$_4$ and concentrated in vacuo. The crude material was purified via Reveleris to afford tert-butyl (Z)-(4-(3-(4-(N,N-dimethylsulfamoyl)benzyl)-5-methoxy-2,6-dimethyl-1H-pyrrolo[3,2-b]pyridin-1-yl)-3-fluorobut-2-en-1-yl)carbamate (41 mg, 49%) as a yellow gum. $^1$H NMR (300 MHz, CDCl$_3$) δ 7.64 (d, J=8.3 Hz, 2H), 7.53 (d, J=8.4 Hz, 2H), 7.26 (d, J=1.0 Hz, 1H), 4.81-4.40 (m, 4H), 4.17 (s, 2H), 4.00 (s, 31-1), 3.76 (s, 2H), 2.68 (s, 6H), 2.35 (s, 3H), 2.29 (s, 3H), 1.42 (s, 9H).

Procedure K: Preparation of (Z)-4-((1-(4-amino-2-fluorobut-2-en-1-yl)-2,6-dimethyl-5-oxo-4,5-dihydro-1H-pyrrolo[3,2-b]pyridin-3-yl)methyl)-N,N-dimethylbenzenesulfonamide hydrochloride

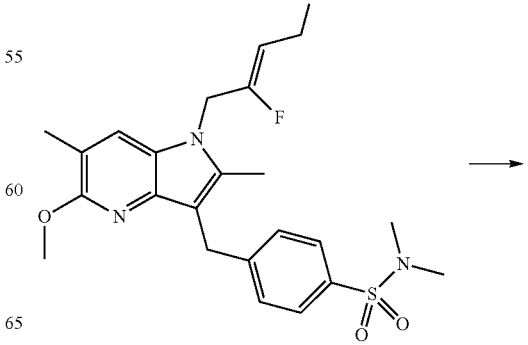

-continued

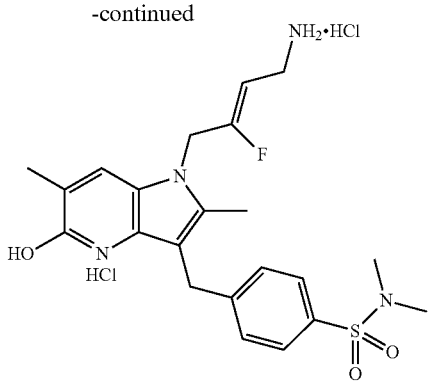

To a stirring solution of tert-butyl (Z)-(4-(3-(4-(N,N-dimethylsulfamoyl)benzyl)-5-methoxy-2,6-dimethyl-1H-pyrrolo[3,2-b]pyridin-1-yl)-3-fluorobut-2-en-1-yl)carbamate (41 mg, 0.07 mmol) in dichloromethane (2.00 mL) under nitrogen at 0° C. (ice bath) was added boron tribromide (219 uL, 0.22 mmol) dropwise. The resulting mixture was stirred at 0° C. for 10 min, and then it was warmed up to rt and stirred for a further 1 h. The reaction was quenched by adding of ice (2 g), and stirring was continued for 10 mins. Then it was diluted/basified with sat. aq. NaHCO₃ (20 mL) and stirred for 30 mins at rt. An off-white solid precipitated during this period. The solid was isolated via filtration, and dried to give crude product. The crude material was purified via reverse phase column to afford (Z)-4-((1-(4-amino-2-fluorobut-2-en-1-yl)-2,6-dimethyl-5-oxo-4,5-dihydro-1H-pyrrolo[3,2-b]pyridin-3-yl)methyl)-N,N-dimethylbenzenesulfonamide hydrochloride (32 mg, 73%) as a yellow gum.

(Z)-4-((1-(4-amino-2-fluorobut-2-en-1-yl)-5-hydroxy-2,6-dimethyl-1H-pyrrolo[3,2-b]pyridin-3-yl)methyl)-N,N-dimethylbenzenesulfonamide dihydrochloride (Compound 19)

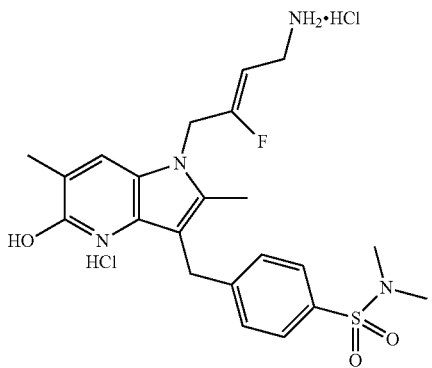

¹H NMR (300 MHz, Methanol-d₄) δ ppm: 8.31 (s, 1H), 7.71 (d, J=8.1 Hz, 2H), 7.40 (d, J=8.0 Hz, 2H), 5.19 (d, J=11.8 Hz, 2H), 5.14 (dt, J=35.1, 7.4 Hz, 1H), 4.29 (s, 2H), 3.65 (d, J=7.4 Hz, 2H), 2.67 (s, 6H), 2.46 (s, 3H), 2.43 (s, 3H).

Example 3

The following compounds were prepared according to procedures and E, L, M, N, O, P, J and Q.

Procedure L: Preparation of ethyl 3-(1-ethoxycarbonyl-2-oxo-propyl)-4-nitro-benzoate

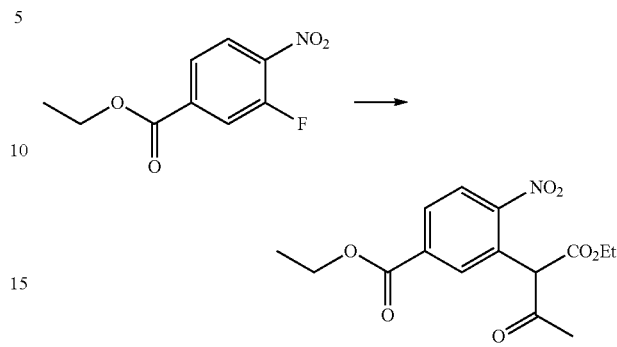

To a stirring mixture of ethyl 3-fluoro-4-nitro-benzoate (5.30 g, 24.9 mmol) and ethyl acetoacetate (3.80 mL, 29.9 mmol) in DMF (25 mL) at rt was added potassium carbonate (6.87 g, 49.8 mmol). The reaction mixture was stirred at rt overnight and then poured onto aq. HCl (1 M, 40 mL). The mixture was further diluted with water (200 mL) and extracted with EtOAc (100 mL×3). The combined organic layers were washed with saturated NH₄Cl solution (50 mL) and brine (50 mL), dried over Na₂SO₄ and concentrated in vacuo to afford ethyl 3-(1-ethoxycarbonyl-2-oxo-propyl)-4-nitro-benzoate (8.70 g, 97%) as a yellow oil. ¹H-NMR (300 MHz; CDCl₃) δ ppm: 1.13 (3H, t, J 6.9 Hz), 1.44 (3H, t, J 7.2 Hz), 1.90 (3H, s), 2.29 (1H, s), 4.17-4.31 (2H, m), 4.44 (2H, q, J 6.9 Hz), 7.99 (1H, d, J 1.8 Hz), 8.02 (1H, d, J 8.5 Hz), 8.12 (1H, d, J 8.5 Hz), 13.07 (1H, s).

Procedure M: Preparation of ethyl 3-acetonyl-4-nitro-benzoate

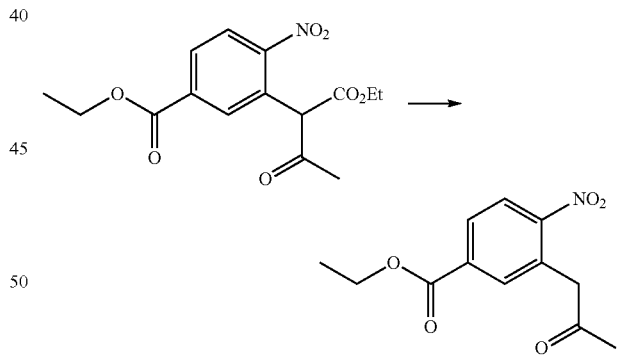

A stirring mixture of ethyl 3-(1-ethoxycarbonyl-2-oxo-propyl)-4-nitro-benzoate (8.70 g, 24.2 mmol) and water (7 mL) in DMSO (70 mL) was heated at 155° C. for 2 h. The mixture was then cooled to rt, diluted with water (250 mL) and extracted with EtOAc (200 mL×3). The combined organic layers were washed with brine (50 mL), dried over Na₂SO₄ and concentrated in vacuo. The crude residue thus obtained was purified over silica gel (100 g), eluting with 25%, then 40% ethyl acetate in n-hexane, to afford ethyl 3-acetonyl-4-nitro-benzoate (5.03 g, 83%) as a light yellow solid. ¹H-NMR (300 MHz; CDCl₃) δ ppm: 1.43 (3H, t, J 7.2 Hz), 2.35 (3H, s), 4.22 (2H, s), 4.45 (2H, q, J 7.2 Hz), 7.96 (1H, d, J 1.2 Hz), 8.10-8.18 (2H, m).

Procedure N: Preparation of methyl 3-(1-(4-(N,N-dimethylsulfamoyl)phenyl)-3-oxobutan-2-yl)-4-nitrobenzoate

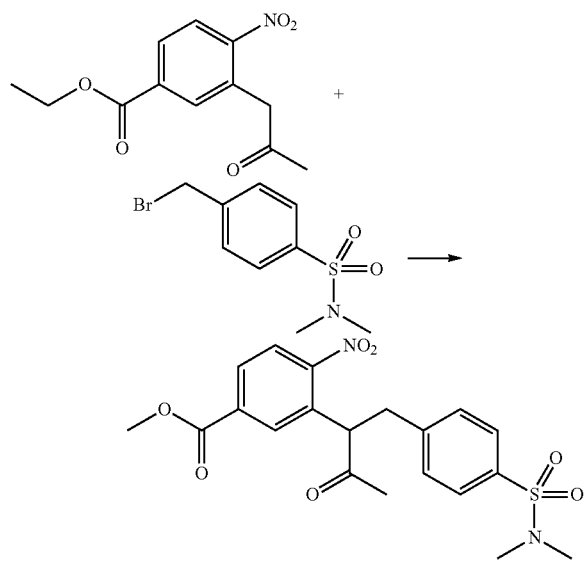

To a stirring solution of methyl 3-acetonyl-4-nitro-benzoate (300 mg, 1.26 mmol) in DMSO (3.5 mL) in a cold water bath, was added sodium methoxide (68 mg, 1.26 mmol) and the mixture allowed to stir for 5 mins. A solution of 4-(bromomethyl)-N,N-dimethylbenzenesulfonamide (422 mg, 1.52 mmol) in DMSO (1.5 mL) was then introduced and the reaction warmed to rt and stirred for 1.5 h. Saturated ammonium chloride solution (10 mL) was then added to quench the reaction and the organic layer extracted with ethyl acetate (10 mL×3). The combined organic layers were washed further with water (10 mL) and brine (10 mL), dried over $Na_2SO_4$ and concentrated in vacuo. The crude residue thus obtained was purified over silica gel (40 g), eluting over a gradient of 30-40% ethyl acetate in n-hexane, to afford methyl 3-(1-(4-(N,N-dimethylsulfamoyl)phenyl)-3-oxobutan-2-yl)-4-nitrobenzoate (197 mg, 31%) as a yellow solid. $^1$H-NMR (300 MHz; $CDCl_3$) δ ppm: 2.15 (3H, s), 2.70 (6H, s), 3.03 (1H, dd, J 13.7, 8.0 Hz), 3.54 (1H, dd, J 13.7, 6.8 Hz), 4.00 (3H, s), 4.59 (1H, dd, J 7.8, 7.0 Hz), 7.17 (2H, d, J 8.3 Hz), 7.62 (2H, d, J 8.3 Hz), 7.81 (1H, d, J 8.4 Hz), 8.06 (1H, d, J 1.6 Hz), 8.10 (1H, dd, J 8.4, 1.8 Hz).

Procedure O: Preparation of methyl 3-(4-(N,N-dimethylsulfamoyl)benzyl)-1-hydroxy-2-methyl-1H-indole-5-carboxylate

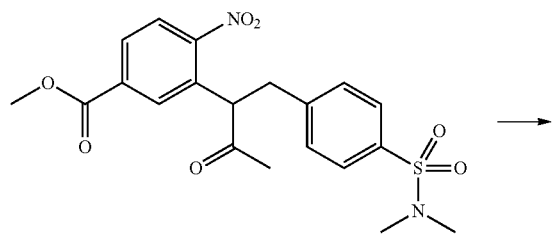

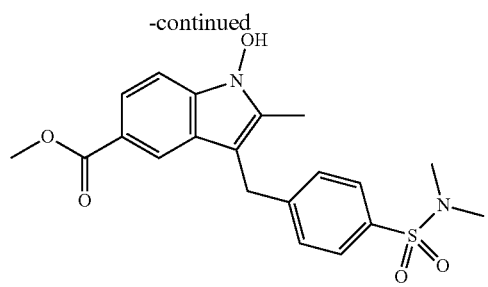

To a stirring solution of methyl 3-(1-(4-(N,N-dimethylsulfamoyl)phenyl)-3-oxobutan-2-yl)-4-nitrobenzoate (197 mg, 0.45 mmol) in THF (2 mL) and saturated ammonium chloride solution (2 mL) was added zinc powder (296 mg, 4.53 mmol) portion-wise. The reaction was then stirred at rt for 2 hours before addition of saturated aqueous sodium bicarbonate. The resulting suspension was stirred vigorously for 10 min, filtered and the filtrate extracted with ethyl acetate (20 mL×2). The combined organic layers were washed further with water (10 mL) and brine (10 mL), dried over $Na_2SO_4$ and concentrated in vacuo. The crude yellow oil thus obtained was used immediately in the preparation of methyl 3-(4-(N,N-dimethylsulfamoyl)benzyl)-2-methyl-1H-indole-5-carboxylate.

Procedure P: Preparation of methyl 3-(4-(N,N-dimethylsulfamoyl)benzyl)-2-methyl-1H-indole-5-carboxylate

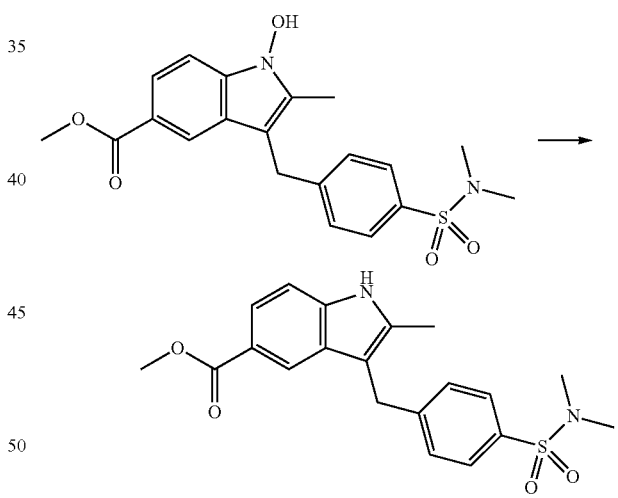

To a stirring solution of crude methyl 3-(4-(N,N-dimethylsulfamoyl)benzyl)-1-hydroxy-2-methyl-1H-indole-5-carboxylate (169 mg, 0.42 mmol) and triethylamine (135 uL, 0.97 mmol) in MeOH (2 mL) at rt was added 2-bromoacetophenone (84 mg, 0.42 mmol) in one portion. The resulting solution was stirred at rt for 3 h and then partitioned between water (10 mL) and ethyl acetate (10 mL). The organic layer was separated and the aqueous phase extracted with further ethyl acetate (10 mL×2). The combined organic layers were washed with water (10 mL) and brine (10 mL), dried over $Na_2SO_4$ and concentrated in vacuo. The material thus obtained was purified over silica gel (12 g), eluting with 40% ethyl acetate in n-hexane, to afford pure methyl 3-(4-(N,N-dimethylsulfamoyl)benzyl)-2-methyl-1H-indole-5- carboxylate (147 mg, 91%) as a yellow oil. $^1$H-NMR (300 MHz; CDCl$_3$) δ ppm: 2.42 (3H, s), 2.70 (6H, s), 3.91 (3H, s), 4.19 (2H, s), 7.33 (1H, d, J 8.8 Hz), 7.36 (2H, d, J 8.5 Hz), 7.67 (2H, d, J 8.4 Hz), 7.87 (1H, dd, J 8.5, 1.6 Hz), 8.06 (1H, br. s), 8.14 (1H, br. s).

Procedure Q: Preparation of methyl (Z)-1-(4-amino-2-fluorobut-2-en-1-yl)-3-(4-(N,N-dimethylsulfamoyl)benzyl)-2-methyl-1H-indole-5-carboxylate hydrochloride

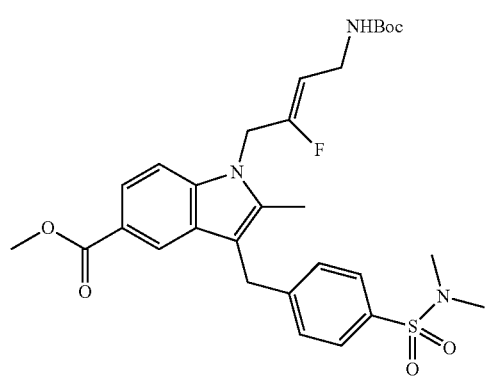

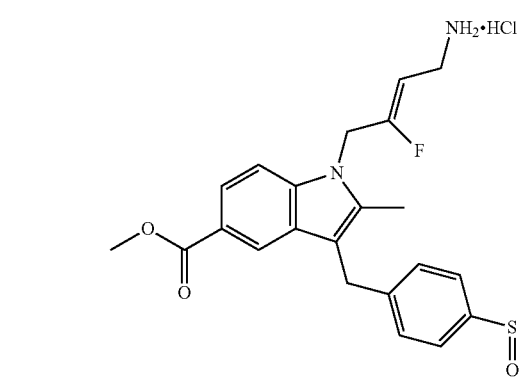

To a stirring solution of methyl (Z)-1-(4-((tert-butoxycarbonyl)amino)-2-fluorobut-2-en-1-yl)-3-(4-(N,N-dimethylsulfamoyl)benzyl)-2-methyl-1H-indole-5-carboxylate (20.0 mg, 0.03 mmol) in MeOH (500 uL) at rt was added HCl (2 M in diethyl ether; 2.00 mL, 4.00 mmol). The resulting mixture was stirred at rt for 1 h. The reaction mixture was then concentrated in vacuo. Ethyl acetate (5.00 mL) was added to the residue, resulting in the formation of a solid precipitate. The mixture was transferred to a vial en masse, and the vial was then spun-down in a centrifuge (4000 rpm, 4 min). The supernatant was decanted, and the solid "cake" was washed with further ethyl acetate (5.0 mL). After brief sonication, the vial was returned to the centrifuge and spun-down. Once again, the supernatant was decanted to leave a solid "cake". This process was repeated a total of 3 times. The solid "cake" was then dried under high vacuum to afford methyl (Z)-1-(4-amino-2-fluorobut-2-en-1-yl)-3-(4-(N,N-dimethylsulfamoyl)benzyl)-2-methyl-1H-indole-5-carboxylate hydrochloride (15 mg, 84%) was obtained as a pink solid.

Methyl (Z)-1-(4-amino-2-fluorobut-2-en-1-yl)-3-(4-(N,N-dimethylsulfamoyl)benzyl)-2-methyl-1H-indole-5-carboxylate hydrochloride (Compound 2)

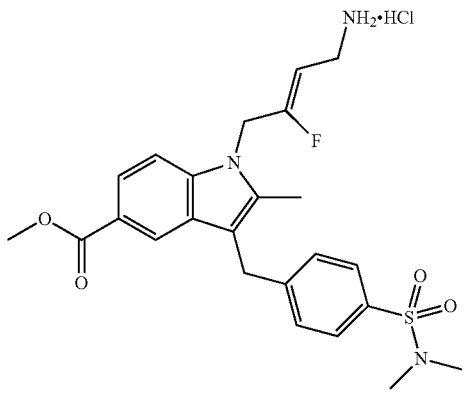

Pale pink solid; m.p 195-198° C.; $^1$H-NMR (300 MHz; Methanol-d$_4$) δ ppm: 2.49 (3H, s), 2.66 (6H, s), 3.61 (2H, br. d, J 7.4 Hz), 3.88 (3H, s), 4.27 (2H, s), 4.72-4.92 (1H, m), 5.10 (2H, d, J 8.9 Hz), 7.46 (3H, apparent d, J 8.6 Hz), 7.68 (2H, d, J 8.1 Hz), 7.84 (1H, d, J 8.8 Hz), 8.09 (1H, s).

(Z)-4-((1-(4-amino-2-fluorobut-2-en-1-yl)-2-methyl-1H-pyrrolo[3,2-b]pyridin-3-yl)methyl)-N,N-dimethylbenzenesulfonamide dihydrochloride (Compound 8)

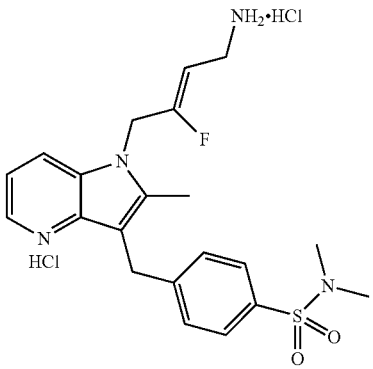

$^1$H NMR (300 MHz, DMSO-d$_6$) δ ppm: 8.70 (s, 1H), 8.59 (d, J=5.7 Hz, 1H), 8.17 (s, 3H), 7.71-7.59 (m, 3H), 7.53 (d, J=8.4 Hz, 2H), 5.40 (d, J=14.3 Hz, 2H), 5.27 (dt, J=36.2, 7.3 Hz, 1H), 4.48 (s, 2H), 3.53-3.40 (m, 2H), 2.59 (s, 6H), 2.57 (s, 2H).

81

(Z)-4-((1-(4-amino-2-fluorobut-2-en-1-yl)-2,5-dimethyl-1H-pyrrolo[3,2-b]pyridin-3-yl)methyl)-N,N-dimethylbenzenesulfonamide dihydrochloride (Compound 9)

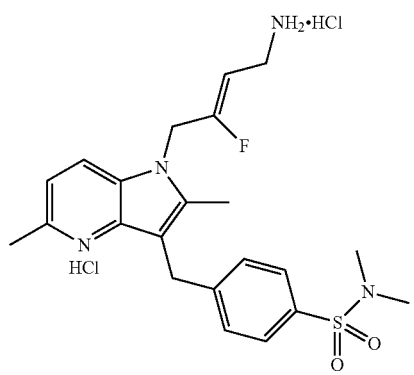

$^1$H NMR (300 MHz, Methanol-$d_4$) δ ppm: 8.59 (d, J=8.3 Hz, 1H), 7.72 (d, J=7.9 Hz, 2H), 7.52 (d, J=8.3 Hz, 1H), 7.43 (d, J=8.0 Hz, 2H), 5.35 (d, J=13.4 Hz, 2H), 4.47 (s, 2H), 5.33 (dt, J=35.3, 7.3 Hz, 1H), 3.66 (d, J=6.9 Hz, 2H), 2.85 (s, 3H), 2.67 (s, 6H), 2.57 (s, 3H).

(Z)-4-((1-(4-amino-2-fluorobut-2-en-1-yl)-2,6-dimethyl-1H-pyrrolo[3,2-b]pyridin-3-yl)methyl)-N,N-dimethylbenzenesulfonamide dihydrochloride (Compound 11)

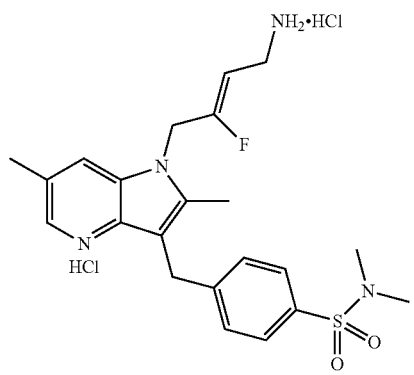

$^1$H NMR (300 MHz, Methanol-$d_4$) δ ppm: 8.61-8.58 (m, 1H), 8.40 (s, 1H), 7.73 (d, J=8.4 Hz, 2H), 7.43 (d, J=8.3 Hz, 2H), 5.34 (d, J=13.2 Hz, 2H), 5.25 (dt, J=35.2, 7.4 Hz, 1H), 4.41 (s, 2H), 3.66 (d, J=7.2 Hz, 2H), 2.67 (s, 6H), 2.66 (s, 3H), 2.61 (s, 3H).

Example 4

The following compound was prepared according to procedures and E, R, J and Q.

82

(Z)-4-((1-(4-amino-2-fluorobut-2-en-1-yl)-2-methyl-1H-indol-3-yl)methyl)-N,N-dimethylbenzene-sulfonamide hydrochloride (Compound 26)

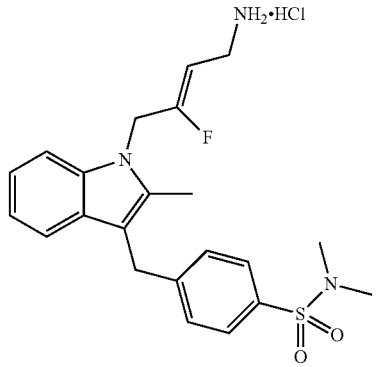

Procedure R: Preparation of N,N-dimethyl-4-((2-methyl-1H-indol-3-yl)methyl)benzenesulfonamide

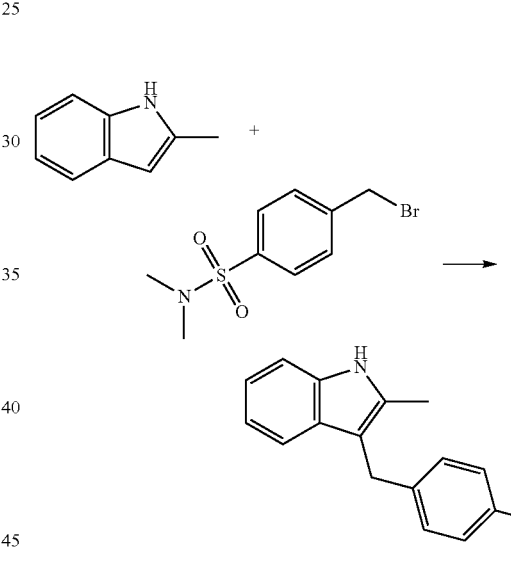

To a round bottom flask charged with 2-methyl-1H-indole (525 mg, 4.00 mmol) and 4-(bromomethyl)-N,N-dimethylbenzenesulfonamide (1.41 g, 4.80 mmol) was added DMF (6.00 mL). The dissolved mixture was then split equally into two microwave vials. Each vial was heated to 120° C. in a microwave reactor for 25 min at 20 W. After cooling, the two reaction mixtures were combined and poured onto water (25 mL). The mixture was stirred for 5 min during which time a brown gum formed. The crude material was extracted with ethyl acetate (50 mL). The organic layer was washed with brine, dried over MgSO$_4$ and then concentrated in vacuo to give a brown tar. Methanol (10 mL) was added and the mixture was stirred for 45 min at rt affording a light brown precipitate. The solid was isolated by filtration, and dried to give N,N-dimethyl-4-((2-methyl-1H-indol-3-yl)methyl)benzenesulfonamide (543 mg, 37%) as a grey/brown solid.

$^1$H NMR (300 MHz, CDCl$_3$) δ 7.92 (s, 1H), 7.66 (d, J=8.4 Hz, 2H), 7.41-7.30 (m, 4H), 7.21-6.98 (m, 2H), 4.15 (s, 2H), 2.69 (s, 6H), 2.42 (s, 3H).

(Z)-4-((1-(4-amino-2-fluorobut-2-en-1-yl)-2-methyl-1H-indol-3-yl)methyl)-N,N-dimethylbenzene-sulfonamide hydrochloride (Compound 26)

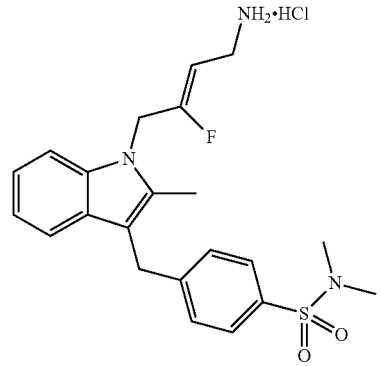

$^1$H NMR (300 MHz, Methanol-$d_4$) δ ppm: 7.66 (d, J=8.3 Hz, 2H), 7.45 (d, J=8.4 Hz, 2H), 7.39 (d, J=3.0 Hz, 1H), 7.36 (d, J=3.0 Hz, 1H), 7.14 (ddd, J=8.2, 7.1, 1.2 Hz, 1H), 7.02 (ddd, J=8.0, 7.1, 1.0 Hz, 1H), 5.03 (dd, J=7.8, 1.3 Hz, 2H), 4.70 (dt, J=34.1, 7.5 Hz, 1H), 4.22 (s, 2H), 3.63-3.56 (m, 2H), 2.65 (s, 6H), 2.46 (s, 3H).

Example 5

The following compound was prepared according to procedures E, L, M, N, P, Q, J, S, and T.

(Z)-1-(4-amino-2-fluorobut-2-en-1-yl)-3-(4-(N,N-dimethylsulfamoyl)benzyl)-2-methyl-1H-indole-5-carboxylic acid hydrochloride (Compound 1)

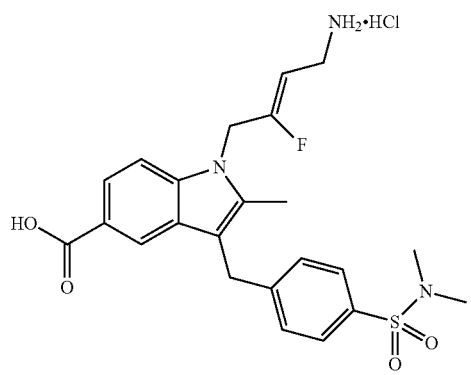

Procedure S: Preparation of ((Z)-1-(4-((tert-butoxycarbonyl)amino)-2-fluorobut-2-en-1-yl)-3-(4-(N,N-dimethylsulfamoyl)benzyl)-2-methyl-1H-indole-5-carboxylic acid

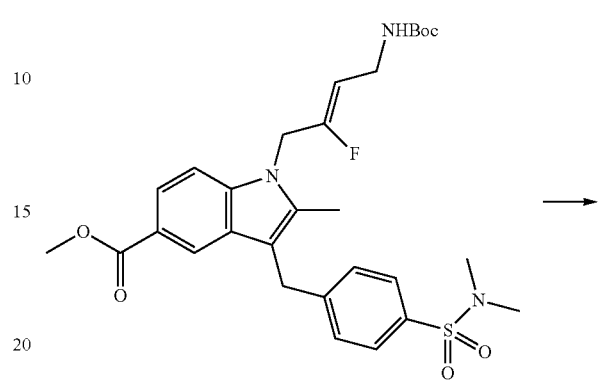

Into a 50 mL round bottom, methyl (Z)-1-(4-((tert-butoxycarbonyl)amino)-2-fluorobut-2-en-1-yl)-3-(4-(N,N-dimethylsulfamoyl)benzyl)-2-methyl-1H-indole-5-carboxylate (20.0 mg, 0.034 mmol) was added, followed by methanol (2.0 mL), THF (2.0 mL) and 10% aqueous KOH (2.0 mL). The mixture was stirred at rt overnight. Tlc after this time indicated only 30% conversion. The reaction mixture was then heated to 60° C. and stirring was continued for a further 6 h. The reaction mixture was concentrated in vacuo, and to the residue was added water (5 mL). It was then acidified by adding 2 M HCl until pH=5. The product was extracted with ethyl acetate (3×15 mL). The combined organics were dried over $Na_2SO_4$ and concentrated in vacuo to afford (Z)-1-(4-((tert-butoxycarbonyl)amino)-2-fluorobut-2-en-1-yl)-3-(4-(N,N-dimethylsulfamoyl)benzyl)-2-methyl-1H-indole-5-carboxylic acid (19 mg, 97%) as a yellow solid. The crude material was progressed to the next step without purification. $^1$H NMR (300 MHz, Chloroform-d) δ 8.16 (d, J=1.6 Hz, 1H), 7.94 (dd, J=8.6, 1.6 Hz, 114), 7.68 (d, J=8.3 Hz, 2H), 7.40-7.29 (m, 3H), 4.97-4.39 (m, 4H), 4.21 (s, 2H), 3.80 (s, 2H), 2.70 (s, 6H), 2.41 (s, 3H), 1.43 (s, 9H).

Procedure T: Preparation of (Z)-1-(4-amino-2-fluorobut-2-en-1-yl)-3-(4-(N,N-dimethylsulfamoyl)benzyl)-2-methyl-1H-indole-5-carboxylic acid hydrochloride (Compound 1)

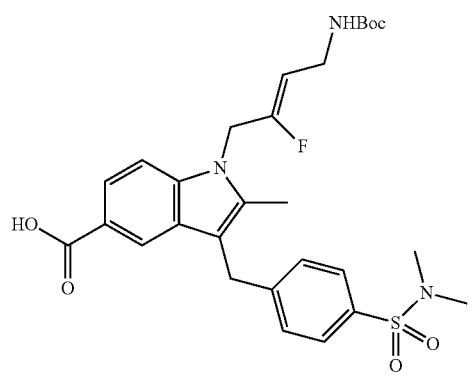

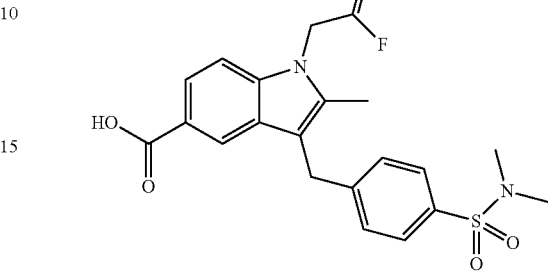

To a stirring solution of (Z)-1-(4-((tert-butoxycarbonyl)amino)-2-fluorobut-2-en-1-yl)-3-(4-(N,N-dimethylsulfamoyl)benzyl)-2-methyl-1H-indole-5-carboxylic acid (19.0 mg, 0.03 mmol) in dichloromethane (1.0 mL) was added HCl (2 M in diethylether; 2.00 mL, 4.00 mmol). The resulting mixture was stirred at rt for 5 hour. The reaction mixture was then concentrated in vacuo to give a pink solid. The solid was washed with ethyl acetate (2×5 mL) and dried under high vacuum to afford (Z)-1-(4-amino-2-fluorobut-2-en-1-yl)-3-(4-(N,N-dimethylsulfamoyl)benzyl)-2-methyl-1H-indole-5-carboxylic acid hydrochloride (14.0 mg, 83%) as a pink solid.

(Z)-1-(4-amino-2-fluorobut-2-en-1-yl)-3-(4-(N,N-dimethylsulfamoyl)benzyl)-2-methyl-1H-indole-5-carboxylic acid hydrochloride (Compound 1)

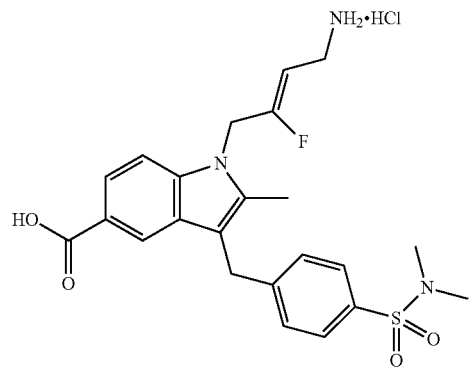

$^1$H NMR (300 MHz, Methanol-$d_4$) δ ppm: 8.09 (d, J=1.6 Hz, 1H), 7.85 (dd, J=8.6, 1.6 Hz, 1H), 7.68 (d, J=8.4 Hz, 1H), 7.51-7.43 (m, 3H), 5.08 (s, 1H), 4.80 (dt, J=35.2, 7.5 Hz, 1H), 4.27 (s, 2H), 3.61 (d, J=7.4 Hz, 2H), 2.65 (s, 6H), 2.50 (s, 3H).

Example 6

The following compounds were prepared according to procedures E, L, M, N, O, P, J, S, U and Q.

Procedure U: Preparation of tert-butyl (Z)-(4-(5-(dimethylcarbamoyl)-3-(4-(N,N-dimethylsulfamoyl)benzyl)-2-methyl-1H-indol-1-yl)-3-fluorobut-2-en-1-yl)carbamate

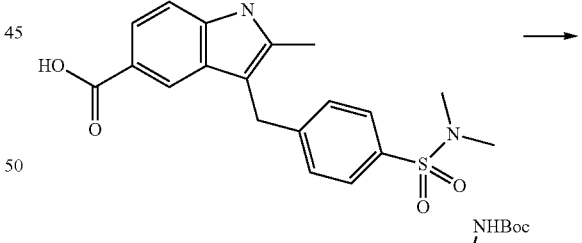

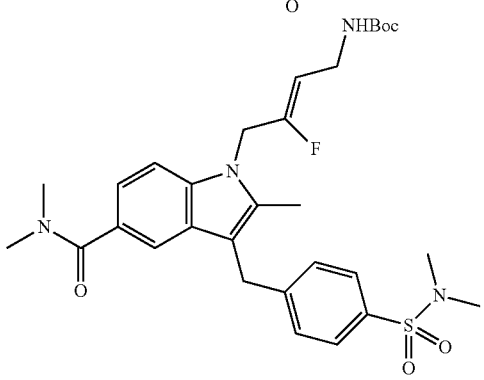

To a stirred mixture of N,N-dimethylamine hydrochloride (8.74 mg, 0.11 mmol) in DMF (1.00 mL) at rt, was added triethylamine (50 uL, 0.36 mmol). After stirring for 10 min, (Z)-1-(4-((tert-butoxycarbonyl)amino)-2-fluorobut-2-en-1-yl)-3-(4-(N,N-dimethylsulfamoyl)benzyl)-2-methyl-1H-indole-5-carboxylic acid (40 mg, 0.072 mmol) was added, followed by HATU (33 mg, 0.09 mmol). The resulting mixture was stirred at rt for 2 h. Water (15 mL) was added and the product was extracted with ethyl acetate (3×20 mL). The combined organic layers were washed sequentially with aq. HCl (1 M, 15 mL), saturated aq. NH$_4$Cl (15 mL) and brine (15 mL). After drying over Na$_2$SO$_4$, the organics were concentrated in vacuo. The crude material was purified over silica gel, eluting with 66% ethyl acetate in hexane, followed by 100% ethyl acetate to afford tert-butyl (Z)-(4-(5-(dimethylcarbamoyl)-3-(4-(N,N-dimethylsulfamoyl)benzyl)-2-methyl-1H-indol-1-yl)-3-fluorobut-2-en-1-yl)carbamate (40.0 mg, 0.07 mmol, 95%) as a yellow oil. $^1$H NMR (300 MHz, CDCl$_3$) δ 7.65 (d, J=8.3 Hz, 2H), 7.46 (s, 1H), 7.33 (d, J=8.1 Hz, 2H), 7.26 (d, J=1.2 Hz, 2H), 4.97-4.45 (m, 4H), 4.16 (s, 2H), 3.79 (s, 2H), 3.04 (s, 6H), 2.69 (s, 6H), 2.40 (s, 3H), 1.42 (s, 9H).

(Z)-1-(4-amino-2-fluorobut-2-en-1-yl)-3-(4-(N,N-dimethylsulfamoyl)benzyl)-N,N,2-trimethyl-1H-indole-5-carboxamide hydrochloride (Compound 3)

Pale pink solid; m.p 130-133° C.; $^1$H-NMR (300 MHz; Methanol-d$_4$) δ ppm: 2.50 (3H, s), 2.65 (6H, s), 2.98 (3H, br. s), 3.09 (3H, br. s), 3.61 (2H, br. d, J 7.1 Hz), 4.24 (2H, s), 4.82 (1H, dt, J 33.8, 7.5 Hz), 5.08 (2H, d, J 9.1 Hz), 7.23 (1H, dd, J 8.3, 1.3 Hz), 7.46 (4H, apparent d, J 8.4 Hz), 7.66 (2H, d, J 8.3 Hz).

(Z)-1-(4-amino-2-fluorobut-2-en-1-yl)-3-(4-(N,N-dimethylsulfamoyl)benzyl)-2-methyl-1H-indole-5-carboxamide hydrochloride (Compound 4)

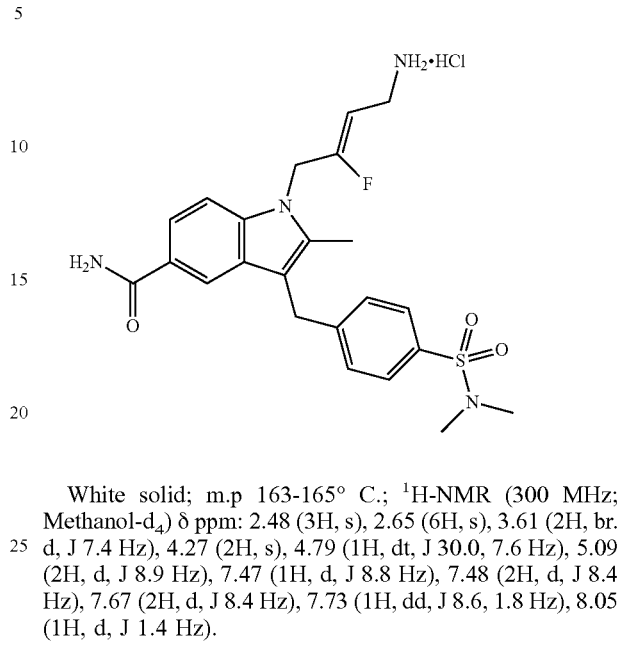

White solid; m.p 163-165° C.; $^1$H-NMR (300 MHz; Methanol-d$_4$) δ ppm: 2.48 (3H, s), 2.65 (6H, s), 3.61 (2H, br. d, J 7.4 Hz), 4.27 (2H, s), 4.79 (1H, dt, J 30.0, 7.6 Hz), 5.09 (2H, d, J 8.9 Hz), 7.47 (1H, d, J 8.8 Hz), 7.48 (2H, d, J 8.4 Hz), 7.67 (2H, d, J 8.4 Hz), 7.73 (1H, dd, J 8.6, 1.8 Hz), 8.05 (1H, d, J 1.4 Hz).

Example 7

The following compounds were prepared according to procedures V, W, L, M, N, O, P, J, and Q.

Procedure V: Preparation of (4-(methylsulfonyl)phenyl)methanol

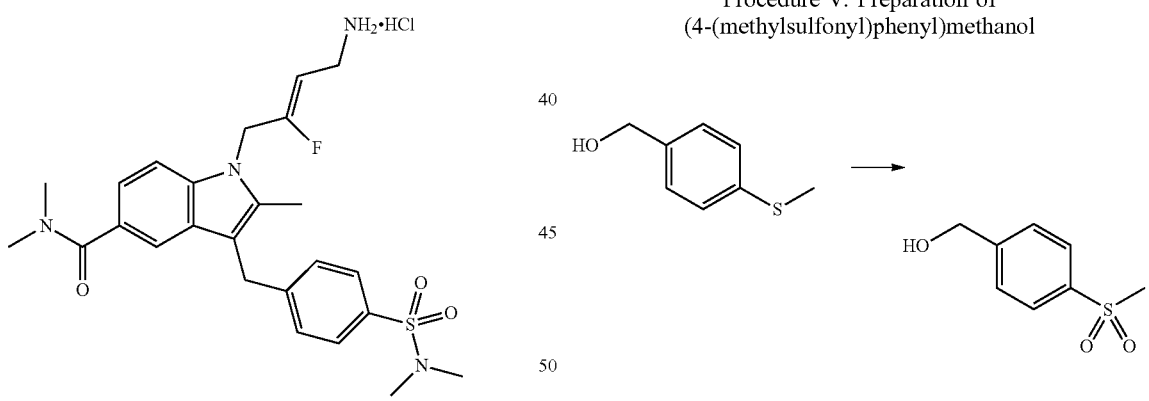

To a stirred solution of (4-(methylthio)phenyl)methanol (5.00 g, 32.4 mmol) in dichloromethane at 0° C. was added 3-chlorobenzenecarboperoxoic acid (23.6 g, 105 mmol) portion-wise. The resulting mixture was stirred at rt for 2 h. The reaction mixture was poured into 10% aq. K$_2$CO$_3$ (300 mL) and stirring was continued at rt for 10 mins. The aqueous layer was extracted with dichloromethane (100 mL×3), ethyl acetate (100 mL×3). The combined organics were washed with 10% aq. Na$_2$S$_2$O$_5$ (100 mL) and brine (100 mL), dried over Na$_2$SO$_4$ and concentrated in vacuo. The crude material was purified over silica gel eluting with 50% ethyl acetate followed by 50% ethyl acetate/5% MeOH in hexane to afford (4-(methylsulfonyl)phenyl)methanol (2.00 g, 33%) as a white solid. $^1$H NMR (300 MHz, CDCl$_3$) δ ppm: 7.95 (d, J=8.4 Hz, 2H), 7.59 (dd, J=7.9, 0.8 Hz, 1H), 4.85 (s, 2H), 3.07 (s, 3H).

Procedure W: Preparation of 1-(bromomethyl)-4-(methylsulfonyl)benzene

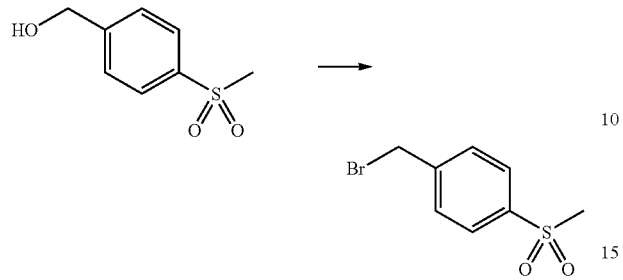

To a stirring solution of (4-(methylsulfonyl)phenyl)methanol (2.00 g, 10.7 mmol) and triethylamine (2.24 mL, 16.1 mmol) in acetone (25 mL) at 0° C. was added methanesulfonyl chloride (1.00 mL, 12.9 mmol) drop-wise. The resulting mixture was stirred at this temperature for 30 mins. The reaction mixture was filtered, and to the filtrate was added lithium bromide (4.66 g, 53.7 mmol) at 0° C., in three portions. The resulting mixture was stirred at this temperature for 5 mins and then warmed up to rt for 1.5 h. The reaction mixture was filtered, and filtrate was concentrated in vacuo. After diluting with water (50 mL), the product was extracted with dichloromethane (50 mL×3). The combined organics were dried over $Na_2SO_4$, and concentrate in vacuo to afford 1-(bromomethyl)-4-(methylsulfonyl)benzene (2.80 g, 100%) as a white solid. $^1$H NMR (300 MHz, $CDCl_3$) δ ppm: 7.95 (d, J=8.4 Hz, 2H), 7.61 (d, J=8.4 Hz, 2H), 4.53 (s, 2H), 3.08 (s, 3H).

(Z)-3-fluoro-4-(2-methyl-3-(4-(methylsulfonyl)benzyl)-1H-pyrrolo[3,2-b]pyridin-1-yl)but-2-en-1-amine dihydrochloride (Compound 10)

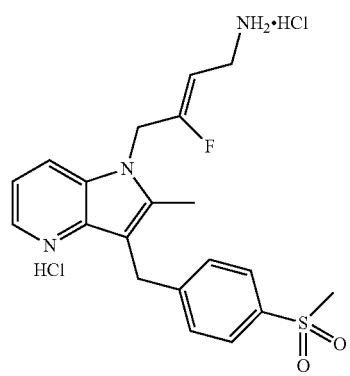

$^1$H NMR (300 MHz, Methanol-$d_4$) δ ppm: 8.75 (d, J=7.6 Hz, 1H), 8.52 (d, J=5.1 Hz, 1H), 7.89 (d, J=7.3 Hz, 2H), 7.71 (s, 1H), 7.48 (d, J=7.5 Hz, 2H), 5.40 (d, J=13.1 Hz, 2H), 4.47 (s, 2H), 5.28 (m, 1H), 3.65 (dd, J=6.7, 4.3 Hz, 2H), 3.10 (s, 3H), 2.64 (s, 3H).

(Z)-4-(2,5-dimethyl-3-(4-(methylsulfonyl)benzyl)-1H-pyrrolo[3,2-b]pyridin-1-yl)-3-fluorobut-2-en-1-amine dihydrochloride (Compound 12)

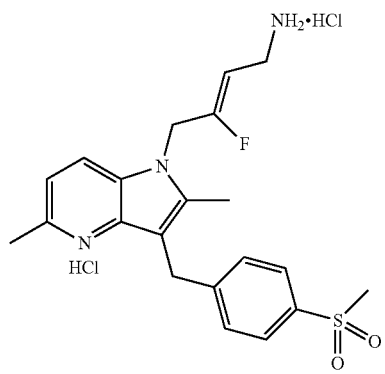

$^1$H NMR (300 MHz, Methanol-$d_4$) δ ppm: 8.59 (d, J=8.4 Hz, 1H), 7.89 (d, J=8.0 Hz, 2H), 7.52 (d, J=8.3 Hz, 1H), 7.45 (d, J=8.0 Hz, 2H), 5.34 (d, J=13.7 Hz, 2H), 5.32 (dt, J=35.1, 7.3 Hz, 1H), 4.47 (s, 2H), 3.70-3.61 (m, 2H), 3.11 (s, 3H), 2.85 (s, 3H), 2.57 (s, 3H).

(Z)-3-fluoro-4-(2-isopropyl-3-(4-(methylsulfonyl)benzyl)-1H-pyrrolo[3,2-b]pyridin-1-yl)but-2-en-1-amine dihydrochloride (Compound 33)

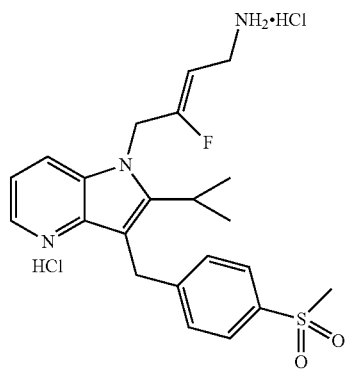

$^1$H NMR (300 MHz, Methanol-$d_4$) δ ppm: 8.77 (d, J=7.1 Hz, 1H), 8.50 (s, 1H), 7.90 (d, J=6.6 Hz, 2H), 7.73 (s, 1H), 7.39 (d, J=7.1 Hz, 2H), 5.49 (d, J=11.3 Hz, 2H), 5.33 (d, J=34.6 Hz, 1H), 4.60 (s, 2H), 3.74-3.53 (m, 3H), 3.11 (s, 3H), 1.40 (d, J=6.2 Hz, 6H).

Example 8

The following compound was prepared according to procedures X, Y, W, L, M, N, O, P, J, and Q.

(Z)-4-(2,5-dimethyl-3-(3-(methylsulfonyl)benzyl)-1H-pyrrolo[3,2-b]pyridin-1-yl)-3-fluorobut-2-en-1-amine dihydrochloride (Compound 17)

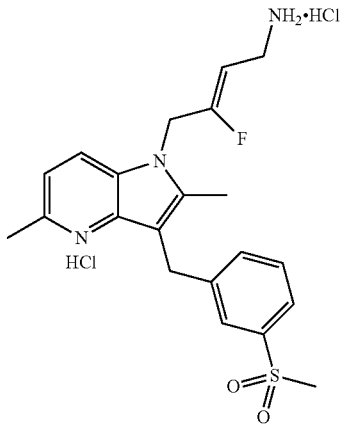

Procedure X: Preparation of methyl 3-(methylsulfonyl)benzoate

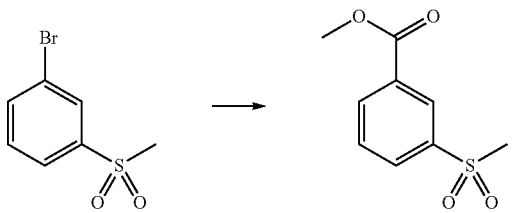

A stirring solution of 1-bromo-3-(methylsulfonyl)benzene (1.00 g, 4.25 mmol) and triethylamine (1.19 mL, 8.51 mmol) in methanol (4 mL) and DMF (8 mL) was degassed by passing through it a stream of $N_2$ gas for 5 mins. Diacetoxypalladium (95.5 mg, 0.43 mmol) and diphenylphosphanylpropyl-(diphenyl)phosphane (175 mg, 0.43 mmol) were then added. Carbon monoxide gas was bubbled through the resulting mixture for 5 mins and the mixture was then heated at 90° C. under a CO atmosphere overnight. After cooling to rt, the reaction mixture was partitioned between ethyl acetate (30 mL) and water (80 mL). The aqueous phase was extracted with further ethyl acetate (30 mL×2). The combined organics were washed with sat aq. $NH_4Cl$, brine, dried over $Na_2SO_4$ and concentrated in vacuo. The crude material was purified over silica gel eluting with 25% ethyl acetate in hexane to afford methyl 3-(methylsulfonyl)benzoate (950 mg, 100%) as a pale yellow solid. $^1$H NMR (300 MHz, $CDCl_3$) δ ppm: 8.63 (dd, J=1.8 Hz, 1H), 8.35 (dt, J=7.8, 1.4 Hz, 1H), 8.17 (ddd, J=7.8, 1.9, 1.2 Hz, 1H), 4.00 (s, 3H), 3.11 (s, 3H).

Procedure Y: Preparation of (3-(methylsulfonyl)phenyl)methanol

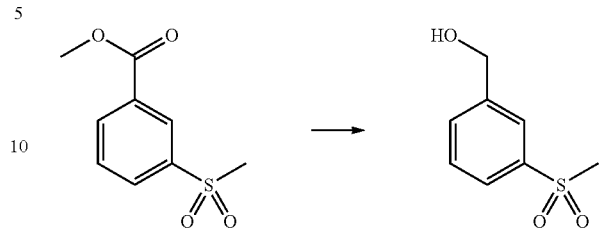

To a stirring solution of methyl 3-(methylsulfonyl)benzoate (950 mg, 4.43 mmol) in ethanol (20 mL) and THF (10 mL) at −10° C. was added calcium chloride (492 mg, 4.43 mmol), followed by sodium borohydride (336 mg, 8.87 mmol). The resulting mixture was then stirred at rt for 30 mins. Tlc after this time showed very low conversion. A further amount of $NaBH_4$ (336 mg, 8.87 mmol) was added and the mixture was stirred at rt for further 1 hour. The reaction mixture was poured into sat. aq. $NaHCO_3$ (30 mL). The product was extracted with ethyl acetate (50 mL×5) and the combined organics was dried over $Na_2SO_4$ and concentrated in vacuo to afford (3-(methylsulfonyl)phenyl)methanol (800 mg, 82%) as a light yellow oil. $^1$H NMR (300 MHz, $CDCl_3$) δ ppm: 7.98 (s, 1H), 7.88 (dt, J=7.6, 1.6 Hz, 1H), 7.68 (d, J=8.1 Hz, 1H), 7.59 (dd, J=7.7 Hz, 1H), 4.83 (s, 2H), 3.08 (s, 3H).

(Z)-3-((1-(4-amino-2-fluorobut-2-en-1-yl)-2,5-dimethyl-1H-pyrrolo[3,2-b]pyridin-3-yl)methyl)-N,N-dimethylbenzenesulfonamide dihydrochloride (Compound 17)

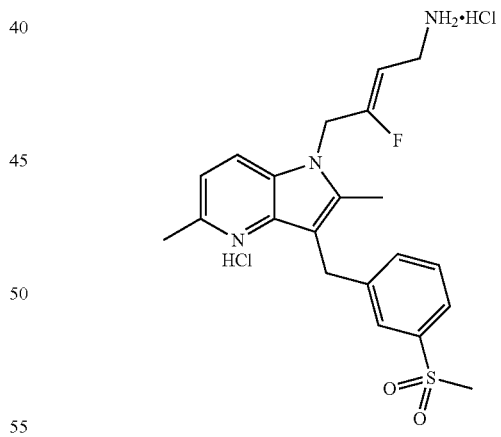

$^1$H NMR (300 MHz, Methanol-$d_4$) δ ppm: 8.59 (d, J=8.4 Hz, 1H), 7.87-7.81 (m, 1H), 7.68 (s, 1H), 7.65-7.57 (m, 2H), 7.52 (d, J=8.5 Hz, 1H), 5.35 (d, J=12.4 Hz, 2H), 5.21 (dt, J=34.2, 7.4 Hz, 1H), 4.48 (s, 2H), 3.66 (d, J=7.3 Hz, 2H), 3.11 (s, 3H), 2.85 (s, 3H), 2.57 (s, 3H).

Example 9

The following compound was prepared according to procedures Y, W, L, M, N, O, P, J, and Q.

(Z)-5-((1-(4-amino-2-fluorobut-2-en-1-yl)-2,5-dimethyl-1H-pyrrolo[3,2-b]pyridin-3-yl)methyl)-N,N-dimethylpyridine-2-sulfonamide trihydrochloride (Compound 16)

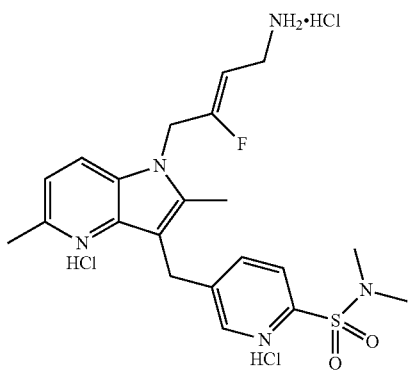

$^1$H NMR (300 MHz, Methanol-d$_4$) δ ppm: 8.59, (d, J=8.1 Hz, 1H), 8.58 (s, 1H), 7.88 (d, J=8.0 Hz, 1H), 7.82 (dd, J=8.2, 2.1 Hz, 1H), 7.53 (d, J=8.4 Hz, 1H), 5.35 (d, J=13.8 Hz, 2H), 5.32 (dt, J=34.5, 7.3 Hz, 1H), 4.48 (s, 2H), 3.66 (d, J=7.5 Hz, 2H), 2.87 (s, 6H), 2.85 (s, 3H), 2.60 (s, 3H).

Example 10

The following compound was prepared according to procedures Z, Y, W, L, M, N, O, P, J, and Q.

(Z)-4-(2,5-dimethyl-3-((5-(methylsulfonyl)pyridin-2-yl)methyl)-1H-pyrrolo[3,2-b]pyridin-1-yl)-3-fluorobut-2-en-1-amine trihydrochloride (Compound 14)

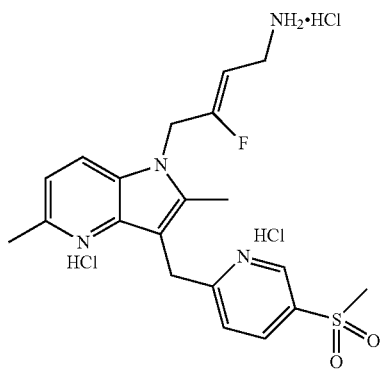

Procedure Z: Preparation of methyl 5-(N,N-dimethylsulfamoyl)picolinate

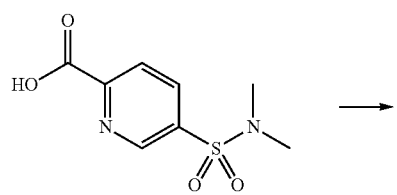

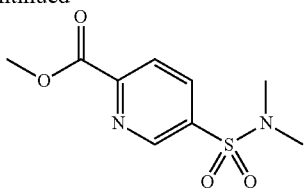

To a stirring solution of 5-(N,N-dimethylsulfamoyl)picolinic acid (230 mg, 1.00 mmol) in dichloromethane (10 mL) and methanol (5 mL) at 0° C. was added diazomethyl(trimethyl)-silane (0.75 mL, 1.50 mmol) drop-wise. The resulting mixture was stirred at this temperature for 30 min. The reaction mixture was concentrated in vacuo to give methyl 5-(N,N-dimethylsulfamoyl)picolinate (235 mg, 96%) as a pink solid. $^1$H NMR (300 MHz, CDCl$_3$) δ ppm: 9.11 (s, 1H), 8.39-8.14 (m, 2H), 7.71 (dd, J=7.7, 7.7 Hz, 1H), 4.08 (s, 3H), 2.80 (s, 6H).

(Z)-4-(2,5-dimethyl-3-((5-(methylsulfonyl)pyridin-2-yl)methyl)-1H-pyrrolo[3,2-b]pyridin-1-yl)-3-fluorobut-2-en-1-amine trihydrochloride (Compound 14)

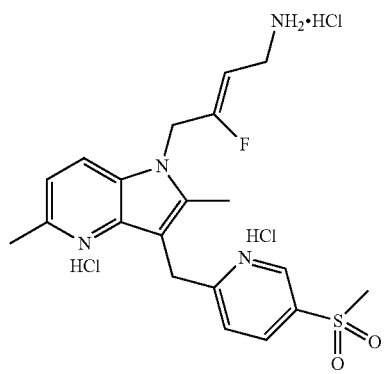

$^1$H NMR (300 MHz, Methanol-d$_4$) δ ppm: 8.98 (dd, J=2.4, 0.8 Hz, 1H), 8.55 (d, J=8.4 Hz, 1H), 8.32 (dd, J=8.2, 2.4 Hz, 1H), 7.67 (d, J=8.2 Hz, 1H), 7.52 (d, J=8.5 Hz, 1H), 5.32 (d, J=13.5 Hz, 2H), 5.28 (dt, J=35.4, 7.4 Hz, 1H), 4.60 (s, 2H), 3.64 (d, J=7.3 Hz, 2H), 3.20 (s, 3H), 2.87 (s, 3H), 2.62 (s, 3H).

Example 11

The following compounds were prepared according to procedures AA, Y, W, L, M, N, O, P, J, and Q.

Procedure AA: Preparation of methyl 6-(methylsulfonyl)nicotinate

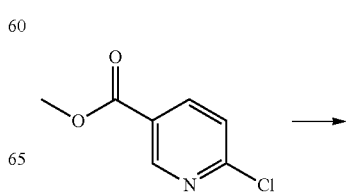

-continued

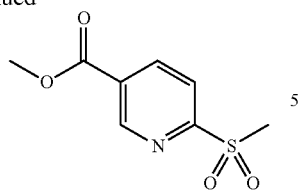

To a stirring solution of methyl 6-chloronicotinate (2.00 g, 11.7 mmol) in DMSO (10 mL), was added sodium methanesulfinate (1.78 g, 17.5 mmol) at rt in one lot. The resulting mixture was heated to 100° C. for 1 h. The reaction mixture was cooled to rt, and then dilute with water (100 mL). The product was then extracted with ethyl acetate (30 mL×3) and the combined organics were washed with water (20 mL) and brine (20 mL). After drying over $Na_2SO_4$, the solvent was removed in vacuo to afford methyl 6-(methylsulfonyl)nicotinate (2.20 g, 88%) as an off-white solid. $^1$H NMR (300 MHz, $CDCl_3$) δ ppm: 9.31 (dd, J=2.1, 0.9 Hz, 1H), 8.59 (dd, J=8.1, 2.0 Hz, 1H), 8.20 (dd, J=8.1, 0.9 Hz, 1H), 4.04 (s, 3H), 3.30 (s, 3H).

(Z)-4-(2,5-dimethyl-3-((6-(methylsulfonyl)pyridin-3-yl)methyl)-1H-pyrrolo[3,2-b]pyridin-1-yl)-3-fluorobut-2-en-1-amine trihydrochloride (Compound 13)

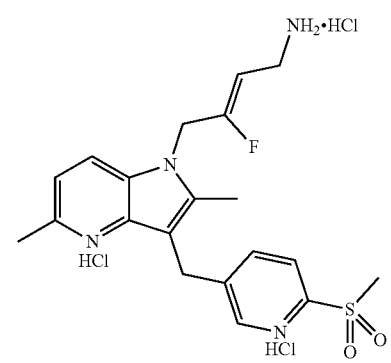

$^1$H NMR (300 MHz, Methanol-$d_4$) δ ppm: 8.63 (d, J=2.6 Hz, 1H), 8.60 (d, J=8.5 Hz, 1H), 8.06-7.98 (m, 1H), 7.87 (dd, J=8.1, 2.2 Hz, 1H), 7.53 (d, J=8.4 Hz, 1H), 5.35 (d, J=13.6 Hz, 2H), 5.31 (dt, J=35.2, 7.4 Hz, 1H), 4.51 (s, 2H), 3.66 (d, J=7.3 Hz, 2H), 3.22 (s, 3H), 2.85 (s, 3H), 2.60 (s, 3H).

(Z)-4-((1-(4-amino-2-fluorobut-2-en-1-yl)-5-fluoro-2-methyl-1H-pyrrolo[3,2-b]pyridin-3-yl)methyl)-N,N-dimethylbenzenesulfonamide trihydrochloride (Compound 22)

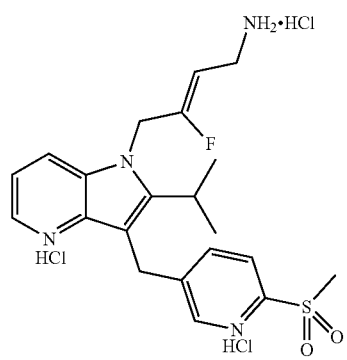

$^1$H NMR (300 MHz, Methanol-$d_4$) δ ppm: 8.74 (d, J=8.2 Hz, 1H), 8.59 (s, 1H), 8.52 (d, J=5.8 Hz, 1H), 8.03 (d, J=8.1 Hz, 1H), 7.80 (d, J=8.1 Hz, 1H), 7.73 (dd, J=8.3, 5.8 Hz, 1H), 5.48 (d, J=11.9 Hz, 2H), 5.30 (dt, J=34.3, 7.3 Hz, 1H), 4.63 (s, 2H), 3.68 (d, J=7.3 Hz, 3H), 3.65-3.55 (m, 1H), 3.23 (s, 3H), 1.43 (d, J=7.1 Hz, 6H).

Example 12

The following compound was prepared according to procedures AA, Y, W, L, M, N, O, P, J, and Q.

(Z)-3-fluoro-4-(2-methyl-3-((6-(methylsulfonyl)pyridin-3-yl)methyl)-5-(trifluoromethyl)-1H-pyrrolo[3,2-b]pyridin-1-yl)but-2-en-1-amine trihydrochloride (Compound 31)

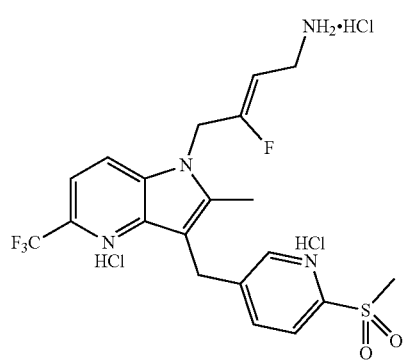

$^1$H NMR (300 MHz, DMSO-$d_6$) δ ppm: 8.79 (dd, J=2.1, 0.9 Hz, 1H), 8.16 (d, J=8.5 Hz, 1H), 8.00 (dd, J=8.1, 2.1 Hz, 2H), 7.94 (dd, J=8.1, 0.9 Hz, 1H), 7.63 (d, J=8.5 Hz, 1H), 5.24 (d, J=13.1 Hz, 2H), 5.06 (dt, J=36.0, 7.2 Hz, 1H), 4.30 (s, 2H), 3.44 (t, J=6.3 Hz, 2H), 3.23 (s, 3H), 2.56 (s, 3H).

Example 13

The following compound was prepared according to procedures E, AB, AC, Y, W, L, M, N, O, P, J, and Q.

(Z)-6-((1-(4-amino-2-fluorobut-2-en-1-yl)-2,5-dimethyl-1H-pyrrolo[3,2-b]pyridin-3-yl)methyl)-N,N-dimethylpyridine-3-sulfonamide trihydrochloride (Compound 15)

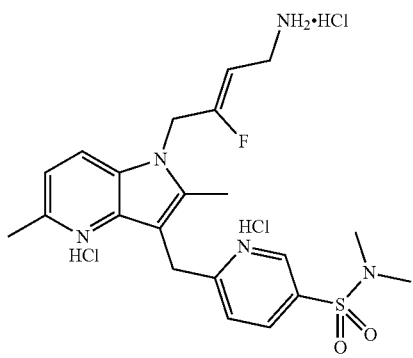

Procedure AB: Preparation of sodium 5-(dimethylsulfamoyl)pyridine-2-carboxylate

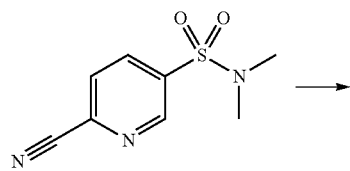

To a stirring solution of 6-cyano-N,N-dimethylpyridine-3-sulfonamide (1.00 g, 4.73 mmol) in 1,4-dioxane at rt was added aqueous sodium hydroxide (6 N, 4.00 mL, 24.0 mmol). The resulting mixture was heated to reflux, and vigorous stirring was continued overnight. After cooling to rt, the white voluminous solid was collected by filtration, and the filter cake was washed with diethyl ether. The solid was then dried under high vacuum to give sodium 5-(dimethylsulfamoyl)pyridine-2-carboxylate (1.25 g, 100%). $^1$H NMR (300 MHz, Deuterium Oxide) δ ppm: 8.89 (s, 1H), 8.26 (s, 1H), 8.04 (s, 1H), 2.71 (s, 6H).

Procedure AC: Preparation of ethyl 5-(N,N-dimethylsulfamoyl)picolinate

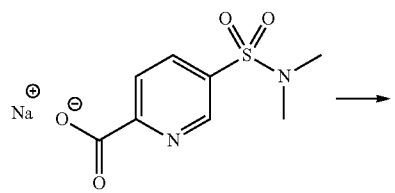

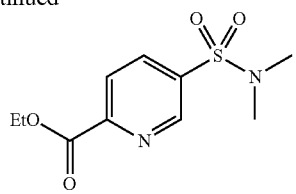

To a stirring suspension of sodium 5-(dimethylsulfamoyl)pyridine-2-carboxylate (1.00 g, 3.96 mmol) in ethanol (20 mL) at rt was added concentrated sulfuric acid (0.1 mL). The resulting mixture was heated at reflux for 2 h. After cooling to rt, the reaction mixture was concentrated to ~½ volume in vacuo. The resulting residue was partitioned between water (40 mL) and ethyl acetate (40 mL). The aqueous layer was extracted with further ethyl acetate (30 mL×2). The combined organics were washed with sat. aq. NaHCO$_3$ (40 mL), sat. aq. NaCl (40 mL), dried over Na$_2$SO$_4$, and then concentrated in vacuo to give ethyl 5-(N,N-dimethylsulfamoyl)picolinate (880 mg, 86%) as a white solid.

(Z)-6-((1-(4-amino-2-fluorobut-2-en-1-yl)-2,5-dimethyl-1H-pyrrolo[3,2-b]pyridin-3-yl)methyl)-N,N-dimethylpyridine-3-sulfonamide trihydrochloride (Compound 15)

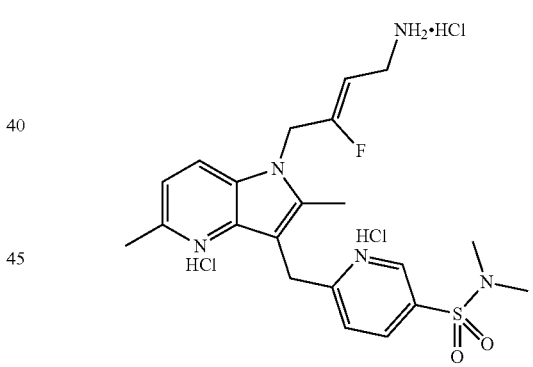

$^1$H NMR (300 MHz, Methanol-d$_4$) δ ppm: 8.85 (d, J=2.3 Hz, 1H), 8.56 (d, J=8.4 Hz, 1H), 8.19 (dd, J=8.2, 2.3 Hz, 1H), 7.67 (d, J=8.2 Hz, 1H), 7.51 (d, J=8.4 Hz, 1H), 5.32 (d, J=13.5 Hz, 2H), 5.30 (dt, J=35.2, 7.4 Hz, 1H), 4.62 (s, 21-1), 3.64 (d, J=7.3 Hz, 2H), 2.87 (s, 3H), 2.74 (s, 6H), 2.64 (s, 3H).

Example 14

The following compound was prepared according to procedures E, AD, W, L, M, N, O, P, J, and Q.

(Z)-3-((1-(4-amino-2-fluorobut-2-en-1-yl)-2,5-dimethyl-1H-pyrrolo[3,2-b]pyridin-3-yl)methyl)-N,N-dimethylbenzenesulfonamide dihydrochloride (Compound 18)

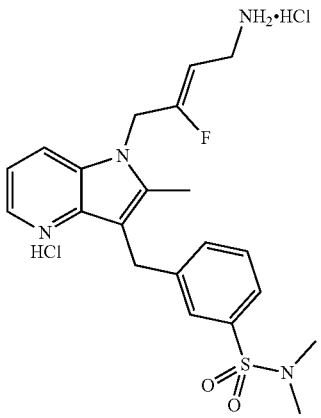

Procedure AD: Preparation of 3-(hydroxymethyl)-N,N-dimethylbenzenesulfonamide

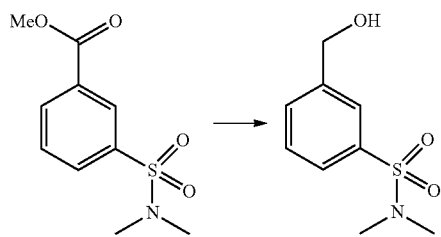 [SMILES: COC(=O)c1cccc(S(=O)(=O)N(C)C)c1 ; CN(C)S(=O)(=O)c1cccc(CO)c1]

To a stirring solution of methyl 3-(N,N-dimethylsulfamoyl)benzoate (910 mg, 3.74 mmol) in ethanol (18 mL) at 0° C. was added lithium borohydride (172 mg, 7.48 mmol). The resulting cloudy solution was stirred at rt overnight. The solvent was removed in vacuo, and resulting residue was taken up in ethyl acetate (50 mL). The organic layer was washed with water, brine and dried over MgSO$_4$. Removal of the solvent in vacuo afforded 3-(hydroxymethyl)-N,N-dimethylbenzenesulfonamide (560 mg, 70%) as a yellow film. $^1$H NMR (300 MHz, CDCl$_3$) δ ppm: 7.80 (dt, J=1.8, 0.8 Hz, 1H), 7.72 (dt, J=7.5, 1.6 Hz, 1H), 7.64 (d, J=7.7 Hz, 1H), 7.56 (dd, J=7.7 Hz, 1H), 4.82 (d, J=5.2 Hz, 2H), 2.74 (s, 6H), 1.94 (t, J=5.8 Hz, 1H).

(Z)-3-((1-(4-amino-2-fluorobut-2-en-1-yl)-2,5-dimethyl-1H-pyrrolo[3,2-b]pyridin-3-yl)methyl)-N,N-dimethylbenzenesulfonamide dihydrochloride (Compound 18)

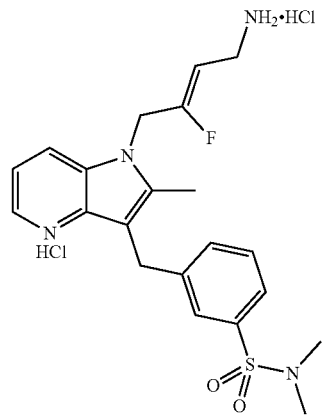

$^1$H NMR (300 MHz, Methanol-d$_4$) δ 8.76 (d, J=7.7 Hz, 1H), 8.53 (dd, J=6.0, 0.9 Hz, 1H), 7.72 (dd, J=8.3, 5.9 Hz, 1H), 7.66 (dt, J=7.0, 2.0 Hz, 1H), 7.62-7.52 (m, 3H), 5.41 (d, J=13.3 Hz, 2H), 5.32 (dt, J=35.2, 7.4 Hz, 1H), 4.47 (s, 2H), 3.70-3.62 (s, 2H), 2.65 (s, 9H).

Example 15

The following compound was prepared according to procedures L, M, N, O, P, J, and Q.

(Z)-4-(3-(2-chloro-4-(methylsulfonyl)benzyl)-2-methyl-1H-pyrrolo[3,2-b]pyridin-1-yl)-3-fluorobut-2-en-1-amine dihydrochloride (Compound 20)

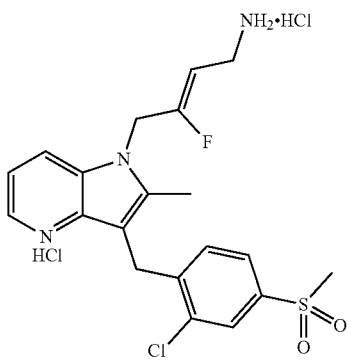

$^1$H NMR (300 MHz, Methanol-d$_4$) δ ppm: 8.77 (d, J=8.1 Hz, 1H), 8.52 (dd, J=6.0, 1.0 Hz, 1H), 8.09 (d, J=1.9 Hz, 1H), 7.78 (dd, J=8.1, 1.9 Hz, 1H), 7.73 (dd, J=8.3, 5.9 Hz, 1H), 7.18 (d, J=8.1 Hz, 1H), 5.41 (d, J=13.5 Hz, 2H), 5.36 (dt, J=34.2, 7.4 Hz, 1H), 4.50 (s, 2H), 3.67 (d, J=7.4 Hz, 2H), 3.15 (s, 3H), 2.58 (s, 3H).

Example 16

The following compounds were prepared according to procedures AE, AF, AG, AH, L, M, N, O, P, J and Q.

Procedure AE: Preparation of 3-chloro-4-(methylthio)benzaldehyde

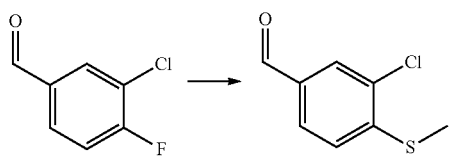

To a solution of 3-chloro-4-fluorobenzaldehyde (24.0 g, 0.15 mol, 1.0 eq) in DMF (120 mL) was added sodium methanethiolate (79.4 g, 0.23 mol, 1.5 eq) at −5° C. The mixture was stirred at r.t. overnight. The mixture was poured into water and extracted with EtOAc. The organic layer was washed with water, brine, dried over $Na_2SO_4$ and concentrated in vacuo. The residue was purified by flash chromatography (petroleum ether/EtOAc, 20:1) silica gel to give 3-chloro-4-(methylthio)benzaldehyde (10.3 g, 36%) as a white solid.

Procedure AF: Preparation of (3-chloro-4-(methylthio)phenyl)methanol

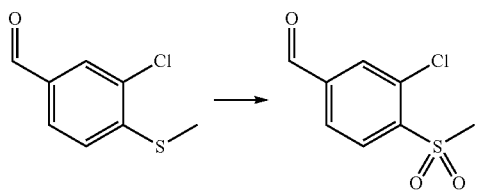

To a solution of 3-chloro-4-(methylthio)benzaldehyde (10.0 g, 0.05 mol, 1.0 eq) in $THF/H_2O$ (120 mL/18 mL) was added $NaBH_4$ (8.2 g, 0.22 mol, 4.4 eq) in one portion at r.t. The mixture was stirred at rt for 2 h. The reaction was quenched with 1 N HCl and the mixture was extracted with EtOAc. The organic layer was washed with water, dried over $Na_2SO_4$ and concentrated in vacuo to give (3-chloro-4-(methylthio)phenyl)methanol (9.70 g, 96%) as a white solid.

Procedure AG: Preparation of (3-chloro-4-(methylsulfonyl)phenyl)methanol

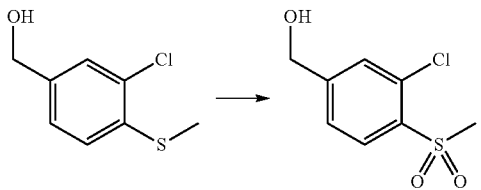

To a mixture of (3-chloro-4-(methylthio)phenyl)methanol (14.2 g, 0.08 mol, 1.0 eq) in $MeOH/H_2O$ (100 mL/500 mL) was added Oxone™ (76.0 g, 045 mol, 6.0 eq) in one portion at r.t. The mixture was stirred at rt overnight. Water was added and the mixture was extracted with EtOAc. The organic layer was washed with water, brine, dried over $Na_2SO_4$ and concentrated in vacuo to give (3-chloro-4-(methylsulfonyl)phenyl)methanol (14.9 g, 90%) as a white solid.

Procedure AH: Preparation of 4-(bromomethyl)-2-chloro-1-(methylsulfonyl)benzene

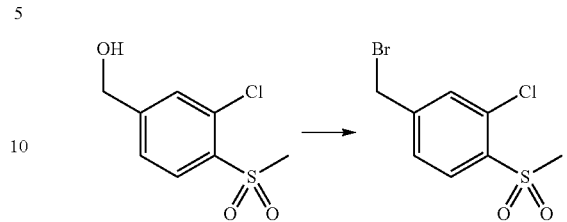

To a solution of (3-chloro-4-(methylsulfonyl)phenyl)methanol (7.0 g, 0.03 mol, 1.0 eq) in dioxane (70 mL) was added $PBr_3$ (6.30 g, 0.02 mol) dropwise at rt. After addition, the mixture was stirred at 100° C. for 1 h. The mixture was cooled to r.t. and the reaction was quenched with ice-water. The mixture was extracted with EtOAc and the combined organic layer, was washed with water, brine, dried over $Na_2SO_4$ and concentrated in vacuo to give 4-(bromomethyl)-2-chloro-1-(methylsulfonyl)benzene (8.70 g, 97%) as a white solid.

(Z)-4-(3-(3-chloro-4-(methylsulfonyl)benzyl)-2-methyl-1H-pyrrolo[3,2-b]pyridin-1-yl)-3-fluorobut-2-en-1-amine dihydrochloride (Compound 35)

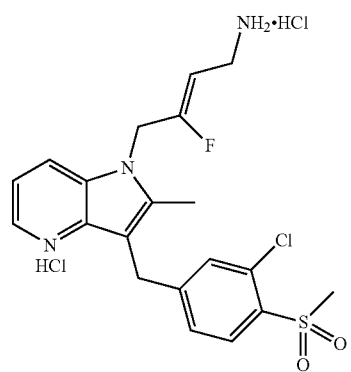

$^1$H NMR (300 MHz, Methanol-$d_4$) δ ppm: 8.74 (d, J=8.3 Hz, 1H), 8.54 (dd, J=5.9, 1.0 Hz, 1H), 8.05 (d, J=8.2 Hz, 1H), 7.72 (dd, J=8.3, 5.9 Hz, 1H), 7.53 (d, J=1.7 Hz, 1H), 7.35 (dd, J=8.3, 1.7 Hz, 1H), 5.40 (d, J=14.2 Hz, 2H), 5.35 (dt, J=35.2, 7.4 Hz, 1H), 4.44 (s, 2H), 3.66 (d, J=7.4 Hz, 2H), 3.29 (s, 3H), 2.65 (s, 3H).

(Z)-3-fluoro-4-(2-methyl-3-(2-methyl-4-(methylsulfonyl)benzyl)-1H-pyrrolo[3,2-b]pyridin-1-yl)but-2-en-1-amine dihydrochloride (Compound 34)

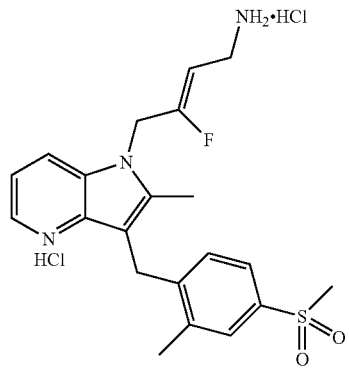

$^1$H NMR (300 MHz, Methanol-d$_4$) δ ppm: 8.76 (d, J=8.2 Hz, 1H), 8.50 (d, J=5.8 Hz, 1H), 7.87 (s, 1H), 7.72 (dd, J=8.3, 5.9 Hz, 1H), 7.63 (dd, J=8.1, 2.0 Hz, 1H), 6.87 (d, J=8.1 Hz, 1H), 5.43 (d, J=13.8 Hz, 2H), 4.37 (s, 2H), 5.37 (dt, J=35.6, 7.4 Hz, 1H), 3.68 (d, J=7.3 Hz, 2H), 3.10 (s, 3H), 2.61 (s, 3H), 2.58 (s, 3H).

Example 17

The following compound was prepared according to procedures V, W, AI, AJ, AK, AL, J, AM and Q.

(Z)-2-(1-(4-amino-2-fluorobut-2-en-1-yl)-3-(4-(methylsulfonyl)benzyl)-1H-pyrrolo[3,2-b]pyridin-2-yl)propan-2-ol dihydrochloride (Compound 25)

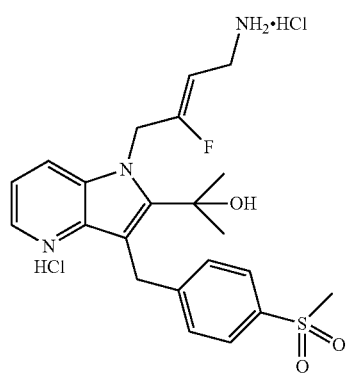

Procedure AI: Preparation of tributyl(4-(methylsulfonyl)benzyl)stannane

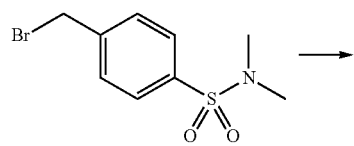

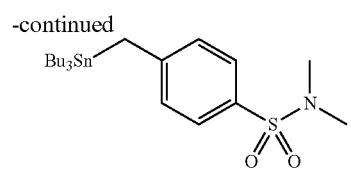

A stirring solution of 4-(bromomethyl)-N,N-dimethylbenzenesulfonamide (2.23 g, 8.00 mmol) and hexa-n-butylditin (4.45 mL, 8.80 mmol) in toluene (30 mL) at rt was degassed by passing a stream of argon gas through it 5 min. Tetrakis(triphenylphosphine)palladium (0) (462 mg, 0.40 mmol) was then added and the mixture was heated at reflux overnight. The reaction mixture was concentrated under vacuum and the crude material was adsorbed directly onto silica gel. Purification was performed over silica gel to afford N,N-dimethyl-4-((tributylstannyl)methyl)benzenesulfonamide (1.81 g, 46%) as a colourless oil. $^1$H NMR (300 MHz, CDCl$_3$) δ ppm: 7.58 (d, J=8.4 Hz, 2H), 7.12 (d, J=8.6 Hz, 2H), 1.50-1.37 (m, 6H), 1.34-1.19 (m, 6H), 0.94-0.80 (m, 9H).

Procedure AJ: Preparation of methyl 1H-pyrrolo[3,2-b]pyridine-2-carboxylate

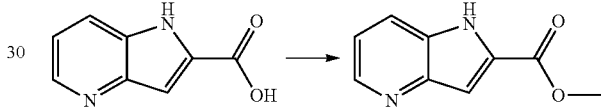

Diazomethyl(trimethyl)silane (2 M in hexane, 2.25 mL, 4.50 mmol) was added drop-wise to a suspension of 1H-pyrrolo[3,2-b]pyridine-2-carboxylic acid (486 mg, 3.00 mmol) in DMF (4.5 mL). After the complete addition, the ice-bath was removed and the mixture was stirred at ambient temperature for 30 min. The reaction mixture was diluted with water (50 mL), and the resulting suspension was stirred at rt for 15 min. The solid was filtered, washed with water, and dried in an oven at 60° C. for 1 h to afford methyl 1H-pyrrolo[3,2-b]pyridine-2-carboxylate (315 mg, 60%) as a pale yellow solid. $^1$H NMR (300 MHz, CDCl$_3$) δ ppm: 9.08 (s, 1H), 8.60 (dd, J=4.5, 1.4 Hz, 1H), 7.78 (dt, J=8.4, 1.2 Hz, 1H), 7.42 (dd, J=2.1, 1.0 Hz, 1H), 7.28 (dd, J=8.4, 4.5 Hz, 1H), 4.01 (s, 3H).

Procedure AK: Preparation of 1-(tert-butyl) 2-methyl 3-bromo-1H-pyrrolo[3,2-b]pyridine-1,2-dicarboxylate

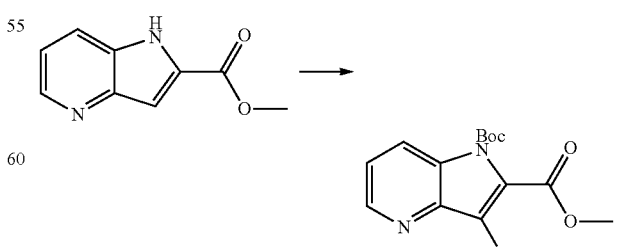

1-bromopyrrolidine-2,5-dione (NBS; 334 mg, 1.88 mmol) was added in one lot to a suspension of methyl 1H-pyrrolo[3,2-b]pyridine-2-carboxylate (315 mg, 1.79 mmol) in DMF (2.0 mL). A clear pale yellow solution was obtained. The mixture was stirred at ambient temperature for 30 min. Tlc after this time indicated the absence of starting material. Di-tert-butyl dicarbonate (859 mg, 3.93 mmol) was added followed by addition of 4-(dimethylamino)pyridine (229 mg, 1.88 mmol). The resulting mixture was stirred for 30 min. after which time, tlc indicated the absence of starting material. The reaction mixture was diluted with water (20 mL). The precipitated solid was filtered, washed with water and dried in an oven at 60° C. for 2 hr to afford 1-(tort-butyl) 2-methyl 3-bromo-1H-pyrrolo[3,2-b]pyridine-1,2-dicarboxylate (600 mg, 94%) as a pale yellow solid. $^1$H NMR (300 MHz, CDCl$_3$) δ 8.69 (dd, J=4.7, 1.4 Hz, 1H), 8.42 (dd, J=8.5, 1.4 Hz, 1H), 7.41 (dd, J=8.5, 4.7 Hz, 1H), 4.04 (s, 3H), 1.65 (s, 91-1).

Procedure AL: Preparation of methyl 3-(4-(methylsulfonyl)benzyl)-1H-pyrrolo[3,2-b]pyridine-2-carboxylate

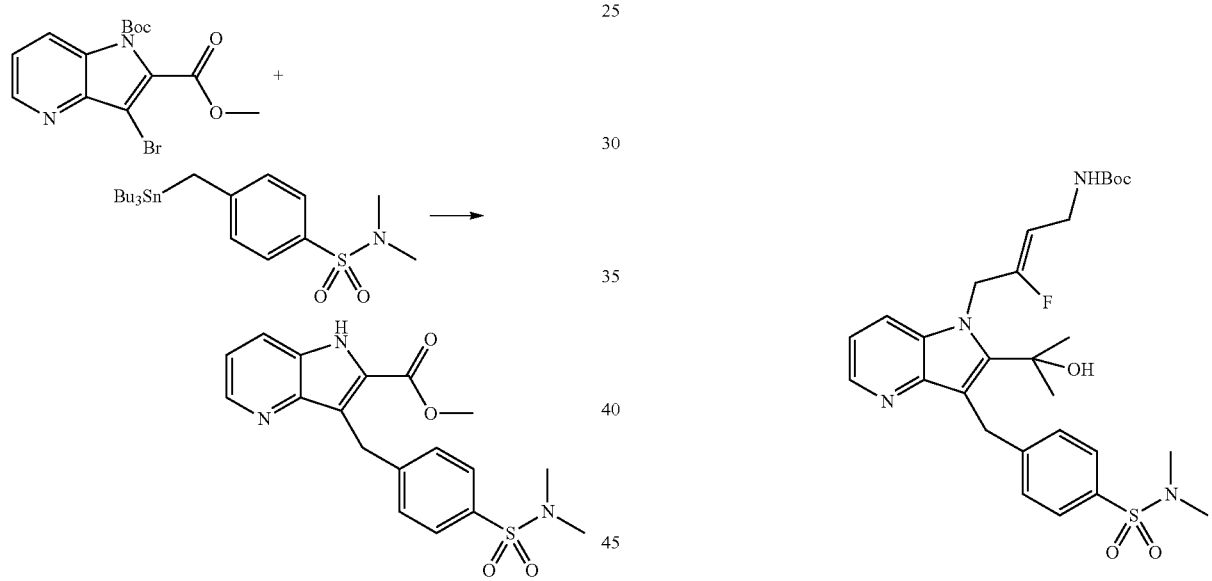

A stirring mixture of N,N-dimethyl-4-(((tributylstannyl)methyl)benzenesulfonamide (439 mg, 0.90 mmol) and 1-(tert-butyl) 2-methyl 3-bromo-1H-pyrrolo[3,2-b]pyridine-1,2-dicarboxylate (200 mg, 0.56 mmol) in DMF (2.5 mL) was degassed by purging Argon through it for 10 min. Tetrakis(triphenylphosphine)palladium(0) (65.1 mg, 0.06 mmol) was then added, and the mixture was heated at 100° C. for 8 hours. The reaction mixture was diluted with water (25 mL), and the product was extracted with ethyl acetate (25 mL×3). The combined organics were dried over Na$_2$SO$_4$, and then concentrated in vacuo. The crude material was purified over silica gel to afford methyl 3-(4-(methylsulfamoyl)benzyl)-1H-pyrrolo[3,2-b]pyridine-2-carboxylate (175 mg, 83%) as a white solid. $^1$H NMR (300 MHz, DMSO-d$_6$) δ ppm: 8.49 (dd, J=4.4, 1.5 Hz, 1H), 7.83 (dd, J=8.4, 1.5 Hz, 1H), 7.61 (d, J=8.6 Hz, 2H), 7.56 (d, J=8.7 Hz, 2H), 7.32 (dd, J=8.4, 4.4 Hz, 1H), 4.56 (s, 2H), 3.91 (s, 3H), 2.55 (s, 6H).

Procedure AM: Preparation of tert-butyl (Z)-(3-fluoro-4-(2-(2-hydroxypropan-2-yl)-3-(4-(methylsulfonyl)benzyl)-1H-pyrrolo[3,2-b]pyridin-1-yl)but-2-en-1-yl)carbamate

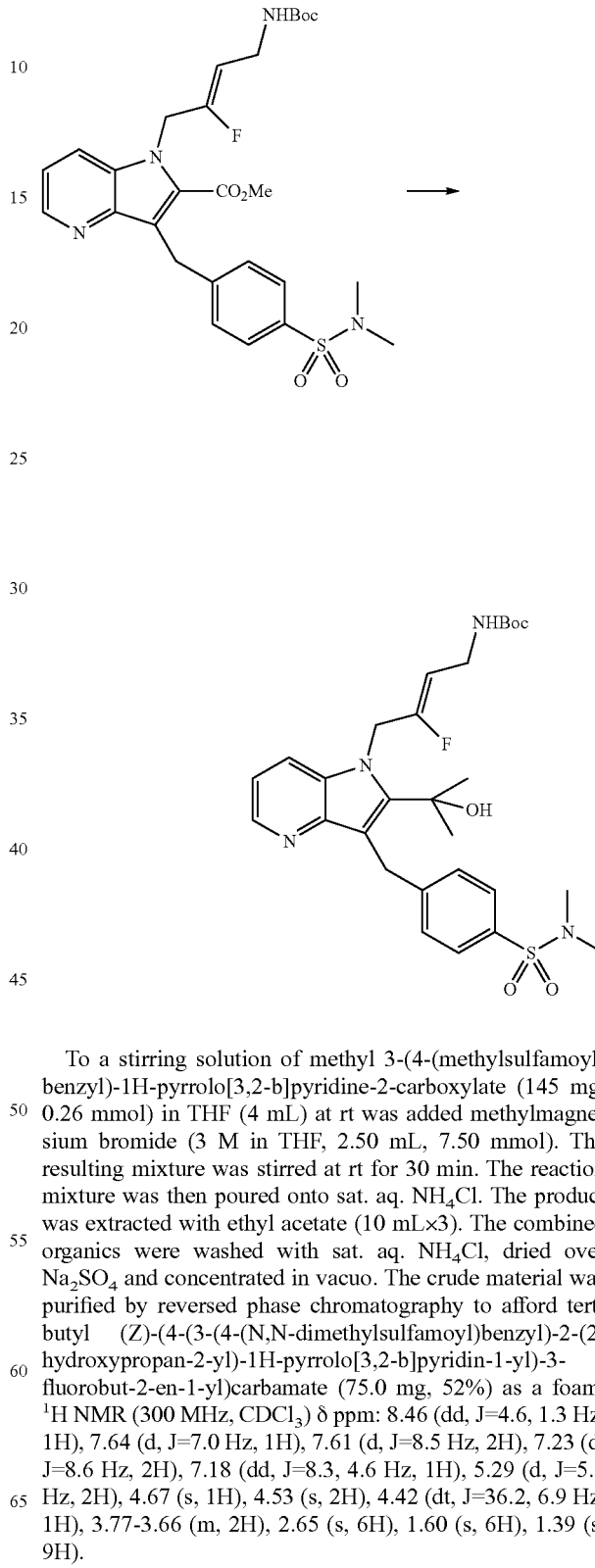

To a stirring solution of methyl 3-(4-(methylsulfamoyl)benzyl)-1H-pyrrolo[3,2-b]pyridine-2-carboxylate (145 mg, 0.26 mmol) in THF (4 mL) at rt was added methylmagnesium bromide (3 M in THF, 2.50 mL, 7.50 mmol). The resulting mixture was stirred at rt for 30 min. The reaction mixture was then poured onto sat. aq. NH$_4$Cl. The product was extracted with ethyl acetate (10 mL×3). The combined organics were washed with sat. aq. NH$_4$Cl, dried over Na$_2$SO$_4$ and concentrated in vacuo. The crude material was purified by reversed phase chromatography to afford tert-butyl (Z)-(4-(3-(4-(N,N-dimethylsulfamoyl)benzyl)-2-(2-hydroxypropan-2-yl)-1H-pyrrolo[3,2-b]pyridin-1-yl)-3-fluorobut-2-en-1-yl)carbamate (75.0 mg, 52%) as a foam. $^1$H NMR (300 MHz, CDCl$_3$) δ ppm: 8.46 (dd, J=4.6, 1.3 Hz, 1H), 7.64 (d, J=7.0 Hz, 1H), 7.61 (d, J=8.5 Hz, 2H), 7.23 (d, J=8.6 Hz, 2H), 7.18 (dd, J=8.3, 4.6 Hz, 1H), 5.29 (d, J=5.6 Hz, 2H), 4.67 (s, 1H), 4.53 (s, 2H), 4.42 (dt, J=36.2, 6.9 Hz, 1H), 3.77-3.66 (m, 2H), 2.65 (s, 6H), 1.60 (s, 6H), 1.39 (s, 9H).

(Z)-4-((1-(4-amino-2-fluorobut-2-en-1-yl)-2-(2-hydroxypropan-2-yl)-1H-pyrrolo[3,2-b]pyridin-3-yl)methyl)-N,N-dimethylbenzenesulfonamide dihydrochloride (Compound 25)

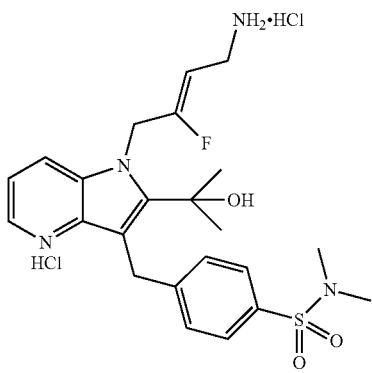

$^1$H NMR (300 MHz, Methanol-d$_4$) δ ppm: 8.76 (d, J=8.1 Hz, 1H), 8.56 (d, J=5.6 Hz, 1H), 7.78 (dd, J=7.7, 5.5 Hz, 1H), 7.74 (d, J=8.0 Hz, 2H), 7.35 (d, J=7.9 Hz, 2H), 5.84 (d, J=9.4 Hz, 2H), 5.05 (dt, J=34.3, 7.1 Hz, 1H), 4.64 (s, 2H), 3.66 (dd, J=6.9, 2.9 Hz, 2H), 2.66 (s, 6H), 1.68 (s, 6H).

Example 18

The following compound was prepared according to procedures and E, AN, AO, AP, J and Q.

(Z)-4-((1-(4-amino-2-fluorobut-2-en-1-yl)-5-fluoro-2-methyl-1H-pyrrolo[3,2-b]pyridin-3-yl)methyl)-N,N-dimethylbenzenesulfonamide dihydrochloride (Compound 23)

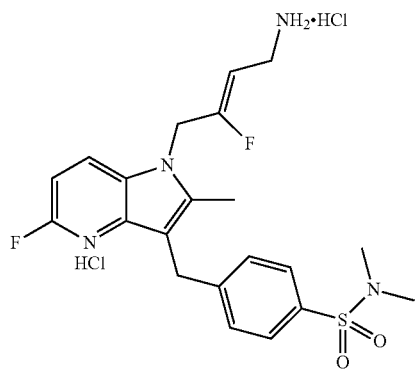

Procedure AN: Preparation of 5-fluoro-2-methyl-3-(methylthio)-1H-pyrrolo[3,2-b]pyridine

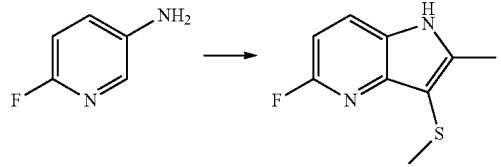

To a suspension of 6-fluoropyridin-3-amine (2.50 g, 22.0 mmol) in dichloromethane (40 mL) was added a solution of t-BuOCl (2.50 mL) in dichloromethane (5 mL) at −65° C. The resulting mixture was then stirred for 0.5 h before addition of a solution of 1-methylthiopropanone (2.3 mL) in dichloromethane (5 mL). Stirring was continued at −65° C. for 2 h. Triethylamine (3.2 mL) was then added the resulting reaction mixture was stirred at rt overnight. Water (15 mL) was added and stirring was continued for 0.5 h. The solid thus formed was filtrated and washed with dichloromethane. The filtrate was transferred to a separatory funnel, and the organic layer was separated and then concentrated. A second crop of solid was filtered, combined with previous solid and dried under high vacuum to afford 5-fluoro-2-methyl-3-(methylthio)-1H-pyrrolo[3,2-b]pyridine (1.8 g, yield: 42%) as an off-white solid. 1H-NMR (300 MHz, CDCl$_3$): δ ppm: 8.41 (bs, 1H), 7.66-7.60 (m, 1H), 6.72-6.68 (m, 1H), 2.58 (s, 6H), 2.35 (s, 3H).

Procedure AO: Preparation of 5-fluoro-2-methyl-1H-pyrrolo[3,2-b]pyridine

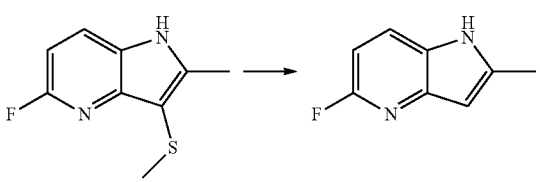

To a mixture of 5-fluoro-2-methyl-3-(methylthio)-1H-pyrrolo[3,2-b]pyridine (1.80 g, 9.20 mmol) in ethanol/acetic acid (9:1, 1.0 L) was added Raney Ni (25.0 g) in portions, at rt. The mixture was then stirred at rt overnight. Water (150 mL) was added, and the solid was filtered off carefully and washed with water. The filtrate was adjusted to pH=8 with saturated aqueous Na$_2$CO$_3$ solution, extracted with ethyl acetate (3×100 mL), dried over Na$_2$SO$_4$ and concentrated in vacuo. The crude material was purified by flash column chromatography on silica gel eluting with petroleum ether/ethyl acetate (5:1) to afford 5-fluoro-2-methyl-1H-pyrrolo[3,2-b]pyridine (1.20 g, 87%). 1H-NMR (300 MHz, CDCl$_3$): δ ppm: 8.84 (bs, 1H), 7.65-7.60 (m, 1H), 6.66-6.63 (m, 1H), 6.30 (s, 1H), 2.49 (s, 3H).

Procedure AP: Preparation of 4-(5-fluoro-2-methyl-1H-pyrrolo[3,2-b]pyridin-3-yl)methyl)-N,N-dimethylbenzenesulfonamide

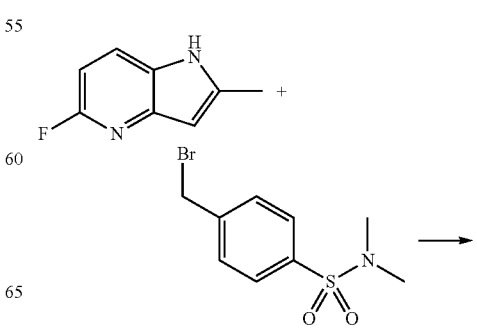

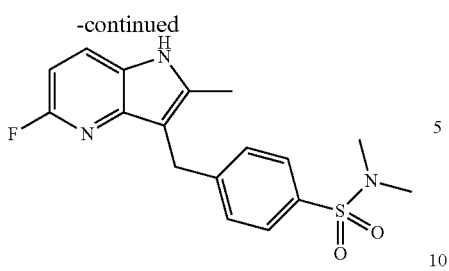

5-fluoro-2-methyl-1H-pyrrolo[3,2-b]pyridine (0.50 g, 3.30 mmol) and 4-(bromomethyl)-N,N-dimethylbenzenesulfonamide (1.10 g, 4.00 mmol) were suspended in water (2.5 mL) in a 10 mL sealable tube. The mixture was heated at 150° C. in a microwave. After cooling to rt, the reaction mixture was basified with sat. aq. Na$_2$CO$_3$. The aqueous phase was then extracted with ethyl acetate (50 mL×3), dried over Na$_2$SO$_4$, and concentrated in vacuo. The crude material was purified using prep-TLC to afford 4-((5-fluoro-2-methyl-1H-pyrrolo[3,2-b]pyridin-3-yl)methyl)-N,N-dimethylbenzenesulfonamide (130 mg, 11%) as a white solid. $^1$H-NMR (300 MHz, CDCl$_3$): δ ppm: 8.18 (s, 1H), 7.64-7.59 (m, 3H), 7.42-7.39 (m, 2H), 6.70-6.66 (m, 1H), 4.17 (s, 2H), 2.66 (s, 6H), 2.37 (s, 3H).

(Z)-4-((1-(4-amino-2-fluorobut-2-en-1-yl)-5-fluoro-2-methyl-1H-pyrrolo[3,2-b]pyridin-3-yl)methyl)-N,N-dimethylbenzenesulfonamide dihydrochloride (Compound 23)

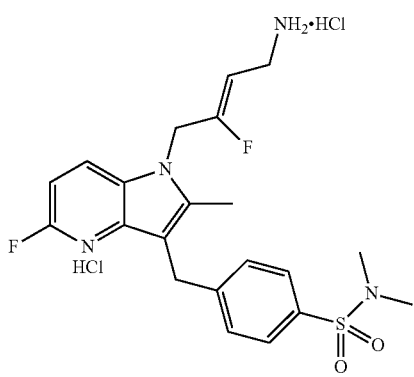

$^1$H NMR (300 MHz, DMSO-d$_6$) δ ppm: 8.09 (s, 3H), 8.08 (dd, J=8.7, 7.1 Hz, 1H), 7.64 (d, J=8.3 Hz, 2H), 7.50 (d, J=8.4 Hz, 2H), 6.85 (dd, J=8.6, 1.5 Hz, 1H), 5.16 (d, J=13.1 Hz, 2H), 5.06 (dt, J 35.4, 7.2 Hz, 1H), 4.14 (s, 2H), 3.44 (t, J=6.3 Hz, 2H), 2.57 (s, 6H), 2.46 (s, 3H).

Example 19

The following compound was prepared according to procedures and E, AQ, AN, AO, AR, J and Q.

(Z)-4-((1-(4-amino-2-fluorobut-2-en-1-yl)-6-fluoro-2-methyl-1H-pyrrolo[3,2-b]pyridin-3-yl)methyl)-N,N-dimethylbenzenesulfonamide dihydrochloride (Compound 24)

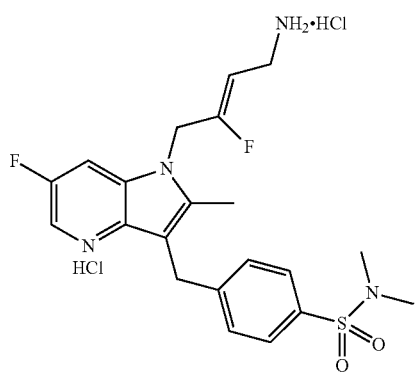

Procedure AQ: Preparation of N,N-dimethyl-4-((4,5,5-tetramethyl-1,3,2-dioxaborolan-2-yl)methyl)benzenesulfonamide To a stirring suspension of (PinB)$_2$ (49.0 g, 0.19 mol), Fe(acac)$_3$ (1.90 g, 5.50 mmol) and TMEDA (0.83 mL in THF (400 mL) at 0° C. was added ethylmagnesiumbromide (1 M, 200 mL) dropwise. The reaction mixture was stirred for 0.5 h at which time a solution of 4-(bromomethyl)-N,N-dimethylbenzenesulfonamide was added in (15.4 g, 0.06 mol) in THF (50 mL). The resulting mixture was stirred at rt overnight. The reaction mixture was quenched with sat. aq. NH$_4$Cl, and the product was extracted with ethyl acetate (100 mL×3). Purification over silica gel eluting with ethyl acetate/hexane (1:15) followed by ethyl acetate/hexane (1:7) afforded N,N-dimethyl-4-((4,4,5,5-tetramethyl-1,3,2-dioxaborolan-2-yl)methyl)benzenesulfonamide (5.30 g, 30%) as a white solid. $^1$H-NMR (300 MHz, CDCl$_3$): δ ppm: 7.65-7.62 (m, 2H), 7.35-7.32 (m, 2H), 2.68 (s, 6H), 2.37 (s, 2H), 1.23 (s, 12H).

111

Procedure AR: Preparation of tert-butyl 3-(4-(N,N-dimethylsulfamoyl)benzyl)-6-fluoro-2-methyl-1H-pyrrolo[3,2-b]pyridine-1-carboxylate

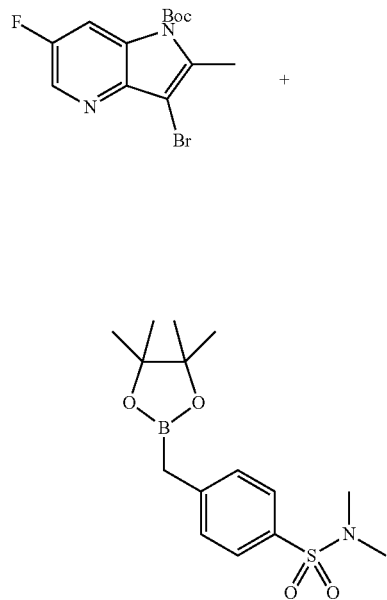

To a stirring solution of tert-butyl 3-bromo-6-fluoro-2-methyl-1H-pyrrolo[3,2-b]pyridine-1-carboxylate (33.0 mg, 0.18 mmol) and N,N-dimethyl-4-((4,4,5,5-tetramethyl-1,3,2-dioxaborolan-2-yl)methyl)benzenesulfonamide (114 mg, 0.35 mmol) in toluene (2 mL) was added a solution of $K_3PO_4$ (85.0 mg, 0.40 mmol) in water (0.2 mL) followed by Pd(dppf)Cl$_2$ (20 mg). The resulting mixture was purged with $N_2$ for 3 min, and then heated at 65° C. overnight. The reaction mixture was diluted with ethyl acetate (20 mL), and the organic phase was washed with water, brine, dried over $Na_2SO_4$ and evaporated to afford crude tert-butyl 3-(4-(N,N-dimethylsulfamoyl)benzyl)-6-fluoro-2-methyl-1H-pyrrolo[3,2-b]pyridine-1-carboxylate, which was directly used in next step without further purification. The reaction was repeated for 20 times to get 110 mg of tert-butyl 3-(4-(N,N-dimethylsulfamoyl)benzyl)-6-fluoro-2-methyl-1H-pyrrolo[3,2-b]pyridine-1-carboxylate.

112

(Z)-4-((1-(4-amino-2-fluorobut-2-en-1-yl)-6-fluoro-2-methyl-1H-pyrrolo[3,2-b]pyridin-3-yl)methyl)-N,N-dimethylbenzenesulfonamide dihydrochloride (Compound 24)

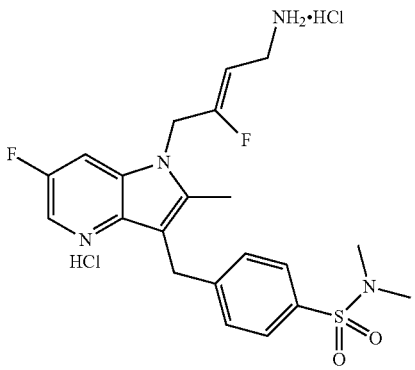

$^1$H NMR (300 MHz, DMSO-d$_6$) δ ppm: 8.50 (dd, J=2.3 Hz, 1H), 8.24 (d, J=9.8 Hz, 1H), 8.14 (s, 3H), 7.63 (d, J=8.3 Hz, 2H), 7.52 (d, J=8.4 Hz, 2H), 5.21 (d, J=13.6 Hz, 2H), 5.15 (dt, J=35.2, 7.2 Hz, 1H), 4.29 (s, 2H), 3.45 (t, J=6.4 Hz, 21-1), 2.57 (s, 6H), 2.50 (s, 3H).

Example 20

The following compound was prepared according to procedures AA, Y, W, AS, AT, AU, AV, AP, AW, AX, AY, J and Q.

(Z)-4-(5-(1,1-difluoroethyl)-2-methyl-3-((6-(methylsulfonyl)pyridin-3-yl)methyl)-1H-pyrrolo[3,2-b]pyridin-1-yl)-3-fluorobut-2-en-1-amine trihydrochloride (Compound 30)

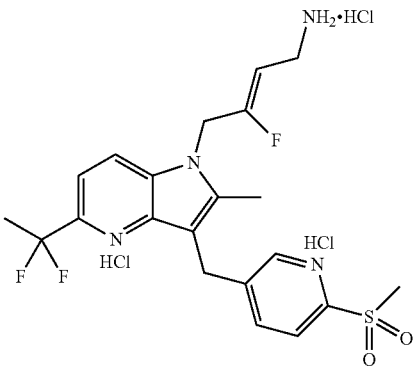

Procedure AS: Preparation of 5-chloro-2-methyl-3-(methylthio)-1H-pyrrolo[3,2-b]pyridine

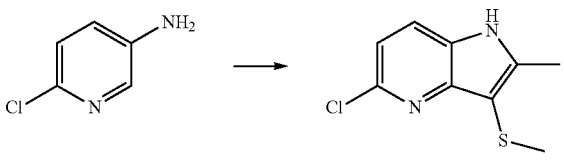

To a solution of 6-chloropyridin-3-amine (5.00 g, 46.0 mmol) in dichloromethane (110 mL) at −78° C. was added a solution of t-BuOCl (92 mmol, 10.4 mL) in dichloromethane (40 mL). The reaction was stirred for 30 min prior to the addition of methylthioacetone (46.0 mmol, 4.80 g) in dichloromethane (40 mL). After 90 min, a solution of NEt₃ (46.0 mmol, 7.10 mL) in dichloromethane (450 mL) was added and the reaction was warmed to ambient temperature. The reaction was quenched by the addition of water, and the aqueous layer was extracted with dichloromethane. The organic layer was dried over Na₂SO₄ and concentrated in vacuo. The residue was purified by flash column chromatography on silica gel (CH₂Cl₂: MeOH=20:1) to afford 5-chloro-2-methyl-3-(methylthio)-1H-pyrrolo[3,2-b]pyridine (7.1 g, 72%)

Procedure AT: Preparation of 2-methyl-3-(methylthio)-1H-pyrrolo[3,2-b]pyridine-5-carbonitrile

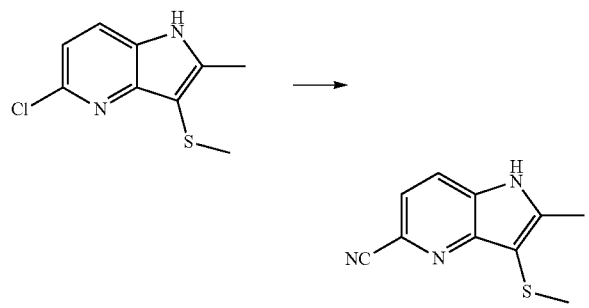

A stirring mixture of 5-chloro-2-methyl-3-(methylthio)-1H-pyrrolo[3,2-b]pyridine (1.00 g, 4.70 mmol), Zn(CN)₂ (0.84 g, 7.10 mmol), Pd(PPh₃)₄ (543 mg, 0.47 mmol) and NMP (10 mL) was heated at 100° C. for 1 h under MW. The reaction mixture was diluted with water, extracted with ethyl acetate (50 ml×3), washed with brine, dried over Na₂SO₄ and concentrated in vacuo to afford 2-methyl-3-(methylthio)-1H-pyrrolo[3,2-b]pyridine-5-carbonitrile (0.70 g), which was used directly in next step without further purification.

Procedure AU: Preparation of 1-(2-methyl-3-(methylthio)-1H-pyrrolo[3,2-b]pyridin-5-yl)ethan-1-one

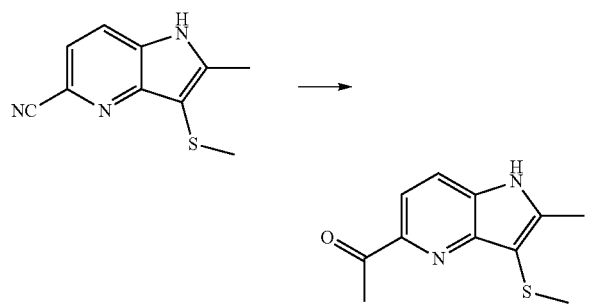

To a stirring solution of 2-methyl-3-(methylthio)-1H-pyrrolo[3,2-b]pyridine-5-carbonitrile (2.8 g, 13.8 mmol) in dry THF (50 mL) under nitrogen was added methylmagnesium bromide (3 M in diethylether, 13.8 mL, 41.4 mmol) drop-wise at 0° C. The resulting mixture was stirred at rt overnight. The reaction mixture was poured into aqueous NH₄Cl, and stirring was continued for 30 min. The aqueous phase was extracted with ethyl acetate (100 mL×3), and the combined organic phases were dried over Na₂SO₄, concentrated in vacuo. The crude material was purified over silica gel ethyl acetate/hexane (5:1) to afford 1-(2-methyl-3-(methylthio)-1H-pyrrolo[3,2-b]pyridin-5-yl)ethan-1-one (2.10 g, 69%) as a white solid.

Procedure AV: Preparation of 1-(2-methyl-1H-pyrrolo[3,2-b]pyridin-5-yl)ethan-1-ol

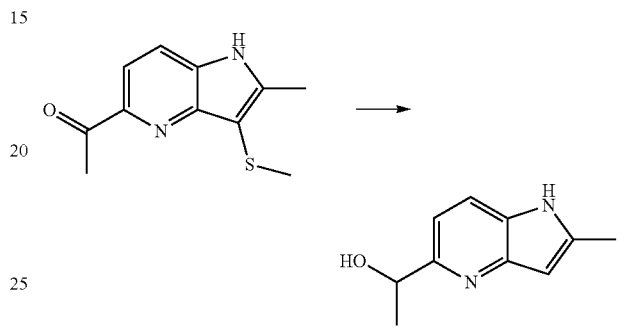

To a mixture of 1-(2-methyl-3-(methylthio)-1H-pyrrolo[3,2-b]pyridin-5-yl)ethan-1-one (2.80 g, 0.01 mol) in ethanol (60 mL) and AcOH (15 mL) at rt was added Raney Ni (30 g) in portions. The resulting mixture was stirred at rt overnight. Water (100 mL) was added, and the resulting solid was filtered and washed with water. The filtrate was adjusted to pH 8 with Na₂CO₃ solution, and then extracted with ethyl acetate (100 mL×3). The combined organics were dried over Na₂SO₄, and concentrated in vacuo. The residue was dissolved in methanol, and NaBH₄ (0.20 g, 5.20 mmol) was added. The resulting mixture was then stirred at rt for 1 h. The reaction was quenched with aq. 2 M HCl, and the pH was adjusted to 8 with Na₂CO₃. After concentrating in vacuo, the reaction mixture was dilute with water (20 mL), extracted with ethyl acetate (50 mL×3). The combined organics were then dried over Na₂SO₄ and concentrated in vacuo. The crude material was purified over silica gel with eluting with dichloromethane/MeOH (20:1) to afford 1-(2-methyl-1H-pyrrolo[3,2-b]pyridin-5-yl)ethan-1-ol (0.80 g, 33%) as a yellow solid, which was used directly in next step without further purification.

Procedure AW: Preparation of 1-(2-methyl-3-((6-(methylsulfonyl)pyridin-3-yl)methyl)-1H-pyrrolo-[3,2-b]pyridin-5-yl)ethan-1-one

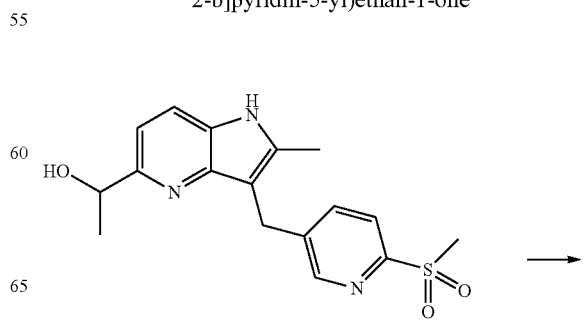

-continued

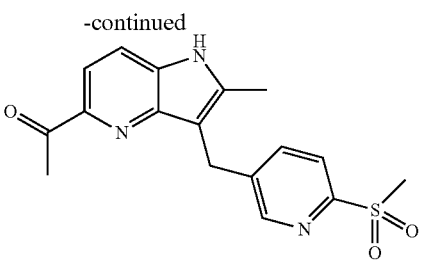

A mixture of 1-(2-methyl-3-((6-(methylsulfonyl)pyridin-3-yl)methyl)-1H-pyrrolo[3,2-b]pyridin-5-yl)ethan-1-ol (0.4 g, 1.15 mmol), dichloromethane (10 mL), MeCN (10 ml) and activated $MnO_2$ (1.00 g) was stirred at rt overnight. The solid was filtered off, and the filtrate was evaporated to afford 1-(2-methyl-3-((6-(methylsulfonyl)pyridin-3-yl)methyl)-1H-pyrrolo[3,2-b]pyridin-5-yl)ethan-1-one (0.30 g, 75%) as a light yellow solid. This material was used directly in next step without further purification.

Procedure AX: Preparation of tert-butyl 5-acetyl-2-methyl-3-((6-(methylsulfonyl)pyridin-3-yl)methyl)-1H-pyrrolo[3,2-b]pyridine-1-carboxylate

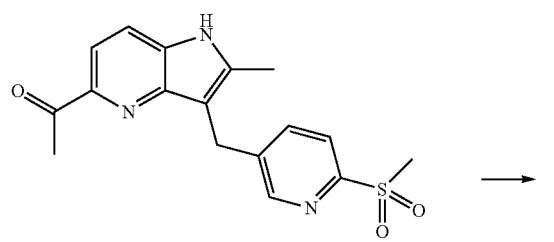

To a stirring solution of 1-(2-methyl-3-((6-(methylsulfonyl)pyridin-3-yl)methyl)-1H-pyrrolo[3,2-b]pyridin-5-yl)ethan-1-one (0.3 g, 0.87 mmol), $Et_3N$ (0.18 g, 1.75 mmol) and $Boc_2O$ (0.29 g, 1.31 mmol) in dichloromethane (10 mL) was added DMAP (20 mg). The resulting mixture was stirred at rt overnight. The reaction mixture was partitioned between ethyl acetate and water, and the organic layer was washed with water, dried over $Na_2SO_4$, and concentrated in vacuo. The crude material was purified by prep-TLC to afford tert-butyl 5-acetyl-2-methyl-3-((6-(methylsulfonyl)pyridin-3-yl)methyl)-1H-pyrrolo[3,2-b]pyridine-1-carboxylate (0.15 g, 39%) as a light yellow solid. $^1$H-NMR (300 MHz, $CDCl_3$): δ ppm: 8.77 (s, 1H), 8.36-8.33 (m, 1H), 8.00-7.88 (m, 3H), 6.50-6.48 (m, 1H), 4.26 (s, 2H), 3.27 (s, 3H), 2.77 (s, 3H), 2.69 (s, 3H).

Procedure AY: Preparation of tert-butyl 3-bromo-5-(1,1-difluoroethyl)-2-methyl-1H-indole-1-carboxylate

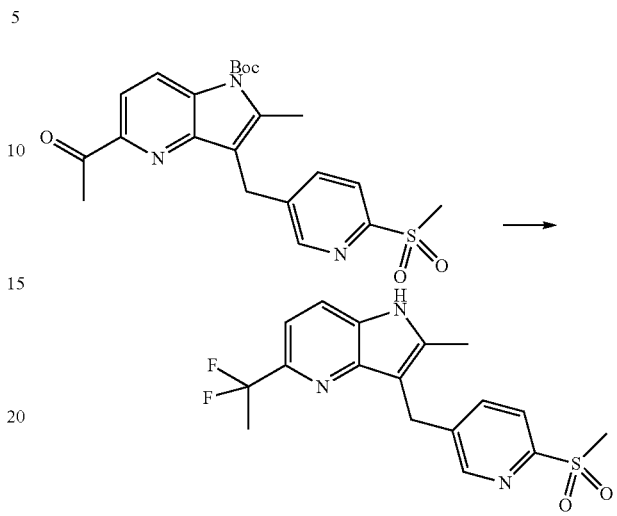

A mixture of tert-butyl 5-acetyl-2-methyl-3-((6-(methylsulfonyl)pyridin-3-yl)methyl)-1H-pyrrolo[3,2-b]pyridine-1-carboxylate (0.15 g, 0.34 mmol) and DAST (15 mL) were stirred at 50° C. overnight. The mixture was cooled to rt, quenched with ice/$NaHCO_3$ sat. to pH >8. The crude product was extracted with dichloromethane (2×50 mL). The combined organics were then dried over $Na_2SO_4$, and concentrated in vacuo. The residue was dissolved in methanol (1 mL), added then HCl (3 M in ethyl acetate; 10 mL) was added. The resulting mixture was then stirred at rt overnight. After concentrating in vacuo, the pH was adjusted to >8 with $Na_2CO_3$. The crude material was then purified on prep-TLC to afford 5-(1,1-difluoroethyl)-2-methyl-3-((6-(methylsulfonyl)pyridin-3-yl)methyl)-1-pyrrolo[3,2-b]pyridine (0.15 g, yield 65%) as an off-white solid. 1H-NMR (400 MHz, DMSO-$d_6$) δ ppm: 11.66-11.64 (m, 1H), 8.81 (s, 1H), 8.05-8.02 (s, 1H), 7.93-7.91 (s, 1H), 7.76-7.74 (m, 1H), 7.36-7.34 (m, 1H), 4.21 (s, 2H), 3.21 (s, 311), 2.49 (s, 3H), 2.10-2.01 (m, 3H).

(Z)-4-(5-(1,1-difluoroethyl)-2-methyl-3-((6-(methylsulfonyl)pyridin-3-yl)methyl)-1H-pyrrolo[3,2-b]pyridin-1-yl)-3-fluorobut-2-en-1-amine trihydrochloride (Compound 30)

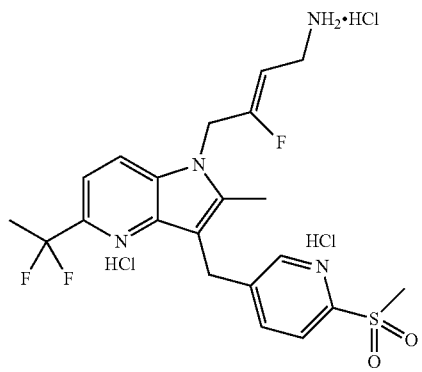

$^1$H NMR (300 MHz, DMSO-d$_6$) δ ppm: 8.82 (dd, J=2.1, 0.8 Hz, 1H), 8.06 (dd, J=8.8, 2.2 Hz, 1H), 8.03 (d, J=8.9 Hz, 1H), 7.95 (d, J=8.8 Hz, 1H), 7.46 (d, J=8.5 Hz, 1H), 5.18 (d, J=12.8 Hz, 2H), 5.01 (dt, J=36.2, 7.2 Hz, 1H), 4.26 (s, 2H), 3.43 (d, J=7.3 Hz, 2H), 3.22 (s, 3H), 2.56 (s, 3H), 2.07 (t, J=18.9 Hz, 3H).

Example 21

The following compound was prepared according to procedures AZ, AAA, AAB, AAC, J and Q.

(Z)-4-((1-(4-amino-2-fluorobut-2-en-1-yl)-2-methyl-1H-indol-3-yl)oxy)-N,N-dimethylbenzene-sulfonamide hydrochloride (Compound 21)

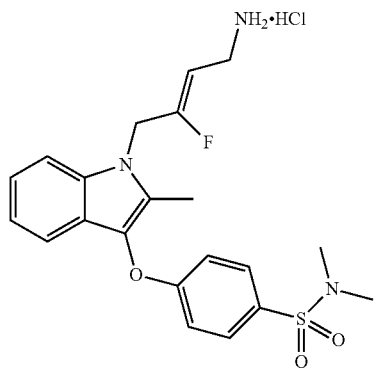

Procedure AZ: Preparation of 4-(chlorosulfonyl)phenyl acetate

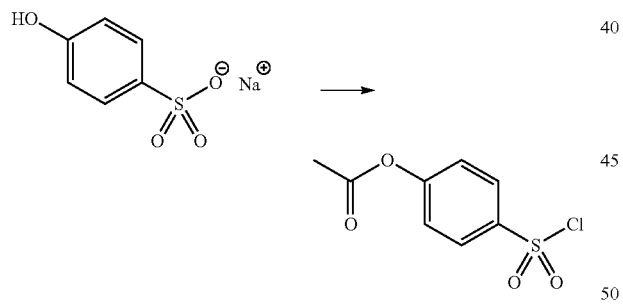

To a stirring mixture of acetic anhydride (33.9 g, 332 mmol) and triethylamine (59.4 mL, 426 mmol) was added sodium 4-hydroxybenzenesulfonate dihydrate (22.0 g, 94.8 mmol). The resulting mixture was stirred at rt overnight. The volatiles were removed in vacuo, and the residual water was removed by azeotrope with toluene. Hot ethyl acetate (250 mL) was added, and the solid was filtered from the hot solution and dried. To a stirring solution of the solid thus obtained, in neat thionyl chloride (66.0 mL, 900 mmol) was added DMF (4.40 mL, 56.9 mmol), and the reaction mixture was stirred at reflux for 2 h. After cooling to rt, the reaction mixture was poured onto ice/water (~250 mL), cautiously, and the product was extracted with dichloromethane (80 mL×2). The combined organics were dried over Na$_2$SO$_4$, and the solvent was removed in vacuo to afford the title compound 4-(chlorosulfonyl)phenyl acetate (14.8 g, 66%) as an off-white solid. $^1$H NMR (300 MHz, CDCl$_3$) δ ppm: 8.07 (d, J=9.1 Hz, 2H), 7.37 (d, J=9.1 Hz, 2H), 2.36 (s, 3H).

Procedure AAA: Preparation of 4-hydroxy-N,N-dimethylbenzenesulfonamide

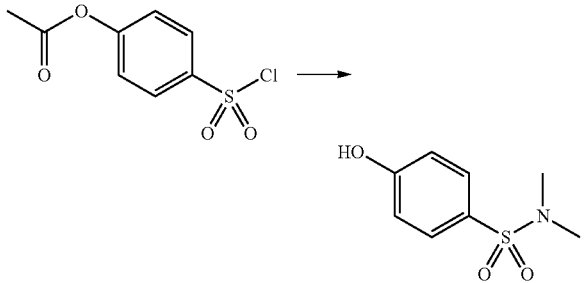

To a stirring mixture of dimethylamine hydrochloride (2.08 g, 25.6 mmol) in dichloromethane (20 mL), at 0° C. was added triethylamine (4.75 mL, 34.1 mmol). The resulting mixture was stirred at this temperature for 30 mins. To this was added pyridine (4.14 mL, 51.1 mmol) followed by a solution of 4-(chlorosulfonyl)phenyl acetate (2.00 g, 8.52 mmol) in dichloromethane (4 mL) dropwise. The reaction mixture was allowed to warm to rt, and stirring was continued overnight. The solvent was removed in vacuo, and the residue was taken up in ethyl acetate (25 mL). The organics were washed with aq. HCl (2 M, 25 mL), water (25 mL) and then brine (25 mL). After drying over Na$_2$SO$_4$, the solvent was removed in vacuo to afford the title compound 4-hydroxy-N,N-dimethylbenzenesulfonamide (1.57 g, 92%). $^1$H NMR (300 MHz, CDCl$_3$) δ ppm: 7.66 (d, J=8.8 Hz, 2H), 7.00 (d, J=8.5 Hz, 2H), 2.70 (s, 6H).

Procedure AAB: Preparation of N,N-dimethyl-4-(2-oxopropoxy)benzenesulfonamide

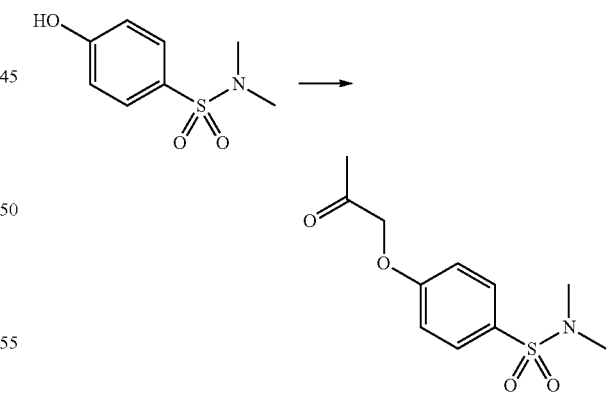

A solution of 1-chloropropan-2-one (0.24 mL, 3.01 mmol), 4-hydroxy-N,N-dimethylbenzenesulfonamide (550 mg, 2.74 mmol) and potassium carbonate (567 mg, 4.10 mmol) in DMF (2.5 mL) was stirred at rt for 1 h. The reaction mixture was diluted with water (25 mL) and the product was extracted with ethyl acetate (20 mL×3). The combined organic layer was washed with water (20 mL×2), dried over Na$_2$SO$_4$, and concentrated in vacuo to afford N,N-dimethyl-4-(2-oxopropoxy)benzenesulfonamide (520 mg, 74%) as a red colored oil that solidified on standing. ¹H NMR (300 MHz, CDCl₃) δ ppm: 7.75 (d, J=8.9 Hz, 2H), 7.01 (d, J=8.4 Hz, 2H), 4.66 (s, 2H), 2.70 (d, J=2.0 Hz, 6H), 2.32 (d, J=2.0 Hz, 3H).

Procedure AAC: Preparation of N,N-dimethyl-4-((2-methyl-1H-indol-3-yl)oxy)benzenesulfonamide

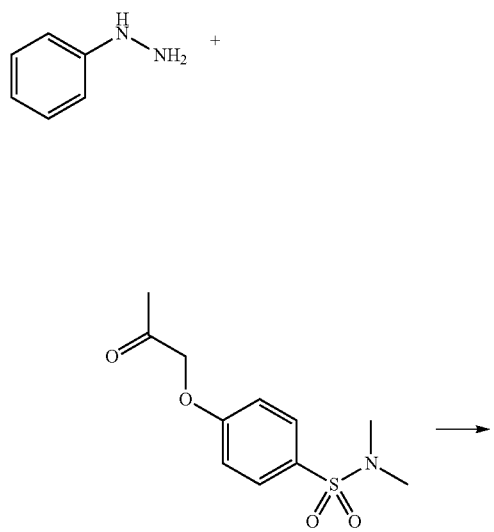

Acetic acid (0.1 mL) was added to a mixture of N,N-dimethyl-4-(2-oxopropoxy)benzenesulfonamide (514 mg, 2.00 mmol) and phenylhydrazine (216 mg, 2.00 mmol) in ethanol (10 mL) at rt. The resulting mixture was heated at reflux for 6 h. The reaction mixture was concentrated under vacuum when a brown colored, viscous residue was obtained. To this residue was added 4% aqueous sulphuric acid (5.00 mL, 2.00 mmol). The mixture was then heated at reflux for 2 h. The reaction mixture was cooled to rt, and the product was extracted with ethyl acetate (20 mL×3). The combined organics were dried over Na₂SO₄, concentrated and adsorbed onto silica gel. The crude material was purified using a Reveleris chromatography system to afford the title compound N,N-dimethyl-4-((2-methyl-1H-indol-3-yl)oxy)benzenesulfonamide (84.0 mg, 11%) as a brown solid. ¹H NMR (300 MHz, CDCl₃) δ ppm: 7.80 (s, 1H), 6.94-7.39 (m, 6H), 7.70 (d, J=6.7 Hz, 2H), 2.72 (s, 6H), 2.36 (d, J=2.1 Hz, 3H).

(Z)-4-((1-(4-amino-2-fluorobut-2-en-1-yl)-2-methyl-1H-indol-3-yl)oxy)-N,N-dimethylbenzene-sulfonamide hydrochloride (Compound 21)

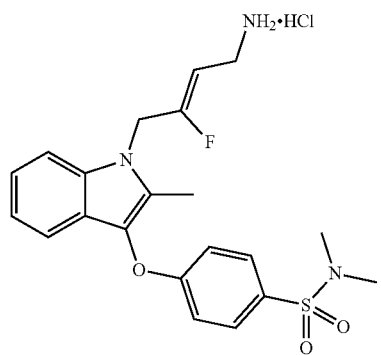

¹H NMR (300 MHz, Methanol-d₄) δ ppm: 7.74 (d, J=9.0 Hz, 2H), 7.48 (dd, J=8.2, 1.1 Hz, 1H), 7.24-7.16 (m, 2H), 7.13 (d, J=9.0 Hz, 2H), 7.05 (ddd, J=8.0, 6.9, 0.9 Hz, 1H), 5.07 (dd, J=8.6, 1.2 Hz, 2H), 4.80-4.73 (m, 2H), 4.82 (dt, J=34.9, 7.3 Hz, 1H), 3.63 (d, J=7.5 Hz, 21-1), 2.68 (s, 6H), 2.36 (s, 3H).

Example 22

The following compound was prepared according to procedures, AAD, AAE, AO, AAF, AAG, AAH, AAI, AAJ, AAK, J and Q.

(Z)-4-(5-cyclopropyl-2-methyl-3-((6-(methylsulfonyl)pyridin-3-yl)methyl)-1H-pyrrolo[3,2-b]pyridin-1-yl)-3-fluorobut-2-en-1-amine trihydrochloride (Compound 27)

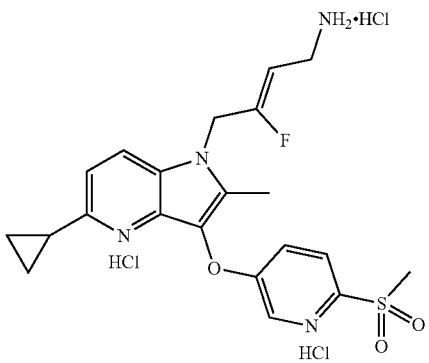

Procedure AAD: Preparation of 6-(methylthio)nicotinaldehyde

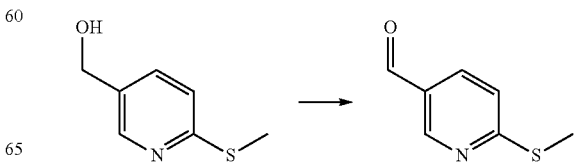

A suspension of (6-(methylthio)pyridin-3-yl)methanol (310 mg, 2.00 mmol) and manganese dioxide (1.39 g, 16.0 mmol) in CHCl$_3$ (10 mL) at rt was stirred overnight. The reaction mixture was filtered through Celite™, and the filtrated was concentrated in vacuo to afford the title compound 6-(methylthio)nicotinaldehyde (309 mg, 100%) as a yellow solid. $^1$H NMR (300 MHz, CDCl$_3$) δ ppm: 10.01 (d, J=0.6 Hz, 1H), 8.85 (dd, J=2.2, 0.8 Hz, 1H), 7.95 (dd, J=8.4, 2.2 Hz, 1H), 7.32 (dt, J=8.4, 0.8 Hz, 1H), 2.65 (s, 3H).

Procedure AAE: Preparation of 5-chloro-2-methyl-3-(methylthio)-1H-pyrrolo[3,2-b]pyridine

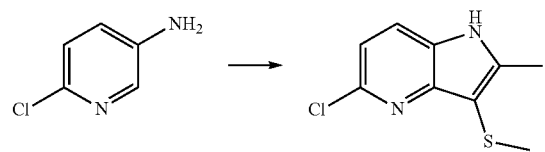

To a solution of 6-chloropyridin-3-amine (6.72 g, 62.0 mmol) in CH$_2$Cl$_2$ (150 mL) at −78° C. was added a solution of t-BuOCl (124 mmol, 14 mL) in CH$_2$Cl$_2$ (50 mL). The reaction stirred for 30 min prior to the addition of methylthioacetone (62.0 mmol, 6.47 g) in CH$_2$Cl$_2$ (50 mL). After 90 min, a solution of NEt$_3$ (62.0 mmol, 9.60 mL) in CH$_2$Cl$_2$ (50 mL) was added and the reaction warmed to ambient temperature. The reaction was quenched by the addition of water and the aqueous layer was extracted with CH$_2$Cl$_2$. The organic layer was dried over Na$_2$SO$_4$ and concentrated in vacuo. The residue was purified over silica gel, eluting with CH$_2$Cl$_2$/MeOH (20:1) to afford 5-chloro-2-methyl-3-(methylthio)-1H-pyrrolo[3,2-b]pyridine (9.50 g, 72%).

Procedure AAF: Preparation of tert-butyl 5-chloro-2-methyl-1H-pyrrolo[3,2-b]pyridine-1-carboxylate

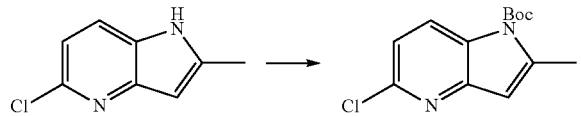 [SMILES: Cc1cc2nc(Cl)ccc2[nH]1 ; Cc1cc2nc(Cl)ccc2n1C(=O)OC(C)(C)C]

To a stirring solution of 5-chloro-2-methyl-1H-pyrrolo[3,2-b]pyridine (250 mg, 1.50 mmol) in DMF (1.5 mL) at rt was added di-tert-butyl dicarbonate (655 mg, 3.00 mmol) followed by 4-(dimethylamino)pyridine (183 mg, 1.50 mmol). The resulting mixture was stirred at rt for 1 h. The reaction mixture was diluted with water (15 mL). The resulting solid was filtered, and washed with water (3 mL×2). The solid thus obtained was dissolved in dichloromethane (50 mL), dried over Na$_2$SO$_4$ and concentrated in vacuo to afford tert-butyl 5-chloro-2-methyl-1H-pyrrolo[3, 2-b]pyridine-1-carboxylate (380 mg, 95%) as a tan solid. $^1$H NMR (300 MHz, CDCl$_3$) δ ppm: 8.28 (dd, J=8.7, 0.7 Hz, 1H), 7.15 (d, J=8.7 Hz, 1H), 6.48 (dq, J=1.0 Hz, 1H), 2.66 (d, J=1.1 Hz, 3H), 1.70 (s, 9H).

Procedure AAG: Preparation of tert-butyl 5-cyclopropyl-2-methyl-1H-pyrrolo[3,2-b]pyridine-1-carboxylate

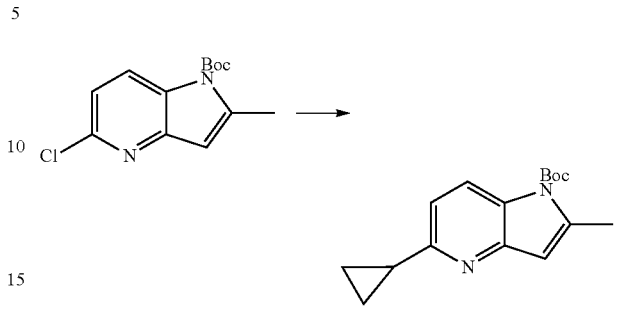

A microwave vessel charged with tert-butyl 5-chloro-2-methyl-1H-pyrrolo[3,2-b]pyridine-1-carboxylate (150 mg, 0.56 mmol), cyclopropylboronic acid (96.6 mg, 1.12 mmol), potassium phosphate tribasic (389 mg, 1.69 mmol) and tricyclohexylphosphane (31.5 mg, 0.11 mmol) in toluene (mL) was degassed by bubbling nitrogen through it for 10 mins. To this was added diacetoxypalladium (12.6 mg, 0.06 mmol) and the vessel was sealed. The reaction vessel was then heated at 120° C. for 2 h. After cooling to rt, the reaction mixture was diluted with ethyl acetate (20 mL), and then filtered through Celite™. The filtrate was washed with water (10 mL) and brine (10 mL), dried over Na$_2$SO$_4$, and concentrated in vacuo. Purification was performed using a 40 g RediSep cartridge, eluting over a gradient of 10-50% ethyl acetate in hexane to afford the title compound tert-butyl 5-cyclopropyl-2-methyl-1H-pyrrolo[3,2-b]pyridine-1-carboxylate (81.0 mg, 53%) as a white solid.

Procedure AAH: Preparation of 5-cyclopropyl-2-methyl-1H-pyrrolo[3,2-b]pyridine

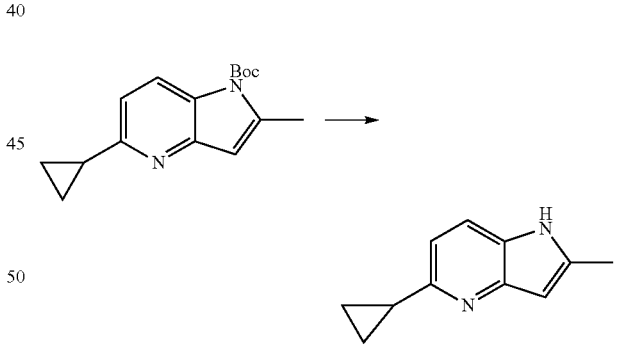

To a stirring solution of tert-butyl 5-cyclopropyl-2-methyl-1H-pyrrolo[3,2-b]pyridine-1-carboxylate (183 mg, 0.67 mmol) in dichloromethane (2 mL) at rt was added trifluoroacetic acid (2.00 mL, 0.67 mmol). The resulting mixture was stirred at rt for 3 h, and the solvent was removed in vacuo. The residue was taken up in ethyl acetate, and washed with sat. aq. NaHCO$_3$, water, brine, dried over Na$_2$SO$_4$, and concentrated in vacuo to afford the title compound 5-cyclopropyl-2-methyl-1H-pyrrolo[3,2-b]pyridine (115 mg, 99%) as a white solid. $^1$H NMR (300 MHz, CDCl$_3$) δ ppm: 10.88 (s, 1H), 7.95 (d, J=8.4 Hz, 1H), 6.72 (d, J=8.4 Hz, 1H), 6.27 (d, J=1.7 Hz, 1H), 2.39-2.28 (m, 1H), 1.39-1.27 (m, 2H), 1.11-1.02 (m, 2H).

123

Procedure AAI: Preparation of tert-butyl 5-cyclopropyl-3-(hydroxy(6-(methylthio)pyridin-3-yl)methyl)-2-methyl-1H-pyrrolo[3,2-b]pyridine-1-carboxylate

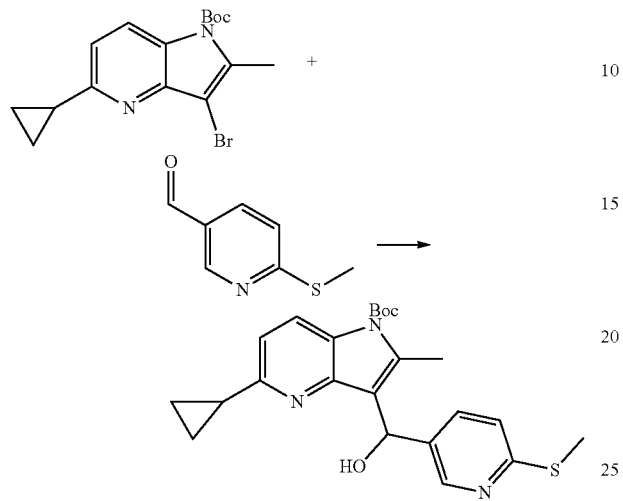

To a stirring solution of tert-butyl 3-bromo-5-cyclopropyl-2-methyl-1H-pyrrolo[3,2-b]pyridine-1-carboxylate (154 mg, 0.44 mmol) in THF (3 mL) at −78° C. under nitrogen was added tert-butyllithium (0.57 mL, 0.96 mmol) dropwise. After Stirring for 2 min, a solution of 6-(methylthio)nicotinaldehyde (73.9 mg, 0.48 mmol) in THF (1 mL) was added. Stirring was continued at −78° C. for 30 min, and then warmed to rt. The reaction mixture was diluted with water (1 mL) and sat. aq. NH$_4$Cl (1 mL), then poured into a mixture of ethyl acetate (20 mL) and water (10 mL). The organic layer was washed with brine, dried over Na$_2$SO$_4$ and concentrated in vacuo. Purification was performed using a 12 g RediSep cartridge eluting over a gradient of 10-40% ethyl acetate in hexane to afford tert-butyl 5-cyclopropyl-3-(hydroxy(6-(methylthio)pyridin-3-yl)methyl)-2-methyl-1H-pyrrolo[3,2-b]pyridine-1-carboxylate (84.0 mg, 38%) as a colorless oil. $^1$H NMR (300 MHz, CDCl$_3$) δ ppm: 8.44 (dt, J=2.4, 0.7 Hz, 1H), 8.15 (d, J=8.6 Hz, 1H), 7.67 (ddd, J=8.3, 2.4, 0.6 Hz, 1H), 7.14 (dd, J=8.3, 0.9 Hz, 1H), 7.05 (d, J=8.6 Hz, 1H), 6.58 (d, J=9.0 Hz, 1H), 5.95 (d, J=7.9 Hz, 1H), 2.15-2.05 (m, 1H), 1.58 (s, 9H), 1.28 (t, J=7.2 Hz, 2H), 1.05-0.97 (m, 2H).

Procedure AAJ: Preparation of 5-cyclopropyl-2-methyl-3-((6-(methylthio)pyridin-3-yl)methyl)-1H-pyrrolo[3,2-b]pyridine

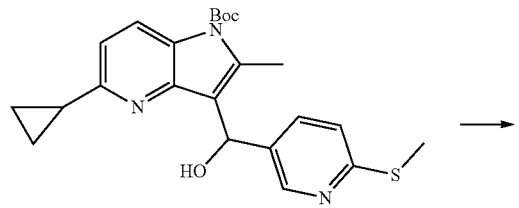

124

-continued

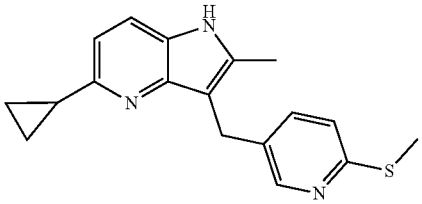

To a stirring solution of tert-butyl 5-cyclopropyl-3-(hydroxy(6-(methylthio)pyridin-3-yl)methyl)-2-methyl-1H-pyrrolo[3,2-b]pyridine-1-carboxylate (84.0 mg, 0.17 mmol) in dichloromethane (2 mL) under nitrogen at rt was added trifluoroacetic acid (0.13 mL, 1.68 mmol) followed by triethylsilane (0.08 mL, 0.50 mmol). The resulting mixture was stirred at rt for 4 h. All volatiles were removed in vacuo to afford crude 5-cyclopropyl-2-methyl-3-((6-(methylthio)pyridin-3-yl)methyl)-1H-pyrrolo[3,2-b]pyridine (60 mg). This material was progressed to the next step without purification.

Procedure AAK: Preparation of 5-cyclopropyl-2-methyl-3-((6-(methylsulfonyl)pyridin-3-yl)methyl)-1H-pyrrolo[3,2-b]pyridine

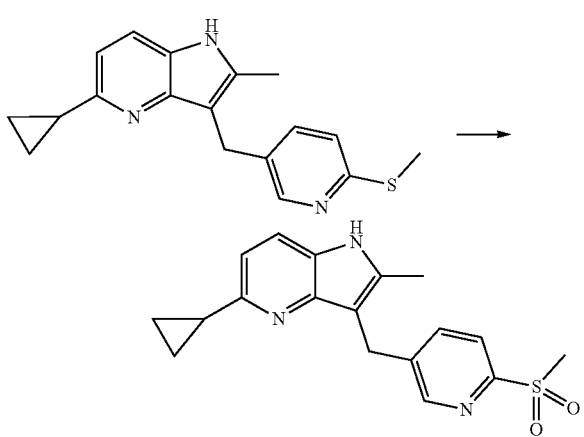

To a stirring solution of 5-cyclopropyl-2-methyl-3-((6-(methylthio)pyridin-3-yl)methyl)-1H-pyrrolo[3,2-b]pyridine (61.0 mg, 0.17 mmol) in THF:MeOH (1:1, 4 mL) was added Oxone™ (412 mg, 0.67 mmol) as a solution in water (4 mL). The resulting mixture was stirred at rt for 20 mins. The reaction was partitioned between ethyl acetate and water, and organic layer was washed with brine, dried over Na$_2$SO$_4$, and concentrated in vacuo. Purification was performed using a 12 g RediSep cartridge, eluting over a gradient of 20-70% ethyl acetate in hexane to afford the title compound 5-cyclopropyl-2-methyl-3-((6-(methylsulfonyl)pyridin-3-yl)methyl)-1H-pyrrolo[3,2-b]pyridine (31.0 mg, 54%) as a colorless foam. $^1$H NMR (300 MHz, CDCl$_3$) δ ppm: 8.69 (s, 1H), 8.46 (s, 1H), 7.96-7.87 (m, 2H), 7.44 (d, J=8.3 Hz, 1H), 6.82 (d, J=8.3 Hz, 1H), 4.18 (s, 2H), 3.19 (s, 3H), 2.38 (s, 3H).

125

(Z)-4-(5-cyclopropyl-2-methyl-3-((6-(methylsulfonyl)pyridin-3-yl)methyl)-1H-pyrrolo[3,2-b]pyridin-1-yl)-3-fluorobut-2-en-1-amine trihydrochloride (Compound 27)

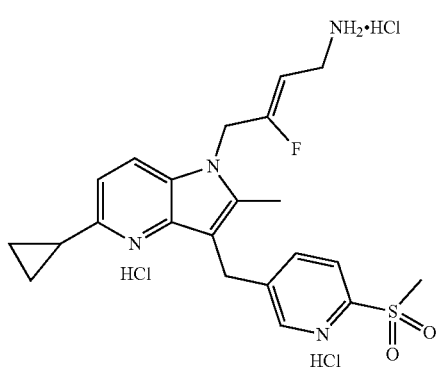

$^1$H NMR (300 MHz, Methanol-d$_4$) δ ppm: 8.64 (dd, J=2.2, 0.9 Hz, 1H), 8.57 (d, J=8.7 Hz, 1H), 8.03 (dd, J=8.1, 0.8 Hz, 1H), 7.87 (dd, J=8.1, 2.2 Hz, 1H), 7.19 (d, J=8.7 Hz, 1H), 5.34 (d, J=13.1 Hz, 2H), 4.54 (s, 2H), 5.30 (dt, J=34.5, 7.4 Hz, 1H), 3.65 (d, J=7.3 Hz, 2H), 3.22 (s, 3H), 2.59 (s, 3H), 2.49 (tt, J=8.3, 5.0 Hz, 1H), 1.46-1.35 (m, 2H), 1.22-1.13 (m, 2H).

Example 23

The following compound was prepared according to procedures E, AI, AJ, AK, AL, AAL, AAM, J, AAN and Q.

(Z)-4-((1-(4-amino-2-fluorobut-2-en-1-yl)-2-(1-hydroxyethyl)-1H-pyrrolo[3,2-b]pyridin-3-yl)methyl)-N,N-dimethylbenzenesulfonamide dihydrochloride (Compound 29)

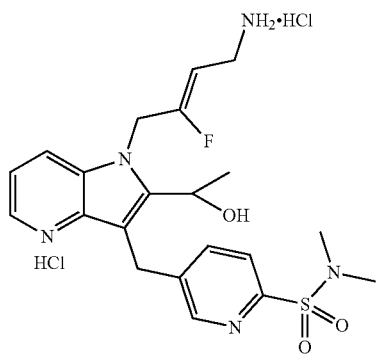

126

Procedure AAL: Preparation of 4-((2-(hydroxymethyl)-1H-pyrrolo[3,2-b]pyridin-3-yl)methyl)-N,N-dimethylbenzenesulfonamide

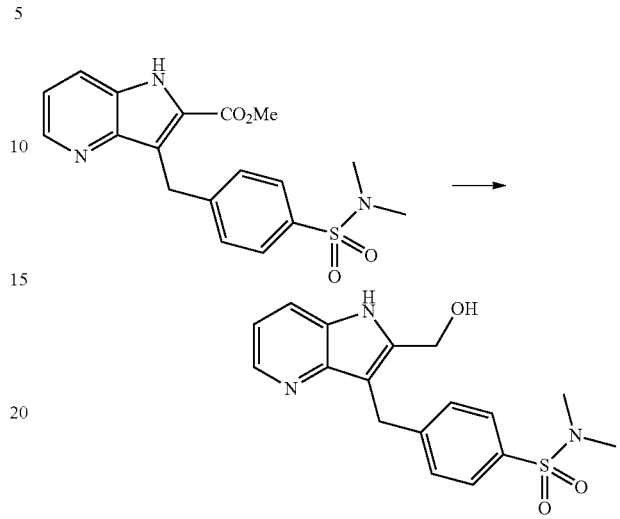

To a stirring solution of methyl 3-(4-(N,N-dimethylsulfamoyl)benzyl)-1H-pyrrolo[3,2-b]pyridine-2-carboxylate (165 mg, 0.4418 mmol) in THF (10 mL) at rt was added diisobutylaluminum hydride (1 M in CH$_2$Cl$_2$, 2.21 mL, 2.21 mmol) drop-wise. The resulting mixture was stirred at rt for 1 h. The reaction mixture was diluted with sat. aq. NH$_4$Cl (25 mL), and the product was extracted with ethyl acetate (20 mL×3). The combined organics were dried over Na$_2$SO$_4$ and concentrated in vacuo to afford 4-((2-(hydroxymethyl)-1H-pyrrolo[3,2-b]pyridin-3-yl)methyl)-N,N-dimethylbenzenesulfonamide (138 mg, 90%) as an off white solid. $^1$H NMR (300 MHz, CDCl$_3$) δ ppm: 8.82 (s, 1H), 8.39 (dd, J=4.7, 1.4 Hz, 1H), 7.64 (dd, J=8.1, 1.4 Hz, 1H), 7.53 (d, J=8.3 Hz, 2H), 7.33 (d, J=8.4 Hz, 2H), 7.10 (dd, J=8.2, 4.7 Hz, 1H), 4.78 (s, 2H), 4.15 (s, 2H), 2.64 (s, 6H).

Procedure AAM: Preparation of 4-((2-formyl-1H-pyrrolo[3,2-b]pyridin-3-yl)methyl)-N,N-dimethylbenzenesulfonamide

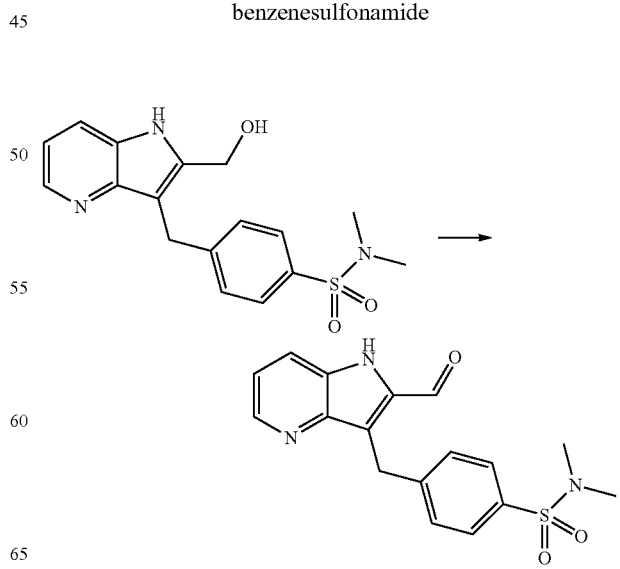

To a stirring solution of 4-((2-(hydroxymethyl)-1H-pyrrolo[3,2-b]pyridin-3-yl)methyl)-N,N-dimethylbenzenesulfonamide (138 mg, 0.40 mmol) in dichloromethane at rt was added Dess-Martin periodinane (237 mg, 0.56 mmol). The resulting mixture was stirred at rt for 1 h. Isopropanol (0.5 mL) was then added to quench unreacted Dess-Martin periodinane. The crude reaction mixture was adsorbed directly onto silica gel and purification was performed on a Reveleris automated chromatography system to give 4-((2-formyl-1H-pyrrolo[3,2-b]pyridin-3-yl)methyl)-N,N-dimethylbenzenesulfonamide (138 mg, 100%) as a white solid. $^1$H NMR (300 MHz, DMSO-$d_6$) δ ppm: 12.08 (s, 1H), 10.26 (s, 1H), 8.52 (dd, J=4.3, 1.4 Hz, 1H), 7.84 (dd, J=8.4, 1.4 Hz, 1H), 7.67-7.59 (m, 4H), 7.36 (dd, J=8.4, 4.4 Hz, 1H), 4.64 (s, 2H), 2.56 (s, 6H).

Procedure AAN: Preparation of tert-butyl (Z)-(4-(3-(4-(N,N-dimethylsulfamoyl)benzyl)-2-(1-hydroxyethyl)-1H-pyrrolo[3,2-b]pyridin-1-yl)-3-fluorobut-2-en-1-yl)carbamate

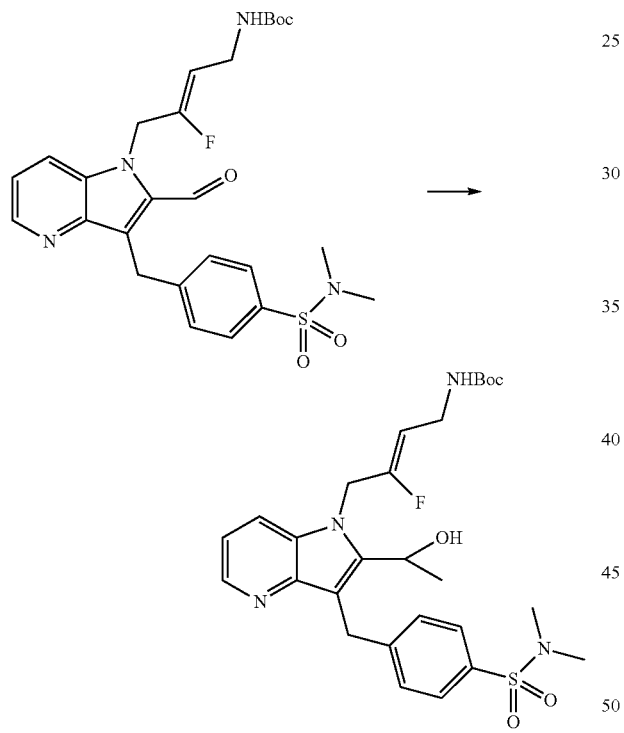

To a stirring solution of tert-butyl (Z)-(4-(3-(4-(N,N-dimethylsulfamoyl)benzyl)-2-formyl-1H-pyrrolo[3,2-b]pyridin-1-yl)-3-fluorobut-2-en-1-yl)carbamate (57.0 mg, 0.11 mmol) in THF (2 mL) at rt was added methylmagnesium bromide (0.32 mL, 0.97 mmol). The resulting mixture was stirred at rt for 1 h. The reaction was quenched by the addition of sat. aq. NH$_4$Cl (0.5 mL), and the product was extracted with ethyl acetate. The combined organics were dried over Na$_2$SO$_4$ and concentrated in vacuo. The crude material was purified by reverse-phase chromatography to afford tert-butyl (Z)-(4-(3-(4-(N,N-dimethylsulfamoyl)benzyl)-2-(1-hydroxyethyl)-1H-pyrrolo[3,2-b]pyridin-1-yl)-3-fluorobut-2-en-1-yl)carbamate (30.0 mg, 51%) as a white solid. $^1$H NMR (300 MHz, CDCl$_3$) δ ppm: 8.43 (dd, J=4.7, 1.3 Hz, 1H), 7.63 (dd, J=8.2, 1.3 Hz, 1H), 7.57 (d, J=8.3 Hz, 2H), 7.35 (d, J=8.3 Hz, 2H), 7.16 (dd, J=8.3, 4.7 Hz, 114), 5.31 (q, J=6.8 Hz, 1H), 5.15 (dd, J=17.3, 7.4 Hz, 1H), 5.00 (dd, J=17.2, 8.4 Hz, 1H), 4.66 (s, 1H), 4.58 (dt, J=36.1, 6.9 Hz, 2H), 4.37 (d, J=16.3 Hz, 1H), 4.18 (d, J=16.9 Hz, 1H), 3.73 (q, J=6.7, 6.0 Hz, 2H), 2.65 (s, 6H), 2.06 (s, 3H), 1.40 (s, 9H).

(Z)-4-((1-(4-amino-2-fluorobut-2-en-1-yl)-2-(1-hydroxyethyl)-1H-pyrrolo[3,2-b]pyridin-3-yl)methyl)-N,N-dimethylbenzenesulfonamide dihydrochloride (Compound 29)

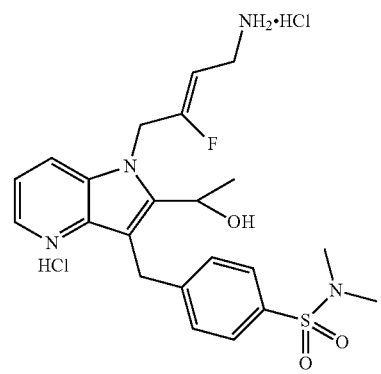

$^1$H NMR (300 MHz, Methanol-$d_4$) δ ppm: 8.75 (d, J=8.3 Hz, 1H), 8.57 (d, J=5.8 Hz, 1H), 7.76 (dd, J=8.4, 5.9 Hz, 1H), 7.73 (d, J=8.3 Hz, 2H), 7.43 (d, J=8.1 Hz, 2H), 5.69 (dd, J=17.1, 10.8 Hz, 1H), 5.55 (dd, J=17.3, 12.5 Hz, 1H), 5.45 (q, J=6.7 Hz, 1H), 5.23 (dt, J=34.5, 7.4 Hz, 1H), 4.60 (d, J=17.4 Hz, 1H), 4.49 (d, J=17.4 Hz, 1H), 3.67 (d, J=7.3 Hz, 2H), 2.66 (s, 6H), 1.47 (d, J=6.8 Hz, 3H).

Example 24

The following compound was prepared according to procedures E, AI, AAO, AK, AL, AAP, J and Q.

(Z)-4-((1-(4-amino-2-fluorobut-2-en-1-yl)-5-(2-hydroxypropan-2-yl)-2-methyl-1H-pyrrolo[3,2-b]pyridin-3-yl)methyl)-N,N-dimethylbenzenesulfonamide dihydrochloride (Compound 28)

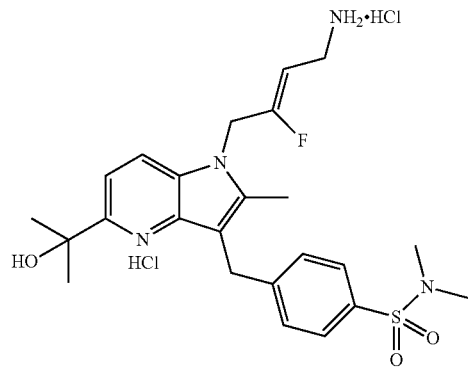

Procedure AAO: Preparation of 2-(2-methyl-1H-pyrrolo[3,2-b]pyridin-5-yl)propan-2-ol

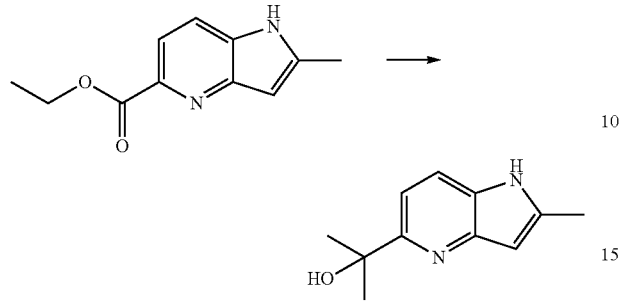

To a stirring solution of ethyl 2-methyl-1H-pyrrolo[3,2-b]pyridine-5-carboxylate (1.23 g, 6.00 mmol) in THF (20 mL) at rt was added methylmagnesiun bromide (3 M in THF, 10.0 mL, 30.0 mmol) over 5 min. The mixture was stirred at rt for 30 min. Additional methylmagnesiun bromide (3 M in THF, 6.00 mL, 18.0 mmol) was added and stirring was continued for 30 min at rt, and then at reflux for 1 h. The reaction mixture was quenched by addition of sat. aq. NH$_4$Cl (45 mL). The product was extracted with ethyl acetate (40 mL×3). The combined organic layer was dried over Na$_2$SO$_4$ and concentrated in vacuo. The crude material was purified over silica gel employing a Revelaris chromatography system to afford 2-(2-methyl-1H-pyrrolo[3,2-b]pyridin-5-yl)propan-2-ol (730 mg, 64%) as a pale yellow solid. $^1$H NMR (300 MHz, CDCl$_3$) δ ppm: 7.99 (s, 1H), 7.58 (dd, J=8.4, 0.9 Hz, 1H), 7.10 (d, J=8.4 Hz, 1H), 6.42 (dq, J=2.2, 1.1 Hz, 1H), 5.68 (s, 1H), 2.53 (d, J=0.9 Hz, 3H), 1.59 (d, J=2.2 Hz, 6H).

Procedure AAP: Preparation of 4-((5-(2-hydroxypropan-2-yl)-2-methyl-1H-pyrrolo[3,2-b]pyridin-3-yl)methyl)-N,N-dimethylbenzenesulfonamide

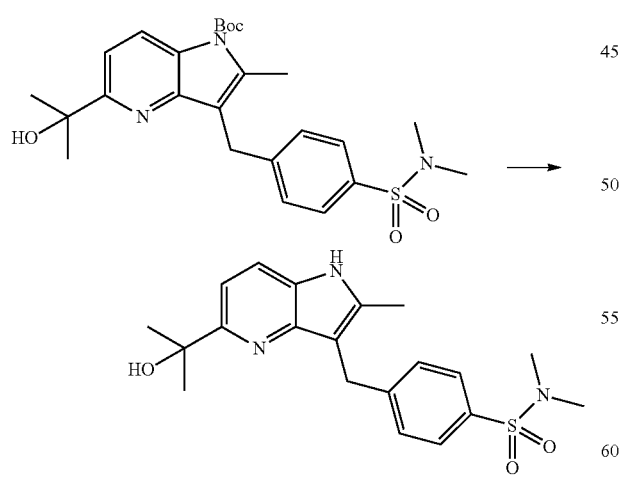

To a stirring mixture of tort-butyl 3-(4-(N,N-dimethylsulfamoyl)benzyl)-5-(2-hydroxypropan-2-yl)-2-methyl-1H-pyrrolo[3,2-b]pyridine-1-carboxylate (67.0 mg, 0.11 mmol) in THF (2 mL) and methanol (2 mL) at rt was added aqueous KOH (10% w/w, 2.00 mL). The resulting mixture was heated at reflux for 8 h. The reaction mixture was concentrated in vacuo to remove organic solvents, and then diluted with water (25 mL). The product was extracted with ethyl acetate (25 mL×3). The combined organics were dried over Na$_2$SO$_4$ and concentrated in vacuo to afford crude 4-((5-(2-hydroxypropan-2-yl)-2-methyl-1H-pyrrolo[3,2-b]pyridin-3-yl)methyl-N,N-dimethylbenzenesulfonamide (49 mg). This material was progressed to the next step without purification. $^1$H NMR (300 MHz, CDCl$_3$) δ ppm: 8.03 (s, 1H), 7.66 (d, J=8.3 Hz, 2H), 7.60 (d, J=8.4 Hz, 1H), 7.46 (d, J=8.5 Hz, 2H), 7.10 (d, J=8.4 Hz, 1H), 4.25 (s, 2H), 2.69 (s, 6H), 2.44 (s, 3H), 1.57 (s, 6H).

(Z)-4-((1-(4-amino-2-fluorobut-2-en-1-yl)-5-(2-hydroxypropan-2-yl)-2-methyl-1H-pyrrolo[3,2-b]pyridin-3-yl)methyl)-N,N-dimethylbenzenesulfonamide dihydrochloride (Compound 28)

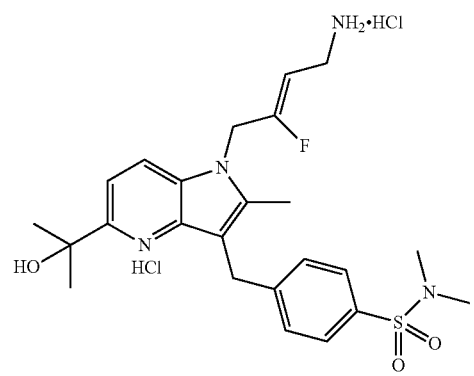

$^1$H NMR (300 MHz, Methanol-d$_4$) δ ppm: 8.67 (d, J=8.3 Hz, 1H), 7.78-7.67 (m, 3H), 7.48 (d, J=7.8 Hz, 2H), 5.38 (d, J=13.2 Hz, 2H), 5.25-5.40 (m, 1H), 4.56 (s, 2H), 3.66 (d, J=6.8 Hz, 2H), 2.67 (s, 6H), 2.64 (s, 3H), 1.69 (s, 6H).

Example 25

The following compound was prepared according to procedures AAQ, AAR, AAS, AAT, AAU and AAV.

(Z)-4-((1-(4-amino-2-fluorobut-2-en-1-yl)-2-methyl-1H-pyrrolo[3,2-c]pyridin-3-yl)methyl)-N,N-dimethylbenzenesulfonamide dihydrochloride (Compound 32)

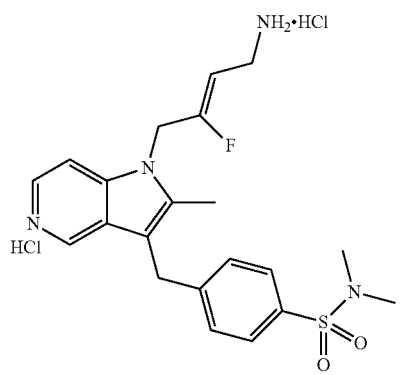

Procedure AAQ: Preparation of tert-butyl (3-(2-hydroxypropyl)pyridin-4-yl)carbamate

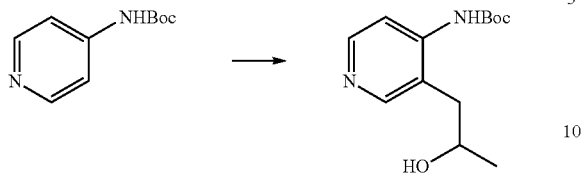

To a solution of tert-butyl pyridin-4-ylcarbamate (12.9 g, 66 mmol) in THF (250 mL) was added t-BuLi (1.6 M, 100 mL, 160 mmol) dropwise at −78° C. followed by propylene oxide (11.2 ml, 160 mmol). The mixture was allowed to warm to rt, and stirring was continued overnight. The reaction mixture was quenched with aq. NH$_4$Cl, extracted with ethyl acetate (100 mL×3), dried over Na$_2$SO$_4$ and concentrated in vacuo. The crude residue was purified over silica gel eluting with petroleum ether/ethyl acetate 5/1 to 2/1) to afford tert-butyl (3-(2-hydroxypropyl)pyridin-4-yl)carbamate (10.0 g, 60% yield) as a slightly yellow solid. $^1$H-NMR (300 MHz, CDCl$_3$): δ ppm: 8.91 (bs, 1H), 8.28-8.27 (m, 1H), 8.13 (s, 1H), 7.93-7.91 (m, 1H), 4.19-4.12 (m, 1H), 2.82-2.76 (m, 1H), 2.70-2.63 (m, 1H), 1.51 (s, 9H), 1.27-1.22 (m, 3H).

Procedure AAR: Preparation of tert-butyl (3-(2-oxopropyl)pyridin-4-yl)carbamate

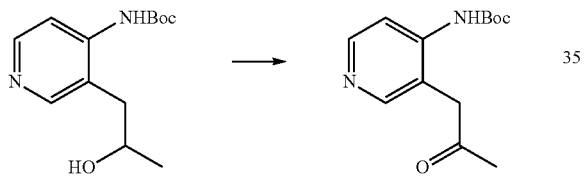

To a solution of tert-butyl (3-(2-hydroxypropyl)pyridin-4-yl)carbamate (3.00 g, 11.8 mmol) in dichloromethane (25 mL) was added PCC (2.00 g, 9.30 mmol), and the resulting mixture was stirred at rt overnight. The pH was adjusted to 9 with aq. Na$_2$CO$_3$, and the product was extracted with ethyl acetate (50 mL×3), dried over Na$_2$SO$_4$ and concentrated in vacuo. The residue was purified over silica gel eluting with petroleum ether/ethyl acetate 5/1 then 2/1 to afford tert-butyl (3-(2-hydroxypropyl)pyridin-4-yl)carbamate (2.00 g, 66% yield) as a white solid. $^1$H-NMR (300 MHz, CDCl$_3$): δ ppm: 8.42-8.407 (m, 1H), 8.32 (s, 1H), 8.02-8.00 (m, 1H), 7.86 (s, 1H), 3.68 (s, 2H), 2.30 (s, 3H), 1.54 (s, 9H).

Procedure AAS: Preparation of tert-butyl (3-(1-(4-(N,N-dimethylsulfamoyl)phenyl)-3-oxobutan-2-yl)pyridin-4-yl)carbamate

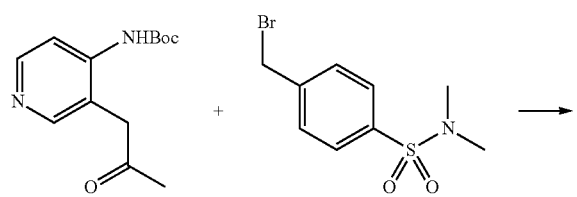

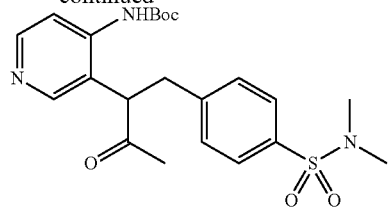

To a solution of tert-butyl (3-(2-oxopropyl)pyridin-4-yl)carbamate (820 mg, 3.30 mmol) in THF (25 mL) at 0° C. was added t-BuONa (314 mg, 3.30 mmol) and TBAB (105 mg, 0.33 mmol). The mixture was stirred for 10 mins before addition of 4-(bromomethyl)-N,N-dimethylbenzenesulfonamide (950 mg, 3.40 mmol). The reaction mixture was then warmed to rt and stirring was continued for 3 h. The mixture was diluted with water, and the product was extracted with ethyl acetate (50 mL×3). The combined organics were dried over Na$_2$SO$_4$ and concentrated in vacuo to give tert-butyl (3-(1-(4-(N,N-dimethylsulfamoyl)phenyl)-3-oxobutan-2-yl)pyridin-4-yl)carbamate (800 mg, 60% yield), which was used directly in next step without further purification.

Procedure AAT: Preparation of N,N-dimethyl-4-((2-methyl-1H-pyrrolo[3,2-c]pyridin-3-yl)methyl)benzenesulfonamide

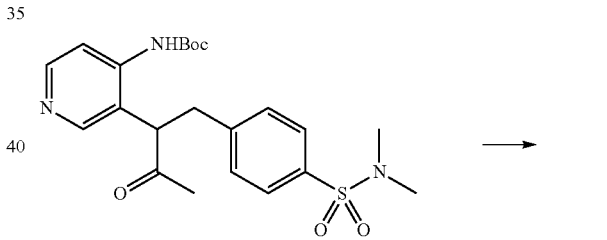

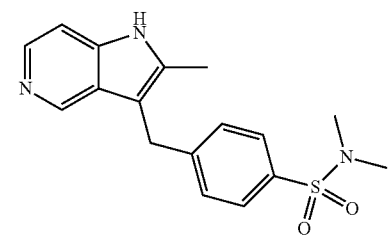

A solution of tert-butyl (3-(1-(4-(N,N-dimethylsulfamoyl)phenyl)-3-oxobutan-2-yl)pyridin-4-yl)carbamate (800 mg, 1.78 mmol) in HCl/dioxane (20 ml, 4 M, 80 mmol) was stirred at rt for 4 h. The solvent was removed and the crude material was purified by prep-HPLC to afford N,N-dimethyl-4-((2-methyl-1H-pyrrolo[3,2-c]pyridin-3-yl)methyl)benzenesulfonamide (320 mg, 54% yield) as white solid. $^1$H-NMR (300 MHz, CDCl$_3$): δ11.30 (s, 1H), 8.56 (s, 1H), 8.05-8.03 (m, 1H), 7.63-7.60 (m, 2H), 7.49-7.46 (m, 2H), 7.22-7.20 (m, 1H), 4.14 (s, 2H), 2.54 (s, 6H), 2.38 (s, 3H).

Procedure AAU: Preparation of tert-butyl (Z)-(4-(3-(4-(N,N-dimethylsulfamoyl)benzyl)-2-methyl-1H-pyrrolo[3,2-c]pyridin-1-yl)-3-fluorobut-2-en-1-yl)carbamate

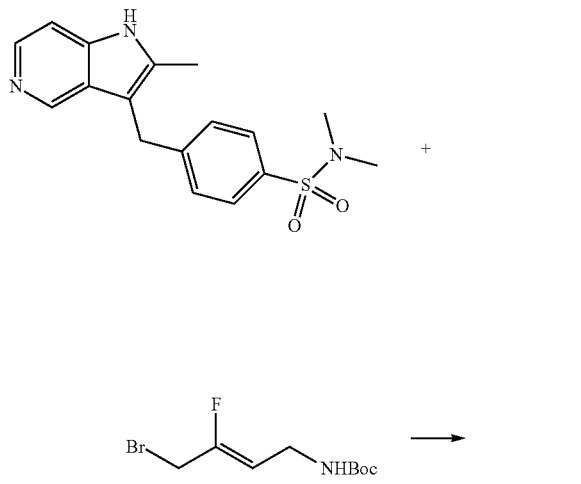

To a stirring solution N,N-dimethyl-4-((2-methyl-1H-pyrrolo[3,2-c]pyridin-3-yl)methyl)benzene-sulfonamide (320 mg, 0.97 mmol) in DMF (10 mL) at 0° C. was added NaH (60%, 42.0 mg, 1.16 mmol) portion-wise. The resulting mixture was stirred for 30 min before addition of text-butyl (Z)-(4-bromo-3-fluorobut-2-en-1-yl)carbamate (260 mg, 0.97 mmol). Stirring was then continued at rt for 3 h. The reaction mixture was partitioned between ethyl acetate (1 L), and water. The organic layer was washed with brine, dried over Na$_2$SO$_4$, and then concentrated in vacuo. The crude residue was purified by prep-HPLC to afford tert-butyl (Z)-(4-(3-(4-(N,N-dimethylsulfamoyl)benzyl)-2-methyl-1H-pyrrolo[3,2-c]pyridin-1-yl)-3-fluorobut-2-en-1-yl)carbamate (150 mg, 30%) as a white solid. $^1$H-NMR (300 MHz, CDCl$_3$): δ ppm: 8.62 (s, 1H), 8.30-8.28 (m, 1H), 7.67-7.64 (m, 2H), 7.35-7.32 (m, 2H), 7.18-7.16 (m, 1H), 4.81-4.57 (m, 4H), 4.18 (s, 2H), 3.78 (s, 2H), 2.67 (s, 6H), 2.42 (s, 3H), 1.41 (s, 9H).

Procedure AAV: Preparation of (Z)-4-((1-(4-amino-2-fluorobut-2-en-1-yl)-2-methyl-1H-pyrrolo[3,2-c]pyridin-3-yl)methyl)-N,N-dimethylbenzenesulfonamide dihydrochloride (Compound 32)

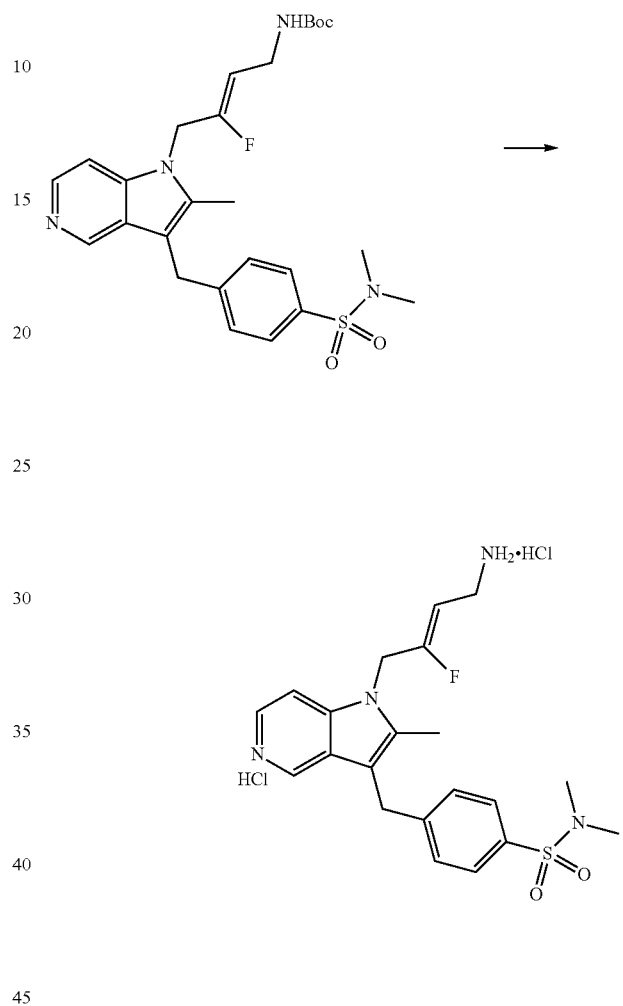

To a solution of tort-butyl (Z)-(4-(3-(4-(N,N-dimethylsulfamoyl)benzyl)-2-methyl-1H-pyrrolo[3,2-c]pyridin-1-yl)-3-fluorobut-2-en-1-yl)carbamate (150 mg, 0.43 mmol) dissolved in dioxane (10 mL) was added HCl (4M, 10 mL, dissolved in dioxane) The resulting mixture was stirred at rt for 2 h. The solvent was evaporated in vacuo, and the crude material was purified by prep-HPLC to afford (Z)-4-((1-(4-amino-2-fluorobut-2-en-1-yl)-2-methyl-1H-pyrrolo[3,2-c]pyridin-3-yl)methyl)-N,N-dimethylbenzene-sulfonamide hydrochloride (120 mg, 90%) as a white solid. $^1$H-NMR (400 MHz, DMSO-d$_6$): δ ppm: 9.19 (s, 1H), 8.51-8.49 (m, 1H), 8.27-8.19 (m, 4H), 7.68-7.65 (m, 2H), 7.53-7.51 (m, 2H), 5.42-5.27 (m, 3H), 4.37 (s, 2H), 3.47-3.46 (m, 2H), 2.58-2.51 (m, 9H).

Example 26

The following compound was made according to procedures AAW, AAX, AAY, AAZ, AAAA, ARAB, AAAC, AAAD, AAU and AAV.

(Z)-4-(2,6-dimethyl-3-(4-(methylsulfonyl)benzyl)-1H-pyrrolo[3,2-c]pyridin-1-yl)-3-fluorobut-2-en-1-amine dihydrochloride (Compound 36)

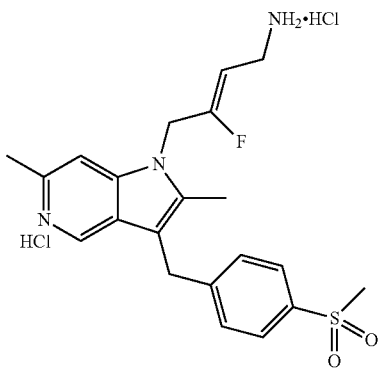

Procedure AAW: Preparation of 5-bromo-2-methylpyridine 1-oxide

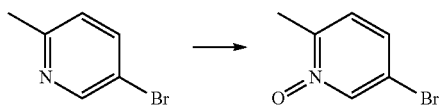

To a solution of 5-bromo-2-methylpyridine (5.0 g, 29.6 mmol) in dichloromethane (50 mL) was added mCPBA (7.50 g, 43.6 mmol). The resulting mixture was stirred at rt for 12 h. The reaction mixture was washed with sat. $Na_2S_2O_3$, dried over $Na_2SO_4$, and evaporated in vacuo. The crude material was purified over silica gel eluting with petroleum ether/ethyl acetate 2/1 then 1/2 to afford 5-bromo-2-methylpyridine 1-oxide (5.10 g, 93% yield) as a yellow solid. $^1$H-NMR (400 MHz, DMSO-$d_6$): δ ppm: 8.41 (s, 1H), 7.32-7.29 (m, 1H), 7.14-7.12 (m, 1H), 2.46 (s, 3H).

Procedure AAX: Preparation of 5-bromo-2-methyl-4-nitropyridine 1-oxide

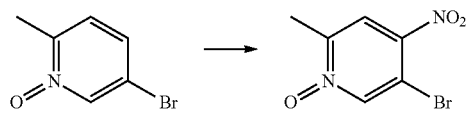

To a solution of 5-bromo-2-methylpyridine 1-oxide (5.10 g, 27.1 mmol) in concentrated sulphuric acid (8.90 mL, 0.18 mol) at 0° C. was added fuming nitric acid (6.80 mL, 0.14 mol). The resulting mixture was then stirred at 90° C. for 5 h. After cooling to rt, the reaction mixture was poured into ice/water, and the resulting solid was filtered, washed with water, and dried to afford 5-bromo-2-methyl-4-nitropyridine 1-oxide (4.10 g, 65%) as a light yellow solid. $^1$H-NMR (300 MHz, CDCl$_3$): δ ppm: 8.52 (s, 1H), 2.50 (s, 3H).

Procedure AAY: Preparation of 5-(1-ethoxy-1,3-dioxobutan-2-yl)-2-methyl-4-nitropyridine 1-oxide

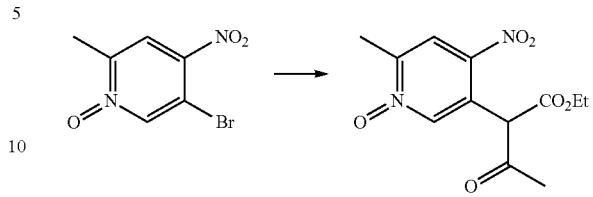

A mixture of 5-bromo-2-methyl-4-nitropyridine 1-oxide (7.15 g, 29.5 mmol), $K_2CO_3$ (6.1 g, 44.3 mmol) and ethyl 3-oxobutanoate (5.76 g, 44.3 mmol) in DMSO (70 mL) at rt was stirred overnight. The mixture was diluted with ethyl acetate (100 mL), and washed with water. The organic layer was then dried over $Na_2SO_4$, and concentrated in vacuo. The crude material was purified over silica gel, eluting with petroleum ether/ethyl acetate 5/1 then 2/1 to afford 5-(1-ethoxy-1,3-dioxobutan-2-yl)-2-methyl-4-nitropyridine 1-oxide (6.60 g, 80%) as a yellow oil. $^1$H-NMR (300 MHz, CDCl$_3$): δ ppm: 13.22 (s, 1H), 8.04 (s, 1H), 7.97 (s, 1H), 4.20-3.98 (m, 2H), 2.52 (s, 3H), 1.89 (s, 3H), 1.10-1.05 (m, 3H).

Procedure AAZ: Preparation of 3-(ethoxycarbonyl)-1-hydroxy-2,6-dimethyl-1H-pyrrolo[3,2-c]pyridine 5-oxide

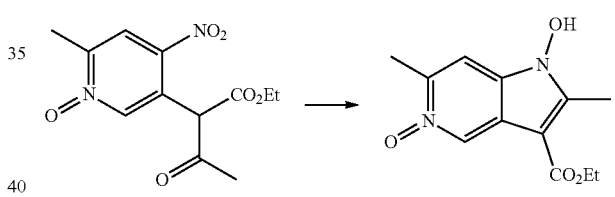

To a stirring solution of 5-(1-ethoxy-1,3-dioxobutan-2-yl)-2-methyl-4-nitropyridine 1-oxide (7.60 g, 26.9 mmol) in ethanol (150 mL) at rt was added Pd/C (10 w %, 0.40 g). The resulting mixture was left to stir at rt for 4 h under 1 atm of $H_2$. The catalyst was filtered, and the filtrate was concentrated in vacuo. The resulting residue was triturated in ethyl acetate to afford 3-(ethoxycarbonyl)-1-hydroxy-2,6-dimethyl-1H-pyrrolo[3,2-c]pyridine 5-oxide (6.70 g) as a yellow solid. The crude material was used directly in next step without further purification.

Procedure AAAA: Preparation of ethyl 2,6-dimethyl-1H-pyrrolo[3,2-c]pyridine-3-carboxylate

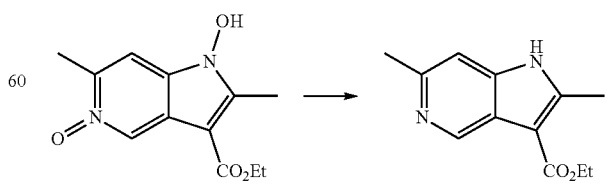

To a stirring suspension of 3-(ethoxycarbonyl)-1-hydroxy-2,6-dimethyl-1H-pyrrolo[3,2-c]pyridine 5-oxide (4.60 g, 18.2 mmol) in DCE (30 mL) was added PCl$_3$ (10 mL). The resulting mixture was stirred at 55° C. for 6 h. DCE and PCl$_3$ were then removed in vacuo. The resulting residue was diluted with water (20 mL), and washed with ethyl acetate (30 mL). The aqueous layer was used directly in next step.

Procedure AAAB: Preparation of 2,6-dimethyl-1H-pyrrolo[3,2-c]pyridine

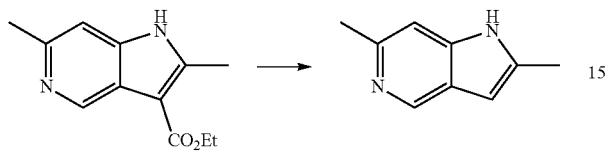

To the aqueous layer obtained in procedure AAAAAB was added concentrated sulfuric acid (6 mL). The resulting mixture was stirred at 120° C. for 8 h. After cooling to rt, the pH of the reaction mixture was adjusted to 6 by the addition of 20% w/w aqueous NaOH. The aqueous mixture was then washed with ethyl acetate, and Na$_2$CO$_3$ was added to the aqueous layer to adjust the pH to 8. The water was then evaporated and the resulting residue was triturated with MeOH/dichloromethane (1:3). The filtrate was evaporated to afford 2,6-dimethyl-1H-pyrrolo[3,2-c]pyridine (2.00 g, 74% over 3 steps) as a light yellow solid. $^1$H-NMR (300 MHz, MeOH-d$_4$): δ ppm: 8.60 (s, 1H), 7.36 (s, 1H), 6.41 (s, 1H), 2.63 (s, 3H), 2.47 (s, 3H).

Procedure AAAC: Preparation of (2,6-dimethyl-1H-pyrrolo[3,2-c]pyridin-3-yl)(4-(methylsulfonyl)-phenyl)methanone

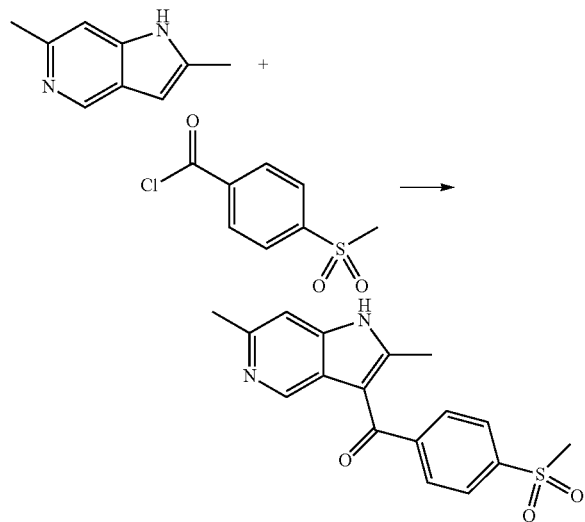

To a suspension of 2,6-dimethyl-1H-pyrrolo[3,2-c]pyridine (0.50 g, 3.40 mmol) in DCE (50 mL) was added AlCl$_3$ (2.30 g, 17.0 mmol). The resulting mixture was stirred at rt for 0.5 h before the addition of 4-(methylsulfonyl)benzoyl chloride (2.50 g, 10.0 mmol). The reaction mixture was stirred at 80° C. for 2 days. After cooling to rt, the reaction mixture was quenched with ice/water and then washed with dichloromethane. The pH of the aqueous layer was adjusted to 8 by the addition of sat. aq. Na$_2$CO$_3$. The resulting solid was filtered, washed with water, and then dried under vacuum to afford (2,6-dimethyl-1H-pyrrolo[3,2-c]pyridin-3-yl)(4-(methylsulfonyl)phenyl)methanone (0.70 g, 63% yield) as an off-white solid. $^1$H-NMR (300 MHz, CDCl$_3$): δ ppm: 8.63 (s, 1H), 7.90-7.86 (m, 4H), 7.34 (s, 1H), 2.74 (s, 6H), 2.65 (s, 3H), 2.52 (s, 3H).

Procedure AAAD: Preparation of 2,6-dimethyl-3-(4-(methylsulfonyl)benzyl)-1H-pyrrolo[3,2-c]pyridine

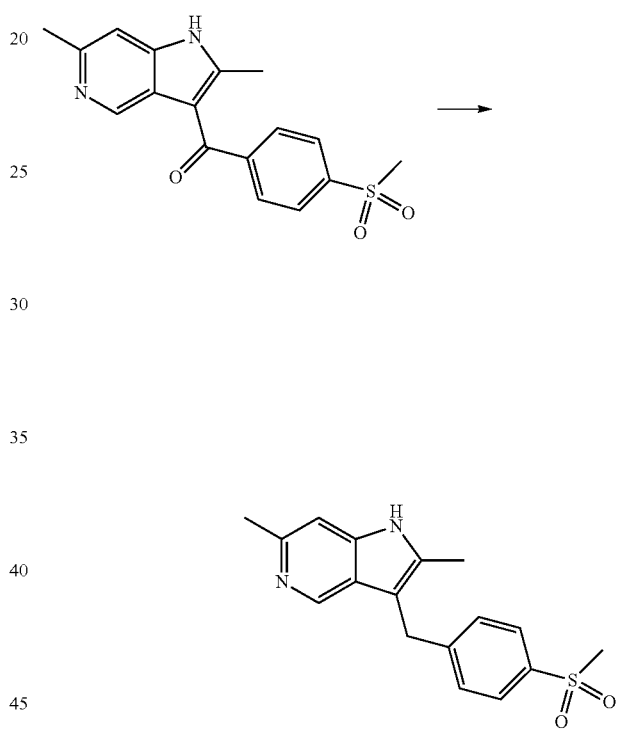

To a solution of (2,6-dimethyl-1H-pyrrolo[3,2-c]pyridin-3-yl)(4-(methylsulfonyl)phenyl)methanone (0.70 g, 2.1 mmol) in methanol (20 mL) at rt was added NaBH$_4$ (0.19 g, 5.00 mmol). The resulting mixture left to stir at rt for 1 h. The methanol solvent was removed, and TFA (20 mL) was added. Stirring was then continued at 60° C. for 1 h. TFA was evaporated in vacuo, and the residue was washed with water and sat. aq. NaHCO$_3$, then triturated with petroleum ether/ethyl acetate (1:2). The resulting solid was filtered and dried to afford 2,6-dimethyl-3-(4-(methylsulfonyl)benzyl)-1H-pyrrolo[3,2-c]pyridine (0.60 g, 89% yield) as an off-white solid. $^1$H-NMR (300 MHz, DMSO-d$_6$): δ ppm: 11.56 (s, 1H), 8.57 (s, 1H), 7.83-7.77 (m, 2H), 7.48-7.45 (m, 2H), 7.20 (s, 1H), 4.14 (s, 2H), 3.13 (s, 3H), 2.48 (s, 3H), 2.37 (s, 3H).

(Z)-4-(2,6-dimethyl-3-(4-(methylsulfonyl)benzyl)-1H-pyrrolo[3,2-c]pyridin-1-yl)-3-fluorobut-2-en-1-amine dihydrochloride (Compound 36)

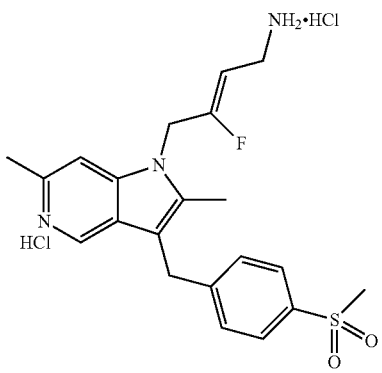

¹H-NMR (400 MHz, DMSO-d₆): δ ppm: 9.05 (s, 1H), 8.36 (bs, 3H), 8.02 (s, 1H), 8.37 (bs, 3H), 7.84-7.82 (m, 2H), 7.54-7.52 (m, 2H), 5.36-5.24 (m, 3H), 4.34 (s, 2H), 3.46 (s, 2H), 3.17 (s, 3H), 2.74 (s, 3H), 2.54 (s, 3H).

Example 27

The following compound was made according to procedures: AAAE, AAX, AAY, AAZ, AAAA, AAAB, AAAF, AAAD, AAU and AAV.

(Z)-4-((5-(4-amino-2-fluorobut-2-en-1-yl)-3,6-dimethyl-5H-pyrrolo[3,2-c]pyridazin-7-yl)methyl)-N,N-dimethylbenzenesulfonamide dihydrochloride (Compound 37)

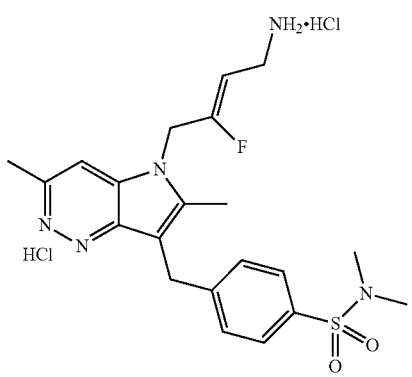

Procedure AAAE: Preparation of 3-chloro-6-methylpyridazine 1-oxide

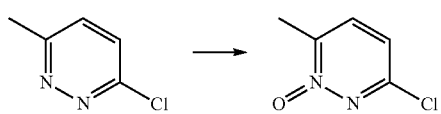

To a stirring solution of 3-chloro-6-methylpyridazine (15.4 g, 0.12 mol) in AcOH (80 mL) was added H₂O₂ (60 mL) in portions at rt. The resulting mixture was stirred at 70° C. overnight. The reaction mixture was partitioned between 20 w % aq. Na₂SO₃ and dichloromethane (100 mL), and the aqueous layer was extracted with further dichloromethane (100 mL×2). The combined organics were dried over Na₂SO₄, and concentrated in vacuo to afford 3-chloro-6-methylpyridazine 1-oxide (11.5 g, 66% yield) as a white solid. ¹H-NMR (300 MHz, CDCl₃): δ ppm: 7.55-7.52 (m, 1H), 7.07-7.05 (m, 1H), 2.46 (s, 3H).

Procedure AAAF: Preparation of 4-(3,6-dimethyl-5H-pyrrolo[3,2-c]pyridazine-7-carbonyl)-N,N-dimethylbenzenesulfonamide

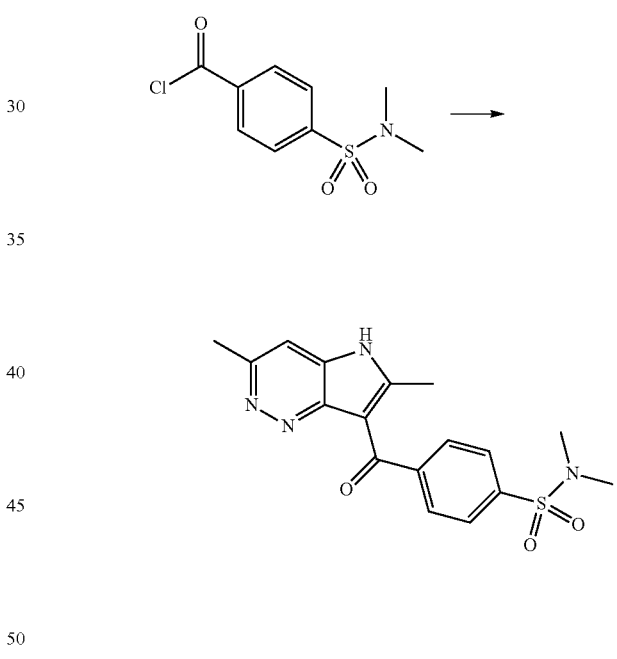

To a suspension of 3,6-dimethyl-5H-pyrrolo[3,2-c]pyridazine (0.5 g, 3.4 mmol) in DCE (50 mL) at rt was added AlCl₃ (2.26 g, 17 mmol). The resulting mixture was left to stir at rt for 0.5 h. To the reaction vessel was then added 4-(N,N-dimethylsulfamoyl)benzoyl chloride (2.5 g, 10 mmol). Stirring was then continued at 80° C. for 2 days. After cooling to rt, the reaction mixture was quenched with ice/water and then washed with dichloromethane. The pH of the aqueous layer was adjusted to 8 by the addition of sat. aq. Na₂CO₃. The resulting solid was filtered, washed with water, and then dried under vacuum to afford 4-(3,6-dimethyl-5H-pyrrolo[3,2-c]pyridazine-7-carbonyl)-N,N-dimethylbenzenesulfonamide (0.60 g, 65% yield) as an off-white solid. ¹H-NMR (300 MHz, DMSO-d₆): δ ppm: 12.99-12.96 (m, 1H), 7.94-7.92 (m, 2H), 7.82-7.80 (m, 2H), 7.50 (s, 1H), 2.75-2.60 (m, 12H).

(Z)-4-((5-(4-amino-2-fluorobut-2-en-1-yl)-3,6-dimethyl-5H-pyrrolo[3,2-c]pyridazin-7-yl)methyl)-N,N-dimethylbenzenesulfonamide dihydrochloride (Compound 37)

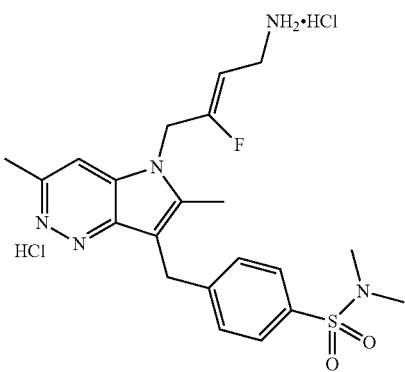

$^1$H-NMR (400 MHz, DMSO-d$_6$): δ ppm: 8.52 (s, 1H), 8.36 (bs, 3H), 7.67-7.65 (m, 2H), 7.55-7.53 (m, 2H), 5.49-5.36 (m, 3H), 4.34 (s, 2H), 3.46-3.45 (m, 2H), 2.90 (s, 3H), 2.68 (s, 3H), 2.57 (s, 6H).

Example 28

The following compound was made according to procedures AAAG, AAAH, AAAI, AAAC, AAAJ, AAAD, AAU and AAV.

(Z)-4-(2,6-dimethyl-7-(4-(methylsulfonyl)benzyl)-5H-pyrrolo[3,2-d]pyrimidin-5-yl)-3-fluorobut-2-en-1-amine dihydrochloride (Compound 38)

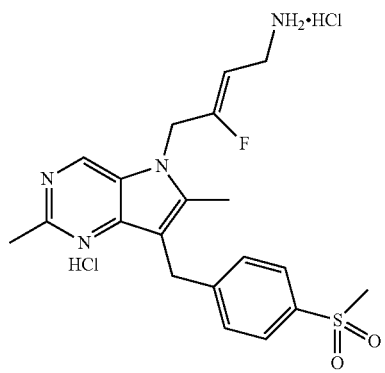

Procedure AAAG: Preparation of ethyl 3-acetimidamido-5-methyl-1H-pyrrole-2-carboxylate

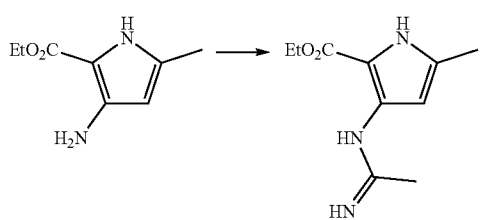

To a solution of ethyl 3-amino-5-methyl-1H-pyrrole-2-carboxylate (2.50 g, 14.8 mmol) in acetonitrile (25 ml) was added HCl/dioxane (4 M, 10 mL). The resulting mixture was stirred at 50° C. overnight. After cooling to rt, MTBE (100 mL) was added, and the resulting solid was filtered, washed with MTBE/acetonitrile (5:1) and dried under vacuum, to afford ethyl 3-acetimidamido-5-methyl-1H-pyrrole-2-carboxylate (4.00 g) as the HCl salt. This material was used directly in next step without further purification.

Procedure AAAH: Preparation of 2,6-dimethyl-3,5-dihydro-4H-pyrrolo[3,2-d]pyrimidin-4-one

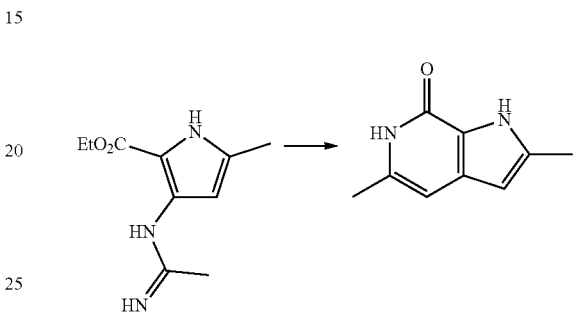

A suspension of ethyl 3-acetimidamido-5-methyl-1H-pyrrole-2-carboxylate (4.00 g, 14.8 mmol) in aqueous NaOH (6 M, 12 mL) was stirred at 90° C. for 4 h. After cooling to rt, the pH was adjusted to 7 with aqueous HCl (4 M). The resulting solid was filtered, washed with water (10 mL) and dried under vacuum to afford 2,6-dimethyl-3,5-dihydro-4H-pyrrolo[3,2-d]pyrimidin-4-one (2.00 g, 83%) as an off-white solid. $^1$H-NMR (300 MHz, DMSO-d$_6$): δ ppm: 11.65-11.61 (m, 2H), 5.95 (s, 1H), 2.26-2.23 (m, 6H).

Procedure AAAI: Preparation of 4-chloro-2,6-dimethyl-5H-pyrrolo[3,2-d]pyrimidine

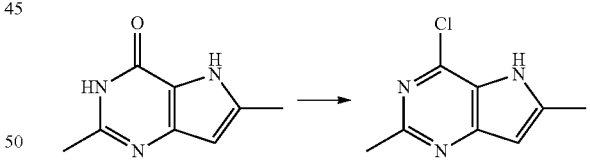

To a suspension of 2,6-dimethyl-3,5-dihydro-4H-pyrrolo[3,2-d]pyrimidin-4-one (2.00 g, 12.3 mmol) in 1,4-dixoane (30 mL) was added POCl$_3$ (10 mL). The resulting mixture was stirred at 85° C. overnight. After cooling to rt, the mixture was evaporated to dryness, and ice/water was added. The aqueous mixture was basified to pH 8 by addition of sat. aq. Na$_2$CO$_3$. The resulting solid was filtered, washed with water, and triturated with ethyl acetate/petroleum ether. Drying under vacuum afforded 4-chloro-2,6-dimethyl-5H-pyrrolo[3,2-d]pyrimidine (1.80 g, 81% yield) as an off-white solid. $^1$H-NMR (300 MHz, DMSO-d$_6$): δ ppm: 12.04 (bs, 1H), 6.34 (s, 1H), 2.57 (s, 3H), 2.47 (s, 3H).

Procedure AAAJ: Preparation of (2,6-dimethyl-5H-pyrrolo[3,2-d]pyrimidin-7-yl)(4-(methylsulfonyl)phenyl)methanone

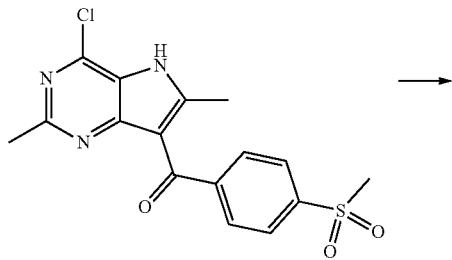

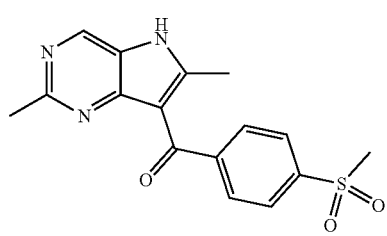

To a stirring mixture of (4-chloro-2,6-dimethyl-5H-pyrrolo[3,2-d]pyrimidin-7-yl)(4-(methylsulfonyl)-phenyl) methanone (1.00 g, 4.70 mmol) in methanol (20 mL) was added Pd/C (10 w %, 0.30 g). The resulting suspension was stirred under 1 atm of $H_2$ at rt for 3 h. The catalyst was filtered off and the filtrate was used directly in next step without further purification.

(Z)-4-(2,6-dimethyl-7-(4-(methylsulfonyl)benzyl)-5H-pyrrolo[3,2-d]pyrimidin-5-yl)-3-fluorobut-2-en-1-amine dihydrochloride (Compound 38)

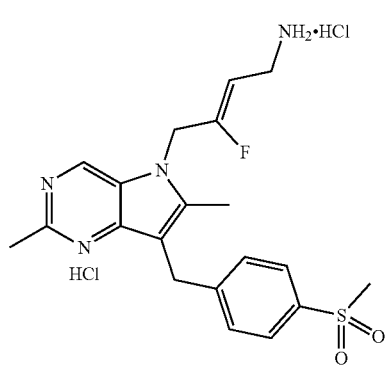

$^1$H-NMR (400 MHz, DMSO-$d_6$): δ ppm: 9.45 (s, 1H), 8.16 (bs, 3H), 7.83-7.81 (m, 2H), 7.53-7.51 (m, 2H), 5.44-5.29 (m, 3H), 4.27 (s, 2H), 3.44-3.40 (m, 2H), 3.17 (s, 3H), 2.81 (s, 3H), 2.64 (s, 3H).

Example 29

The following compound was made according to procedures AAAG, AAAA, AAAI, AAAF, AAAJ, AAAD, AAU and AAV.

(Z)-4-((5-(4-amino-2-fluorobut-2-en-1-yl)-2,6-dimethyl-5H-pyrrolo[3,2-d]pyrimidin-7-yl)methyl)-N,N-dimethylbenzenesulfonamide dihydrochloride (Compound 39)

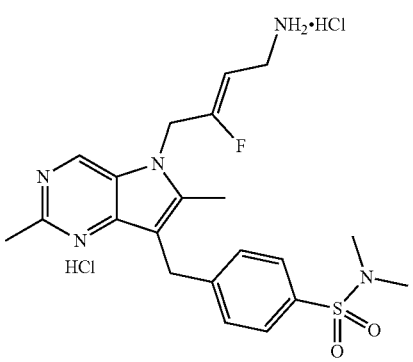

$^1$H-NMR (400 MHz, DMSO-$d_6$): δ ppm: 9.52 (s, 1H), 8.28 (bs, 3H), 7.66-7.64 (m, 2H), 7.52-7.50 (m, 2H), 5.48-5.318 (m, 3H), 4.28 (s, 2H), 3.46-3.43 (m, 2H), 2.83 (s, 3H), 2.64 (s, 3H), 2.58 (s, 6H).

Example 30

The following compound was made according to procedures AAAK, AAAL, AAAM, AAAN, AAAO, AAAP, AAAQ, AAAR, and AAAS.

(Z)-4-(2,5-dimethyl-3-(4-(methylsulfonyl)phenethyl)-1H-pyrrolo[3,2-b]pyridin-1-yl)-3-fluorobut-2-en-1-amine dihydrochloride (Compound 40)

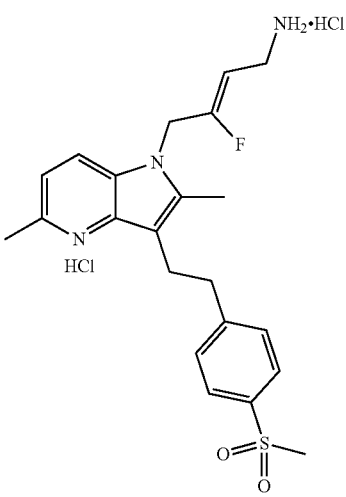

Procedure AAAK: Preparation of 6-methyl-2-(prop-1-yn-1-yl)pyridin-3-amine

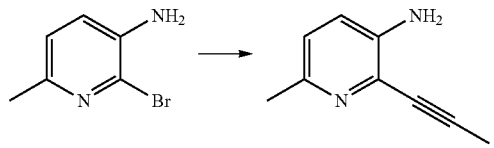

Into a 500 mL 3-necked round-bottom flask purged and maintained with an inert atmosphere of nitrogen, was placed 2-bromo-6-methylpyridin-3-amine (25.0 g, 134 mmol), acetonitrile (100 mL), triethylamine (100 mL), copper (I) iodide (1.30 g, 6.83 mmol), Pd(PPh$_3$)$_2$Cl$_2$ (1.40 g, 1.99 mmol). The resulting solution was stirred for 3 h at 80° C. with continued bubbling of propyne gas. The solids were filtered, and the filtrate was concentrated under vacuum. The residue was purified over silica gel, eluting with ethyl acetate/petroleum ether (1:3) to afford 6-methyl-2-(prop-1-yn-1-yl)pyridin-3-amine (18.0 g, 92%) as a yellow solid. (300 MHz, DMSO-d$_6$) δ ppm: 6.96 (d, J=8.4 Hz, 1H), 6.88 (d, J=8.4 Hz, 1H), 5.16 (brs, 2H), 2.24 (s, 3H), 2.08 (s, 3H).

Procedure AAAL: Preparation of 2,5-dimethyl-1H-pyrrolo[3,2-b]pyridine

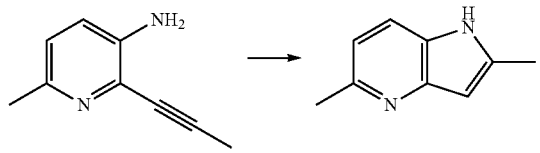

Into a 500 mL round-bottom flask, was placed a solution of 6-methyl-2-(prop-1-yn-1-yl)pyridin-3-amine (18.0 g, 123 mmol) in DMF (300 mL). To this was added KO$^t$Bu (28.0 g, 250 mmol), in portions at 0° C. The resulting solution was then stirred at rt for 3 h. The reaction was then quenched by the addition of water/ice (1.0 L). The resulting solution was extracted with of ethyl acetate (200 mL×6), and the combined were washed with of brine (1.0 L×2). The organics were dried over anhydrous sodium sulfate and concentrated under vacuum to afford 2,5-dimethyl-1H-pyrrolo[3,2-b]pyridine (16.0 g, 89%) as a yellow solid. (300 MHz, DMSO-d$_6$) δ ppm: 10.96 (brs, 1H), 7.50-7.42 (m, 1H), 6.84 (d, J=8.4 Hz, 1H), 6.14 (s, 1H), 2.51 (s, 3H), 2.40 (s, 3H).

Procedure AAAM: Preparation of 2,5-dimethyl-1H-pyrrolo[3,2-b]pyridine-3-carbaldehyde

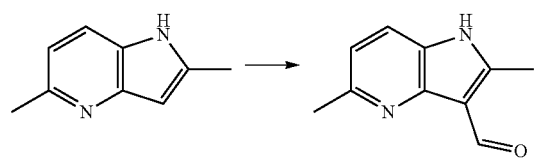

Into a 2.0 L 3-necked round-bottom flask, was placed a solution of 2,5-dimethyl-1H-pyrrolo[3,2-b]pyridine (15.0 g, 103 mmol) in chloroform/EtOH (90/240 mL). To this was added a solution of potassium hydroxide (150 g, 2.67 mol) in water (180 mL). The resulting solution was stirred for 2 h at 80° C. An additional amount of potassium hydroxide (150 g, 2.67 mol) in water (180 mL) was added, and stirring was continued at 80° C. for 2 h. After cooling to rt, the reaction mixture was concentrated under vacuum. The resulting solution was extracted with of ethyl acetate (200 mL×3), and the combined organic layers were washed with brine (300 mL). The organics were dried over anhydrous sodium sulfate and concentrated under vacuum. The residue was purified over silica gel column, eluting with ethyl acetate/petroleum ether (1:1) to afford of 2,5-dimethyl-1H-pyrrolo[3,2-b]pyridine-3-carbaldehyde (10.0 g, 56%) as a yellow solid. (300 MHz, DMSO-d$_6$) δ ppm: 12.15 (brs, 1H), 10.31 (s, 1H), 7.65 (d, J=8.1 Hz, 1H), 6.84 (d, J=8.1 Hz, 1H), 2.73 (s, 3H), 2.55 (s, 3H).

Procedure AAAN: Preparation of tert-butyl 3-formyl-2,5-dimethyl-1H-pyrrolo[3,2-b]pyridine-1-carboxylate

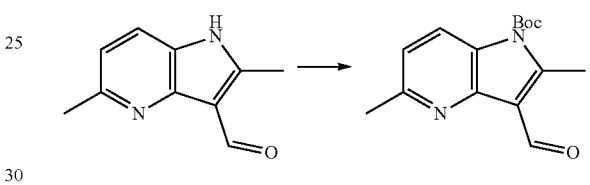

Into a 500 mL round-bottom flask, was placed a solution of 2,5-dimethyl-1H-pyrrolo[3,2-b]pyridine-3-carbaldehyde (10.0 g, 57.4 mmol) in dichloromethane (100 mL), triethylamine (9.50 mL, 68.2 mmol). This was followed by the addition of (Boc)$_2$O (15.0 g, 68.7 mmol) in several batches, at 0° C. The resulting solution was then stirred at room temperature for 2 h. The resulting mixture was concentrated under vacuum. The residue was purified over silica gel, eluting with ethyl acetate/petroleum ether (1:3) to afford tert-butyl 3-formyl-2,5-dimethyl-1H-pyrrolo[3,2-b]pyridine-1-carboxylate (12.0 g, 76%) as an off-white solid. (300 MHz, CDCl$_3$) δ ppm: 10.69 (s, 1H), 8.23 (d, J=8.7 Hz, 1H), 7.13 (d, J=8.7 Hz, 1H), 3.05 (s, 3H), 2.71 (s, 3H), 1.72 (s, 9H).

Procedure AAAO: Preparation of (4-(methylsulfonyl)benzyl)triphenylphosphonium chloride

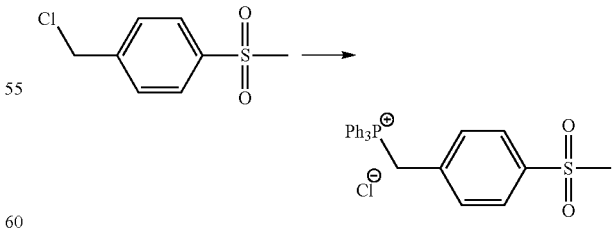

Into a 250 mL round-bottom flask, purged and maintained with an inert atmosphere of nitrogen, was placed a solution of 1-(chloromethyl)-4-(methylsulfonyl)benzene (5.00 g, 24.4 mmol) in toluene (100 mL). Triphenylphosphine (6.40 g, 24.4 mmol) was added, and the resulting solution was stirred at 100° C., overnight. The reaction mixture was cooled with a water/ice bath, and the resulting solid was collected by filtration. After drying, (4-(methylsulfonyl) benzyl)triphenylphosphonium chloride (6.20 g, 54%) was obtained as an off-white solid. (300 MHz, CDCl₃) δ ppm: 7.85-7.73 (m, 9H), 7.63-7.50 (m, 8H), 7.49-7.47 (m, 2H), 6.03 (d, J=15.6 Hz, 2H), 2.99 (s, 3H).

Procedure AAAP: Preparation of (E)-2,5-dimethyl-3-(4-(methylsulfonyl)styryl)-1H-pyrrolo[3,2-b]pyridine

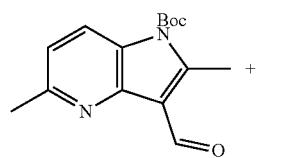

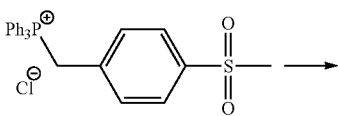

Into a 50 mL round-bottom flask, was placed tert-butyl 3-formyl-2,5-dimethyl-1H-pyrrolo[3,2-b]pyridine-1-carboxylate (5.20 g, 19.0 mmol), (4-(methylsulfonyl)benzyl)triphenylphosphonium chloride (3.06 g, 6.55 mmol), methanol (30 mL) and ᵗBuOK (1.88 g, 16.8 mmol). The resulting solution was stirred at 50° C. for 30 min, and then cooled to rt. The solids were collected by filtration, and the filter cake was washed with cold MeOH (5 mL). After drying, (E)-2,5-dimethyl-3-(4-(methylsulfonyl)styryl)-1H-pyrrolo[3,2-b]pyridine (1.50 g, 24%) was obtained as a yellow solid. (300 MHz, DMSO-d₆) δ ppm: 11.28 (brs, 1H), 7.73 (d, J=8.7 Hz, 2H), 7.52 (d, J=8.1 Hz, 1H), 7.41 (d, J=8.1 Hz, 2H), 6.94-6.89 (m, 2H), 6.64 (d, J=12.0 Hz, 1H), 3.21 (s, 3H) 2.39 (s, 3H), 1.97 (s, 3H).

Procedure AAAA: Preparation of 2,5-dimethyl-3-(4-methylsulfonyl)phenethyl)-1H-pyrrolo[3,2-b]pyridine

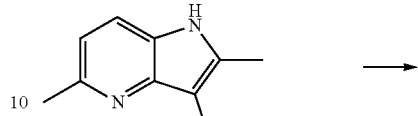

Into a 100 mL round-bottom flask, was placed a solution of (E)-2,5-dimethyl-3-(4-(methylsulfonyl)styryl)-1H-pyrrolo[3,2-b]pyridine (1.00 g, 3.06 mmol) in methanol/THF (6/6 mL) followed by palladium on carbon (10% w/w; 326 mg). The resulting solution was stirred at rt for 1 h under a hydrogen atmosphere (balloon). The solids were filtered and the filtrate was concentrated under vacuum to afford 2,5-dimethyl-3-(4-(methylsulfonyl)phenethyl)-1H-pyrrolo[3,2-b]pyridine (660 mg, 66%) as a yellow solid. (300 MHz, DMSO-d₆) δ ppm: 10.72 (brs, 1H), 7.80 (d, J=8.4 Hz, 2H), 7.46-7.40 (m, 3H), 6.85 (d, J=8.1 Hz, 1H), 3.17 (s, 3H), 3.07-2.94 (m, 4H), 2.12 (s, 3H).

Procedure AAAR: Preparation of tert-butyl (Z)-(4-(2,5-dimethyl-3-(4-(methylsulfonyl)phenethyl)-1H-pyrrolo[3,2-b]pyridin-1-yl)-3-fluorobut-2-en-1-yl)carbamate

-continued

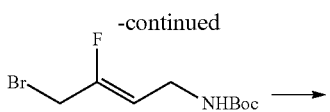

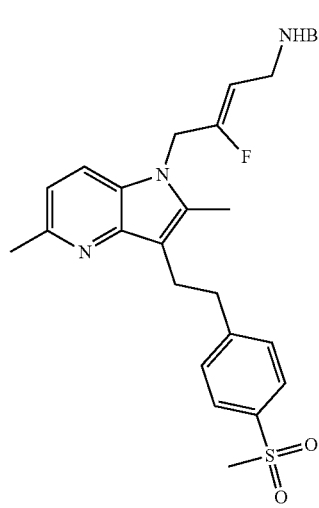

Procedure AAAS: Preparation of (Z)-4-(2,5-dimethyl-3-(4-(methylsulfonyl)phenethyl)-1H-pyrrolo[3,2-b]pyridin-1-yl)-3-fluorobut-2-en-1-amine dihydrochloride (Compound 40)

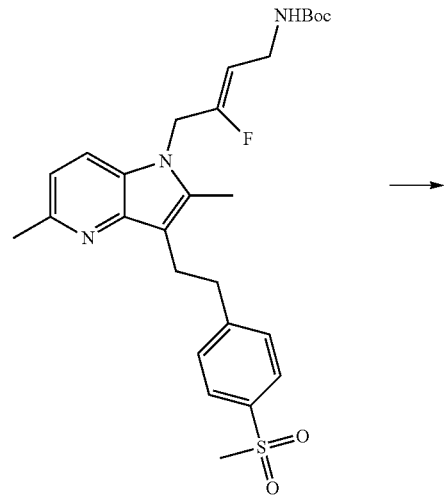

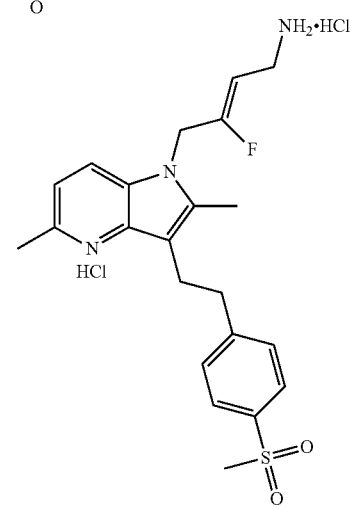

Into a 50 mL round-bottom flask, was placed 2,5-dimethyl-3-(4-(methylsulfonyl)phenethyl)-1H-pyrrolo[3,2-b]pyridine (660 mg, 2.01 mmol), DMF (4 mL) and potassium hydroxide (150 mg, 2.67 mmol). The resulting solution was stirred at room temperature for 5 min. Tert-butyl (Z)-(4-bromo-3-fluorobut-2-en-1-yl)carbamate (591 mg, 2.20 mmol) was added and the resulting solution was left to stir at rt for an additional 5 h. The reaction was then quenched by the addition of water (5 mL). The resulting solution was extracted with ethyl acetate (10 mL×3), and the combined organics were dried over $Na_2SO_4$ and then concentrated under vacuum. The crude product was purified by Flash-Prep-HPLC (silica gel; mobile phase: water (0.1% FA)/$CH_3CN$=20% increasing to water (0.1% FA)/$CH_3CN$=80% within 10 min; Detector, UV 254 nm) to afford tert-butyl (Z)-(4-(2,5-dimethyl-3-(4-(methylsulfonyl)phenethyl)-1H-pyrrolo[3,2-b]pyridin-1-yl)-3-fluorobut-2-en-1-yl)carbamate (500 mg, 48%) as a yellow solid. (300 MHz, DMSO-$d_6$) δ ppm: 12.71 (brs, 1H), 8.14 (s, 1H), 7.80 (d, J=8.4 Hz, 2H), 7.73-7.71 (m, 1H), 7.42 (d, J=8.1 Hz, 2H), 6.96-6.93 (m, 1H), 4.93-4.72 (m, 3H), 3.53 (brs, 2H), 3.17 (s, 3H), 3.01 (s, 4H), 2.54 (s, 3H), 2.11 (s, 3H), 1.35 (s, 9H).

Into a 50 mL round-bottom flask, was placed tert-butyl (Z)-(4-(2,5-dimethyl-3-(4-(methylsulfonyl)phenethyl)-1H-pyrrolo[3,2-b]pyridin-1-yl)-3-fluorobut-2-en-1-yl)carbamate (350 mg, 0.68 mmol), methanol (10 mL), hydrogen chloride (2 M solution in dioxane; 4 mL). The resulting solution was stirred at room temperature for 2 h. The reaction mixture was concentrated under vacuum, and the resulting solution was diluted with diethyl ether (20 mL). The solids were collected by filtration and the filter cake was washed with diethyl ether. The solid was then air dried to afford (Z)-4-(2,5-dimethyl-3-(4-(methylsulfonyl)phenethyl)-1H-pyrrolo[3,2-b]pyridin-1-yl)-3-fluorobut-2-en-1-amine dihydrochloride (218 mg, 71%) as a grey solid. (300 MHz, DMSO-$d_6$) δ ppm: 8.57-8.54 (m, 1H), 7.81-7.78 (m, 2H), 7.51-7.45 (m, 3H), 5.29-5.11 (m, 311), 3.50-3.44 (m, 2H), 3.22-3.16 (m, 5H), 2.97-2.81 (m, 2H), 2.97 (s, 3H), 2.29 (s, 3H).

Example 31

The following compounds were made according to procedures: AAAT, L, M, AAAU, AAAV, AAAW, J and Q.

Procedure AAAT: Preparation of
3-fluoro-N,N-dimethyl-4-nitrobenzenesulfonamide

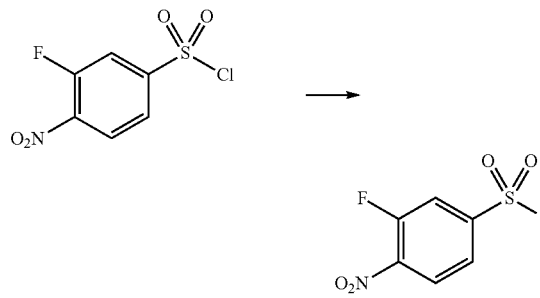

To a stirring solution of dimethylamine hydrochloride (340 mg, 4.17 mmol) in dichloromethane at 0° C. was added triethylamine (1.28 mL, 9.18 mmol). After stirring for 2 mins, 3-fluoro-4-nitrobenzenesulfonyl chloride (1.00 g, 4.17 mmol) was added in one portion. The resulting mixture was stirred at 0° C. for a further 20 mins. The reaction mixture was partitioned between dichloromethane (30 mL) and water (10 mL) and the organic layer was washed with sat. aq. NaCl, dried over MgSO$_4$ and concentrated in vacuo to afford 3-fluoro-N,N-dimethyl-4-nitrobenzenesulfonamide (1.02 g, 98%) as a yellow solid. $^1$H NMR (300 MHz, CDCl$_3$) δ ppm: 8.23 (dd, J=8.7, 6.8 Hz, 1H), 7.77-7.69 (m, 2H), 2.83 (s, 6H), 1.57 (s, 3H).

Procedure AAAU: Preparation of
N,N,2-trimethyl-1H-indole-5-sulfonamide

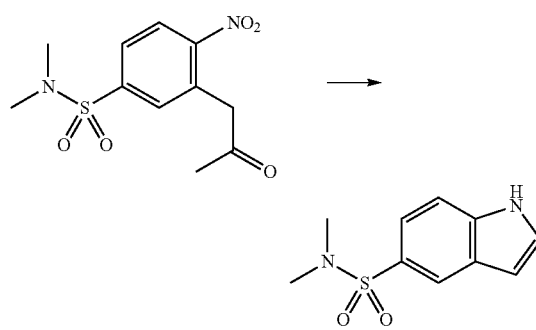

To a stirred solution of N,N-dimethyl-4-nitro-3-(2-oxopropyl)benzenesulfonamide (1.16 g, 4.05 mmol) and ammonium formate (1.79 g, 28.4 mmol) in methanol (20 mL) at rt was added a slurry of palladium on carbon (647 ing, 6.08 mmol) in water (1 mL). The resulting mixture was then heated at reflux for 1.5 h. After cooling to rt the reaction mixture diluted with dichloromethane (10 mL) and filtered through a plug of Celite™, washing with further methanol (50 mL). After concentration of the filtrate in vacuo the resulting residue was taken up in ethyl acetate, and water was added. The phases were separated and the aqueous phase extracted with further ethyl acetate. The organics were combined and washed with brine, dried over Na$_2$SO$_4$, and concentrated in vacuo to afford crude title compound N,N,2-trimethyl-1H-indole-5-sulfonamide (890 mg, 92%) as a yellow solid. The crude material was progressed to the next step without further purification. $^1$H NMR (300 MHz, Chloroform-d) δ 8.21 (s, 1H), 8.09-7.88 (m, 1H), 7.53 (dd, J=8.5, 1.8 Hz, 1H), 7.39 (dt, J=8.5, 0.8 Hz, 1H), 6.37 (p, J=2.1, 1.0 Hz, 1H), 2.71 (s, 6H), 2.51 (s, 3H).

Procedure AAAV: Preparation of
3-formyl-N,N-dimethylbenzenesulfonamide

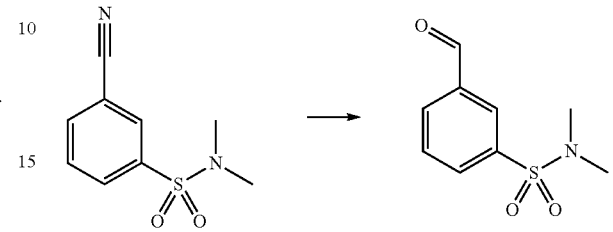

To a suspension of 3-cyano-N,N-dimethylbenzenesulfonamide (2.00 g, 9.51 mmol) in formic acid (12 mL) at rt was added Raney nickel (1.50 g). The resulting mixture was heated to reflux and stirring was continued for 1 h. After cooling to rt the reaction mixture was filtered through celite and the filtrate was transferred to a separatory funnel containing water (50 mL). The organic phase was washed with sat. aq. NaHCO$_3$ (50 mL×3), sat.aq. NaCl (50 mL), dried over Na$_2$SO$_4$ and concentrated in vacuo to give a pale yellow oil that solidified upon freezing. The crude 3-formyl-N,N-dimethylbenzenesulfonamide (1.85 g, 82%) was progressed to the next step without purification. $^1$H NMR (300 MHz, CDCl$_3$) δ ppm: 10.12 (s, 1H), 8.29 (dd, J=1.6 Hz, 1H), 8.14 (dt, J=7.7, 1.4 Hz, 1H), 8.09-8.01 (m, 1H), 7.76 (dd, J=7.7 Hz, 1H), 2.78 (s, 8H).

Procedure AAAW: Preparation of 3-(3-(N,N-dimethylsulfamoyl)benzyl)-N,N,2-trimethyl-1H-indole-5-sulfonamide

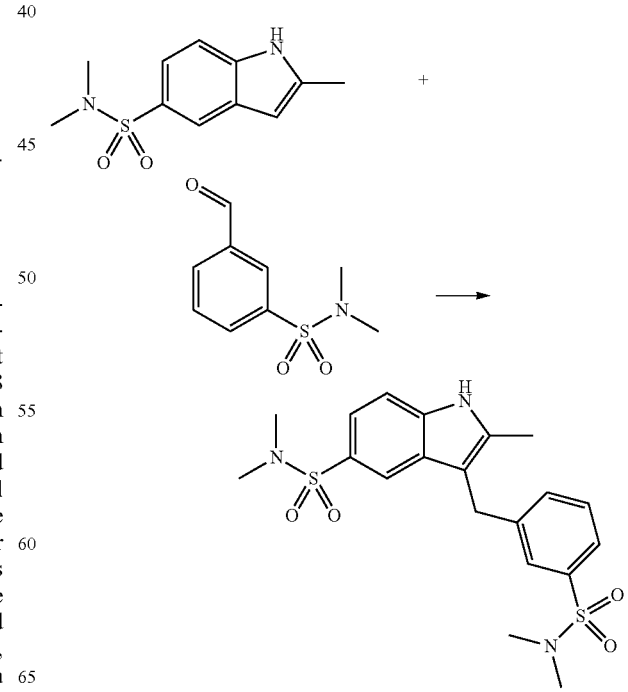

To a stirred solution of N,N,2-trimethyl-1H-indole-5-sulfonamide (100 mg, 0.42 mmol) and 3-formyl-N,N-dimethylbenzenesulfonamide (89.5 mg, 0.42 mmol) in $CH_2Cl_2$ (1 mL), at rt was added triethylsilane (0.20 mL, 1.26 mmol) and trifluoroacetic acid (0.16 mL, 2.10 mmol). The resulting orange-coloured solution was left to stir at rt overnight. The reaction mixture was cooled to 0° C. and carefully neutralised with sat. aq. $NaHCO_3$ solution. The mixture was transferred to a separatory funnel and the aqueous layer was extracted with $CH_2Cl_2$ (20 mL). The combined organics were washed with sat. aq. NaCl (20 mL), dried over $Na_2SO_4$ and concentrated in vacuo. The crude material was purified over silica gel, eluting with ethyl acetate:$CH_2Cl_2$:hexane (1:1:3) to afford product 3-(3-(N,N-dimethylsulfamoyl)benzyl)-N,N,2-trimethyl-1H-indole-5-sulfonamide (130 mg, 71%) as an off-white solid. $^1$H NMR (300 MHz, $CDCl_3$) δ ppm: 8.31 (s, 1H), 7.71 (d, J=1.7 Hz, 1H), 7.64-7.57 (m, 1H), 7.58-7.54 (m, 1H), 7.52 (dd, J=8.5, 1.7 Hz, 1H), 7.48-7.44 (m, 2H), 7.41 (t, J=7.7 Hz, 1H), 4.20 (s, 2H), 2.64 (s, 6H), 2.62 (s, 6H), 2.46 (s, 3H).

(Z)-1-(4-amino-2-fluorobut-2-en-1-yl)-3-(3-(N,N-dimethylsulfamoyl)benzyl)-N,N,2-trimethyl-1H-indole-5-sulfonamide hydrochloride (Compound 7)

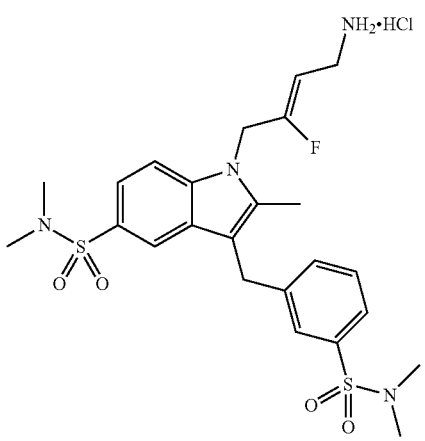

$^1$H NMR (300 MHz, DMSO-$d_6$) δ 7.97 (s, 3H), 7.74-7.69 (m, 2H), 7.61 (s, 1H), 7.57-7.50 (m, 3H), 7.44 (dd, J=8.6, 1.7 Hz, 1H), 5.19 (d, J=13.3 Hz, 2H), 5.09 (dt, J=35.1, 7.5 Hz, 1H), 4.28 (s, 2H), 3.46 (d, J=7.2 Hz, 21-1), 2.53 (s, 6H), 2.51 (s, 3H), 2.48 (s, 6H).

(Z)-1-(4-amino-2-fluorobut-2-en-1-yl)-3-(4-(N,N-dimethylsulfamoyl)benzyl)-N,N,2-trimethyl-1H-indole-5-sulfonamide hydrochloride (Compound 6)

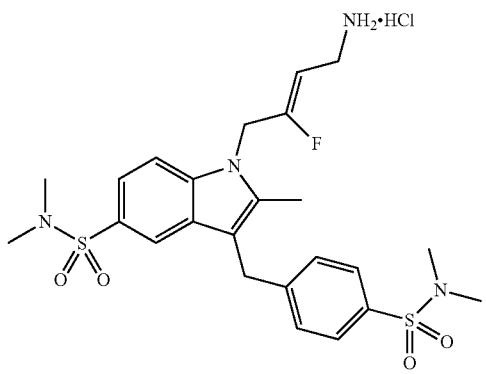

$^1$H NMR (300 MHz, Methanol-$d_4$) δ 7.67 (d, J=8.3 Hz, 2H), 7.55-7.50 (m, 2H), 7.47 (d, J=8.3 Hz, 2H), 7.31 (ddd, J=8.4, 7.0, 1.1 Hz, 1H), 7.13 (dd, J=7.6 Hz, 1H), 5.17-4.88 (m, 3H), 4.95 (dt, J=34.4, 7.4 Hz, 1H), 4.29 (d, J=16.0 Hz, 1H), 4.17 (d, J=16.9 Hz, 1H), 3.59 (d, J=7.4 Hz, 2H), 3.10 (s, 4H), 2.97 (s, 3H), 2.65 (s, 6H).

Example 32

The following compound was made according to procedures: AAAX, AAAV, AAAW, J and Q.

(Z)-1-(4-amino-2-fluorobut-2-en-1-yl)-3-(4-(N,N-dimethylsulfamoyl)benzyl)-N,N-dimethyl-1H-indole-2-carboxamide hydrochloride (Compound 5)

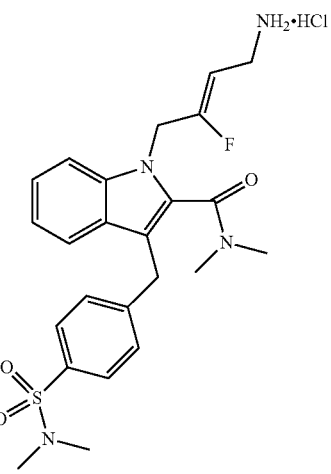

Procedure AAAX: Preparation of N,N-dimethyl-1H-indole-2-carboxamide

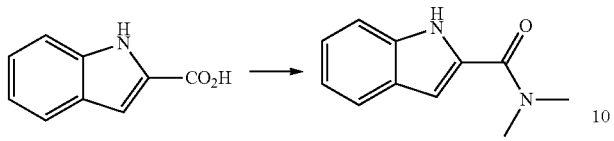

To a stirring solution of dimethylamine hydrochloride (0.76 g, 9.31 mmol) in DMF (30 mL) at rt under $N_2$ was added triethylamine (4.32 mL, 31.0 mmol). The resulting mixture was left to stir at rt for 10 min at which time indole-2-carboxylic acid (1.00 g, 6.21 mmol) was added, followed by HATU (2.83 g, 7.45 mmol). The resulting solution was left to stir at rt for 4 h. The reaction mixture was poured into cold (0° C.) water resulting in the precipitation of a tan colored solid. The solid was isolated by filtration, washed with further water and air dried overnight to afford N,N-dimethyl-1H-indole-2-carboxamide (1.11 g, 95%). $^1$H NMR (300 MHz, $CDCl_3$) δ ppm: 9.45 (s, 1H), 7.69 (dd, J=8.0, 1.0 Hz, 1H), 7.46 (dd, J=8.2, 0.9 Hz, 1H), 7.32 (dd, J=7.0, 1.2 Hz, 1H), 7.16 (ddd, J=8.0, 7.0, 1.0 Hz, 1H), 6.88 (dd, J=2.1, 1.0 Hz, 1H), 3.43 (s, 3H), 3.27 (s, 3H).

(Z)-1-(4-amino-2-fluorobut-2-en-1-yl)-3-(4-(N,N-dimethylsulfamoyl)benzyl)-N,N-dimethyl-1H-indole-2-carboxamide hydrochloride (Compound 5)

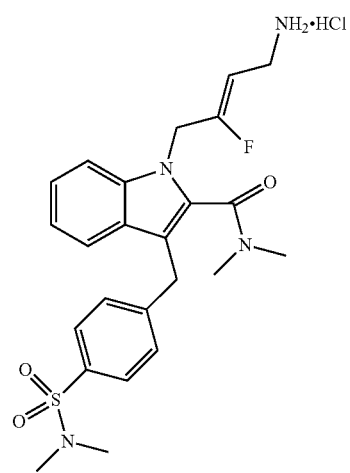

$^1$H NMR (300 MHz, Methanol-$d_4$) δ 7.67 (d, J=8.3 Hz, 21-1), 7.55-7.50 (m, 2H), 7.47 (d, J=8.3 Hz, 2H), 7.31 (ddd, J=8.4, 7.0, 1.1 Hz, 1H), 7.13 (dd, J=7.6 Hz, 1H), 5.17-4.88 (m, 3H), 4.29 (d, J=16.0 Hz, 1H), 4.17 (d, J=16.9 Hz, 1H), 3.59 (d, J=7.4 Hz, 2H), 3.10 (s, 4H), 2.97 (s, 3H), 2.65 (s, 6H).

Example 33

The following compounds were prepared according to procedures AA, Y, W, L, M, N, O, P, J and Q.

(Z)-4-(3-((6-(ethylsulfonyl)pyridin-3-yl)methyl)-2-isopropyl-1H-pyrrolo[3,2-b]pyridin-1-yl)-3-fluorobut-2-en-1-amine dihydrochloride (Compound 43)

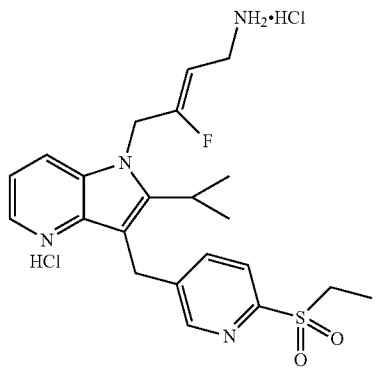

$^1$H-NMR (300 MHz, Methanol-$d_4$) δ ppm: 8.79 (d, J=7.9 Hz, 1H), 8.62 (s, 1H), 8.52 (d, J=5.5 Hz, 1H), 8.03 (d, J=7.4 Hz, 1H), 7.82 (d, J=7.6 Hz, 1H), 7.75 (t, J=6.9 Hz, 1H), 5.49 (d, J=11.6 Hz, 2H), 5.37 (dd, J=33.5, 6.8 Hz, 1H), 4.65 (s, 2H), 3.63 (d, J=7.9 Hz, 1H), 3.41 (q, J=7.5 Hz, 2H), 3.37 (s, 2H), 1.42 (d, J=6.8 Hz, 6H), 1.24 (t, J=7.4 Hz, 3H).

(Z)-3-fluoro-4-(2-isopropyl-3-((6-(isopropylsulfonyl)pyridin-3-yl)methyl)-1H-pyrrolo[3,2-b]pyridin-1-yl)but-2-en-1-amine hydrochloride (Compound 41)

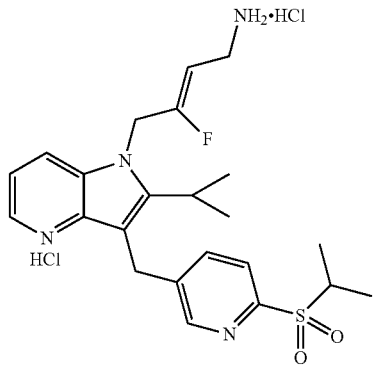

$^1$H-NMR (300 MHz, DMSO-$d_6$) δ ppm: 8.79 (d, J=8.3 Hz, 1H), 8.68 (d, J=2.1 Hz, 1H), 8.60 (d, J=5.7 Hz, 1H), 8.21 (s, 3H), 7.95 (d, J=8.1 Hz, 1H), 7.77 (dd, J=8.1, 2.2 Hz, 1H), 7.71 (dd, J=8.3, 5.7 Hz, 1H), 5.50 (d, J=12.3 Hz, 2H), 5.26 (dt, J=36.2, 7.2 Hz, 1H), 4.67 (s, 2H), 3.68 (p, J=6.8 Hz, 1H), 3.61-3.40 (m, 3H), 1.26 (d, J=7.0 Hz, 6H), 1.16 (dd, J=7.0, 2.0 Hz, 7H).

157

(Z)-4-(3-((6-(cyclopropylsulfonyl)pyridin-3-yl)methyl)-2-isopropyl-1H-pyrrolo[3,2-b]pyridin-1-yl)-3-fluorobut-2-en-1-amine dihydrochloride (Compound 44)

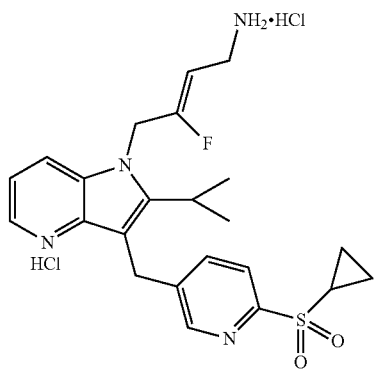

¹H-NMR (300 MHz, Methanol-d₄) δ ppm: 8.77 (d, J=8.1 Hz, 1H), 8.59 (d, J=1.6 Hz, 1H), 8.52 (dd, J=5.9, 1.0 Hz, 1H), 7.98 (dd, J=8.1, 0.8 Hz, 1H), 7.80 (dd, J=8.1, 2.2 Hz, 1H), 7.75 (dd, J=8.3, 5.9 Hz, 1H), 5.55-5.45 (m, 2H), 5.32 (dt, J=34.3, 7.4 Hz, 1H), 4.64 (s, 2H), 3.74-3.56 (m, 3H), 2.86 (tt, J=7.9, 4.8 Hz, 1H), 1.43 (d, J=7.1 Hz, 6H), 1.32-1.18 (m, 2H), 1.16-1.01 (m, 2H).

Example 34

The following compound was prepared according to procedures AAAK, AAAL, AA, Y, AAD, AAAY, J and Q.

(Z)-(1-(4-amino-2-fluorobut-2-en-1-yl)-2-isopropyl-1H-pyrrolo[3,2-b]pyridin-3-yl)(6-(methylsulfonyl)pyridin-3-yl)methanol dihydrochloride (Compound 42)

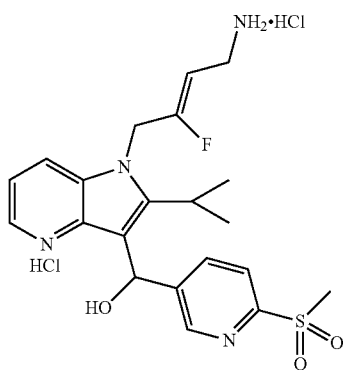

Procedure AAAY: Preparation of (2-isopropyl-1H-pyrrolo[3,2-b]pyridin-3-yl)(6-(methylsulfonyl)pyridin-3-yl)methanol

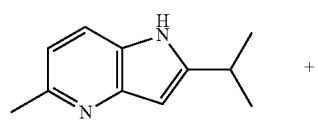 +

158

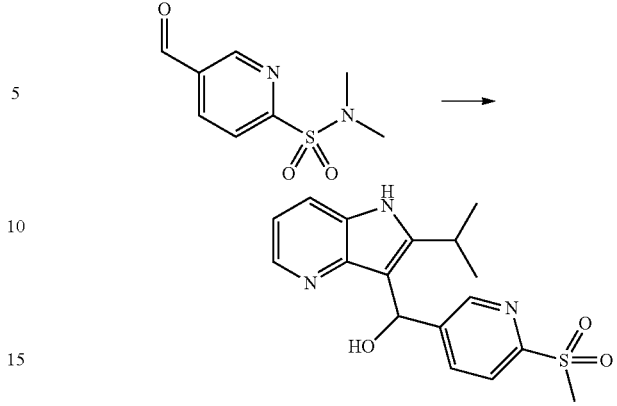

Into a 250-mL round-bottom flask, was placed a solution of 2-isopropyl-5-methyl-1H-pyrrolo[3,2-b]pyridine (1.60 g, 9.99 mmol) in anhydrous THF (30 mL). This was followed by the addition of LiHMDS (12 mL, 12.0 mmol) drop-wise with stirring at 0° C. The mixture was stirred for 10 min. To this was added a solution of 6-(methylsulfonyl)nicotinaldehyde (2.30 g, 12.4 mmol) in THF (20 mL) drop-wise with stirring at 0° C. The resulting solution was stirred for 1 hr at 0° C. The reaction was then quenched by the addition of brine (50 mL). The resulting solution was extracted with ethyl acetate (100 mL×3) and the organic layers combined, dried over anhydrous sodium sulfate, and concentrated under vacuum. The residue was purified over silica gel, eluting with dichloromethane/methanol (10:1) to afford (2-isopropyl-1H-pyrrolo[3,2-b]pyridin-3-yl)(6-(methylsulfonyl)pyridin-3-yl)methanol (2.80 g, 81%) as a light yellow solid. ¹H-NMR (300 MHz, DMSO-d₆): δ ppm: 11.17 (brs, 1H), 8.82 (s, 1H), 8.29-8.22 (m, 1H), 8.15-8.08 (m, 1H), 7.97 (d, J=8.1 Hz, 1H), 7.68-7.60 (m, 1H), 7.10-6.99 (m, 1H), 6.43 (d, J=4.1 Hz, 1H), 6.03 (d, J=4.2 Hz, 1H), 3.56-3.40 (m, 1H), 3.17 (s, 3H), 1.29 (d, J=6.9 Hz, 3H), 1.09 (d, J=7.0 Hz, 3H).

(Z)-(1-(4-amino-2-fluorobut-2-en-1-yl)-2-isopropyl-1H-pyrrolo[3,2-b]pyridin-3-yl)(6-(methylsulfonyl)pyridin-3-yl)methanol dihydrochloride (Compound 42)

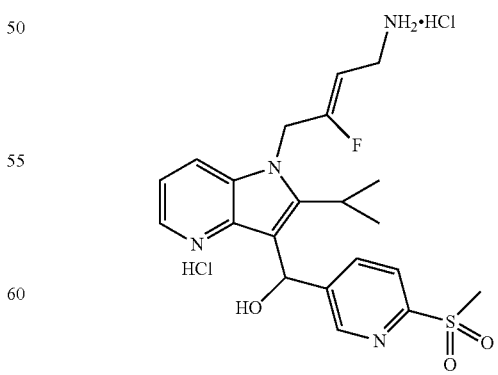

¹H-NMR (300 MHz, Methanol-d₄) δ 8.91-8.70 (m, 2H), 8.45 (dd, J=5.9, 0.9 Hz, 1H), 8.19-7.96 (m, 2H), 7.74 (dd, J=8.3, 5.9 Hz, 1H), 6.62 (s, 1H), 5.49 (d, J=11.5 Hz, 2H), 5.31 (dt, J=34.3, 7.4 Hz, 1H), 3.66 (dd, J=10.6, 7.3 Hz, 311), 3.24 (s, 3H), 1.52 (d, J=7.1 Hz, 3H), 1.35 (d, J=7.2 Hz, 3H).

Example 35

Method to Determine the Ability of Compounds of the Invention to Inhibit LOX and LOXL1-4 from Different Sources Lysyl oxidase (LOX) is an extracellular copper dependent enzyme which oxidizes peptidyl lysine and hydroxylysine residues in collagen and lysine residues in elastin to produce peptidyl alpha-aminoadipic-delta-semialdehydes. This catalytic reaction can be irreversibly inhibited by β-aminopropionitrile (BAPN) that binds to the active site of LOX (Tang S. S., Trackman P. C. and Kagan H. M., Reaction of aortic lysyl oxidase with beta-aminopropionitrile. *J Biol Chem* 1983; 258: 4331-4338). There are five LOX family members; these are LOX, LOXL1, LOXL2, LOXL3 and LOXL4. LOX and LOXL family members can be acquired as recombinant active proteins from commercial sources, or extracted from animal tissues like bovine aorta, tendons, pig skin; or prepared from cell cultures. The inhibitory effects of the compounds of the present invention were tested against the given LOX-LOXL preparation using a high-throughput coupled colorimetric method (Holt A. and Palcic M., A peroxidase-coupled continuous absorbance plate-reader assay for flavin monoamine oxidases, copper-containing amine oxidases and related enzymes. *Nat. Protoc.* 2006; 1: 2498-2505). The assay was developed using either 384 or 96 well format. Briefly, in a standard 384 well plate assay 25 µL of a dilution of any of the isoenzymes and orthologues in 1.2 M urea, 50 mM sodium borate buffer (pH 8.2) were added into each well in the presence of 1 µM mofegiline and 0.5 mM pargyline (to inhibit SSAO and MAO-B and MAO-A, respectively). Test compounds were dissolved in DMSO and tested in a Concentration Response Curve (CRC) with 11 data points, typically in the micromolar or nanomolar range after incubation with the enzyme for 30 min at 37° C. Twenty five µL of a reaction mixture containing twice the $K_M$ concentration of putrescine (Sigma Aldrich, e.g. 20 mM for LOX, or 10 mM for LOXL2 and LOXL3), 120 µM Amplex Red (Sigma Aldrich) and 1.5 U/mL horseradish peroxidase (Sigma Aldrich) prepared in 1.2 M urea, 50 mM sodium borate buffer (pH 8.2) were then added to the corresponding wells. The above volumes were doubled in the case of 96 wells plate. The fluorescence (RFU) was read every 2.5 min for 30 min at a range of temperatures from 37° to 45° C., excitation 565 nm and emission 590 (Optima; BMG labtech). The slope of the kinetics for each well was calculated using MARS data analysis software (BMG labtech) and this value was used to deduce the $IC_{50}$ value (Dotmatics). The ability of the inventive compounds to inhibit the amine oxidase activity LOX and other family members is shown in Table 2.

TABLE 2

LOX and LOXL2 inhibitory activities of examples of compounds of the invention

| Compound | Bovine LOX Activity $IC_{50}$ (nanomolar) | Human LOXL2 Activity $IC_{50}$ (nanomolar) |
|---|---|---|
| BAPN | >1000 | <1000 |
| 1 | >300 | <300 |
| 2 | >300 | <300 |
| 3 | >300 | <300 |

TABLE 2-continued

LOX and LOXL2 inhibitory activities of examples of compounds of the invention

| Compound | Bovine LOX Activity $IC_{50}$ (nanomolar) | Human LOXL2 Activity $IC_{50}$ (nanomolar) |
|---|---|---|
| 4 | >300 | <300 |
| 5 | >300 | <300 |
| 6 | >300 | <300 |
| 7 | >300 | <300 |
| 8 | >300 | <300 |
| 9 | >300 | <300 |
| 10 | >300 | <300 |
| 11 | >300 | <300 |
| 12 | >300 | <300 |
| 13 | >300 | <300 |
| 14 | >300 | <300 |
| 15 | >300 | <300 |
| 16 | >300 | <300 |
| 17 | >300 | <300 |
| 18 | >300 | <300 |
| 19 | >300 | <300 |
| 20 | >300 | <300 |
| 21 | >300 | <300 |
| 22 | >300 | <300 |
| 23 | >300 | <300 |
| 24 | >300 | <300 |
| 25 | >300 | <300 |
| 26 | >300 | <300 |
| 27 | >300 | <300 |
| 28 | >300 | <300 |
| 29 | >300 | <300 |
| 30 | >300 | <300 |
| 31 | >300 | <300 |
| 32 | >300 | <300 |
| 33 | >300 | <300 |
| 34 | >300 | <300 |
| 35 | >300 | <300 |
| 36 | >300 | <300 |
| 37 | >300 | <300 |
| 38 | >300 | <300 |
| 39 | >300 | <300 |
| 40 | >300 | <300 |
| 41 | >300 | <300 |
| 42 | >300 | <300 |
| 43 | >300 | <300 |
| 44 | >300 | <300 |

Example 36

Method to Determine the Ability of Compounds of Formula I to Inhibit Human Recombinant SSAO/VAP-1

Human recombinant SSAO/VAP-1 amine oxidase activity was determined using the coupled colorimetric method as described for monoamine oxidase, copper-containing amine oxidases and related enzymes (Holt A. and Palcic M., A peroxidase-coupled continuous absorbance plate-reader assay for flavin monoamine oxidases, copper-containing amine oxidases and related enzymes. *Nat Protoc* 2006; 1: 2498-2505). Briefly, a cloned cDNA template corresponding to residues 34-763 of human SSAO/VAP-1, and incorporating a mouse Ig kappa (κ) signal sequence, N-terminal flag epitope tag and tobacco etch virus (TEV) cleavage site, was assembled in a mammalian expression vector (pLO-CMV) by Geneart AG. This vector containing human SSAO/VAP-1 residues was transfected into CHO-K1 glycosylation mutant cell line, Lec 8. A clone stably expressing human SSAO/VAP-1 was isolated and cultured in large scale. Active human SSAO/VAP-1 was purified and recovered using immunoaffinity chromatography. This was used as the source for SSAO/VAP-1 activity. A high-throughput colorimetric assay was developed using either 96 or 384 well format. Briefly, in a standard 96 well plate assay 50 μL of purified human SSAO/VAP-1 (0.25 μg/mL) in 0.1 M sodium phosphate buffer (pH 7.4) was added into each well. Test compounds were dissolved in DMSO and tested in a Concentration Response Curve (CRC) with 4-11 data points, typically in the micromolar or nanomolar range after incubation with human SSAO/VAP-1 for 30 min at 37° C. After 30 min incubation, 50 μL of the reaction mixture containing 600 μM benzylamine (Sigma Aldrich), 120 μM Amplex Red (Sigma Aldrich) and 1.5 U/mL horseradish peroxidase (Sigma Aldrich) prepared in 0.1 M sodium phosphate buffer (pH 7.4) were added to the corresponding well. The fluorescence unit (RFU) was read every 2.5 min for 30 min at 37° C. excitation 565 nm and emission 590 (Optima; BMG labtech). The slope of the kinetics for each well was calculated using MARS data analysis software (BMG labtech) and this value was used to deduce the $IC_{50}$ value (Dotmatics). The ability of the compounds of Formula I to inhibit SSAO/VAP-1 is shown in Table 3.

Example 37

Method to Determine the Ability of Compounds of Formula I to Inhibit Human Recombinant MAO-B The specificity of the compounds of this invention was tested by determining their ability to inhibit MAO-B activities in vitro. Recombinant human MAO-B (0.06 mg/mL; Sigma Aldrich) was used as source of MAO-B enzyme activities. The assay was performed in a similar way as for human SSAO/VAP-1 (Example 36) except, the substrate benzylamine was used at 100 μM. The ability of compounds of Formula I to inhibit MAO-B is shown in Table 3.

TABLE 3

Selectivity of Compounds of Formula I for LOX and LOXL2 compared to SSAO/VAP-1 and MAO-B

| Compound | SSAO/VAP-1 Activity $IC_{50}$ (micromolar) | MAO-B Activity $IC_{50}$ (micromolar) |
|---|---|---|
| BAPN | >3 | >3 |
| 1 | >3 | >3 |
| 2 | >3 | >3 |
| 3 | >3 | >3 |
| 4 | >3 | >3 |
| 5 | >3 | >3 |
| 6 | >3 | >3 |
| 7 | >3 | >3 |
| 8 | >3 | >3 |
| 9 | >3 | >3 |
| 10 | >3 | >3 |
| 11 | >3 | >3 |
| 12 | >3 | >3 |
| 13 | >3 | >3 |
| 14 | >3 | >3 |
| 15 | >3 | >3 |
| 16 | >3 | >3 |
| 17 | >3 | >3 |
| 18 | >3 | >3 |
| 19 | >3 | >3 |
| 20 | >3 | >3 |
| 21 | >3 | >3 |
| 22 | >3 | >3 |
| 23 | >3 | >3 |
| 24 | >3 | >3 |
| 25 | >3 | >3 |
| 26 | >3 | >3 |
| 27 | >3 | >3 |
| 28 | >3 | >3 |
| 29 | >3 | >3 |
| 30 | >3 | >3 |
| 31 | >3 | >3 |

TABLE 3-continued

Selectivity of Compounds of Formula I for LOX and LOXL2 compared to SSAO/VAP-1 and MAO-B

| Compound | SSAO/VAP-1 Activity $IC_{50}$ (micromolar) | MAO-B Activity $IC_{50}$ (micromolar) |
|---|---|---|
| 32 | >3 | >3 |
| 33 | >3 | >3 |
| 34 | >3 | >3 |
| 35 | >3 | >3 |
| 36 | >3 | >3 |
| 37 | >3 | >3 |
| 38 | >3 | >3 |
| 39 | >3 | >3 |
| 40 | >3 | >3 |
| 41 | >3 | >3 |
| 42 | >3 | >3 |
| 43 | nt | nt |
| 44 | nt | nt |

LOX and LOXL1-4 enzymes are members of a large family of flavin-dependent and copper-dependent amine oxidases, which includes SSAO/VAP-1 and monoamine oxidase-B (MAO-B). Compounds of the present invention selectively inhibit members of the LOX family of enzymes with respect to SSAO/VAP-1, MAO-B and other family member amine oxidases. Examples of the magnitude of selectivity can be seen in Table 3.

Example 38

Inhibition of $CCl_4$ Induced Liver Fibrosis

An analysis of the use of LOXL2 inhibitors to treat inflammatory/fibrotic diseases is performed through the use of a $CCl_4$ induced liver fibrosis model. Liver injury is frequently followed by complete parenchymal regeneration due to regenerative potency of hepatocytes. Continuous liver injury due to the administration of $CCl_4$ leads to extracellular matrix accumulation, accompanied by recurrent hepatocyte necrosis, inflammation, and regenerative processes, causing liver fibrosis and consequently liver cirrhosis (see Natsume, M, et al., *Attenuated liver fibrosis and depressed serum albumin levels in carbon tetrachloride-treated IL-6-deficient mice. J. Leukoc. Biol.*, 1999, 66, 601-608 also See Yao, Q, Y, et al. *Inhibition by curcumin of multiple sites of the transforming growth factor-beta1 signalling pathway ameliorates the progression of liver fibrosis induced by carbon tetrachloride in rats. BMC Complement Altern Med.* 2012 Sep. 16; 12(1):156.)

Rats are administered orally with $CCl_4$ at a concentration of 0.25 μL/g in olive oil, 3 times per week for 6 weeks. Compound 22 is given 0.1-100 mg/Kg throughout the period of the experimental procedure or only 3 weeks after $CCl_4$ administration and then throughout the entire study. Compared with the vehicle-treated group that show increases in fibrosis in the liver, Compound 22 administration shows up to 50% reduction as demonstrated by liver sirius red staining with quantification (See FIG. 1). In addition, Compound 22 treated mice results in a statistically significant reduction in the liver collagen with inhibition of >30% of collagen by hydroxyproline analysis.

Example 39

Streptozotocin and High Fat Diet Induced Liver Fibrosis

High fat/carbohydrate diet induced liver fibrosis is the most common reason for liver dysfunction and ultimately liver failure. NASH is induced in male mice by a single subcutaneous injection of 200 μg streptozotocin solution 2 days after birth and feeding with high fat diet after 4 weeks of age (STAM™ model). The STAM™ model demonstrates NASH progression that resembles the disease in humans: STAM™ mice manifest NASH at 8 weeks, which progresses to fibrosis at 12 weeks (K Saito et al. *Characterization of hepatic lipid profiles in a mouse model with nonalcoholic steatohepatitis and subsequent fibrosis Sci Rep.* 2015 Aug. 20; 5:12466).

Figure 2:
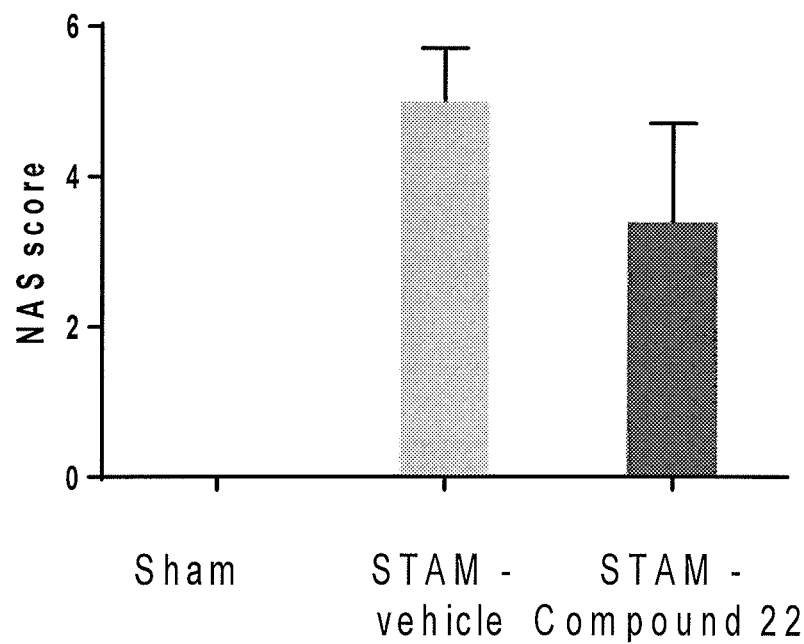
FIG. 2 shows the ability of Compound 22 to reduce fibrosis in a mouse model of streptozotocin and high fat diet induced liver fibrosis.

LOXL2 inhibitor compound 22 was administered by daily oral gavage at doses between 10-30 mg/kg 8 weeks after streptozotocin application. Mice were sacrificed after NASH had been established and whole blood samples were taken via cardiac puncture. Liver samples were collected and washed with cold saline. Liver weight was measured. The left lateral, right and caudate lobes of livers were snap frozen in liquid nitrogen and stored at −80° C. For HE staining, sections were cut from paraffin blocks of liver tissue prefixed in Bouin's solution and stained with Lillie-Mayer's Hematoxylin and eosin solution. NAFLD Activity score (NAS) was calculated according to the criteria of Kleiner (Kleiner D E. et al., *Design and validation of a histological scoring system for nonalcoholic fatty liver disease. Hepatology,* 2005; 41: 1313). To visualize collagen deposition, Bouin's fixed liver sections were stained using picro-Sirius red solution and the area of fibrosis was quantified (See FIG. 2).

Example 40

Reduction of Collagen Cross-Link Formation in an in vitro Fibroblastic Foci Model of IPF The lung tissue of patients with idiopathic pulmonary fibrosis (IPF) is characterised by dense collections of myofibroblasts and extracellular matrix (ECM) termed 'fibroblastic foci'. Using a novel in vitro model of fibroblastic foci (Jones et al., AJRCCM 191; 2015:A4912) the formation of lysyl oxidase (LOX) mediated collagen cross-links and the effects of the nonselective LOX inhibitor β-aminopropionitrile (BAPN) as well lysyl oxidase like-2 (LOXL2)-selective inhibitors were investigated.

Cultures of primary fibroblasts were grown out from clinical diagnostic biopsies of fibrotic lung and stored in liquid nitrogen. Fibroblasts from confirmed cases of IPF were subsequently expanded and seeded onto transwell membranes under optimised conditions for mature collagen matrix deposition in the presence of BAPN or a LOXL2-selective inhibitor (Compound 22). Following stimulation with transforming growth factor β1 (TGF-β1) multicellular foci formed which were histochemically similar in organisation to fibroblastic foci in vivo. The foci were cultured for a further six weeks in the presence of TGF-β1 and the inhibitors. Cultures were then harvested and snap frozen in liquid nitrogen.

To quantify collagen cross-links (Robins Biochem Soc Trans 2007; 35(5): 849-852; Saito et al Anal. Biochem. 1997; 253: 26-32; Sims, Avery & Bailey Methods in Molecular Biology 2000; vol 139: 11-26), cultures were treated with potassium borohydride to stabilise the reducible immature cross-links, and hydrolysed in 6N HCl at 100° C. for 16 hr. Total collagen content was assessed by hydroxyproline assay. Immature cross-links were assessed by LC/MS/MS and mature pyridinoline cross-links by ELISA. Cross-link data is expressed as moles of cross-link per mole collagen.

Figure 3:
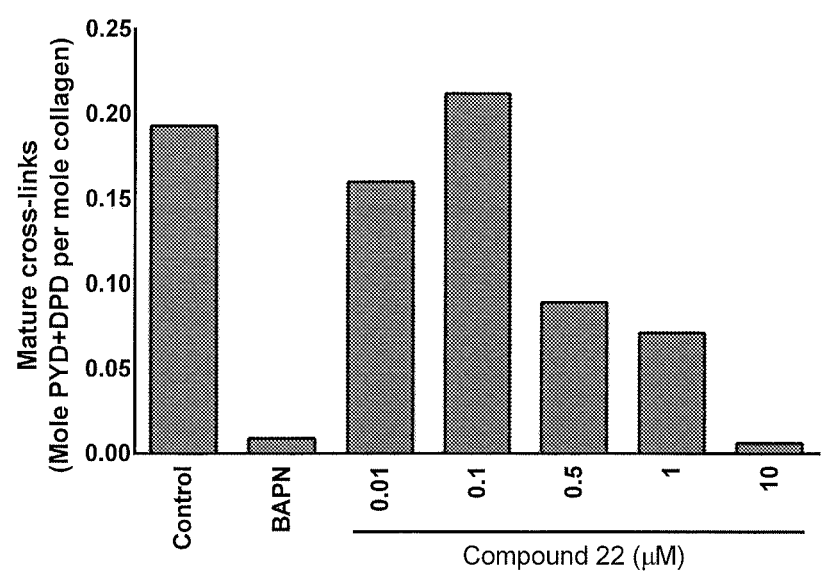
FIG. 3 shows the ability of Compound 22 to reduce collagen cross-link formation in an in vitro fibroblastic foci model of idiopathic pulmonary fibrosis (IPF).

The number of mature LOX family-mediated collagen crosslinks increased over the 6 week duration of the model. Both BAPN and the LOXL2-selective inhibitor (Compound 22) reduced cross-link formation in a concentration dependent manner (see FIG. 3).

The invention claimed is:
1. A compound of Formula I:

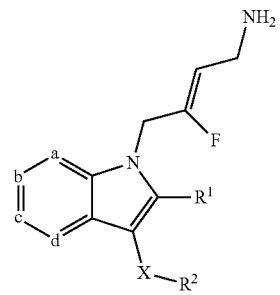

Formula I or a stereoisomer, pharmaceutically acceptable salt, or tautomeric form thereof;
wherein:
a is N or $CR^3$;
b is N or $CR^4$;
c is N or $CR^5$;
d is N or $CR^6$;
and from 0 to 2 of a, b, c and d are N;
X is O or —$(CHR^7)_m$—
m is 1 or 2;
$R^1$ is selected from the group consisting of hydrogen, halogen, $C_{1-6}$alkyl, $C_{3-7}$cycloalkyl, —O—$C_{1-6}$alkyl, —O—$C_{3-7}$cycloalkyl, —C(O)$OR^8$, —C(O)$NR^9R^{10}$ and —$NR^9C(O)R^{11}$; wherein each $C_{1-6}$alkyl is a straight or branched chain alkyl; and wherein each $C_{1-6}$-alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$;
$R^2$ is aryl or heteroaryl; wherein each $R^2$ is optionally substituted by one or more $R^{12}$;
$R^3$, $R^4$, $R^5$ and $R^6$ are each independently selected from the group consisting of hydrogen, halogen, hydroxyl, $C_{1-6}$alkyl, $C_{3-7}$cycloalkyl, —O—$C_{1-6}$alkyl, —O—$C_{3-7}$cycloalkyl, —CN, —$NO_2$, —$NR^9R^{10}$, —C(O)$OR^8$, —C(O)$NR^9R^{10}$, —$NR^9C(O)R^{11}$, —S($O_2$)$NR^9R^{10}$, —$NR^9S(O_2)R^{11}$, —S(O)$R^{11}$, —S($O_2$)$R^{11}$, tetrazole and oxadiazole; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$;
each $R^7$ is independently selected from the group consisting of hydrogen, hydroxyl and $C_{1-3}$alkyl;
$R^8$ is selected from the group consisting of hydrogen, $C_{1-6}$alkyl, and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$;
$R^9$ and $R^{10}$ are independently selected from the group consisting of hydrogen, $C_{1-6}$alkyl and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —C$_{1-3}$alkyl, —O—C$_{1-3}$alkyl, —CF$_3$, —CH$_2$CF$_3$, and —O—CF; or R$^9$ and R$^{10}$ when attached to the same nitrogen atom are combined to form a 3- to 7-membered ring having from 0 to 2 additional heteroatoms as ring members;

R$^{11}$ is selected from the group consisting of C$_{1-6}$alkyl and C$_{3-7}$cycloalkyl; wherein each C$_{1-6}$alkyl is a straight or branched chain alkyl; and wherein each C$_{1-6}$alkyl and C$_{3-7}$cycloalkyl is optionally substituted by one or more substituents selected from the group consisting of halogen, —OH, —SH, —C$_{1-3}$alkyl, —O—C$_{1-3}$alkyl, —CF$_3$, —CH$_2$CF$_3$, and —O—CF$_3$; and R$^{12}$ is selected from the group consisting of halogen, C$_{1-6}$alkyl, —O—C$_{1-6}$alkyl, —S—C$_{1-6}$alkyl, C$_{3-7}$cycloalkyl, —O—C$_{3-7}$cycloalkyl, —C(O)OR$^8$, —C(O)NR$^9$R$^{10}$, —NR$^9$C(O)R$^{11}$, —S(O$_2$)NR$^9$R$^{10}$, —NR$^9$S(O$_2$)R$^{11}$, —S(O)R$^{11}$ and —S(O$_2$)R$^{11}$; wherein each C$_{1-6}$alkyl is a straight or branched chain alkyl; and wherein each C$_{1-6}$alkyl and C$_{3-7}$cycloalkyl is optionally substituted by one or more substituents selected from the group consisting of halogen, —OH, —C$_{1-3}$alkyl, —O—C$_{1-3}$alkyl, —CF$_3$, —CH$_2$CF$_3$, and —O—CF$_3$.

2. A compound according to claim 1, of Formula Ia:

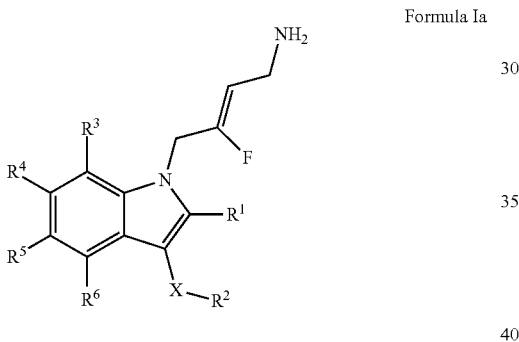

Formula Ia or a pharmaceutically acceptable salt thereof;
wherein:
X is O or —(CHR$^7$)$_m$—
m is 1 or 2;

R$^1$ is selected from the group consisting of hydrogen, halogen, C$_{1-6}$alkyl, C$_{3-7}$cycloalkyl, —O—C$_{1-6}$alkyl, —O—C$_{3-7}$cycloalkyl, —C(O)OR$^8$, —C(O)NR$^9$R$^{10}$ and —NR$^9$C(O)R$^{11}$; wherein each C$_{1-6}$alkyl is a straight or branched chain alkyl; and wherein each C$_{1-6}$alkyl and C$_{3-7}$cycloalkyl is optionally substituted by one or more substituents selected from the group consisting of halogen, —OH, —SH, —C$_{1-3}$alkyl, —O—C$_{1-3}$alkyl, —CF$_3$, —CH$_2$CF$_3$, and —O—CF$_3$;

R$^2$ is aryl or heteroaryl; wherein each R$^2$ is optionally substituted by one or more R$^{12}$;

R$^3$, R$^4$, R$^5$ and R$^6$ are each independently selected from the group consisting of hydrogen, halogen, hydroxyl, C$_{1-6}$alkyl, C$_{3-7}$cycloalkyl, —O—C$_{1-6}$alkyl, —O—C$_{3-7}$cycloalkyl, —CN, —NO$_2$, —NR$^9$R$^{10}$, —C(O)OR$^8$, —C(O)NR$^9$R$^{10}$, —NR$^9$C(O)R$^{11}$, —S(O$_2$)NR$^9$R$^{10}$, —NR$^9$S(O$_2$)R$^{11}$, —S(O)R$^{11}$, —S(O$_2$)R$^{11}$, tetrazole and oxadiazole; wherein each C$_{1-6}$alkyl is a straight or branched chain alkyl; and wherein each C$_{1-6}$alkyl and C$_{3-7}$cycloalkyl is optionally substituted by one or more substituents selected from the group consisting of halogen, —OH, —SH, —C$_{1-3}$alkyl, —O—C$_{1-3}$alkyl, —CF$_3$, —CH$_2$CF$_3$, and —O—CF$_3$;

each R$^7$ is independently selected from the group consisting of hydrogen, hydroxyl and C$_{1-3}$alkyl;

R$^8$ is selected from the group consisting of hydrogen, C$_{1-6}$alkyl, and C$_{3-7}$cycloalkyl; wherein each C$_{1-6}$alkyl is a straight or branched chain alkyl; and wherein each C$_{1-6}$alkyl and C$_{3-7}$cycloalkyl is optionally substituted by one or more substituents selected from the group consisting of halogen, —OH, —SH, —C$_{1-3}$alkyl, —O—C$_{1-3}$alkyl, —CF$_3$, —CH$_2$CF$_3$, and —O—CF$_3$;

R$^9$ and R$^{10}$ are independently selected from the group consisting of hydrogen, C$_{1-6}$alkyl and C$_{3-7}$cycloalkyl; wherein each C$_{1-6}$alkyl is a straight or branched chain alkyl; and wherein each C$_{1-6}$alkyl and C$_{3-7}$cycloalkyl is optionally substituted by one or more substituents selected from the group consisting of halogen, —OH, —SH, —C$_{1-3}$alkyl, —O—C$_{1-3}$alkyl, —CF$_3$, —CH$_2$CF$_3$, and —O—CF$_3$; or R$^9$ and R$^{10}$ when attached to the same nitrogen atom are combined to form a 3- to 7-membered ring having from 0 to 2 additional heteroatoms as ring members;

R$^{11}$ is selected from the group consisting of C$_{1-6}$alkyl and C$_{3-7}$cycloalkyl; wherein each C$_{1-6}$alkyl is a straight or branched chain alkyl; and wherein each C$_{1-6}$alkyl and C$_{3-7}$cycloalkyl is optionally substituted by one or more substituents selected from the group consisting of halogen, —OH, —SH, —C$_{1-3}$alkyl, —O—C$_{1-3}$alkyl, —CF$_3$, —CH$_2$CF$_3$, and —O—CF$_3$; and R$^{12}$ is selected from the group consisting of halogen, C$_{1-6}$alkyl, —O—C$_{1-6}$alkyl, —S—C$_{1-6}$alkyl, C$_{3-7}$cycloalkyl, —O—C$_{3-7}$cycloalkyl, —C(O)OR$^8$, —C(O)NR$^9$R$^{10}$, —NR$^9$C(O)R$^{11}$, —S(O$_2$)NR$^9$R$^{10}$, —NR$^9$S(O$_2$)R$^{11}$, —S(O)R$^{11}$ and —S(O$_2$)R$^{11}$; wherein each C$_{1-6}$alkyl is a straight or branched chain alkyl; and wherein each C$_{1-6}$alkyl and C$_{3-7}$cycloalkyl is optionally substituted by one or more substituents selected from the group consisting of halogen, —OH, —C$_{1-3}$alkyl, —O—C$_{1-3}$alkyl, —CF$_3$, —CH$_2$CF$_3$, and —O—CF$_3$.

3. A compound according to claim 1, of Formula Ib:

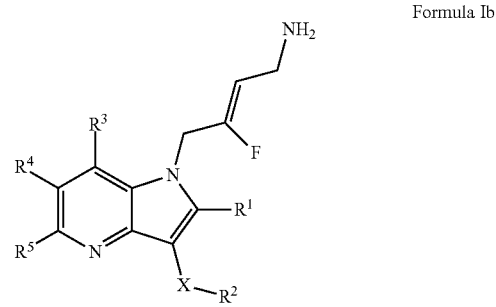

Formula Ib or a pharmaceutically acceptable salt thereof;
X is O or —(CHR$^7$)$_m$—
m is 1 or 2;

R$^1$ is selected from the group consisting of hydrogen, halogen, C$_{1-6}$alkyl, C$_{3-7}$cycloalkyl, —O—C$_{1-6}$alkyl, —O—C$_{3-7}$cycloalkyl, —C(O)OR$^8$, —C(O)NR$^9$R$^{10}$ and —NR$^9$C(O)R$^{11}$; wherein each C$_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$;

$R^2$ is aryl or heteroaryl; wherein each $R^2$ is optionally substituted by one or more $R^{12}$;

$R^3$, $R^4$ and $R^5$ are each independently selected from the group consisting of hydrogen, halogen, hydroxyl, $C_{1-6}$alkyl, $C_{3-7}$cycloalkyl, —O—$C_{1-6}$alkyl, —O—$C_{3-7}$cycloalkyl, —CN, —$NO_2$, —$NR^9R^{10}$, —C(O)$OR^8$, —C(O)$NR^9R^{10}$, —$NR^9$C(O)$R^{11}$, —S($O_2$)$NR^9R^{10}$, —$NR^9$S($O_2$)$R^{11}$, —S(O)$R^{11}$, —S($O_2$)$R^{11}$, tetrazole and oxadiazole; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$;

each $R^7$ is independently selected from the group consisting of hydrogen, hydroxyl and $C_{1-3}$alkyl;

$R^8$ is selected from the group consisting of hydrogen, $C_{1-6}$alkyl, and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$;

$R^9$ and $R^{10}$ are independently selected from the group consisting of hydrogen, $C_{1-6}$alkyl and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$; or $R^9$ and $R^{10}$ when attached to the same nitrogen atom are combined to form a 3- to 7-membered ring having from 0 to 2 additional heteroatoms as ring members;

$R^{11}$ is selected from the group consisting of $C_{1-6}$alkyl and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$; and $R^{12}$ is selected from the group consisting of halogen, $C_{1-6}$alkyl, —O—$C_{1-6}$-alkyl, —S—$C_{1-6}$alkyl, $C_{3-7}$cycloalkyl, —O—$C_{3-7}$cycloalkyl, —C(O)$OR^8$, —C(O)$NR^9R^{10}$, —$NR^9$C(O)$R^{11}$, —S($O_2$)$NR^9R^{10}$, —$NR^9$S($O_2$)$R^{11}$, —S(O)$R^{11}$ and —S($O_2$)$R^{11}$; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —$C_{1-3}$alkyl, —O—$C_{1-3}$alkyl, —$CF_3$, —$CH_2CF_3$, and —O—$CF_3$.

4. A compound according to claim 1, of Formula Ic:

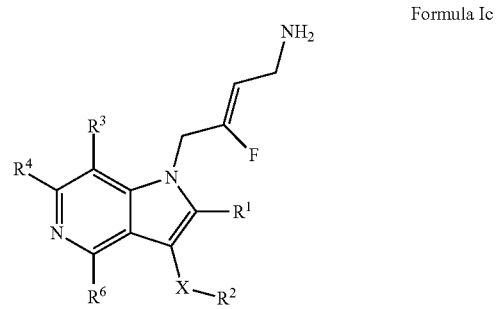

Formula Ic or a pharmaceutically acceptable salt thereof;

X is O or —(CHR$^7$)$_m$— m is 1 or 2;

$R^1$ is selected from the group consisting of hydrogen, halogen, $C_{1-6}$alkyl, $C_{3-7}$cycloalkyl, —O—$C_{1-6}$alkyl, —O—$C_{3-7}$cycloalkyl, —C(O)$OR^8$, —C(O)$NR^9R^{10}$ and —$NR^9$C(O)$R^{11}$; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$;

$R^2$ is aryl or heteroaryl; wherein each $R^2$ is optionally substituted by one or more $R^{12}$;

$R^3$, $R^4$ and $R^6$ are each independently selected from the group consisting of hydrogen, halogen, hydroxyl, $C_{1-6}$alkyl, $C_{3-7}$cycloalkyl, —O—$C_{1-6}$alkyl, —O—$C_{3-7}$cycloalkyl, —CN, —$NO_2$, —$NR^9R^{10}$, —C(O)$OR^8$, —C(O)$NR^9R^{10}$, —$NR^9$C(O)$R^{11}$, —S($O_2$)$NR^9R^{10}$, —$NR^9$S($O_2$) $R^{11}$, —S(O)$R^{11}$, —S($O_2$)$R^{11}$, tetrazole and oxadiazole; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$;

each $R^7$ is independently selected from the group consisting of hydrogen, hydroxyl and $C_{1-3}$alkyl;

$R^8$ is selected from the group consisting of hydrogen, $C_{1-6}$alkyl, and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$;

$R^9$ and $R^{10}$ are independently selected from the group consisting of hydrogen, $C_{1-6}$alkyl and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$; or $R^9$ and $R^{10}$ when attached to the same nitrogen atom are combined to form a 3- to 7-membered ring having from 0 to 2 additional heteroatoms as ring members;

$R^{11}$ is selected from the group consisting of $C_{1-6}$alkyl and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$; and $R^{12}$ is selected from the group consisting of halogen, $C_{1-6}$alkyl, —O—$C_{1-6}$alkyl, —S—$C_{1-6}$alkyl, $C_{3-7}$cycloalkyl, —O—$C_{3-7}$cycloalkyl, —C(O)OR$^8$, —C(O)NR$^9$R$^{10}$, —NR$^9$C(O)R$^{11}$, —S(O$_2$)NR$^9$R$^{10}$, —NR$^9$S(O$_2$)R$^{11}$, —S(O)R$^{11}$ and —S(O$_2$)R$^{11}$; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —$C_{1-3}$alkyl, —O—$C_{1-3}$alkyl, —$CF_3$, —$CH_2CF_3$, and —O—$CF_3$.

5. A compound according to claim 1, of Formula If:

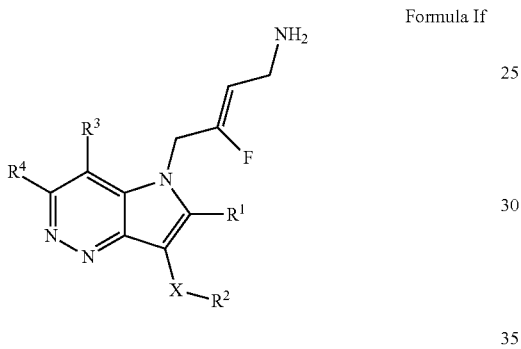

Formula If or a pharmaceutically acceptable salt thereof;

X is O or —(CHR$^7$)$_m$— m is 1 or 2;

$R^1$ is selected from the group consisting of hydrogen, halogen, $C_{1-6}$alkyl, $C_{3-7}$cycloalkyl, —O—$C_{1-6}$alkyl, —O—$C_{3-7}$cycloalkyl, —C(O)OR$^8$, —C(O)NR$^9$R$^{10}$ and —NR$^9$C(O)R$^{11}$; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$;

$R^2$ is aryl or heteroaryl; wherein each $R^2$ is optionally substituted by one or more $R^{12}$;

$R^3$ and $R^4$ are each independently selected from the group consisting of hydrogen, halogen, hydroxyl, $C_{1-6}$alkyl, $C_{3-7}$cycloalkyl, —O—$C_{1-6}$alkyl, —O—$C_{3-7}$cycloalkyl, —CN, —NO$_2$, —NR$^9$R$^{10}$, —C(O)OR$^8$, —C(O)NR$^9$R$^{10}$, —NR$^9$C(O)R$^{11}$, —S(O$_2$)NR$^9$R$^{10}$, —NR$^9$S(O$_2$)R$^{11}$, —S(O)R$^{11}$, —S(O$_2$)R$^{11}$, tetrazole and oxadiazole; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$;

each $R^7$ is independently selected from the group consisting of hydrogen, hydroxyl and $C_{1-3}$alkyl;

$R^8$ is selected from the group consisting of hydrogen, $C_{1-6}$alkyl, and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$;

$R^9$ and $R^{10}$ are independently selected from the group consisting of hydrogen, $C_{1-6}$alkyl and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$; or $R^9$ and $R^{10}$ when attached to the same nitrogen atom are combined to form a 3- to 7-membered ring having from 0 to 2 additional heteroatoms as ring members;

$R^{11}$ is selected from the group consisting of $C_{1-6}$alkyl and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$; and $R^{12}$ is selected from the group consisting of halogen, $C_{1-6}$alkyl, —O—$C_{1-6}$alkyl, —S—$C_{1-6}$alkyl, $C_{3-7}$cycloalkyl, —O—$C_{3-7}$cycloalkyl, —C(O)OR$^8$, —C(O)NR$^9$R$^{10}$, —NR$^9$C(O)R$^{11}$, —S(O$_2$)NR$^9$R$^{10}$, —NR$^9$S(O$_2$)R$^{11}$, —S(O)R$^{11}$ and —S(O$_2$)R$^9$R$^{11}$; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —$C_{1-3}$alkyl, —O—$C_{1-3}$alkyl, —$CF_3$, —$CH_2CF_3$, and —O—$CF_3$.

6. A compound according to claim 1, of Formula Ig:

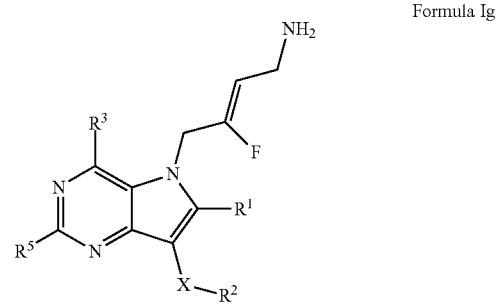

Formula Ig or a pharmaceutically acceptable salt thereof;

X is O or —(CHR$^7$)$_m$— m is 1 or 2;

$R^1$ is selected from the group consisting of hydrogen, halogen, $C_{1-6}$alkyl, $C_{3-7}$cycloalkyl, —O—$C_{1-6}$alkyl, —O—$C_{3-7}$cycloalkyl, —C(O)OR$^8$, —C(O)NR$^9$R$^{10}$ and —NR$^9$C(O)R$^{11}$; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$;

$R^2$ is aryl or heteroaryl; wherein each $R^2$ is optionally substituted by one or more $R^{12}$;

$R^3$ and $R^5$ are each independently selected from the group consisting of hydrogen, halogen, hydroxyl, $C_{1-6}$alkyl, $C_{3-7}$cycloalkyl, —O—$C_{1-6}$alkyl, —O—$C_{3-7}$cycloalkyl, —CN, —NO$_2$, —NR$^9$R$^{10}$, —C(O)OR$^8$, —C(O)NR$^9$R$^{10}$, —NR$^9$C(O)R$^{11}$, —S(O$_2$)NR$^9$R$^{10}$, —NR$^9$S(O$_2$)R$^{11}$, —S(O)R$^{11}$, —S(O$_2$)R$^{11}$, tetrazole and oxadiazole; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —CF$_3$, —CH$_2$CF$_3$, and —O—CF$_3$;

each $R^7$ is independently selected from the group consisting of hydrogen, hydroxyl and $C_{1-3}$alkyl;

$R^8$ is selected from the group consisting of hydrogen, $C_{1-6}$alkyl, and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —CF$_3$, —CH$_2$CF$_3$, and —O—CF$_3$;

$R^9$ and $R^{10}$ are independently selected from the group consisting of hydrogen, $C_{1-6}$alkyl and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —CF$_3$, —CH$_2$CF$_3$, and —O—CF$_3$; or $R^9$ and $R^{10}$ when attached to the same nitrogen atom are combined to form a 3- to 7-membered ring having from 0 to 2 additional heteroatoms as ring members;

$R^{11}$ is selected from the group consisting of $C_{1-6}$alkyl and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —CF$_3$, —CH$_2$CF$_3$, and —O—CF$_3$; and $R^{12}$ is selected from the group consisting of halogen, $C_{1-6}$alkyl, —O—$C_{1-6}$alkyl, —S—$C_{1-6}$alkyl, $C_{3-7}$cycloalkyl, —O—$C_{3-7}$cycloalkyl, —C(O)OR$^8$, —C(O)NR$^9$R$^{10}$, —NR$^9$C(O)R$^{11}$, —S(O$_2$)NR$^9$R$^{10}$, —NR$^9$S(O$_2$)R$^{11}$, —S(O)R$^{11}$ and —S(O$_2$)R$^{11}$; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —$C_{1-3}$alkyl, —O—$C_{1-3}$alkyl, —CF$_3$, —CH$_2$CF$_3$, and —O—CF$_3$.

7. A compound according to claim 1, wherein m is 1 and $R^7$ is hydrogen.

8. A compound according to claim 1, wherein $R^1$ is selected from the group consisting of hydrogen, methyl, ethyl, isopropyl, 1-hydroxyethyl, 2-hydroxyisopropyl, chloro and —C(O)N(CH$_3$)$_2$.

9. A compound according to claim 1, selected from the group consisting of:

1 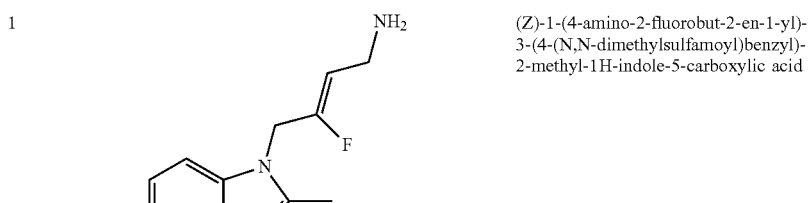

(Z)-1-(4-amino-2-fluorobut-2-en-1-yl)-3-(4-(N,N-dimethylsulfamoyl)benzyl)-2-methyl-1H-indole-5-carboxylic acid 2 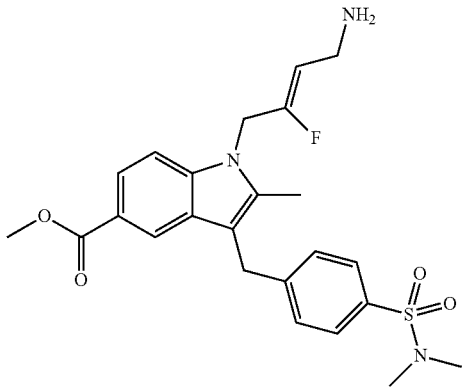

(Z)-methyl 1-(4-amino-2-fluorobut-2-en-1-yl)-3-(4-(N,N-dimethylsulfamoyl)benzyl)-2-methylindole-5-carboxylate -continued
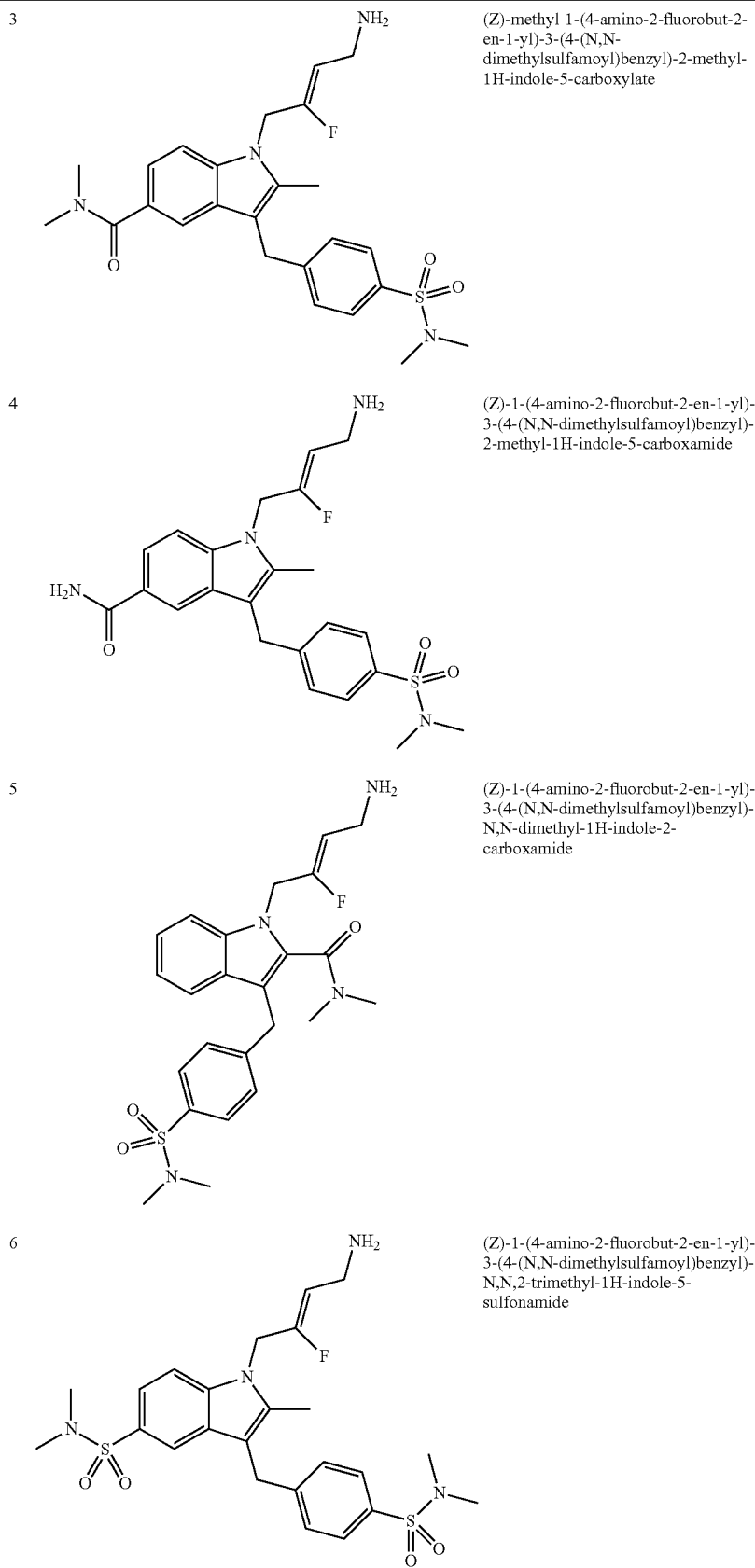
3    (Z)-methyl 1-(4-amino-2-fluorobut-2-en-1-yl)-3-(4-(N,N-dimethylsulfamoyl)benzyl)-2-methyl-1H-indole-5-carboxylate
4    (Z)-1-(4-amino-2-fluorobut-2-en-1-yl)-3-(4-(N,N-dimethylsulfamoyl)benzyl)-2-methyl-1H-indole-5-carboxamide
5    (Z)-1-(4-amino-2-fluorobut-2-en-1-yl)-3-(4-(N,N-dimethylsulfamoyl)benzyl)-N,N-dimethyl-1H-indole-2-carboxamide
6    (Z)-1-(4-amino-2-fluorobut-2-en-1-yl)-3-(4-(N,N-dimethylsulfamoyl)benzyl)-N,N,2-trimethyl-1H-indole-5-sulfonamide

| # | | |
|---|---|---|
| 7 | 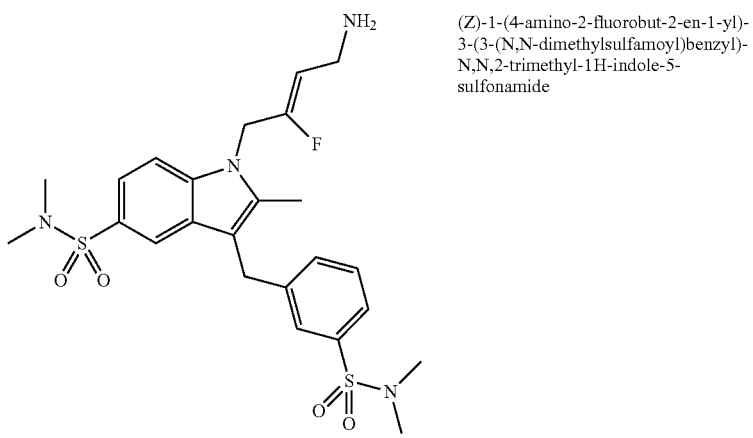 | (Z)-1-(4-amino-2-fluorobut-2-en-1-yl)-3-(3-(N,N-dimethylsulfamoyl)benzyl)-N,N,2-trimethyl-1H-indole-5-sulfonamide |
| 8 | 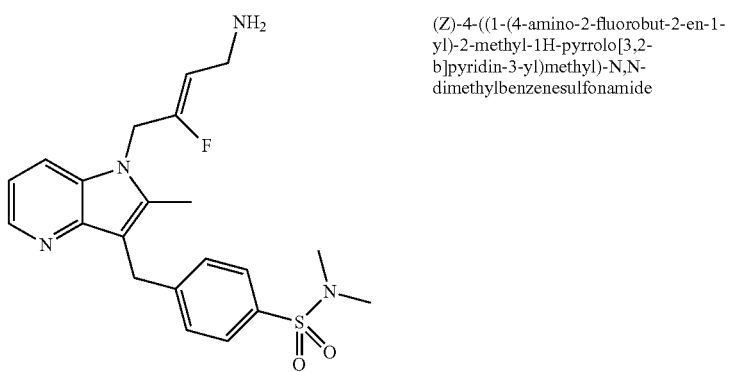 | (Z)-4-((1-(4-amino-2-fluorobut-2-en-1-yl)-2-methyl-1H-pyrrolo[3,2-b]pyridin-3-yl)methyl)-N,N-dimethylbenzenesulfonamide |
| 9 | 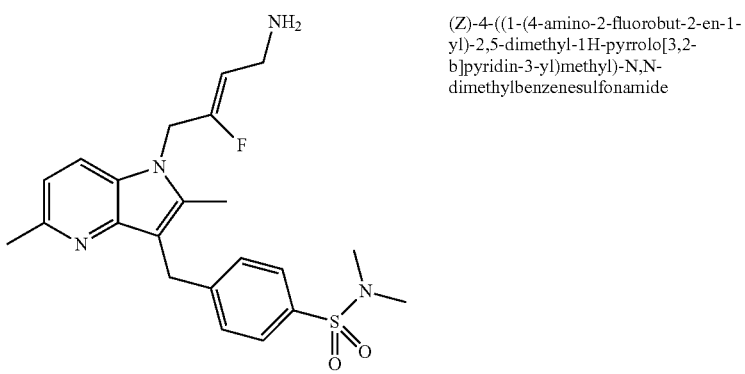 | (Z)-4-((1-(4-amino-2-fluorobut-2-en-1-yl)-2,5-dimethyl-1H-pyrrolo[3,2-b]pyridin-3-yl)methyl)-N,N-dimethylbenzenesulfonamide |
| 10 | 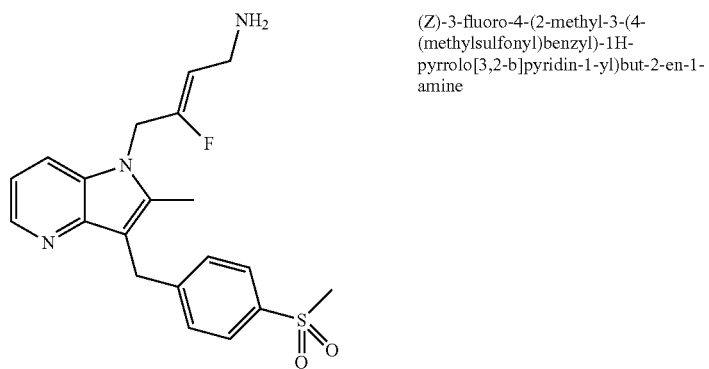 | (Z)-3-fluoro-4-(2-methyl-3-(4-(methylsulfonyl)benzyl)-1H-pyrrolo[3,2-b]pyridin-1-yl)but-2-en-1-amine |

| | | |
|---|---|---|
| 11 | 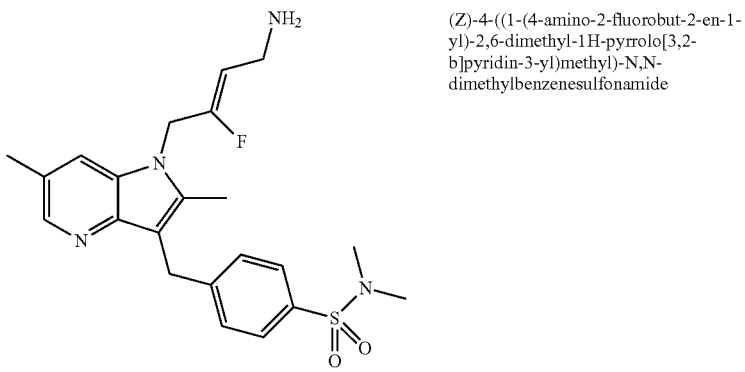 | (Z)-4-((1-(4-amino-2-fluorobut-2-en-1-yl)-2,6-dimethyl-1H-pyrrolo[3,2-b]pyridin-3-yl)methyl)-N,N-dimethylbenzenesulfonamide |
| 12 | 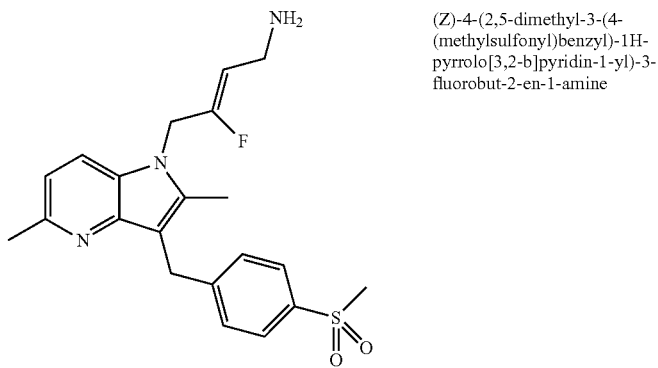 | (Z)-4-(2,5-dimethyl-3-(4-(methylsulfonyl)benzyl)-1H-pyrrolo[3,2-b]pyridin-1-yl)-3-fluorobut-2-en-1-amine |
| 13 | 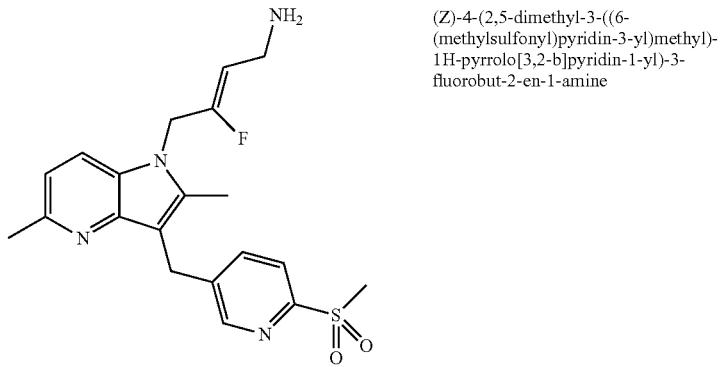 | (Z)-4-(2,5-dimethyl-3-((6-(methylsulfonyl)pyridin-3-yl)methyl)-1H-pyrrolo[3,2-b]pyridin-1-yl)-3-fluorobut-2-en-1-amine |
| 14 | 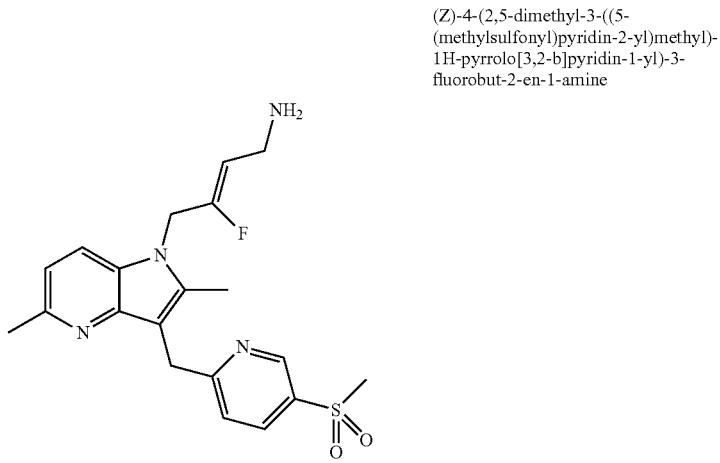 | (Z)-4-(2,5-dimethyl-3-((5-(methylsulfonyl)pyridin-2-yl)methyl)-1H-pyrrolo[3,2-b]pyridin-1-yl)-3-fluorobut-2-en-1-amine |

| | | |
|---|---|---|
| 15 | 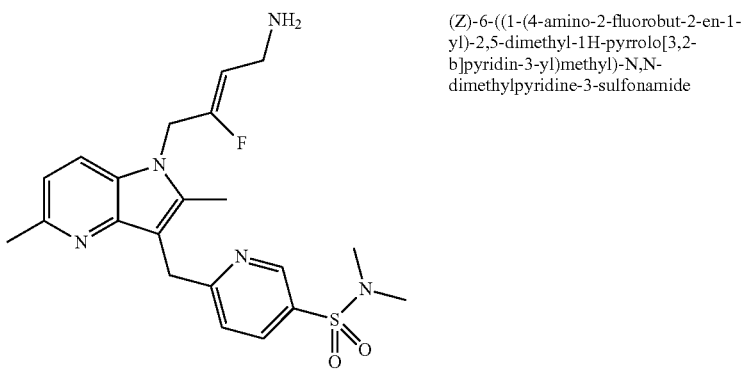 | (Z)-6-((1-(4-amino-2-fluorobut-2-en-1-yl)-2,5-dimethyl-1H-pyrrolo[3,2-b]pyridin-3-yl)methyl)-N,N-dimethylpyridine-3-sulfonamide |
| 16 | 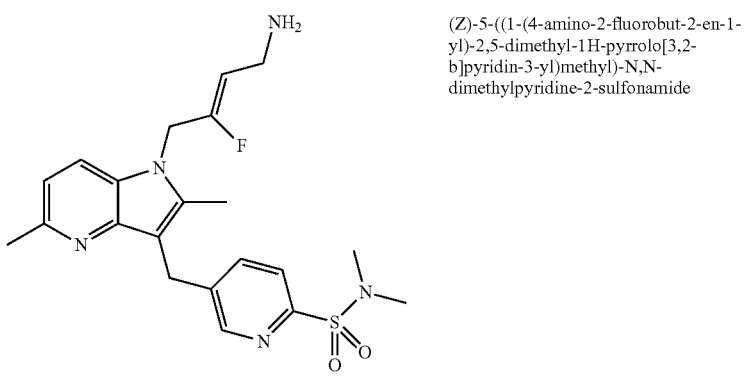 | (Z)-5-((1-(4-amino-2-fluorobut-2-en-1-yl)-2,5-dimethyl-1H-pyrrolo[3,2-b]pyridin-3-yl)methyl)-N,N-dimethylpyridine-2-sulfonamide |
| 17 | 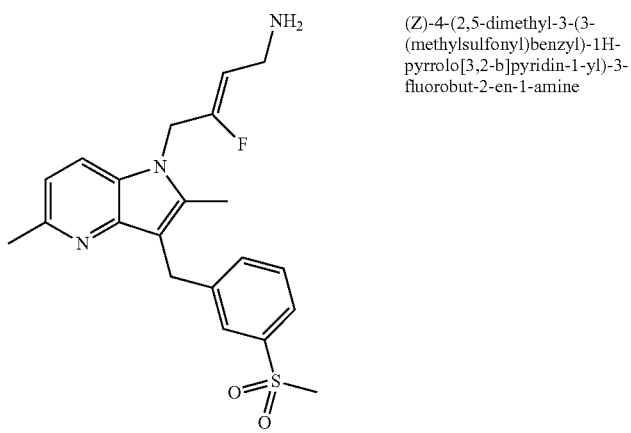 | (Z)-4-(2,5-dimethyl-3-(3-(methylsulfonyl)benzyl)-1H-pyrrolo[3,2-b]pyridin-1-yl)-3-fluorobut-2-en-1-amine |
| 18 | 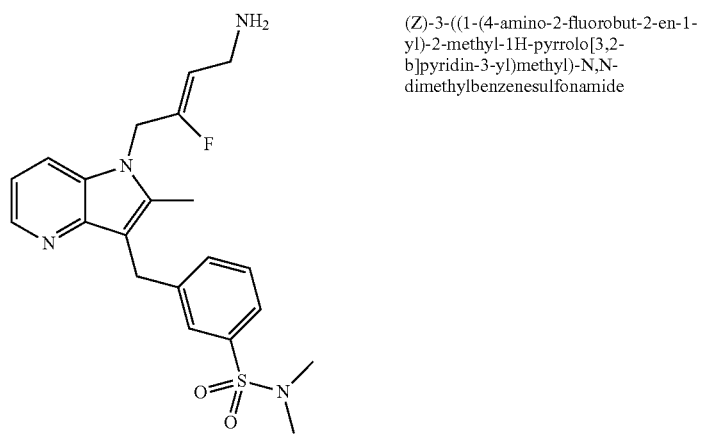 | (Z)-3-((1-(4-amino-2-fluorobut-2-en-1-yl)-2-methyl-1H-pyrrolo[3,2-b]pyridin-3-yl)methyl)-N,N-dimethylbenzenesulfonamide |

| | | |
|---|---|---|
| 19 | 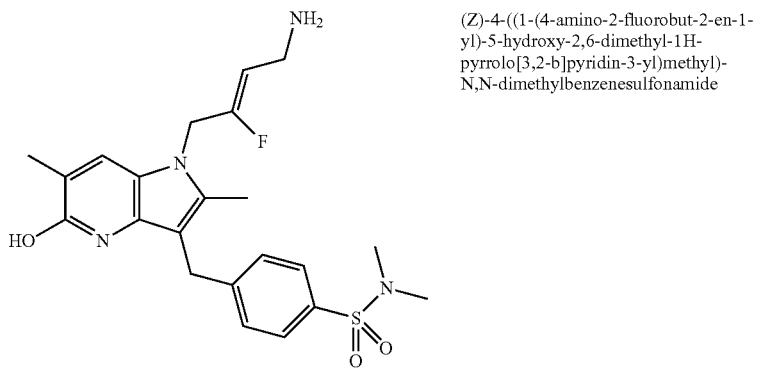 | (Z)-4-((1-(4-amino-2-fluorobut-2-en-1-yl)-5-hydroxy-2,6-dimethyl-1H-pyrrolo[3,2-b]pyridin-3-yl)methyl)-N,N-dimethylbenzenesulfonamide |
| 20 | 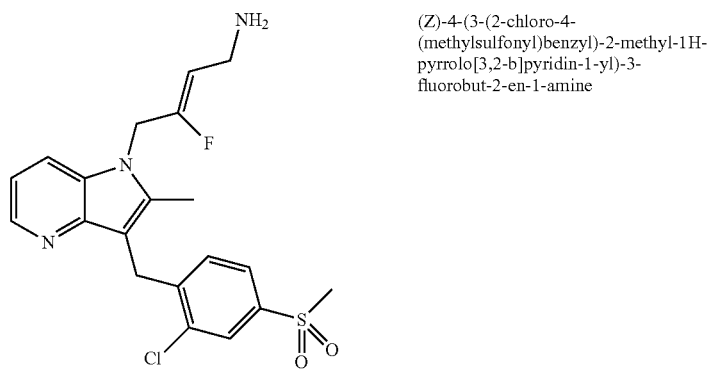 | (Z)-4-(3-(2-chloro-4-(methylsulfonyl)benzyl)-2-methyl-1H-pyrrolo[3,2-b]pyridin-1-yl)-3-fluorobut-2-en-1-amine |
| 21 | 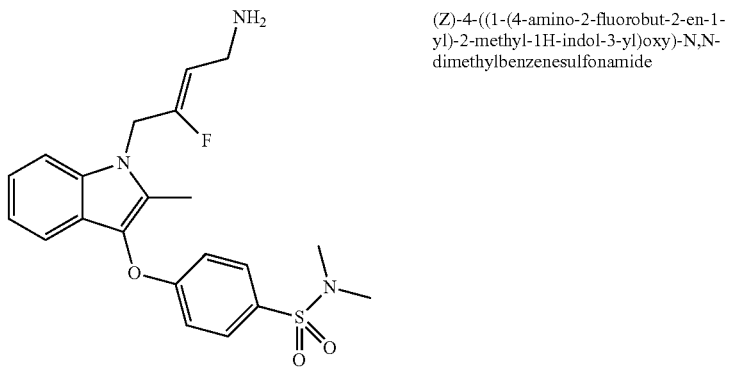 | (Z)-4-((1-(4-amino-2-fluorobut-2-en-1-yl)-2-methyl-1H-indol-3-yl)oxy)-N,N-dimethylbenzenesulfonamide |
| 22 | 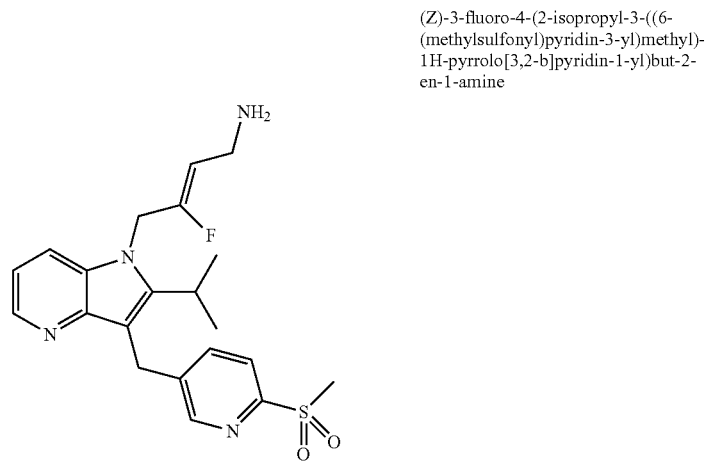 | (Z)-3-fluoro-4-(2-isopropyl-3-((6-(methylsulfonyl)pyridin-3-yl)methyl)-1H-pyrrolo[3,2-b]pyridin-1-yl)but-2-en-1-amine |

| | | |
|---|---|---|
| 23 | 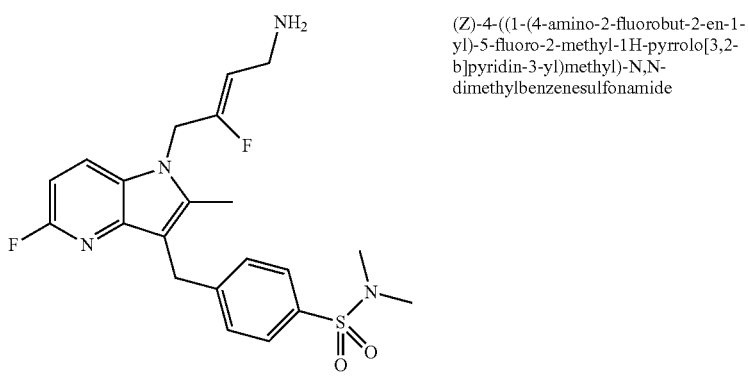 | (Z)-4-((1-(4-amino-2-fluorobut-2-en-1-yl)-5-fluoro-2-methyl-1H-pyrrolo[3,2-b]pyridin-3-yl)methyl)-N,N-dimethylbenzenesulfonamide |
| 24 | 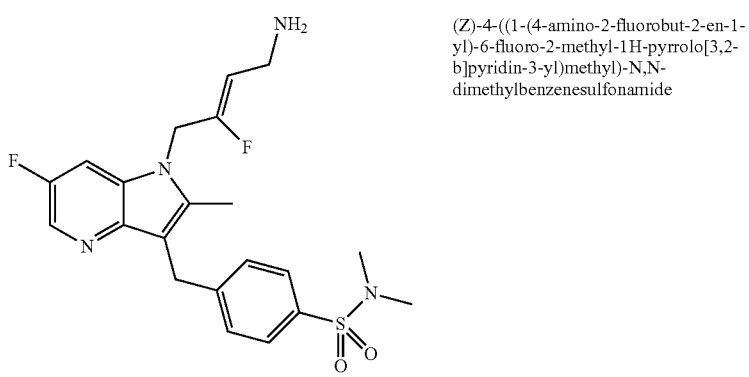 | (Z)-4-((1-(4-amino-2-fluorobut-2-en-1-yl)-6-fluoro-2-methyl-1H-pyrrolo[3,2-b]pyridin-3-yl)methyl)-N,N-dimethylbenzenesulfonamide |
| 26 | 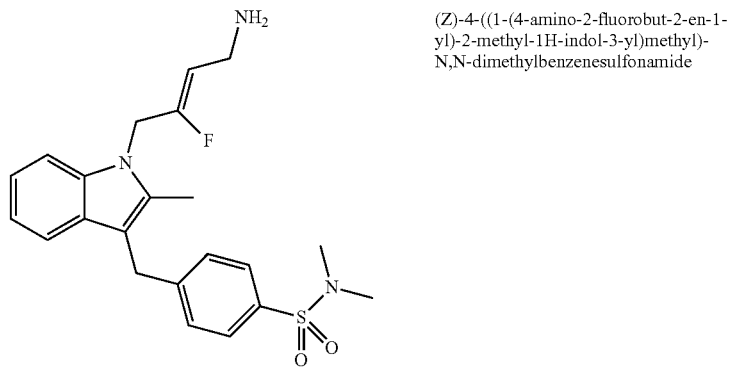 | (Z)-4-((1-(4-amino-2-fluorobut-2-en-1-yl)-2-methyl-1H-indol-3-yl)methyl)-N,N-dimethylbenzenesulfonamide |
| 27 | 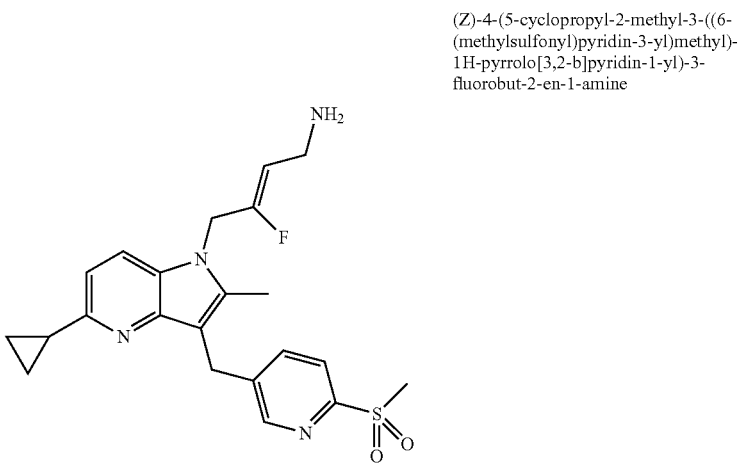 | (Z)-4-(5-cyclopropyl-2-methyl-3-((6-(methylsulfonyl)pyridin-3-yl)methyl)-1H-pyrrolo[3,2-b]pyridin-1-yl)-3-fluorobut-2-en-1-amine |

| | | |
|---|---|---|
| 28 | 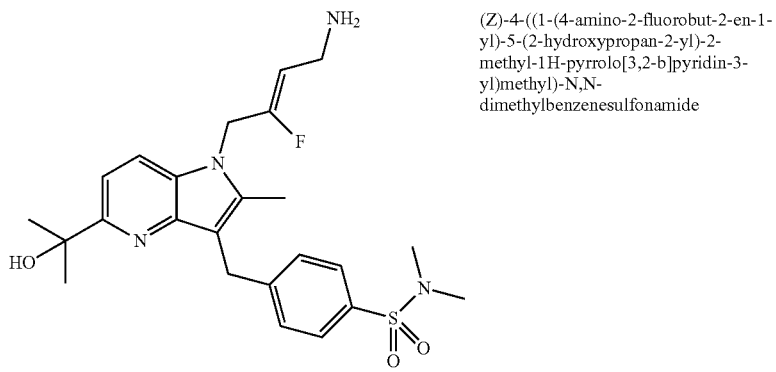 | (Z)-4-((1-(4-amino-2-fluorobut-2-en-1-yl)-5-(2-hydroxypropan-2-yl)-2-methyl-1H-pyrrolo[3,2-b]pyridin-3-yl)methyl)-N,N-dimethylbenzenesulfonamide |
| 29 | 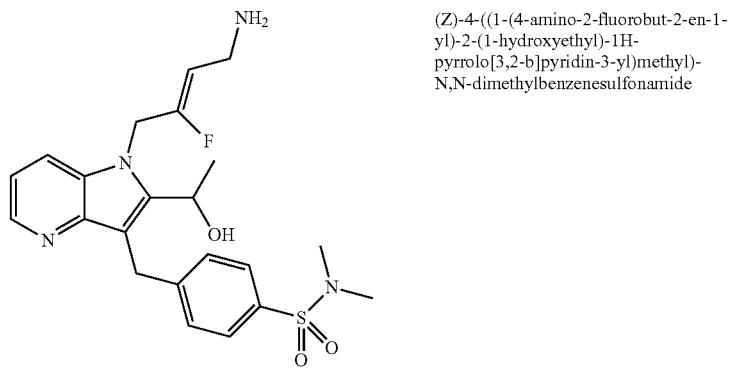 | (Z)-4-((1-(4-amino-2-fluorobut-2-en-1-yl)-2-(1-hydroxyethyl)-1H-pyrrolo[3,2-b]pyridin-3-yl)methyl)-N,N-dimethylbenzenesulfonamide |
| 30 | 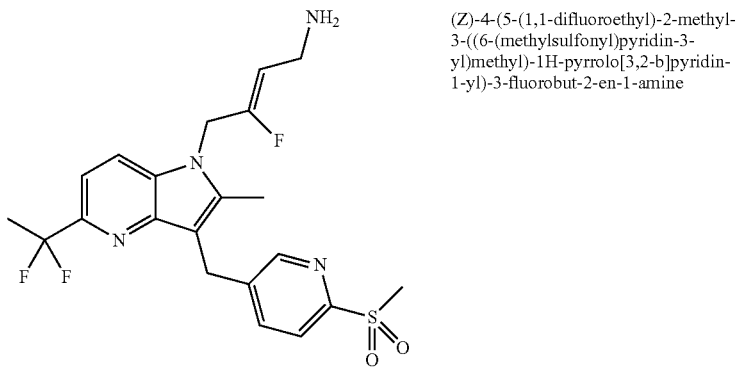 | (Z)-4-(5-(1,1-difluoroethyl)-2-methyl-3-((6-(methylsulfonyl)pyridin-3-yl)methyl)-1H-pyrrolo[3,2-b]pyridin-1-yl)-3-fluorobut-2-en-1-amine |
| 31 | 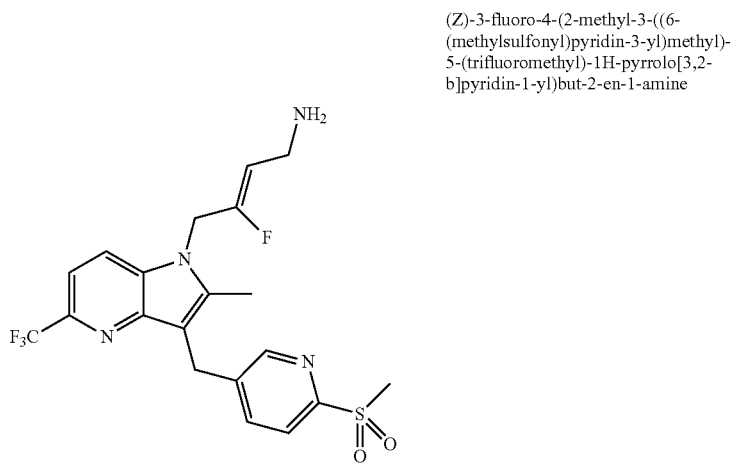 | (Z)-3-fluoro-4-(2-methyl-3-((6-(methylsulfonyl)pyridin-3-yl)methyl)-5-(trifluoromethyl)-1H-pyrrolo[3,2-b]pyridin-1-yl)but-2-en-1-amine |

| | | |
|---|---|---|
| 32 | 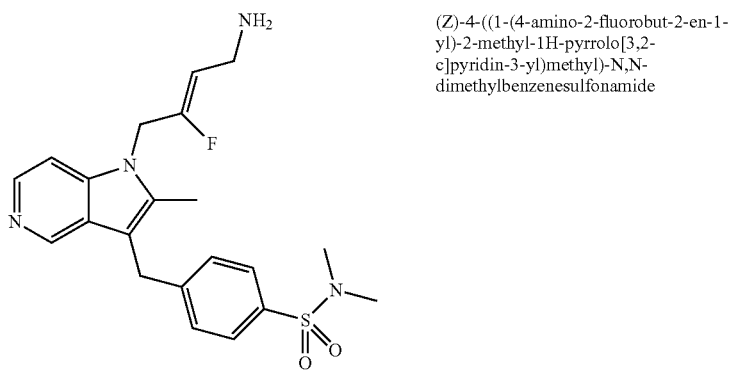 | (Z)-4-((1-(4-amino-2-fluorobut-2-en-1-yl)-2-methyl-1H-pyrrolo[3,2-c]pyridin-3-yl)methyl)-N,N-dimethylbenzenesulfonamide |
| 33 | 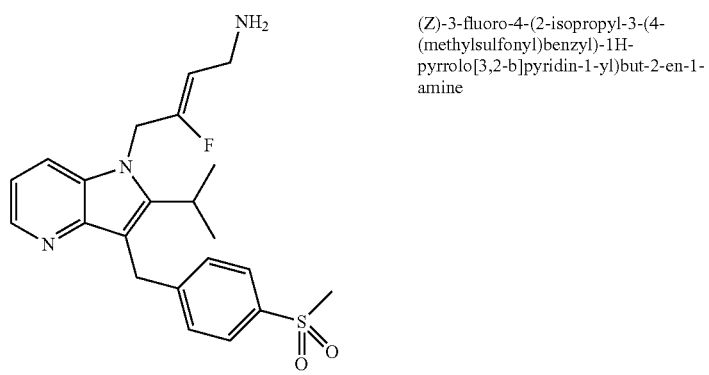 | (Z)-3-fluoro-4-(2-isopropyl-3-(4-(methylsulfonyl)benzyl)-1H-pyrrolo[3,2-b]pyridin-1-yl)but-2-en-1-amine |
| 34 | 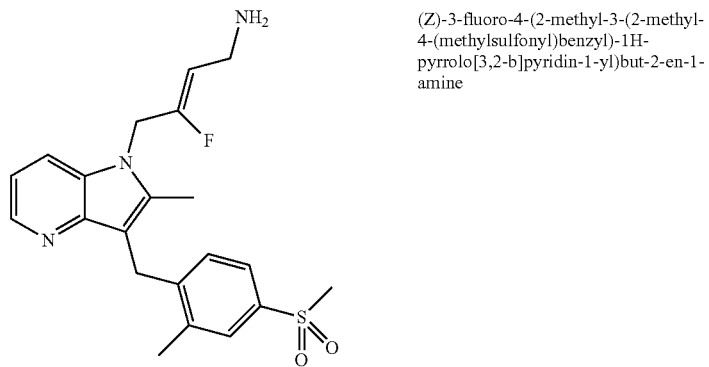 | (Z)-3-fluoro-4-(2-methyl-3-(2-methyl-4-(methylsulfonyl)benzyl)-1H-pyrrolo[3,2-b]pyridin-1-yl)but-2-en-1-amine |
| 35 | 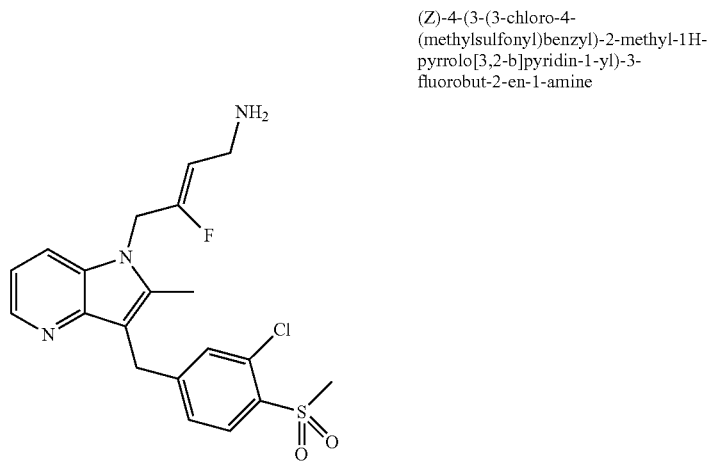 | (Z)-4-(3-(3-chloro-4-(methylsulfonyl)benzyl)-2-methyl-1H-pyrrolo[3,2-b]pyridin-1-yl)-3-fluorobut-2-en-1-amine |

| | | |
|---|---|---|
| 36 | 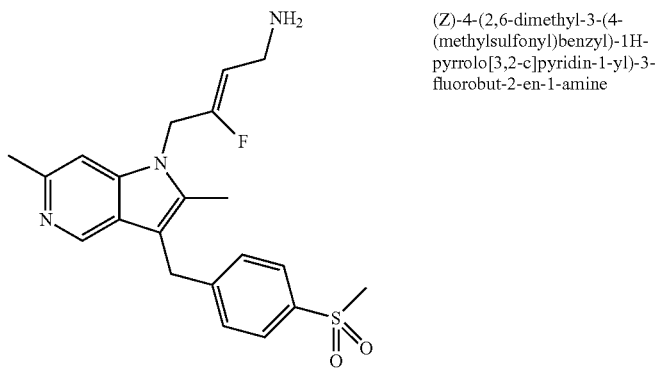 | (Z)-4-(2,6-dimethyl-3-(4-(methylsulfonyl)benzyl)-1H-pyrrolo[3,2-c]pyridin-1-yl)-3-fluorobut-2-en-1-amine |
| 37 | 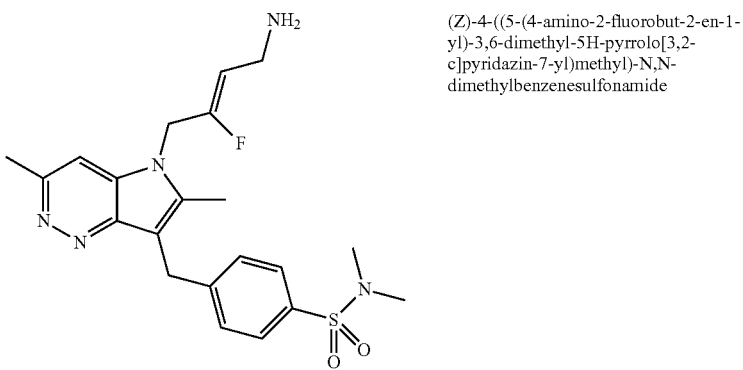 | (Z)-4-((5-(4-amino-2-fluorobut-2-en-1-yl)-3,6-dimethyl-5H-pyrrolo[3,2-c]pyridazin-7-yl)methyl)-N,N-dimethylbenzenesulfonamide |
| 38 | 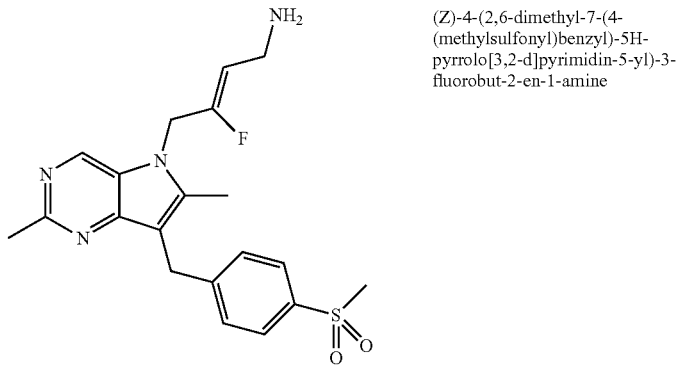 | (Z)-4-(2,6-dimethyl-7-(4-(methylsulfonyl)benzyl)-5H-pyrrolo[3,2-d]pyrimidin-5-yl)-3-fluorobut-2-en-1-amine |
| 39 | 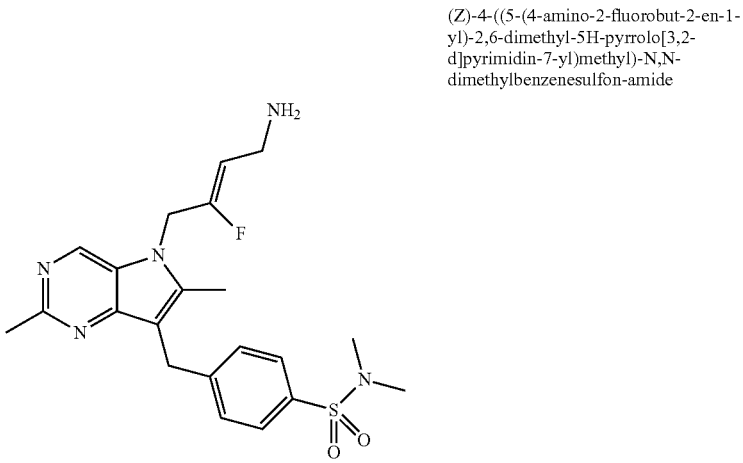 | (Z)-4-((5-(4-amino-2-fluorobut-2-en-1-yl)-2,6-dimethyl-5H-pyrrolo[3,2-d]pyrimidin-7-yl)methyl)-N,N-dimethylbenzenesulfon-amide |

| | | |
|---|---|---|
| 40 | 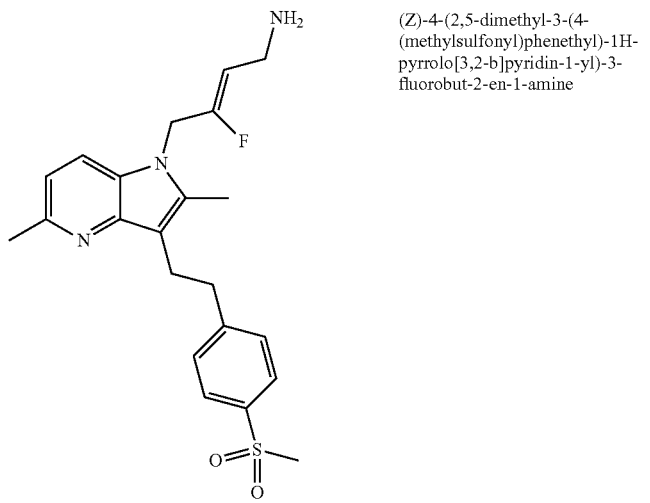 | (Z)-4-(2,5-dimethyl-3-(4-(methylsulfonyl)phenethyl)-1H-pyrrolo[3,2-b]pyridin-1-yl)-3-fluorobut-2-en-1-amine |
| 41 | 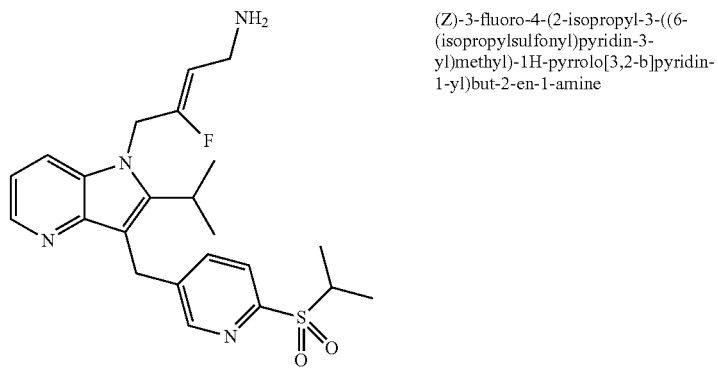 | (Z)-3-fluoro-4-(2-isopropyl-3-((6-(isopropylsulfonyl)pyridin-3-yl)methyl)-1H-pyrrolo[3,2-b]pyridin-1-yl)but-2-en-1-amine |
| 42 | 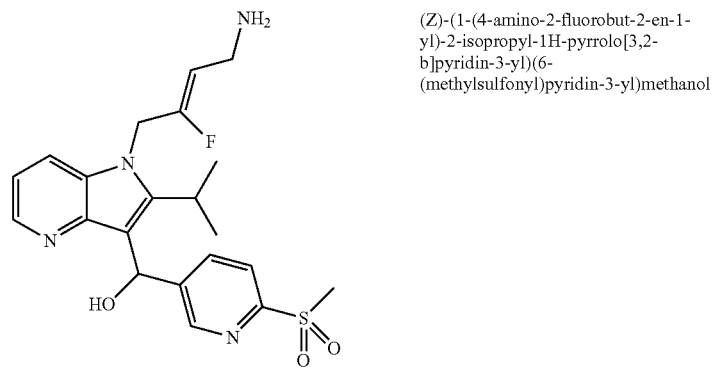 | (Z)-(1-(4-amino-2-fluorobut-2-en-1-yl)-2-isopropyl-1H-pyrrolo[3,2-b]pyridin-3-yl)(6-(methylsulfonyl)pyridin-3-yl)methanol |
| 43 | 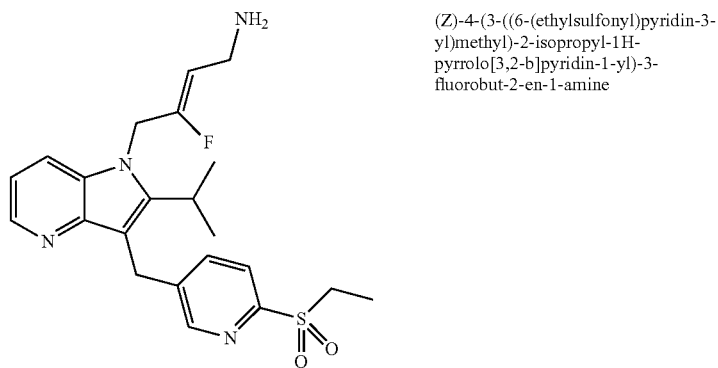 | (Z)-4-(3-((6-(ethylsulfonyl)pyridin-3-yl)methyl)-2-isopropyl-1H-pyrrolo[3,2-b]pyridin-1-yl)-3-fluorobut-2-en-1-amine |

| 44 | 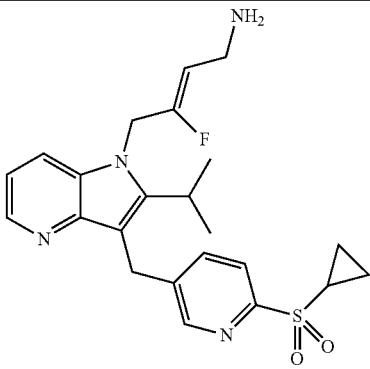 | (Z)-4-(3-((6-(cyclopropylsulfonyl)pyridin-3-yl)methyl)-2-isopropyl-1H-pyrrolo[3,2-b]pyridin-1-yl)-3-fluorobut-2-en-1-amine | or a pharmaceutically acceptable salt thereof.

10. A pharmaceutical composition comprising a compound according to claim 1, or a pharmaceutically acceptable salt thereof, and at least one pharmaceutically acceptable excipient, carrier or diluent.

11. A method of inhibiting the amine oxidase activity of LOX, LOXL1, LOXL2, LOXL3 and LOXL4 in a subject in need thereof, comprising administering to the subject an effective amount of a compound according to claim 1, or a pharmaceutically acceptable salt thereof.

12. A compound according to claim 1 of Formula I:

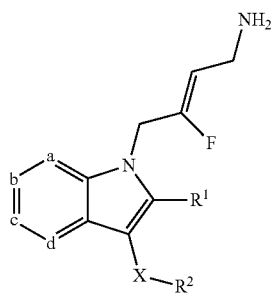

Formula I or a stereoisomer or pharmaceutically acceptable salt thereof;
wherein:
a is N or $CR^3$;
b is N or $CR^4$;
c is N or $CR^5$;
d is N or $CR^6$;
and from 0 to 2 of a, b, c and d are N;
X is O or —$(CHR^7)_m$—;
m is 1 or 2;
$R^1$ is selected from the group consisting of $C_{1-6}$alkyl and —$C(O)NR^9R^{10}$; wherein each $C_{1-6}$alkyl is a straight or branched chain alkyl; and wherein each $C_{1-6}$alkyl is optionally substituted by one —OH;
$R^2$ is selected from the group consisting of phenyl and pyridinyl; wherein each R is optionally substituted by one or more $R^{12}$;
$R^3$ is hydrogen;
$R^4$ is selected from the group consisting of hydrogen, halogen and $C_{1-6}$alkyl;
$R^5$ is selected from the group consisting of hydrogen, halogen, hydroxyl, $C_{1-6}$alkyl, C-cycloalkyl, —C(O)OR$^8$, —C(O)NR$^9$R$^{10}$ and —S(O$_2$)NR$^9$R$^{10}$; wherein each $C_{1-6}$alkyl is a straight or branched chain alkyl; and wherein each $C_{1-6}$alkyl is optionally substituted by one or more substituents selected from the group consisting of halogen and —OH;
$R^6$ is hydrogen;
each $R^7$ is independently selected from the group consisting of hydrogen and hydroxyl;
$R^8$ is selected from the group consisting of hydrogen and $C_{1-6}$alkyl;
$R^9$ and $R^{10}$ are independently selected from the group consisting of hydrogen and $C_{1-6}$alkyl;
$R^{11}$ is selected from the group consisting of $C_{1-6}$alkyl and $C_{3-7}$cycloalkyl; wherein each $C_{1-6}$alkyl is a straight or branched chain alkyl; and
$R^{12}$ is selected from the group consisting of —$S(O_2)NR^9R^{10}$ and —$S(O_2)R^{11}$.

13. A compound according to claim 1, wherein
X is selected from the group consisting of O and —$CH_2$—;
$R^1$ is selected from the group consisting of methyl, isopropyl, 1-hydroxyethyl, and —$C(O)N(CH_3)_2$;
$R^2$ is selected from the group consisting of phenyl,

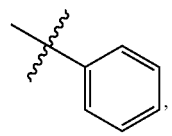, 2-pyridinyl,

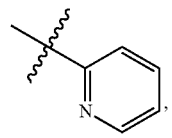, and 3-pyridinyl

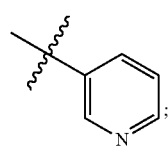;

wherein each $R^2$ is substituted by one or more $R^{12}$;
$R^4$ is selected from the group consisting of hydrogen, methyl and fluorine;
$R^5$ is selected from the group consisting of hydrogen, fluorine, hydroxyl, methyl, —$CF_3$, —$CHF_2CH_3$, —$C(CH_3)_2OH$, cyclopropyl, —C(O)OH, —C(O)OCH_3, —C(O)N(CH_3)_2, —C(O)NH_2 and —$S(O_2)N(CH_3)_2$; and
$R^{12}$ is selected from the group consisting of —$S(O_2)N(CH_3)_2$, —$S(O_2)CH_3$, —$S(O_2)Et$, —$S(O_2)^iPr$, and —$S(O_2)$cyclopropyl.

14. A compound according to claim 1, of Formula Ib:

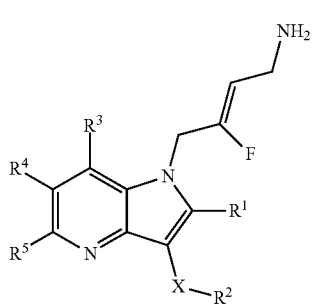

Formula Ib or a pharmaceutically acceptable salt thereof; wherein:
X is —$(CHR^7)_m$—;
m is 1 or 2;
$R^1$ is selected from the group consisting of hydrogen and $C_{1-6}$alkyl; wherein each $C_{1-6}$alkyl is a straight or branched chain alkyl; and wherein each $C_{1-6}$alkyl is optionally substituted by one —OH;
$R^2$ is selected from the group consisting of phenyl and pyridinyl; wherein each $R^2$ is optionally substituted by one or more $R^{12}$;
$R^3$ is hydrogen;
$R^4$ is selected from the group consisting of hydrogen, halogen and $C_{1-6}$alkyl;
$R^5$ is selected from the group consisting of hydrogen, halogen, hydroxyl, $C_{1-6}$alkyl and $C_{3-7}$cycloalkyl; wherein each $C_{1-6}$alkyl is a straight or branched chain alkyl; and wherein each $C_{1-6}$alkyl is optionally substituted by one or more substituents selected from the group consisting of halogen and, —OH;
each $R^7$ is independently selected from the group consisting of hydrogen and hydroxyl;
$R^9$ and $R^{10}$ are independently selected from $C_{1-6}$alkyl;
$R^{11}$ is selected from the group consisting of $C_{1-6}$alkyl and $C_{3-7}$cycloalkyl; wherein each $C_{1-6}$alkyl is a straight or branched chain alkyl; and
$R^{12}$ is selected from the group consisting of —$S(O_2)NR^9R^{10}$ and —$S(O_2)R^{11}$.

15. A compound according to claim 14, of Formula Ib wherein:
X is —$CH_2$—;
$R^1$ is selected from the group consisting of methyl, isopropyl and 1-hydroxyethyl;
$R^2$ is selected from the group consisting of phenyl

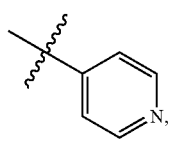 [SMILES: *c1ccncc1]

2-pyridinyl

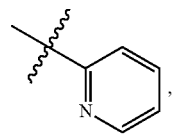 [SMILES: *c1ccccn1]

and 3-pyridinyl

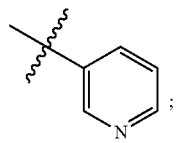

wherein each $R^2$ is substituted by one or more $R^{12}$;
$R^3$ is hydrogen;
$R^4$ is selected from the group consisting of hydrogen, methyl and fluorine;
$R^5$ is selected from the group consisting of hydrogen, fluorine, hydroxyl, methyl, —$CF_3$, —$C(CH_3)_2OH$ and cyclopropyl; and
$R^{12}$ is selected from the group consisting of —$S(O_2)N(CH_3)_2$, —$S(O_2)CH_3$, —$S(O_2)Et$, —$S(O_2)^iPr$, and —$S(O_2)$cyclopropyl.

16. The compound of claim 1 having the structure:

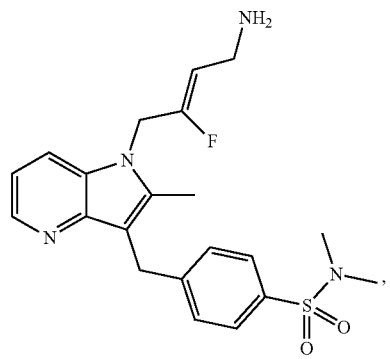 [SMILES: Cc1c(Cc2ccc(S(=O)(=O)N(C)C)cc2)c2ncccc2n1C/C(F)=C/CN]

or a pharmaceutically acceptable salt thereof.

17. The compound of claim 1 having the structure:

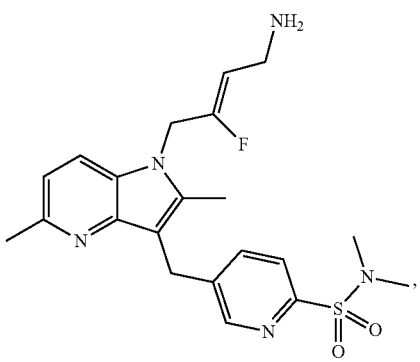

or a pharmaceutically acceptable salt thereof.

18. The compound of claim 1 having the structure:
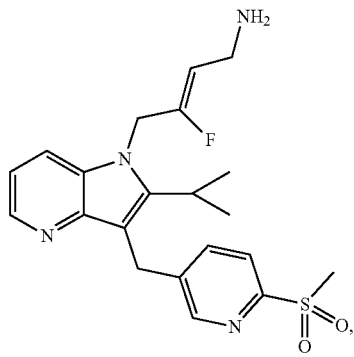 [SMILES: CC(C)c1c(Cc2ccc(S(C)(=O)=O)nc2)c2ncccc2n1C/C(F)=C/CN]
or a pharmaceutically acceptable salt thereof.
19. The compound of claim 1 having the structure:
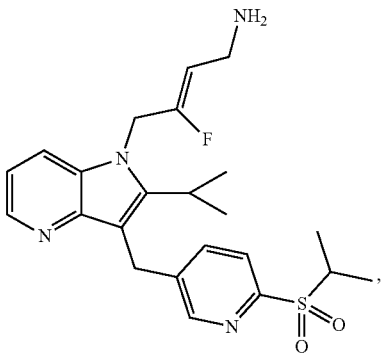 [SMILES: CC(C)c1c(Cc2ccc(S(=O)(=O)C(C)C)nc2)c2ncccc2n1C/C(F)=C/CN]
or a pharmaceutically acceptable salt thereof.
* * * * *